(12) United States Patent
Hirai et al.

(10) Patent No.: US 8,846,885 B2
(45) Date of Patent: Sep. 30, 2014

(54) OLIGONUCLEOTIDE WITH PROTECTED BASE

(71) Applicant: Ajinomoto Co., Inc., Tokyo (JP)

(72) Inventors: Kunihiro Hirai, Kawasaki (JP); Satoshi Katayama, Kawasaki (JP); Takayoshi Torii, Kawasaki (JP); Ryotaro Nakaya, Kawasaki (JP); Daisuke Takahashi, Yokkaichi (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/768,486

(22) Filed: Feb. 15, 2013

(65) Prior Publication Data

US 2013/0267697 A1    Oct. 10, 2013

Related U.S. Application Data

(60) Provisional application No. 61/600,191, filed on Feb. 17, 2012, provisional application No. 61/728,952, filed on Nov. 21, 2012.

(51) Int. Cl.
| | |
|---|---|
| *C07H 21/02* | (2006.01) |
| *C07H 21/04* | (2006.01) |
| *C07H 21/00* | (2006.01) |
| *C07H 1/00* | (2006.01) |
| *C07H 19/06* | (2006.01) |
| *C07H 19/173* | (2006.01) |
| *C07H 19/073* | (2006.01) |

(52) U.S. Cl.
CPC ............... *C07H 21/00* (2013.01); *C07H 1/00* (2013.01); *C07H 19/06* (2013.01); *C07H 19/173* (2013.01); *C07H 19/073* (2013.01)
USPC ...... 536/23.1; 536/22.1; 536/25.3; 536/25.31

(58) Field of Classification Search
None
See application file for complete search history.

(56) References Cited

U.S. PATENT DOCUMENTS 5,459,255 A    10/1995    Cook et al.

FOREIGN PATENT DOCUMENTS

| | | |
|---|---|---|
| JP | 9-500398 A | 1/1997 |
| JP | 2010-275254 A | 12/2010 |
| WO | WO 2005/070859 A1 | 8/2005 |

OTHER PUBLICATIONS

Oligonucleotide. (n.d.) *The American Heritage® Dictionary of the English Language, Fourth Edition*. (2003). Retrieved Jan. 12, 2014 from http://www.thefreedictionary.com/oligonucleotide.*

Martin Egli et al., "Current Protocols in Nucleic Acid Chemistry", John Wiley & Sons, Inc., vol. 1, 2000, pp. 3.0.1-3.0.3 and 3.1.1-3.1.28.

Gian Maria Bonora et al., "HELP (High Efficiency Liquid Phase) new oligonucleotide synthesis on soluble polymeric support", Nucleic Acids Research, vol. 18, No. 11, 1990, pp. 3155-3159.

Robert A. Donga et al., "A Novel Approach to Oligonucleotide Synthesis Using an Imidazolium Ion Tag as a Soluble Support", J. Org. Chem., vol. 71, 2006, pp. 7907-7910.

S. Yu. Andreev et al., "Synthesis of Oligodeoxyribonucleotides Containing Oleylamine Moieties", Russian Journal of Bioorganic Chemistry, vol. 27, No. 3, 2001, pp. 184-190.

T.S. Oretskaya et al., "A novel method of introducing hydrophobic moieties into oligonucleotides for covalent and non-covalent immobilization on electrode surfaces", Bioelectrochemistry, vol. 56, 2002, pp. 47-51.

* cited by examiner

*Primary Examiner* — Patrick Lewis
(74) *Attorney, Agent, or Firm* — Oblon, Spivak, McClelland, Maier & Neustadt, L.L.P.

(57) ABSTRACT

The present invention provides a protected nucleotide for elongation, which can be purified efficiently and in a high yield by a liquid-liquid extraction operation, and can achieve an oligonucleotide production method by a phosphoramidite method.

It has been found that the above-mentioned problem can be solved by a particular oligonucleotide comprising a protected base and/or particular oligonucleotide protected by a branched chain-containing aromatic group at 3'-position.

22 Claims, No Drawings

OLIGONUCLEOTIDE WITH PROTECTED BASE

TECHNICAL FIELD OF THE INVENTION

The present invention relates to a particular oligonucleotide comprising a protected base and a production method of an oligonucleotide using the same. In addition, the present invention relates to a particular branched chain-containing aromatic protecting group, an oligonucleotide having a 3'-hydroxyl group protected by said protecting group, and a production method of an oligonucleotide using the oligonucleotide having a 3'-hydroxyl group protected by said protecting group.

BACKGROUND OF THE INVENTION

The synthesis method of oligonucleotide includes a phosphate triester method, an H-phosphonate method, a phosphoramidite method and the like, and solid phase synthesis (solid phase method) using a phosphoramidite method is most widely used at present (non-patent document 1). The solid phase method is advantageous from the aspect of speed, since process has been optimized and automation has progressed. However, it is associated with defects in that scaling-up is limited due to facility restriction, reagents and starting materials are used in excess, and confirmation of the progress status of the reaction in an intermediate step, analysis of intermediate structure and the like are difficult.

The synthesis methods of oligonucleotide by a liquid phase method have also been studied. Generally, however, treatments after each reaction are performed by a method including (1) directly concentrating the reaction mixture, followed by isolation and purification by silica gel column chromatography, (2) extracting with a solvent such as methylene chloride, chloroform and the like, washing with an aqueous solution, concentrating, purifying by silica gel column chromatography, and the like, and the operation is complicated and the yield is low. In particular, a large-scale, rapid synthesis of a long oligonucleotide is difficult, and the methods are impractical as industrial production processes.

In recent years, a pseudo-solid phase method-like approach has been reported as an attempt to solve the respective defects of the liquid phase method and the solid phase method, and an oligonucleotide production method using a soluble polymer such as monomethoxypolyethylene glycol (MPEG) and the like as a protecting group is disclosed as one example thereof (non-patent document 2). However, while synthetic examples of up to 20mer DNA are disclosed, a crystallization isolation operation is essential for each reaction, and the progress status of the reaction and the like are difficult to confirm, since MPEG molecule itself is not a unimolecule.

In addition, as a pseudo-solid phase method-like method, a production method of oligonucleotide including use of an ionic liquid as a protecting group has been reported, and Synthetic Examples of DNA up to pentamers are shown (non-patent document 3). However, the method is inferior to a solid phase method in the speed and efficiency, since a crystallization isolation operation is essential for each reaction and an operation time is necessary therefor.

Furthermore, a synthesis method of oligonucleotide comprising use of a hydrophobic group-linked nucleoside is disclosed (patent document 1). While it has been reported that the method affords synthesis of 21mer oligonucleotide, it is markedly complicated, since the method requires solidification isolation in every step of deprotection of 5'-protecting group, coupling and oxidation.

DOCUMENT LIST

Patent Document patent document 1: JP-A-2010-275254

Non-Patent Documents non-patent document 1: S. L. Beaucage, D. E. Bergstorm, G. D. Glick, R. A. Jones, Current Protocols in Nucleic Acid Chemistry; John Wiley & Sons (2000)
non-patent document 2: Nucleic Acid Res., 1990, Vol. 18, No. 11, 3155-3159
non-patent document 3: J. Org. Chem., 2006, Vol. 71, No. 20, 7907-7910

SUMMARY OF THE INVENTION

Problems to be Solved by the Invention

The problem of the present invention is provision of a protected nucleotide for elongation, which can afford a production method of oligonucleotide by a phosphoramidite method, which enables efficient purification in a high yield by a liquid-liquid extraction operation.

Means of Solving the Problems

As a result of the intensive studies, the present inventors have found that the above-mentioned problem can be achieved by a particular oligonucleotide comprising a protected base, which resulted in the completion of the present invention.

The present invention includes the following.
[1] An oligonucleotide comprising a protected base, which is represented by the formula (I):

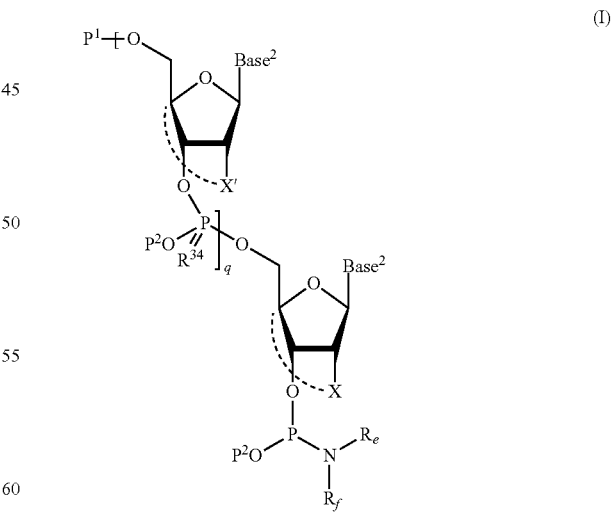

wherein q is any integer of not less than 0;
Base$^2$ in the number of q+1 are each independently a nucleic acid base protected by a group having a $C_{5-30}$ straight chain or branched chain alkyl group and/or a $C_{5-30}$ straight chain or branched chain alkenyl group;

P¹ is a hydrogen atom, or a temporary protecting group removable under acidic conditions;

X is a hydrogen atom, an optionally protected hydroxyl group, a halogen atom or an organic group crosslinked with the 4-position carbon atom;

X' in the number of q are each independently a hydrogen atom, an optionally protected hydroxyl group, a halogen atom or an organic group crosslinked with the 4-position carbon atom;

P² in the number of q+1 are each independently a protecting group removable under basic conditions;

$R^{34}$ in the number of q are each independently an oxygen atom or a sulfur atom; and $R_e$ and $R_f$ are each independently a $C_{1-6}$ alkyl group, or a 5- or 6-membered saturated cyclic amino group formed together with the adjacent nitrogen atom.

[2] The oligonucleotide comprising a protected base of [1], wherein q is 0.

[3] The oligonucleotide comprising a protected base of [1] or [2], wherein the group having a $C_{5-30}$ straight chain or branched chain alkyl group and/or a $C_{5-30}$ straight chain or branched chain alkenyl group is
a group represented by the formula (k):

(k)

wherein * indicates the bonding position to a nucleic acid base;

$R^{27}$ is a $C_{5-30}$ straight chain or branched chain alkyl group or a $C_{5-30}$ straight chain or branched chain alkenyl group,
a group represented by the formula (l):

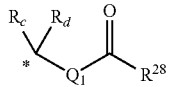

(l)

wherein * indicates the bonding position to a nucleic acid base;

$Q_1$ is —O—, —S— or —NR³⁰— wherein $R^{30}$ is a hydrogen atom or a $C_{1-22}$ alkyl group;

$R_c$ and $R_d$ are each independently a hydrogen atom or a $C_{1-22}$ alkyl group; and $R^{28}$ is a $C_{5-30}$ straight chain or branched chain alkyl group or a $C_{5-30}$ straight chain or branched chain alkenyl group,
a group represented by the formula (m):

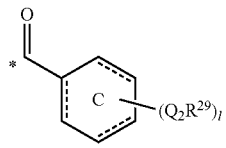

(m)

wherein * indicates the bonding position to a nucleic acid base;

l is an integer of 1 to 5;

$Q_2$ in the number of l are each independently a single bond, or —O—, —S—, —OC(=O)—, —C(=O)O—, —O—CH₂—, —NH—, —NHC(=O)—, —C(=O)NH—, —NH—CH₂— or —CH₂—;

$R^{29}$ in the number of l are each independently a $C_{5-30}$ straight chain or branched chain alkyl group or a $C_{5-30}$ straight chain or branched chain alkenyl group;

ring C is a benzene ring or a cyclohexane ring, each optionally having, in addition to $Q_2R^{29}$ in the number of l and *C=O, a substituent selected from the group consisting of a halogen atom, a $C_{1-6}$ alkyl group optionally substituted by one or more halogen atoms, and a $C_{1-6}$ alkoxy group optionally substituted by one or more halogen atoms, or
a group represented by the formula (s):

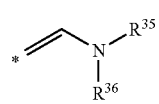

(s)

wherein * indicates the position at which an imino bond is formed with an amino group of a nucleic acid base; and $R^{35}$ and $R^{36}$ are each independently a $C_{5-30}$ straight chain or branched chain alkyl group or a $C_{5-30}$ straight chain or branched chain alkenyl group.

[4] The oligonucleotide comprising a protected base of [3], wherein $R^{27}$, $R^{28}$, $R^{29}$ in the number of l, $R^{35}$ and $R^{36}$ are each independently a branched chain alkyl group or branched chain alkenyl group selected from the group consisting of a 2,6,10,14-tetramethylpentadecyl group, a 2,6,10-trimethylundecyl group, a 2,2,4,8,10,10-hexamethyl-5-undecyl group, a 2,6,10-trimethylundeca-1,5,9-trienyl group, a 2,6-dimethylheptyl group, a 2,6-dimethylhept-5-enyl group, a 2,6-dimethylhepta-1,5-dienyl group, a 9-nonadecyl group, a 12-methyltridecyl group, an 11-methyltridecyl group, an 11-methyldodecyl group, a 10-methylundecyl group, an 8-heptadecyl group, a 7-pentadecyl group, a 7-methyloctyl group, a 3-methyloctyl group, a 3,7-dimethyloctyl group, a 3-methylheptyl group, a 3-ethylheptyl group, a 5-undecyl group, a 2-heptyl group, a 2-methyl-2-hexyl group, a 2-hexyl group, a 3-heptyl group, a 4-heptyl group, a 4-methyl-pentyl group, a 3-methyl-pentyl group, and a 2,4,4-trimethylpentyl group; or a straight chain alkyl group selected from the group consisting of a tetradecyl group, a tridecyl group, a dodecyl group, an undecyl group, a decyl group, a nonyl group, an octyl group, a heptyl group, a hexyl group, and a pentyl group.

[5] The oligonucleotide comprising a protected base of any one of [1] to [4], wherein the $C_{5-30}$ straight chain or branched chain alkyl group and/or $C_{5-30}$ straight chain or branched chain alkenyl group is a $C_{5-30}$ branched chain alkyl group and/or a $C_{5-30}$ branched chain alkenyl group.

[6] The oligonucleotide comprising a protected base of any one of [1] to [5], wherein P¹ is a monomethoxytrityl group or a dimethoxytrityl group.

[7] A method of producing an oligonucleotide, comprising using the oligonucleotide comprising a protected base of any one of [1] to [6].

[8] A method of producing an n+p-mer oligonucleotide, comprising (2) a step of condensing a p-mer oligonucleotide comprising a protected base (p is any integer of one or more) wherein the 3'-hydroxyl group is phosphoramidited, the 5'-hydroxyl group is protected by a temporary protecting group removable under acidic conditions, and the nucleic acid base is protected by a group having a $C_{5-30}$ straight chain or branched chain alkyl group and/or a $C_{5-30}$ straight chain or branched chain alkenyl group, with an n-mer oligonucleotide (n is an integer of one or more) wherein the 5'-hydroxyl group is not protected and the 3'-hydroxyl group is protected, by forming a phosphite triester bond via the 5'-hydroxyl group thereof.

[9] The production method of [8], wherein p is 1.

[10] The production method of [8] or [9], further comprising the following step (3):

(3) a step of converting the phosphite triester bond of the n+p-mer oligonucleotide obtained in the condensation step to a phosphate triester bond or a thiophosphate triester bond by adding an oxidizing agent or a sulfurizing agent to the reaction mixture obtained in the condensation step (2).

[11] The production method of any one of [8] to [10], further comprising the following step (1):

(1) a step of removing the temporary protecting group removable under acidic conditions of the 5'-hydroxyl group by reacting, in a non-polar solvent prior to the condensation step (2), an n-mer oligonucleotide wherein the 3'-hydroxyl group is protected, and the 5'-hydroxyl group is protected by a temporary protecting group, with an acid.

[12] The production method of [11], wherein the step (1) is performed in the presence of at least one kind of cation scavenger selected from a pyrrole derivative and an indole derivative, and further comprises a step of neutralization with an organic base after removal of the temporary protecting group of the 5'-hydroxyl group.

[13] The production method of any one of [10] to [12], further comprising the following step (4):

(4) a step of isolating the n+p-mer oligonucleotide from the reaction mixture obtained in step (3) by an extraction operation alone.

[14] The method of [13], further comprising the following step (5):

(5) a step of removing all the protecting groups of the n+p-mer oligonucleotide obtained in step (4).

[15] The production method of any one of [8] to [14], wherein the p-mer oligonucleotide comprising a protected base, wherein the 3'-hydroxyl group is phosphoramidited, the 5'-hydroxyl group is protected by a temporary protecting group removable under acidic conditions, and the nucleic acid base is protected by a group having a $C_{5-30}$ straight chain or branched chain alkyl group and/or a $C_{5-30}$ straight chain or branched chain alkenyl group, is the oligonucleotide comprising a protected base of any one of [1] to [6].

[16] The production method of any one of [8] to [15], wherein the 3'-hydroxyl group of the n-mer oligonucleotide is protected by a group represented by the formula (III):

-L-Y—Z    (III)

wherein
L is a group represented by the formula (a1):

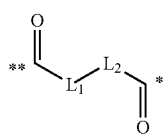

(a1)

wherein * shows the bonding position to Y; ** indicates the bonding position to a 3'-hydroxy group of the nucleotide;
$L_1$ is an optionally substituted divalent $C_{1-22}$ hydrocarbon group; and
$L_2$ is a single bond, or a group represented by C(=O)N($R^2$)—$R^1$—N($R^3$)* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or
$R^2$ and $R^3$ are optionally joined to form an optionally substituted $C_{1-22}$ alkylene bond,
Y is an oxygen atom or NR wherein R is a hydrogen atom, an alkyl group or an aralkyl group, and
Z is a group represented by the formula (a2):

(a2)

wherein * shows the bonding position to Y;
$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;
Q in the number of k are each independently a single bond, or —O—, —S—, —OC(=O)—, —NHC(=O)— or —NH—;
$R^5$ in the number of k are each independently an organic group having at least one aliphatic hydrocarbon group having one or more branched chains and the total carbon number of not less than 14 and not more than 300;
k is an integer of 1 to 4;
ring A optionally further has, in addition to $R^4$, $QR^5$ in the number of k and *C($R_a$)($R_b$), a substituent selected from the group consisting of a halogen atom, a $C_{1-6}$ alkyl group optionally substituted by one or more halogen atoms, and a $C_{1-6}$ alkoxy group optionally substituted by one or more halogen atoms;
$R_a$ is a hydrogen atom; and
$R_b$ is a hydrogen atom, or a group represented by the formula (a3):

(a3)

wherein * indicates a bonding position;
j is an integer of 0 to 4;
Q in the number of j are each independently as defined above;
$R^7$ in the number of j are each independently an organic group having at least one aliphatic hydrocarbon group having one or more branched chains and the total carbon number of not less than 14 and not more than 300;
$R^6$ is a hydrogen atom, or optionally a single bond or —O— in combination with $R^4$ to form a fluorenyl group or a xanthenyl group together with ring A; and
ring B optionally further has, in addition to $QR^7$ in the number of j and $R^6$, a substituent selected from the group consisting of a halogen atom, a $C_{1-6}$ alkyl group optionally substituted by one or more halogen atoms, and a $C_{1-6}$ alkoxy group optionally substituted by one or more halogen atoms.

[17] The production method of any one of [8] to [16], wherein at least one nucleic acid base of the n-mer oligonucleotide is protected by a group having a $C_{5-30}$ straight chain or branched chain alkyl group and/or a $C_{5-30}$ straight chain or branched chain alkenyl group.

[18] The production method of any one of [8] to [17], wherein the group having a $C_{5-30}$ straight chain or branched chain alkyl group and/or a $C_{5-30}$ straight chain or branched chain alkenyl group is a group represented by the formula (k):

(k)

wherein * indicates the bonding position to a nucleic acid base; and $R^{27}$ is a $C_{5-30}$ straight chain or branched chain alkyl group or a $C_{5-30}$ straight chain or branched chain alkenyl group, a group represented by the formula (l):

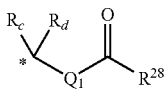

(l)

wherein * indicates the bonding position to a nucleic acid base;

$Q_1$ is —O—, —S— or —$NR^{30}$— wherein $R^{30}$ is a hydrogen atom or a $C_{1-22}$ alkyl group;

$R_c$ and $R_d$ are each independently a hydrogen atom or a $C_{1-22}$ alkyl group; and $R^{28}$ is a $C_{5-30}$ straight chain or branched chain alkyl group or a $C_{5-30}$ straight chain or branched chain alkenyl group, a group represented by the formula (m):

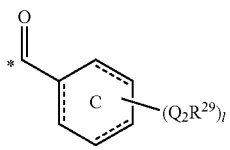

(m)

wherein * indicates the bonding position to a nucleic acid base;

l is an integer of 1 to 5;

Q2 in the number of l are each independently a single bond, or —O—, —S—, —CO(=O)—, —C(=O)O—, —O—CH$_2$—, —NH—, —NHC(=O)—, —C(=O) NH—, —NH—CH$_2$— or —CH$_2$—;

$R^{29}$ in the number of l are each independently a $C_{5-30}$ straight chain or branched chain alkyl group or a $C_{5-30}$ straight chain or branched chain alkenyl group; and ring C is a benzene ring or a cyclohexane ring each optionally having, in addition to $Q_2R^{29}$ in the number of l and *C=O, a substituent selected from the group consisting of a halogen atom, a $C_{1-6}$ alkyl group optionally substituted by one or more halogen atoms, and a $C_{1-6}$ alkoxy group optionally substituted by one or more halogen atoms), or a group represented by the formula (s):

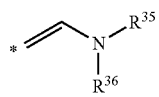

(s)

wherein * indicates the position at which an imino bond is formed with an amino group of a nucleic acid base; and $R^{35}$ and $R^{36}$ are each independently a $C_{5-30}$ straight chain or branched chain alkyl group or a $C_{5-30}$ straight chain or branched chain alkenyl group.

[19] The production method of [18], wherein $R^{27}$, $R^{28}$, $R^{29}$ in the number of 1, $R^{35}$ and $R^{36}$ are each independently a branched chain alkyl group or branched chain alkenyl group selected from the group consisting of a 2,6,10,14-tetramethylpentadecyl group, a 2,6,10-trimethylundecyl group, a 2,2,4,8,10,10-hexamethyl-5-undecyl group, a 2,6,10-trimethylundeca-1,5,9-trienyl group, a 2,6-dimethylheptyl group, a 2,6-dimethylhept-5-enyl group, a 2,6-dimethylhepta-1,5-dienyl group, a 9-nonadecyl group, a 12-methyltridecyl group, an 11-methyltridecyl group, an 11-methyldodecyl group, a 10-methylundecyl group, an 8-heptadecyl group, a 7-pentadecyl group, a 7-methyloctyl group, a 3-methyloctyl group, a 3,7-dimethyloctyl group, a 3-methylheptyl group, a 3-ethylheptyl group, a 5-undecyl group, a 2-heptyl group, a 2-methyl-2-hexyl group, a 2-hexyl group, a 3-heptyl group, a 4-heptyl group, a 4-methyl-pentyl group, a 3-methyl-pentyl group, and a 2,4,4-trimethylpentyl group; or a straight chain alkyl group selected from the group consisting of a tetradecyl group, a tridecyl group, a dodecyl group, an undecyl group, a decyl group, a nonyl group, an octyl group, a heptyl group, a hexyl group, and a pentyl group.

[20] The production method of any one of [8] to [19], wherein the $C_{5-30}$ straight chain or branched chain alkyl group and/or $C_{5-30}$ straight chain or branched chain alkenyl group are/is a $C_{5-30}$ branched chain alkyl group and/or a $C_{5-30}$ branched chain alkenyl group.

[21] A pharmaceutical product comprising the oligonucleotide produced by the production method of any one of [7] to [20].

[22] An oligonucleotide protected by a branched chain-containing aromatic group, which is represented by the formula (II):

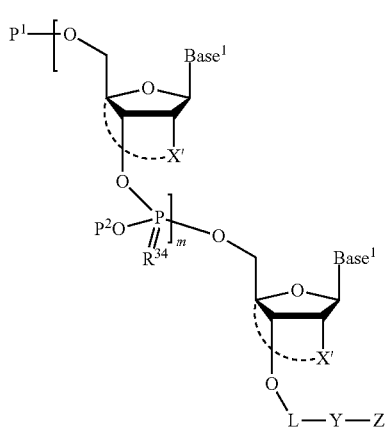

(II)

wherein m is any integer of 0 or more;

Base¹ in the number of m+1 are each independently an optionally protected nucleic acid base;

$P^1$ is a hydrogen atom, or a temporary protecting group removable under acidic conditions;

X is a hydrogen atom, an optionally protected hydroxyl group, a halogen atom or an organic group crosslinked with the 4-position carbon atom;

X' in the number of m are each independently a hydrogen atom, an optionally protected hydroxyl group, a halogen atom or an organic group crosslinked with the 4-position carbon atom;

$P^2$ in the number of m are each independently a protecting group removable under basic conditions;

$R^{34}$ in the number of m are each independently an oxygen atom or a sulfur atom;

L is a group represented by the formula (a1):

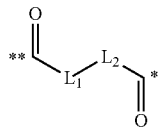
(a1)

wherein * shows the bonding position to Y; ** indicates the bonding position to a 3'-hydroxy group of the nucleotide;

$L_1$ is an optionally substituted divalent $C_{1-22}$ hydrocarbon group; and $L_2$ is a single bond, or a group represented by C(=O)N($R^2$)—$R^1$—N($R^3$)* wherein shows the bonding position to $L_1$, *** shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond, Y is an oxygen atom or NR wherein R is a hydrogen atom, an alkyl group or an aralkyl group, and Z is a group represented by the formula (a2):

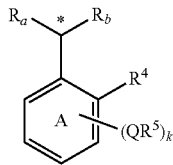
(a2)

wherein * shows the bonding position to Y;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

Q in the number of k are each independently a single bond, or —O—, —S—, —OC(=O)—, —NHC(=O)— or —NH—;

$R^5$ in the number of k are each independently an organic group having at least one aliphatic hydrocarbon group having one or more branched chains, and the total carbon number of not less than 14 and not more than 300;

k is an integer of 1 to 4;

ring A optionally further has, in addition to $R^4$, $QR^5$ in the number of k and *C($R_a$)($R_b$), a substituent selected from the group consisting of a halogen atom, a $C_{1-6}$ alkyl group optionally substituted by one or more halogen atoms, and a $C_{1-6}$ alkoxy group optionally substituted by one or more halogen atoms;

$R_a$ is a hydrogen atom; and $R_b$ is a hydrogen atom, or a group represented by the formula (a3):

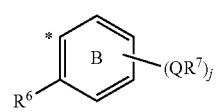
(a3)

wherein * indicates the bonding position;

j is an integer of 0 to 4;

Q in the number of j are each independently as defined above;

$R^7$ in the number of j are each independently an organic group having at least one aliphatic hydrocarbon group having one or more branched chains and the total carbon number of not less than 14 and not more than 300;

$R^6$ is a hydrogen atom, or optionally a single bond or —O— in combination with $R^4$ to form a fluorenyl group or a xanthenyl group together with ring A; and ring B optionally further has, in addition to $QR^7$ in the number of j and $R^6$, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms.

[23] The oligonucleotide of [22], wherein m is 0.

[24] The oligonucleotide of [22] or [23], wherein $R^5$ and $R^7$ are each independently a 3,7,11,15-tetramethylhexadecyl group, a 3,7,11-trimethyldodecyl group, a 2,2,4,8,10,10-hexamethyl-5-dodecanoyl group, a 3,4,5-tri(3',7',11',15'-tetramethylhexadecyloxy)benzyl group, or a 3,5-di(3',7',11',15'-tetramethylhexadecyloxy)benzyl group.

[25] The oligonucleotide of [22] or [23], wherein -L-Y—Z is selected from the group consisting of a 2-{2,4-di(2',3'-dihydrophytyloxy)benzylaminocarbonyl}ethylcarbonyl group; a 3,5-di(2',3'-dihydrophytyloxy)benzylsuccinyl group; a 4-(2',3'-dihydrophytyloxy)benzylsuccinyl group; a 2-{1-[(2-chloro-5-(2',3'-dihydrophytyloxy)phenyl)]benzylaminocarbonyl}ethylcarbonyl group; a 3,4,5-tri(2',3'-dihydrophytyloxy)benzylsuccinyl group; a 2-{3,4,5-tri(2',3'-dihydrophytyloxy)benzylaminocarbonyl}ethylcarbonyl group; a 2-{4-(2',3'-dihydrophytyloxy)benzylaminocarbonyl}ethylcarbonyl group; a 2-{2-[3',4',5'-tri(2",3"-dihydrophytyloxy)benzyloxy]-4-methoxybenzylaminocarbonyl}ethylcarbonyl group; a 2-{4-(2',3'-dihydrophytyloxy)-2-methoxybenzylaminocarbonyl}ethylcarbonyl group; a 4-(2',3'-dihydrophytyloxy)-2-methylbenzylsuccinyl group; a 2-{4-(2',3'-dihydrophytyloxy)-2-methylbenzylaminocarbonyl}ethylcarbonyl group; a 4-[2,2,4,8,10,10-hexamethyl-5-dodecanoylamino]benzylsuccinyl group; a 2-{4-[2,2,4,8,10,10-hexamethyl-5-dodecanoylamino]benzylaminocarbonyl}ethylcarbonyl group; a 4-(3,7,11-trimethyldodecyloxy)benzylsuccinyl group; a 2-{4-(3,7,11-trimethyldodecyloxy)benzylaminocarbonyl}ethylcarbonyl group; a 2-{3,5-di(2',3'-dihydrophytyloxy)benzylaminocarbonyl}ethylcarbonyl group; a 2-{1-[2,3,4-tri(2',3'-dihydrophytyloxy)phenyl]benzylaminocarbonyl}ethylcarbonyl group; a 2-{1-[4-(2',3'-dihydrophytyloxy)phenyl]-4'-(2',3'-dihydrophytyloxy)benzylaminocarbonyl}ethylcarbonyl group; a 3,4,5-tris[3, 4,5-tri(2',3'-dihydrophytyloxy)benzyl]benzylsuccinyl group; and a 2-{3,4,5-tris[3,4,5-tri(2',3'-dihydrophytyloxy)benzyl]benzylaminocarbonyl}ethylcarbonyl group.

[26] The oligonucleotide of any one of [22] to [25], wherein at least one of the nucleic acid bases is protected by a group having a $C_{5-30}$ straight chain or branched chain alkyl group and/or a $C_{5-30}$ straight chain or branched chain alkenyl group.

[27] A protecting group of nucleotide 3'-hydroxyl group, which is represented by the formula (III):

-L-Y—Z    (III)

wherein
L is a group represented by the formula (a1):

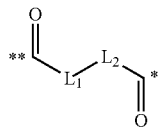

(a1)

wherein * shows the bonding position to Y; ** indicates the bonding position to a 3'-hydroxy group of the nucleotide;
$L_1$ is an optionally substituted divalent $C_{1-22}$ hydrocarbon group; and
$L_2$ is a single bond, or a group represented by C(=O)N($R^2$)—$R^1$—N($R^3$)* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or
$R^2$ and $R^3$ are optionally joined to form an optionally substituted $C_{1-22}$ alkylene bond,
Y is an oxygen atom or NR wherein R is a hydrogen atom, an alkyl group or an aralkyl group, and
Z is a group represented by the formula (a2):

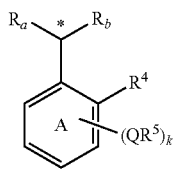

(a2)

wherein * shows the bonding position to Y;
$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;
Q in the number of k are each independently a single bond, or —O—, —S—, —OC(=O)—, —NHC(=O)— or —NH—;
$R^5$ in the number of k are each independently an organic group having at least one aliphatic hydrocarbon group having one or more branched chains and the total carbon number of not less than 14 and not more than 300;
k is an integer of 1 to 4;
ring A optionally further has, in addition to $R^4$, $QR^5$ in the number of k and *C($R_a$)($R_b$), a substituent selected from the group consisting of a halogen atom, a $C_{1-6}$ alkyl group optionally substituted by one or more halogen atoms, and a $C_{1-6}$ alkoxy group optionally substituted by one or more halogen atoms;

$R_a$ is a hydrogen atom; and
$R_b$ is a hydrogen atom, or a group represented by the formula (a3):

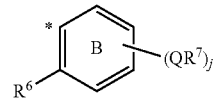

(a3)

wherein * indicates the bonding position;
j is an integer of 0 to 4;
Q in the number of j are each independently as defined above;
$R^7$ in the number of j are each independently an organic group having at least one aliphatic hydrocarbon group having one or more branched chains and the total carbon number of not less than 14 and not more than 300;
$R^6$ is a hydrogen atom, or optionally a single bond or —O— in combination with $R^4$ to form a fluorenyl group or a xanthenyl group together with ring A; and
ring B optionally further has, in addition to $QR^7$ in the number of j and $R^6$, a substituent selected from the group consisting of a halogen atom, a $C_{1-6}$ alkyl group optionally substituted by one or more halogen atoms, and a $C_{1-6}$ alkoxy group optionally substituted by one or more halogen atoms.

[28] The protecting group of [27], wherein $R^5$ and $R^7$ are each independently a 3,7,11,15-tetramethylhexadecyl group, a 3,7,11-trimethyldodecyl group, a 2,2,4,8,10,10-hexamethyl-5-dodecanoyl group, a 3,4,5-tri(3',7',11',15'-tetramethylhexadecyloxy)benzyl group, or a 3,5-di(3',7',11',15'-tetramethylhexadecyloxy)benzyl group.

[29] The protecting group of [27], which is selected from the group consisting of a 2-{2,4-di(2',3'-dihydrophytyloxy)benzylaminocarbonyl}ethylcarbonyl group; a 3,5-di(2',3'-dihydrophytyloxy)benzylsuccinyl group; a 4-(2',3'-dihydrophytyloxy)benzylsuccinyl group; a 2-{1-[(2-chloro-5-(2',3'-dihydrophytyloxy)phenyl)]benzylaminocarbonyl}ethylcarbonyl group; a 3,4,5-tri(2',3'-dihydrophytyloxy)benzylsuccinyl group; a 2-{3,4,5-tri(2',3'-dihydrophytyloxy)benzylaminocarbonyl}ethylcarbonyl group; a 2-{4-(2',3'-dihydrophytyloxy)benzylaminocarbonyl}ethylcarbonyl group; a 2-{2-[3',4',5'-tri(2'',3''-dihydrophytyloxy)benzyloxy]-4-methoxybenzylaminocarbonyl}ethylcarbonyl group; a 2-{4-(2',3'-dihydrophytyloxy)-2-methoxybenzylaminocarbonyl}ethylcarbonyl group; a 4-(2',3'-dihydrophytyloxy)-2-methylbenzylsuccinyl group; a 2-{4-(2',3'-dihydrophytyloxy)-2-methylbenzylaminocarbonyl}ethylcarbonyl group; a 4-[2,2,4,8,10,10-hexamethyl-5-dodecanoylamino]benzylsuccinyl group; a 2-{4-[2,2,4,8,10,10-hexamethyl-5-dodecanoylamino]benzylaminocarbonyl}ethylcarbonyl group; a 4-(3,7,11-trimethyldodecyloxy)benzylsuccinyl group; a 2-{4-(3,7,11-trimethyldodecyloxy)benzylaminocarbonyl}ethylcarbonyl group; a 2-{3,5-di(2',3'-dihydrophytyloxy)benzylaminocarbonyl}ethylcarbonyl group; a 2-{1-[2,3,4-tri(2',3'-dihydrophytyloxy)phenyl]benzylaminocarbonyl}ethylcarbonyl group; a 2-{1-[4-(2',3'-dihydrophytyloxy)phenyl]-4'-(2',3'-dihydrophytyloxy)benzylaminocarbonyl}ethylcarbonyl group; a 3,4,5-tris[3,4,5-tri(2',3'-dihydrophytyloxy)benzyl]benzylsuccinyl group; and a 2-{3,4,5-tris[3,4,5-tri(2',3'-dihydrophytyloxy)benzyl]benzylaminocarbonyl}ethylcarbonyl group.

[30] A method of producing an n'+p'-mer oligonucleotide comprising:

(2') a step of condensing a p'-mer oligonucleotide (p' is any integer of one or more) wherein the 3'-hydroxyl group is phosphoramidited, the 5'-hydroxyl group is protected by a temporary protecting group removable under acidic conditions, and the nucleic acid base is optionally protected, with an n'-mer oligonucleotide (n' is any integer of one or more) wherein the 5'-hydroxyl group is not protected, and the 3'-hydroxyl group is protected by the protecting group according to any one of [27] to [29], by forming a phosphite triester bond via the 5'-hydroxyl group thereof.

[31] The production method of [30], wherein p' is 1.

[32] The production method of [30] or [31], further comprising the following step (3'):

(3') a step of converting the phosphite triester bond of the n'+p'-mer oligonucleotide obtained by the condensation step to a phosphate triester bond or a thiophosphate triester bond by adding an oxidizing agent or a sulfurizing agent to the reaction mixture obtained in the condensation step (2').

[33] The production method of any one of [30] to [32], further comprising the following step (1'):

(1') a step of removing a temporary protecting group removable under acidic conditions of the 5'-hydroxyl group by reacting, in a non-polar solvent prior to the condensation step (2'), the n'-mer oligonucleotide wherein the 3'-hydroxyl group is protected by the protecting group according to any one of [27] to [29], and the 5'-hydroxyl group is protected by the temporary protecting group, with an acid.

[34] The production method of [33], wherein step (1') is performed in the presence of at least one kind of cation scavenger selected from a pyrrole derivative and an indole derivative, and further comprises a step of neutralization with an organic base after removal of the temporary protecting group of the 5'-hydroxyl group.

[35] The production method of any one of [32] to [34], further comprising the following step (4'):

(4') a step of isolating the n'+p'-mer oligonucleotide from the reaction mixture obtained in step (3') by an extraction operation alone.

[36] The production method of [35], further comprising the following step (5'):

(5') a step of removing all the protecting groups of the n'+p'-mer oligonucleotide obtained in step (4').

Effect of the Invention

Using the particular oligonucleotide comprising a protected base of the present invention, a production method of an oligonucleotide by a phosphoramidite method, which enables efficient purification in a high yield by a liquid-liquid extraction operation, can be provided.

Using the oligonucleotide comprising a protected base, particularly an oligonucleotide comprising a branched chain-protected base, of the present invention, liposolubility and solubility in an organic solvent (particularly, non-polar solvent) of an intermediate oligonucleotide obtained in each step of the nucleotide elongation reaction are strikingly improved to enable isolation and purification by an extraction operation alone, and therefore, a complicated, time-consuming operation such as solidification isolation and the like is not necessary, the speed increases, and the efficiency and producibility are strikingly improved.

Furthermore, since an elongated oligonucleotide can be isolated and purified by an extraction operation alone, an elongation reaction in the next cycle can be sequentially performed without taking out the resultant product from the reaction apparatus, whereby an oligonucleotide can be produced continuously in one pot.

It has been clarified that, as another embodiment of the present invention, the same kind of solubility improving effect can also be obtained by protecting a nucleotide 3'-hydroxyl group with a protecting group having a particular structure of a branched chain-containing aromatic group, and further, a synergistic effect can be obtained by a combined use with an oligonucleotide comprising a protected base.

DESCRIPTION OF EMBODIMENTS

The present invention relates to a novel oligonucleotide comprising a protected base, wherein the 3'-hydroxyl group is phosphoramidited, the 5'-hydroxyl group is protected by a temporary protecting group removable under acidic conditions, and the nucleic acid base is protected by a protecting group having a $C_{5-30}$ straight chain or branched chain alkyl group and/or a $C_{5-30}$ straight chain or branched chain alkenyl group.

In another embodiment, the present invention relates to a production method of an oligonucleotide comprising using an oligonucleotide comprising a protected base wherein the nucleic acid base is protected by a group having a $C_{5-30}$ straight chain or branched chain alkyl group and/or a $C_{5-30}$ straight chain or branched chain alkenyl group, which preferably includes the following step (2):

(2) a step of condensing a p-mer oligonucleotide comprising a protected base (p is any integer of one or more) wherein the 3'-hydroxyl group is phosphoramidited, the 5'-hydroxyl group is protected by a temporary protecting group removable under acidic conditions, and the nucleic acid base is protected by a group having a $C_{5-30}$ straight chain or branched chain alkyl group and/or a $C_{5-30}$ straight chain or branched chain alkenyl group, with an n-mer oligonucleotide (n is an integer of one or more) wherein the 5'-hydroxyl group is not protected and the 3'-hydroxyl group is protected, by forming a phosphite triester bond via the 5'-hydroxyl group thereof to give an n+p-mer oligonucleotide.

In a still another embodiment, the present invention relates to a novel oligonucleotide protected by a branched chain-containing aromatic group, wherein the 3'-hydroxyl group is protected by a particular branched chain-containing aromatic protecting group, and the 5'-hydroxyl group is protected by a temporary protecting group removable under acidic conditions.

In a yet another embodiment, the present invention relates to a particular branched chain-containing aromatic protecting group used for protecting the nucleotide 3'-hydroxyl group.

In another embodiment, furthermore, the present invention relates to a production method of an oligonucleotide, comprising using an oligonucleotide wherein the 3'-hydroxyl group is protected by the aforementioned branched chain-containing aromatic protecting group, and preferably includes the following step (2'):

(2') a step of condensing a p'-mer oligonucleotide (p' is any integer of one or more) wherein the 3'-hydroxyl group is phosphoramidited, the 5'-hydroxyl group is protected by a temporary protecting group removable under acidic conditions, and the nucleic acid base is optionally protected, with an n'-mer oligonucleotide (n' is any integer of one or more) wherein the 5'-hydroxyl group is not protected, and the 3'-hydroxyl group is protected by the aforementioned branched chain-containing aromatic protecting group, by forming a phosphite triester bond via the 5'-hydroxyl group thereof to give an n'+p'-mer oligonucleotide.

Explanations are given below.

1. Explanation of Terms

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the specification are hereby incorporated by reference so as to describe and disclose constructed products and methodology described in, for example, publications usable in relation to the described invention.

In the present specification, the "nucleoside" means a compound wherein a nucleic acid base is bonded to the 1'-position of a sugar (e.g., ribose, 2-deoxyribose, ribose crosslinked between the 2-position and the 4-position and the like) by N-glycosidation.

Examples of the ribose wherein the 2-position and the 4-position are crosslinked include compounds represented by the following formulas.

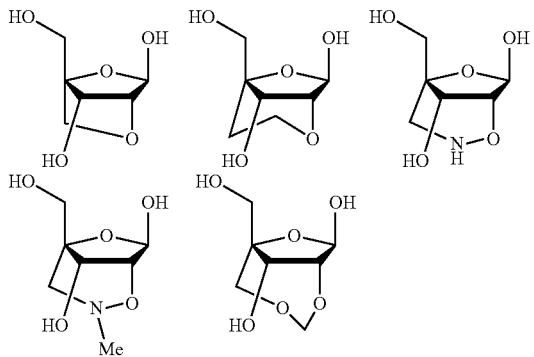

In the present specification, the "nucleic acid base" is not particularly limited as long as it can be used for the synthesis of nucleic acid and includes, for example, a pyrimidine base such as cytosyl group, uracil group, thyminyl group and the like, and a purine base such as adenyl group, guanyl group and the like.

Moreover, in addition to the above-mentioned groups, a modified nucleic acid base (e.g., a 8-bromoadenyl group, a 8-bromoguanyl group, a 5-bromocytosyl group, a 5-iodocytosyl group, a 5-bromouracil group, a 5-iodouracil group, a 5-fluorouracil group, a 5-methylcytosyl group, a 8-oxoguanyl group, a hypoxanthinyl group etc.), which is a nucleic acid base substituted by any 1 to 3 substituents (e.g., a halogen atom, an alkyl group, an aralkyl group, an alkoxy group, an acyl group, an alkoxyalkyl group, a hydroxy group, an amino group, a monoalkylamino group, a dialkylamino group, a carboxy group, a cyano group, a nitro group etc.) at any position(s), are also encompassed in the "nucleic acid base".

In the present specification, the "halogen atom" means a fluorine atom, a chlorine atom, a bromine atom or iodine atom.

In the present specification, examples of the "hydrocarbon group" include an aliphatic hydrocarbon group, an aromatic-aliphatic hydrocarbon group, a monocyclic saturated hydrocarbon group, an aromatic hydrocarbon group and the like. Specific examples thereof include a monovalent group such as an alkyl group, an alkenyl group, an alkynyl group, a cycloalkyl group, an aryl group, an aralkyl group, an acyl group and the like, and a divalent group derived therefrom.

In the present specification, examples of the "alkyl (group)" include a linear or branched chain alkyl group having one or more carbon atoms. When the carbon number is not particularly limited, it is preferably a $C_{1-10}$ alkyl group, more preferably a $C_{1-6}$ alkyl group. When the carbon number is not particularly limited, for example, methyl, ethyl, propyl, isopropyl, butyl, isobutyl, sec-butyl, tert-butyl, pentyl, hexyl and the like are preferable, and methyl and ethyl are particularly preferable.

In the present specification, the "aralkyl (group)" means a $C_{7-20}$ aralkyl group, preferably a $C_{7-16}$ aralkyl group (a $C_{6-10}$ aryl-$C_{1-6}$ alkyl group).

Preferable specific examples include benzyl, 1-phenylethyl, 2-phenylethyl, 1-phenylpropyl, naphthylmethyl, 1-naphthylethyl, 1-naphthylpropyl and the like, and benzyl is particularly preferable.

In the present specification, examples of the "alkoxy (group)" include an alkoxy group having one or more carbon atoms. When the carbon number is not particularly limited, it is preferably a $C_{1-10}$ alkoxy group, more preferably a $C_{1-6}$ alkoxy group. When the carbon number is not particularly limited, methoxy, ethoxy, propoxy, isopropoxy, butoxy, isobutoxy, sec-butoxy, tert-butoxy, pentyloxy, hexyloxy and the like are preferable, and methoxy and ethoxy are particularly preferable.

In the present specification, examples of the "acyl (group)" include a linear or branched chain $C_{1-6}$ alkanoyl group, a $C_{7-13}$ aroyl group and the like. Specific examples thereof include formyl, acetyl, n-propionyl, isopropionyl, n-butyryl, isobutyryl, pivaloyl, valeryl, hexanoyl, benzoyl, naphthoyl, levulinyl and the like, each of which is optionally substituted.

In the present specification, examples of the "alkenyl (group)" include a linear or branched chain $C_{2-6}$ alkenyl group and the like. Preferable examples thereof include vinyl, 1-propenyl, allyl, isopropenyl, butenyl, isobutenyl and the like. Among them, a $C_2$-$C_4$ alkenyl group is preferable.

In the present specification, examples of the "alkynyl (group)" include a $C_{2-6}$ alkynyl group and the like. Preferable examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Among them, a $C_2$-$C_4$ alkynyl group is preferable.

In the present specification, the "cycloalkyl (group)" means a cyclic alkyl group, and examples thereof include cyclopropyl, cyclobutyl, cyclopentyl, cyclohexyl, cycloheptyl, cyclooctyl and the like. Among them, a $C_3$-$C_6$ cycloalkyl group such as cyclopropyl, cyclobutyl, cyclopentyl, cyclohexyl and the like is preferable, and cyclohexyl is particularly preferable.

In the present specification, the "aryl (group)" means a monocyclic aromatic or polycyclic (fused) hydrocarbon group. Specific examples thereof include a $C_{6-14}$ aryl group such as phenyl, 1-naphthyl, 2-naphthyl, biphenylyl, 2-anthryl and the like, and the like. Among them, a $C_{6-10}$ aryl group is more preferably and phenyl is particularly preferable.

In the present specification, the "organic group having a hydrocarbon group" means a group having the aforementioned "hydrocarbon group", and the moiety other than the "hydrocarbon group" of the "organic group having a hydrocarbon group" can be determined freely. For example, the organic group optionally has, as a linker, a moiety such as —O—, —S—, —COO—, —OCONH—, —CONH— and the like.

In the present specification, examples of the "alkylene (group)" include a linear or branched chain alkylene group having one or more carbon atoms. When the carbon number is not particularly limited, it is preferably a $C_{1-10}$ alkylene group, more preferably a $C_{1-6}$ alkylene group. When the carbon number is not particularly limited, for example, methylene, ethylene, propylene, butylene, pentylene, hexylene and the like are preferable, and methylene and ethylene are particularly preferable.

2. Oligonucleotide Comprising a Protected Base

The oligonucleotide comprising a protected base to be used for oligonucleotide synthesis in the present invention can be obtained by protecting a nucleic acid base of a nucleotide wherein the 3'-hydroxyl group is phosphoramidited and the 5'-hydroxyl group is protected by a temporary protecting group removable under acidic conditions by a group having a $C_{5-30}$ straight chain or branched chain alkyl group and/or a $C_{5-30}$ straight chain or branched chain alkenyl group, and can provide a production method of an oligonucleotide suitable for liquid phase synthesis, since liposolubility and solubility in an organic solvent (particularly, non-polar solvent) of an intermediate oligonucleotide is remarkably improved.

From the aspect of solubility in an organic solvent, the group having a $C_{5-30}$ straight chain or branched chain alkyl group and/or a $C_{5-30}$ straight chain or branched chain alkenyl group are/is preferably a $C_{5-30}$ branched chain alkyl group and/or a $C_{5-30}$ branched chain alkenyl group.

As a solvent that shows improved solubility of an oligonucleotide by the oligonucleotide comprising a protected base of the present specification, a non-polar solvent is preferable.

In the present specification, examples of the "non-polar solvent" include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like can be mentioned. Two or more kinds of these solvents may be used in a mixture at an appropriate ratio. Among them, aromatic solvents, aliphatic solvents and a combination thereof are preferable, benzene, toluene, hexane, pentane, heptane, nonane, cyclohexane, and a combination thereof and the like are preferable, toluene, heptane, nonane and a combination thereof are more preferable, and toluene, heptane and a combination thereof are particularly preferable.

Particularly, in the object method for production of an oligonucleotide, an oligonucleotide comprising a protected base, which is preferable for achieving speeding up, high yield and high efficiency, is, for example, a novel compound represented by the following formula (I) (hereinafter sometimes to be referred to as the compound (I) of the present invention).

When q is 0, the oligonucleotide comprising a protected base, which is represented by the formula (I), is understood as "nucleoside comprising a protected base".

Formula (I):

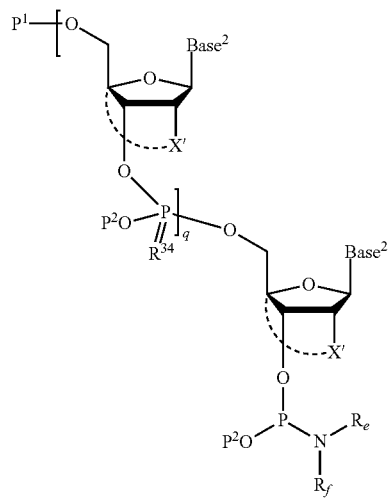

wherein q is any integer of not less than 0;
Base² in the number of q+1 are each independently a nucleic acid base protected by a group having a $C_{5-30}$ straight chain or branched chain alkyl group and/or a $C_{5-30}$ straight chain or branched chain alkenyl group;

$P^1$ is a hydrogen atom, or a temporary protecting group removable under acidic conditions;

X is a hydrogen atom, an optionally protected hydroxyl group, a halogen atom or an organic group crosslinked with the 4-position carbon atom;

X' in the number of q are each independently a hydrogen atom, an optionally protected hydroxyl group, a halogen atom or an organic group crosslinked with the 4-position carbon atom;

$P^2$ in the number of q+1 are each independently a protecting group removable under basic conditions;

$R^{34}$ in the number of q are each independently an oxygen atom or a sulfur atom; and $R_e$ and $R_f$ are each independently a $C_{1-6}$ alkyl group, or a 5- or 6-membered saturated cyclic amino group formed together with the adjacent nitrogen atom.

q is any integer of 0 or more, preferably 0. While the upper limit of q is not particularly set, it is preferably 49 or less, more preferably 29 or less, further preferably 19 or less, still more preferably 4 or less, still further preferably 2 or less and particularly preferably 1.

The groups X and X' in the number of q at the 2-position of ribose residues constituting the oligonucleotide comprising a protected base, which is the compound (I) of the present invention, are each independently a hydrogen atom, an optionally protected hydroxyl group, a halogen atom or an organic group crosslinked with the 4-position carbon atom.

The protecting group of the "optionally protected hydroxyl group" is not particularly limited and, for example, any protecting groups described in Greene's PROTECTIVE GROUPS IN ORGANIC SYNTHESIS, 4th ed., JOHN WILLY&SONS (2006) and the like can be mentioned. Specific examples thereof include a methyl group, a benzyl group, a p-methoxybenzyl group, a tert-butyl group, a methoxymethyl group, a methoxyethyl group, a 2-tetrahydropyranyl group, an ethoxyethyl group, a cyanoethyl group, a cyanoethoxymethyl group, a phenylcarbamoyl group, a 1,1-dioxothiomorpholine-4-thiocarbamoyl group, an acetyl group, a pivaloyl group, a benzoyl group, a trimethylsilyl group, a triethylsilyl group, a triisopropylsilyl group, a tert-butyldimethylsilyl group, a [(triisopropylsilyl)oxy]methyl (Tom) group, an 1-(4-chlorophenyl)-4-ethoxypiperidin-4-yl (Cpep) group and the like. Among these, a triethylsilyl group, a triisopropylsilyl group and a tert-butyldimethylsilyl group are preferable. From the aspects of economic efficiency and easy availability, a tert-butyldimethylsilyl group is particularly preferable.

As the halogen atom for X or X', a fluorine atom, a chlorine atom and the like are preferable, and a fluorine atom is more preferable.

While the "organic group crosslinked with the 4-position carbon atom" for X or X' is not particularly limited as long as the 2-position and the 4-position of the nucleoside is crosslinked, for example, a $C_{2-7}$ alkylene group can be mentioned. The alkylene group may be interrupted at one or more moieties (preferably 1 or 2 moieties) by a linker selected from, for example, —O—, —NR³⁷— ($R^{37}$ is a hydrogen atom or a $C_{1-6}$ alkyl group), —S—, —CO—, —COO—, —COO—, NR³⁸— ($R^{38}$ is a hydrogen atom or a $C_{1-6}$ alkyl group), —CONR³⁹— ($R^{39}$ is a hydrogen atom or a $C_{1-6}$ alkyl group) and the like.

Preferable examples of the "organic group crosslinked with the 4-position carbon atom" include —ORi (Ri is a $C_{1-6}$ alkylene group crosslinked with the 4-position), —O—NR³⁷-Rj (Rj is a $C_{1-6}$ alkylene group crosslinked with the 4-position, and $R^{37}$ is as defined above), —O—Rk-O-Rl (Rk is a $C_{1-6}$ alkylene group, and Rl is a $C_{1-6}$ alkylene group crosslinked with the 4-position) and the like. The $C_{1-6}$ alkylene groups for Ri, Rj, Rk and Rl are preferably each independently a methylene group or an ethylene group.

As the "organic group crosslinked with the 4-position carbon atom", —O—CH$_2$—, —O—CH$_2$—CH$_2$—, —O—NR$^{37}$—CH$_2$— (R$^{37}$ is as defined above), —O—CH$_2$—O—CH$_2$— and the like are preferable, and —O—CH$_2$—, —O—CH$_2$—CH$_2$—, —O—NH—CH$_2$—, —O—NMe-CH$_2$—, —O—CH$_2$—O—CH$_2$— (in all of which the left side binds to the 2-position and the right side binds to the 4-position) and the like are more preferable.

The temporary protecting group P$^1$ that can be used as the 5'-hydroxyl-protecting group of the compound (I) of the present invention is not particularly limited as long as it can be deprotected under acidic conditions and can be used as a hydroxyl-protecting group. Examples thereof include a trityl group, 9-(9-phenyl)xanthenyl group, a 9-phenylthioxanthenyl group, di(C$_{1-6}$ alkoxy)trityl groups such as a 1,1-bis(4-methoxyphenyl)-1-phenylmethyl group and the like, monomethoxytrityl group such as mono(C$_{1-18}$ alkoxy)trityl groups such as a 1-(4-methoxyphenyl)-1,1-diphenylmethyl group and the like. Among these, a monomethoxytrityl group and a dimethoxytrityl group are preferable, and a dimethoxytrityl group is more preferable, in view of easiness of deprotection and easy availability.

The 5- or 6-membered saturated cyclic amino group formed by R$_e$ and R$_f$ together with the adjacent nitrogen atom may have, as a ring-constituting atom besides nitrogen atom, one of oxygen atom or sulfur atom. For example, a pyrrolidinyl group, a piperidinyl group, a morpholinyl group, a thiomorpholinyl group, an N-methylpyrazinyl group and the like can be mentioned.

As R$_e$ and R$_f$, an isopropyl group is preferable.

The protecting group P$^2$ in the number of q+1 that can be used as a protecting group of phosphoramidite or a protecting group of a nucleotide phosphate group of the compound (I) of the present invention is not particularly limited as long as it can be deprotected under base conditions and used as a hydroxyl-protecting group. A group represented by —CH$_2$CH$_2$WG (WG is an electron-withdrawing group) is preferable, and a cyano group is preferable as WG. R$^{34}$ in the number of q is each independently an oxygen atom or a sulfur atom, preferably an oxygen atom.

While the "group having a C$_{5-30}$ straight chain or branched chain alkyl group and/or a C$_{5-30}$ straight chain or branched chain alkenyl group" of the "nucleic acid base protected by a group having a C$_{5-30}$ straight chain or branched chain alkyl group and/or a C$_{5-30}$ straight chain or branched chain alkenyl group" for Base$^2$ in the number of q+1 is not particularly limited as long as it is a protecting group having one or more "C$_{5-30}$ straight chain or branched chain alkyl group and/or C$_{5-30}$ straight chain or branched chain alkenyl group" in the molecular structure thereof, a group represented by the following formula (k), (l), (m) or (s) is preferable.

A group represented by the formula (k):

(k)

wherein * indicates the bonding position to a nucleic acid base;
R$^{27}$ is a C$_{5-30}$ straight chain or branched chain alkyl group or a C$_{5-30}$ straight chain or branched chain alkenyl group, a group represented by the formula (l):

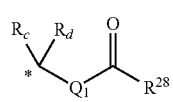

(l)

wherein * indicates the bonding position to a nucleic acid base;
Q$_1$ is —O—, —S— or —NR$^{30}$— wherein R$^{30}$ is a hydrogen atom or a C$_{1-22}$ alkyl group;
R$_c$ and R$_d$ are each independently a hydrogen atom or a C$_{1-22}$ alkyl group;
R$^{28}$ is a C$_{5-30}$ straight chain or branched chain alkyl group or a C$_{5-30}$ straight chain or branched chain alkenyl group, a group represented by the formula (m):

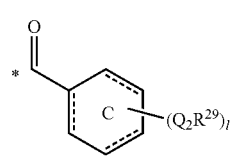

(m)

wherein * indicates the bonding position to a nucleic acid base;
l is an integer of 1-5;
Q$_2$ in the number of l are each independently a single bond, or —O—, —S—, —OC(=O)—, —C(=O)O—, —O—CH$_2$—, —NH—, —NHC(=O)—, —(=O)NHC—, —NH—CH$_2$— or —CH$_2$—;
R$^{29}$ in the number of l are each independently a C$_{5-30}$ straight chain or branched chain alkyl group or a C$_{5-30}$ straight chain or branched chain alkenyl group;
ring C is a benzene ring or a cyclohexane ring each optionally having, in addition to Q$_2$R$^{29}$ in the number of l and *C=O, a substituent selected from the group consisting of a halogen atom, a C$_{1-6}$ alkyl group optionally substituted by one or more halogen atoms, and a C$_{1-6}$ alkoxy group optionally substituted by one or more halogen atoms, or a group represented by the formula (s):

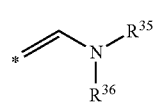

(s)

wherein * indicates the position at which an imino bond is formed with an amino group of a nucleic acid base; and
R$^{35}$ and R$^{36}$ are each independently a C$_{5-30}$ straight chain or branched chain alkyl group or a C$_{5-30}$ straight chain or branched chain alkenyl group.

In the formula (l), Q$_1$ is preferably —O—, and R$_c$ and R$_d$ are each preferably a hydrogen atom.

In the formula (m), l is preferably 1, Q$_2$ is preferably —O—, and ring C is preferably a benzene ring.

The lower limit of the carbon atoms of the "C$_{5-30}$ straight chain or branched chain alkyl group" and "C$_{5-30}$ straight chain or branched chain alkenyl group" of the "C$_{5-30}$ straight chain or branched chain alkyl group or a C$_{5-30}$ straight chain or branched chain alkenyl group" for R$^{27}$, R$^{28}$, R$^{29}$ in the number of l, R$^{35}$ and R$^{36}$ in the formulas (k), (l), (m) and (s), respectively, is 5 or more, preferably 16 or more, more preferably 18 or more. The upper limit of the carbon number is 30 or less, preferably or less, more preferably 20 or less.

While the "$C_{5-30}$ straight chain or branched chain alkyl group or $C_{5-30}$ straight chain or branched chain alkenyl group" for $R^{27}$, $R^{28}$, $R^{29}$ in the number of l, $R^{35}$ or $R^{36}$ is not particularly limited, a branched chain alkyl group represented by the following formula (n) or (e') is preferable.

The carbon numbers, the number of repeat units ($n_{19}$, $n_{20}$ or $n_{21}$) and the like in the definition of each symbol in the formulas (n) and (e') are shown for convenience, and can be appropriately changed within the above-mentioned definition range to achieve the total carbon number of 5 or more (preferably 16 or more, more preferably 18 or more) and 30 or less (preferably 25 or less, more preferably 20 or less). In the following, the formulas (n) and (e') are successively explained.

The formula (n) is as follows.

A branched chain alkyl group represented by

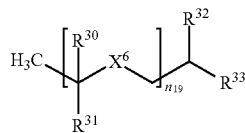

(n)

wherein * shows a bonding position;
$n_{19}$ is an integer of 2 to 6;
$R^{30}$ and $R^{31}$ in the number of $n_{19}$ are each independently a hydrogen atom or a $C_{1-4}$ alkyl group;
$X_6$ in the number of $n_{19}$ are each independently a single bond or a $C_{1-4}$ alkylene group; and
$R^{32}$ is a hydrogen atom or a $C_{1-4}$ alkyl group; and
$R^{33}$ is a $C_{1-4}$ alkyl group,
provided that $R^{30}$ and $R^{31}$ are not hydrogen atoms at the same time, and when $n_{19}$ is 2, $R_{32}$ is a $C_{1-4}$ alkyl group.

In the group of the formula (n), a group wherein $R^{30}$ and $R^{31}$ in the number of $n_{19}$ are each independently a hydrogen atom, a methyl group or an ethyl group;
$X_6$ in the number of $n_{19}$ are each independently a single bond, a methylene group or an ethylene group;
$R^{32}$ is a hydrogen atom, a methyl group or an ethyl group; and $R^{33}$ is a methyl group or an ethyl group is preferable, provided that $R^{30}$ and $R^{31}$ are not hydrogen atoms at the same time, and when $n_{19}$ is 2, $R_{32}$ is a methyl group or an ethyl group.

Examples of more preferable group of the formula (n) include a 2,6,10,14-tetramethylpentadecyl group, a 2,6,10-trimethylundecyl group, a 2,6-dimethylheptyl group and the like.

A branched chain alkyl group represented by the formula (e'):

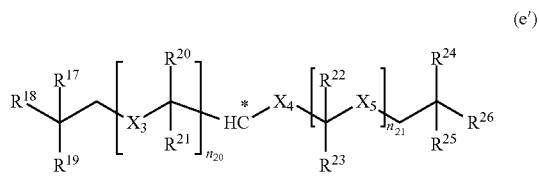

(e')

wherein * shows a bonding position;
$n_{20}$ is an integer of 1 to 5;
$n_{21}$ is an integer of 1 to 5;
$R^{20}$ and $R^{21}$ in the number of $n_{20}$ are each independently a hydrogen atom or a $C_{1-4}$ alkyl group;
$X_3$ in the number of $n_{20}$ are each independently a single bond or a $C_{1-4}$ alkylene group;
$R^{22}$ and $R^{23}$ in the number of $n_{21}$ are each independently a hydrogen atom or a $C_{1-4}$ alkyl group;
$X_5$ in the number of $n_{21}$ are each independently a single bond or a $C_{1-4}$ alkylene group;
$X_4$ is a single bond or a $C_{1-4}$ alkylene group; and
$R^{17}$, $R^{18}$, $R^{19}$, $R^{24}$, $R^{25}$ and $R^{26}$ are each independently a hydrogen atom or a $C_{1-4}$ alkyl group,
provided that $R^{20}$ and $R^{21}$ and/or $R^{22}$ and $R^{23}$ are not hydrogen atoms at the same time, and when $n_{20}+n_{21}$ is 2, two or more of $R^{17}$, $R^{18}$ and $R^{19}$ are each independently a $C_{1-4}$ alkyl group, or two or more of $R^{24}$, $R^{25}$ and $R^{26}$ are each independently a $C_{1-4}$ alkyl group.

A group of the formula (e'), wherein
$n_{20}$ is an integer of 1 to 5;
$n_{21}$ is an integer of 1 to 5;
$R^{20}$ and $R^{21}$ in the number of $n_{20}$ are each independently a hydrogen atom, a methyl group or an ethyl group;
$X_3$ in the number of $n_{20}$ are each independently a single bond, a methylene group or an ethylene group;
$R^{22}$ and $R^{23}$ in the number of $n_{21}$ are each independently a hydrogen atom, a methyl group or an ethyl group;
$X_5$ in the number of $n_{21}$ are each independently a single bond, a methylene group or an ethylene group;
$X_4$ is a single bond, a methylene group or an ethylene group;
$R^{17}$, $R^{18}$, $R^{19}$, $R^{24}$, $R^{25}$ and $R^{26}$ are each independently a hydrogen atom or a $C_{1-4}$ alkyl group is preferable, provided that $R^{20}$ and $R^{21}$ and/or $R^{22}$ and $R^{23}$ are not hydrogen atoms at the same time, and when $n_{20}+n_{21}$ is 2, two or more of $R^{17}$, $R^{18}$ and $R^{19}$ are each independently a $C_{1-4}$ alkyl group, or two or more of $R^{24}$, $R^{25}$ and $R^{26}$ are each independently a $C_{1-4}$ alkyl group.

A group of the formula (e'), wherein
$n_{20}$ is an integer of 1 to 5;
$n_{21}$ is an integer of 1 to 5;
$R^{20}$ and $R^{21}$ in the number of $n_{20}$ are each independently a hydrogen atom or a methyl group;
$X_3$ in the number of $n_{20}$ are each independently a single bond or a methylene group;
$R^{22}$ and $R^{23}$ in the number of $n_{21}$ are each independently a hydrogen atom or a methyl group;
$X_5$ in the number of $n_{21}$ are each independently a single bond or a methylene group;
$X_4$ is a single bond or a methylene group; and
$R^{17}$, $R^{18}$, $R^{19}$, $R^{24}$, $R^{25}$ and $R^{26}$ are methyl groups, provided that $R^{20}$ and $R^{21}$ and/or $R^{22}$ and $R^{23}$ are not hydrogen atoms at the same time, is particularly preferable.

More preferable group of the formula (e') includes a 2,2,4,8,10,10-hexamethyl-5-undecyl group and the like.

Other preferable examples of the "$C_{5-30}$ straight chain or branched chain alkyl group or $C_{5-30}$ straight chain or branched chain alkenyl group" for $R^{27}$, $R^{28}$, $R^{29}$ in the number of l, $R^{35}$ or $R^{36}$ include a branched chain alkyl group and a branched chain alkenyl group selected from the group consisting of a 2,6,10,14-tetramethylpentadecyl group, a 2,6,10-trimethylundecyl group, a 2,2,4,8,10,10-hexamethyl-5-undecyl group, a 2,6,10-trimethylundeca-1,5,9-trienyl group, a 2,6-dimethylheptyl group, a 2,6-dimethylhept-5-enyl group, a 2,6-dimethylhepta-1,5-dienyl group, a 9-nonadecyl group, a 12-methyltridecyl group, an 11-methyltridecyl group, an 11-methyldodecyl group, a 10-methylundecyl group, an 8-heptadecyl group, a 7-pentadecyl group, a 7-methyloctyl group, a 3-methyloctyl group, a 3,7-dimethyloctyl group, a 3-methylheptyl group, a 3-ethylheptyl group, a 5-undecyl group, a 2-heptyl group, a 2-methyl-2-hexyl group, a 2-hexyl group, a 3-heptyl group, a 4-heptyl group, a 4-methyl-pentyl group, a 3-methyl-pentyl group, and a 2,4,4-trimethylpentyl group; and a straight chain alkyl group selected from the group consisting of a tetradecyl group, a tridecyl group, a dodecyl group, an undecyl group, a decyl group, a nonyl group, an octyl group, a heptyl group, a hexyl group, and a pentyl group.

Examples of the nucleic acid base protected by a group having a $C_{5-30}$ straight chain or branched chain alkyl group and/or a $C_{5-30}$ straight chain or branched chain alkenyl group include the following formulas $(A_1)$-$(A_{12})$

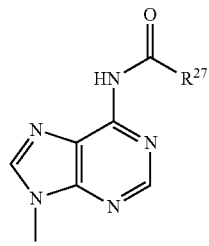 (A$_1$)

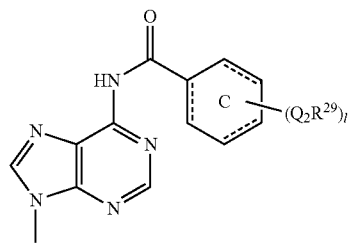 (A$_2$)

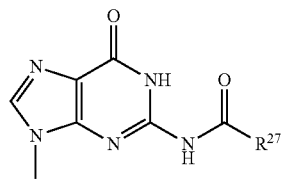 (A$_3$)

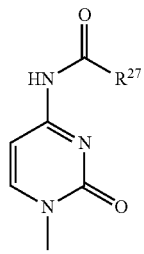 (A$_4$)

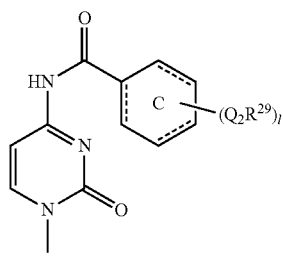 (A$_5$)

-continued

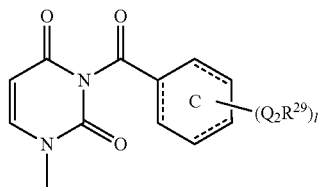 (A$_6$)

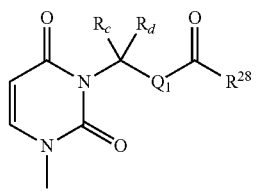 (A$_7$)

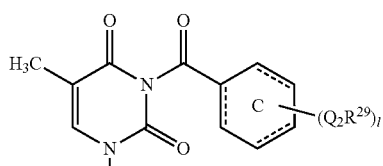 (A$_8$)

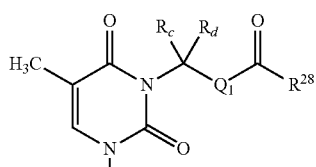 (A$_9$)

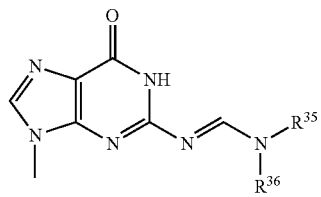 (A$_{10}$)

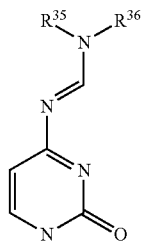 (A$_{11}$)

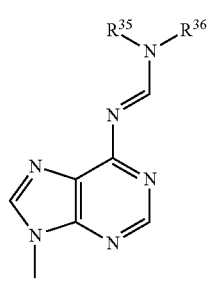 (A$_{12}$)

wherein each symbol is as defined above.

A method of introducing a group having a $C_{5-30}$ straight chain or branched chain alkyl group and/or a $C_{5-30}$ straight chain or branched chain alkenyl group into a nucleic acid base can be performed according to a known method described in Greene's PROTECTIVE GROUPS IN ORGANIC SYNTHESIS, 4th Edition, published by JOHN WILLY & SONS (2006), ORGANIC LETTERS, 2005, Vol. 7, No. 24, 5389-5392, JOURNAL OF AMERICAN CHEMICAL SOCIETY, 1982, Vol. 104, 1316-1319 and the like and using, as a protecting reagent, an activated derivative of the protecting group.

Examples of the activated derivative of the group having a $C_{5-30}$ straight chain or branched chain alkyl group and/or a $C_{5-30}$ straight chain or branched chain alkenyl group include a compound wherein a halogen atom (e.g., chlorine atom, bromine atom etc.) is bonded to * in a group represented by the above-mentioned formula (k), (l) or (m); a symmetric acid anhydride wherein two groups represented by the above-mentioned formula (k) or (m) are bonded to an oxygen atom at *; a mixed acid anhydride wherein a group represented by the above-mentioned formula (k) or (m) is bonded to other acyl group (e.g., isobutyryl group) at *, a compound represented by $(MeO)_2CH-NR^{35}R^{36}$ and the like.

The activated derivative of the protecting group is available as a commercially available product, or can be produced by a method known per se or a method analogous thereto.

A preferable embodiment of the compound represented by the formula (I) of the present invention is a compound of the formula (I), wherein q is 0;

$Base^2$ is a cytosyl group, a uracil group, a thyminyl group, an adenyl group, or a guanyl group, each of which is optionally protected by a group having a $C_{5-30}$ straight chain or branched chain alkyl group and/or a $C_{5-30}$ straight chain or branched chain alkenyl group;

$P^1$ is a di ($C_{1-6}$ alkoxy)trityl group, or a mono ($C_{1-6}$ alkoxy) trityl group;

X is a hydrogen atom, an optionally protected hydroxyl group, a fluorine atom, $-ORi$ (Ri is as defined above), $-O-NR^{37}-Rj$ (Rj and $R^{37}$ are as defined above, or $-O-Rk-O-Rl$ (Rk and Rl is as defined above);

$R_e$ and $R_f$ are each independently a $C_{1-6}$ alkyl group; and $P^2$ is a group represented by $-CH_2CH_2WG$ (WG is an electron-withdrawing group).

Another preferable embodiment of the compound represented by the formula (I) of the present invention is a compound of the formula (I), wherein q is 0;

$Base^2$ is a cytosyl group, a uracil group, a thyminyl group, an adenyl group, or a guanyl group, each of which is optionally protected by a group having a $C_{5-30}$ straight chain or branched chain alkyl group and/or a $C_{5-30}$ straight chain or branched chain alkenyl group;

$P^1$ is a dimethoxytrityl group or a monomethoxytrityl group;

X is a hydrogen atom, an optionally protected hydroxyl group, a fluorine atom, $-O-CH_2-$, $-O-CH_2-CH_2-$, or $-O-NR^{37}-CH_2-$ ($R^{37}$ is as defined above) or $-O-CH_2-O-CH_2-$ (in all of which the left side binds to the 2-position and the right side binds to the 4-position);

$R_e$ and $R_f$ are each an isopropyl group; and $P^2$ is a group represented by $-CH_2CH_2WG$ (WG is an electron-withdrawing group).

A still another preferable embodiment of the compound represented by the formula (I) of the present invention is a compound of the formula (I), wherein q is 0;

$Base^2$ is a cytosyl group, a uracil group, a thyminyl group, an adenyl group, or a guanyl group, each of which is optionally protected by a group having a $C_{5-30}$ straight chain or branched chain alkyl group and/or a $C_{5-30}$ straight chain or branched chain alkyl group and/or a $C_{5-30}$ straight chain or branched chain alkenyl group;

$P^1$ is a dimethoxytrityl group;

X is a hydrogen atom, a methoxy group, a tert-butyldimethylsilyloxy group, a fluorine atom, $-O-CH_2-$, $-O-CH_2-CH_2-$, $-O-NH-CH_2-$, $-O-NMe-CH_2-$ or $-O-CH_2-O-CH_2-$ (in all of which the left side binds to the 2-position and the right side binds to the 4-position);

$R_e$ and $R_f$ are each an isopropyl group; and $P^2$ is a group represented by $-CH_2CH_2CN$.

3. Production Method of Oligonucleotide Comprising Protected Base

Of the oligonucleotides comprising a protected base represented by the following formula (I) of the present invention, an oligonucleoside comprising a protected base represented by the formula (I'), wherein q is 0, can be produced according to a known method (M. H. Caruthers et al., Method in Enzymology 1987, 154, 287-313; S. L. Beaucage and M. H. Caruthers, Tetrahedron Letters 1981, 22, 1859-1862) comprising reacting a nucleoside represented by the formula (Ia), wherein the 5'-hydroxyl group is protected by a temporary protecting group $P^1$ and the nucleic acid base is protected by a group having a $C_{5-30}$ straight chain or branched chain alkyl group and/or a $C_{5-30}$ straight chain or branched chain alkenyl group, with a phosphoramiditing reagent represented by the following formula (o) or (p)

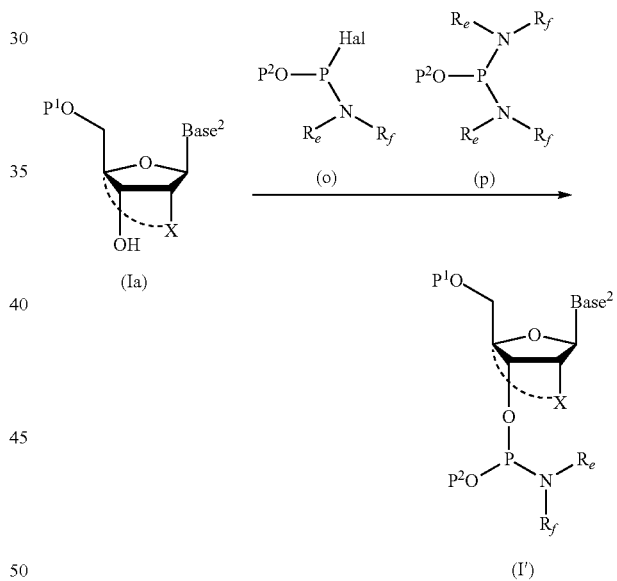

wherein Hal is a halogen atom, and other symbols are as defined above.

A compound represented by the formula (Ia) to be used as a starting material can be produced from a corresponding nucleoside wherein the nucleic acid base is not protected, by protecting the nucleic acid base with a "group having a $C_{5-30}$ straight chain or branched chain alkyl group and/or a $C_{5-30}$ straight chain or branched chain alkenyl group" according to the above-mentioned "method for introducing a group having a $C_{5-30}$ straight chain or branched chain alkyl group and/or a $C_{5-30}$ straight chain or branched chain alkenyl group into a nucleic acid base". The corresponding nucleoside wherein the nucleic acid base is not protected is available as a commercially available product, or can be produced according to a method known per se or a method analogous thereto.

The nucleoside comprising a protected base represented by the formula (I') of the present invention can also be produced by a known method (ORGANIC LETTERS, 2005, Vol. 7, No. 24, 5389-5392) comprising reacting a nucleoside represented by the formula (Ib), wherein the 3'-hydroxyl group is phosphoramidited, the 5'-hydroxyl group is protected by a temporary protecting group $P^1$, and the nucleic acid base is not protected, with a protecting reagent having a $C_{5-30}$ straight chain or branched chain alkyl group and/or a $C_{5-30}$ straight chain or branched chain alkenyl group.

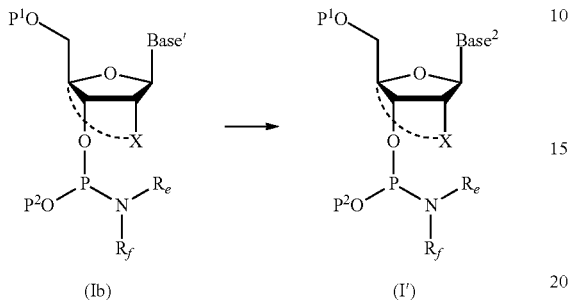

wherein Base' is an unprotected nucleic acid base, and other symbols are as defined above.

A compound represented by the formula (Ib) to be used as a starting material can be produced by deprotecting a corresponding nucleoside wherein the nucleic acid base is protected by a protecting group conventionally used for nucleic acid synthesis (e.g., acetyl group, phenoxyacetyl group, p-isopropylphenoxyacetyl group, benzoyl group, isobutyryl group etc.) according to a known method described in ORGANIC LETTERS, 2005, Vol. 7, No. 24, 5389-5392 and the like. The corresponding nucleoside wherein the nucleic acid base is protected by a protecting group conventionally used for nucleic acid synthesis is available as a commercially available product, or can be produced according to a method known per se or a method analogous thereto.

An oligonucleotide comprising a protected base represented by of the formula (I) wherein q is 1 or more can be produced by appropriately applying, for example, the method described in Aust. J. Chem. 2010, 63, 227-235 and the production method of oligonucleoside described in the present specification to produce a corresponding oligonucleotide comprising a protected base wherein the 3'-hydroxyl group is protected, removing the 3'-hydroxyl-protecting group, and reacting the resulting compound with a phosphoramiditing reagent represented by the formula (o) or (p) according to a known method (M. H. Caruthers et al., Method in Enzymology 1987, 154, 287-313; S. L. Beaucage and M. H. Caruthers, Tetrahedron Letters 1981, 22, 1859-1862.).

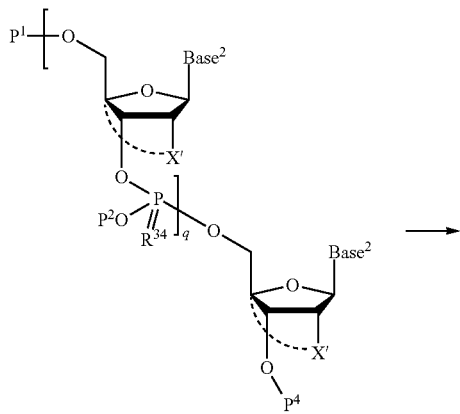

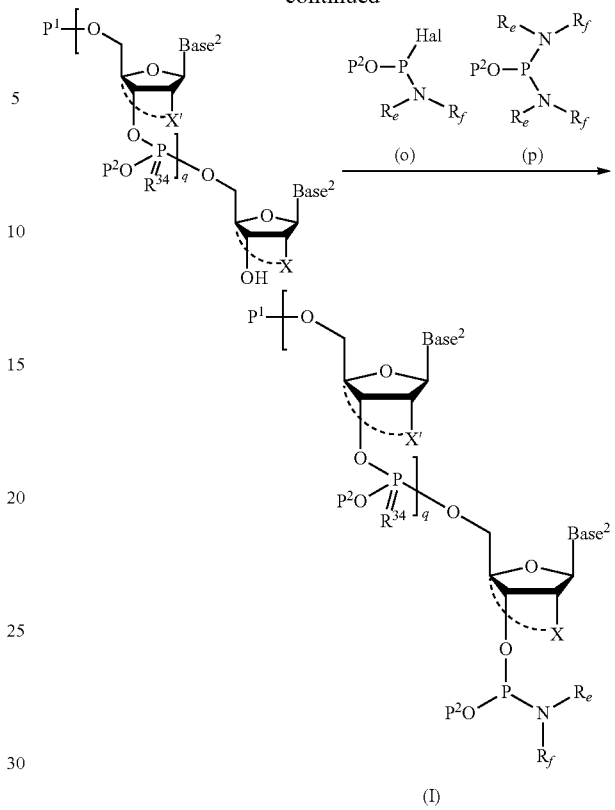

wherein $P^4$ is a nucleotide 3'-hydroxyl-protecting group, and other symbols are as defined above.

As the protecting group of nucleotide 3'-hydroxyl group for $P^4$, a protecting group capable of deprotection under the conditions under which the 5'-hydroxyl-protecting group $P^1$, the protecting group when the nucleic acid base has a protecting group and a phosphate-protecting group $P^2$ are not deprotected is used. For example, a protecting group capable of deprotection with hydrazine can be mentioned. Preferable examples of the protecting group capable of deprotection with hydrazine include a levulyl group and the like (see Aust. J. Chem. 2010, 63, 227-235).

4. Production Method of Oligonucleotide

Next, the production method of oligonucleotide relating to the present invention (hereinafter to be also referred to as "the production method of the present invention") is explained.

The production method of the present invention characteristically comprises using the aforementioned oligonucleotide comprising a protected base. To be specific, a production method of an n+p-mer oligonucleotide from an n-mer oligonucleotide is explained. For example, when n=1, an n-mer oligonucleotide is to be understood as "nucleoside", when p=1, a p-mer oligonucleotide comprising a protected base is to be understood as "nucleoside comprising a protected base", and an n+p-mer oligonucleotide is to be understood as "dinucleoside".

The production method of the present invention preferably includes the following step (2):

(2) a step of condensing a p-mer oligonucleotide comprising a protected base (p is any integer of one or more) wherein the 3'-hydroxyl group is phosphoramidited, the 5'-hydroxyl group is protected by a temporary protecting group removable under acidic conditions, and the nucleic acid base is protected by a group having a $C_{5-30}$ straight chain or branched chain alkyl group and/or a $C_{5-30}$ straight chain or branched chain alkenyl group, with an n-mer oligonucleotide (n is an integer of one or more) wherein the 5'-hydroxyl group is not protected and the 3'-hydroxyl group is protected, by forming a phosphite triester bond via the 5'-hydroxyl group thereof to give an n+p-mer oligonucleotide.

The production method of the present invention preferably further includes the following step (3), by which the phosphite triester bond of the n+p-mer oligonucleotide obtained in step (2) is converted to a phosphate triester bond or thiophosphate triester bond.

(3) a step of converting the phosphite triester bond of the n+p-mer oligonucleotide obtained in the condensation step to a phosphate triester bond or a thiophosphate triester bond by adding an oxidizing agent or a sulfurizing agent to the reaction mixture obtained in the condensation step (2).

The production method of the present invention preferably further includes the following step (1), whereby an n-mer oligonucleotide wherein the 5'-hydroxyl group is not protected and the 3'-hydroxyl group is protected, which is used in step (2), is prepared:

(1) a step of removing the temporary protecting group removable under acidic conditions of the 5'-hydroxyl group by reacting, in a non-polar solvent prior to the condensation step (2), an n-mer oligonucleotide wherein the 3'-hydroxyl group is protected, and the 5'-hydroxyl group is protected by a temporary protecting group, with an acid.

Step (1) is preferably performed in the presence of at least one kind of cation scavenger selected from a pyrrole derivative and an indole derivative, and further includes a step of removing the temporary protecting group of the 5'-hydroxyl group and neutralizing the compound with an organic base. This enables continuous performance of steps (1), (2) and (3) in a solution, and an oligonucleotide wherein nucleoside in the number of p has elongated can be isolated and purified by an extraction operation alone.

Furthermore, by including the following step (4), an n+p-mer oligonucleotide is purified by removing an excess starting material and by-product conveniently and effectively, without the need for complicated solidification-isolation, and can be led to the next step without taking out the resultant product from the reaction vessel:

(4) a step of isolating the n+p-mer oligonucleotide from the reaction mixture obtained in step (3) by an extraction operation alone.

When the amount of the by-product can be controlled by the management of equivalent amounts of the starting materials and the control of the reaction, it is preferable to repeat step (1) to step (3) as a basic unit, and include step (4).

Moreover, since occurrence of by-product can be strictly managed and controlled and highly pure oligonucleotide can be obtained, it is preferable to repeat step (1) to step (4) as a basic unit.

By repeating such cycle in the liquid phase method, the final oligonucleotide can be produced in one-pot, without changing the reaction vessel.

In the production method of the present invention, an oligonucleotide can be isolated and produced by further including step (5):

(5) a step of removing all the protecting groups of the n+p-mer oligonucleotide obtained in step (4).

n is an integer of one or more. While the upper limit thereof is not particularly limited, it is generally 100 or less, preferably 75 or less, more preferably 50 or less, and still more preferably 30 or less p is an integer of one or more, preferably 1. While the upper limit thereof is not particularly limited, it is preferably 50 or less, more preferably 30 or less, more preferably 20 or less, still more preferably 5 or less, and particularly preferably 3 or less.

4-1. Explanation of "n-mer oligonucleotide"

First of all, the n-mer oligonucleotide to be used as a starting material of steps (1) and (2) is explained.

The n-mer oligonucleotide to be used in step (1) is, for example, an n-mer oligonucleotide represented the following formula (i) wherein $P^1$ is a temporary protecting group removable under acidic conditions, the 3'-position hydroxyl group is protected and the 5'-position hydroxyl group is protected by a temporary protecting group removable under acidic conditions. The n-mer oligonucleotide to be used in step (2) shows, for example, an n-mer oligonucleotide represented by the following formula (II) wherein the 5'-position hydroxyl group is not protected, and the 3'-position hydroxyl group is protected.

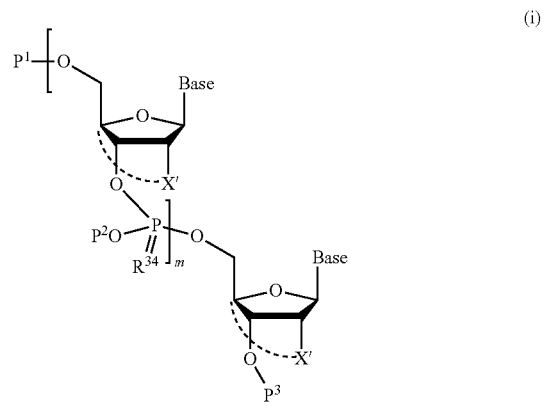

(i)

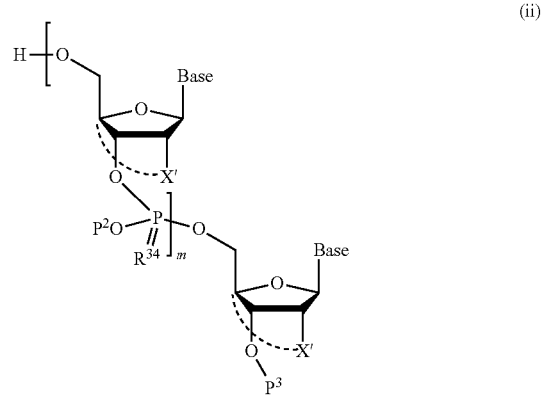

(ii)

wherein m is any integer of not less than 0, Base in the number of m+1 are each independently an optionally protected nucleic acid base, $R^{34}$ in the number of m are each independently an oxygen atom or a sulfur atom, $P^2$ in the number of m are each independently a protecting group removable under basic conditions, $P^3$ is a nucleotide 3'-hydroxyl-protecting group, X' in the number of m+1 are each independently as defined for X, and other symbols are as defined above.

While the upper limit of m is not particularly limited, it is generally 99 or less, preferably 74 or less, more preferably 49 or less, still more preferably 29 or less.

The "protecting group removable under basic conditions" for $P^2$ is as defined for $P^2$ in the formula (I).

Each symbol in the formulas (i) and (ii) is explained below.

4-2. Explanation of "Nucleotide 3'-Hydroxyl-Protecting Group"

The "nucleotide 3'-hydroxyl-protecting group" for $P^3$ in the formulas (i) and (ii) is not particularly limited as long as it is a group stable under acidic conditions capable of removing the 5'-hydroxyl-protecting group, and can dissolve an n-mer oligonucleotide in a non-polar reaction solvent so that the reaction will proceed in steps (1) and (2). It is preferably a group represented by the following formula (III')

$$\text{-L-Y-Z'} \quad \text{(III')}$$

wherein

L is a group represented by the formula (a1):

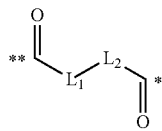

(a1)

wherein * shows the bonding position to Y; ** indicates the bonding position to a 3'-hydroxy group of the nucleotide;
$L_1$ is an optionally substituted divalent $C_{1-22}$ hydrocarbon group; and
$L_2$ is a single bond, or a group represented by $C(=O)N(R^2)-R^1-N(R^3)$* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or
$R^2$ and $R^3$ are optionally joined to form an optionally substituted $C_{1-22}$ alkylene bond,
Y is an oxygen atom or NR wherein R is a hydrogen atom, an alkyl group or an aralkyl group, and
Z' is an organic group having a hydrocarbon group.

A preferable embodiment of the linker L represented by the above-mentioned formula (a1) is a group wherein, in the formula (a1),
$L_1$ is an ethylene group or $CH_2$-O-1,4-phenylene-O-$CH_2$; and
$L_2$ is a single bond, or a group represented by $C(=O)N(R^2)-R^1-N(R^3)$* wherein  shows the bonding position to $L_1$, * shows the bonding position to C=O, $R^1$ is a $C_{1-6}$ alkylene group, and $R^2$ and $R^3$ are each independently a hydrogen atom or an optionally substituted $C_{1-6}$ alkyl group, or $R^2$ and $R^3$ are optionally joined to form an optionally substituted $C_{1-6}$ alkylene bond.

Another preferable embodiment of the linker L represented by the above-mentioned formula (a1) is a group wherein, in the formula (a1),
$L_1$ is an ethylene group; and
$L_2$ is a single bond.

Another preferable embodiment of the linker L represented by the above-mentioned formula (a1) is a group wherein, in the formula (a1),
$L_1$ is an ethylene group; and
the moiety $N(R^2)-R^1-N(R^3)$ for $L_2$ is a piperazinylene group.

Another preferable embodiment of the linker L represented by the above-mentioned formula (a1) is a group wherein, in the formula (a1),
$L_1$ is an ethylene group; and
$L_2$ is a group represented by $C(=O)N(R^2)-R^1-N(R^3)$* wherein  shows the bonding position to $L_1$, * shows the bonding position to C=O, $R^1$ is a pentylene group or a hexylene group, and $R^2$ and $R^3$ are each independently a hydrogen atom or a methyl group.

A particularly preferable example of the above-mentioned linker L is a succinyl group since it is economical and easily available.

Y in the above-mentioned formula (III') is an oxygen atom, or NR wherein R is a hydrogen atom, an alkyl group or an aralkyl group.

In the present specification, the "alkyl group" for R is a $C_{1-30}$ alkyl group, preferably a $C_{1-10}$ alkyl group, more preferably a $C_{1-6}$ alkyl group. Specific preferable examples thereof include methyl, ethyl, propyl, isopropyl, butyl, isobutyl, sec-butyl, tert-butyl and the like, and methyl and ethyl are particularly preferable.

In the present specification, the "aralkyl group" for R is a $C_{7-30}$ aralkyl group, preferably a $C_{7-20}$ aralkyl group, more preferably a $C_{7-16}$ aralkyl group (a $C_{6-10}$ aryl-$C_{1-6}$ alkyl group). Specific preferable examples thereon include benzyl, 1-phenylethyl, 2-phenylethyl, 1-phenylpropyl, α-naphthylmethyl, 1-(α-naphthyl)ethyl, 2-(α-naphthyl)ethyl, 1-(α-naphthyl)propyl, p-naphthylmethyl, 1-(β-naphthyl)ethyl, 2-(β-naphthyl)ethyl, 1-(β-naphthyl)propyl and the like, and benzyl is particularly preferable.

R is preferably a hydrogen atom, a $C_{1-6}$ alkyl group or a $C_{7-16}$ aralkyl group, more preferably a hydrogen atom, methyl, ethyl or benzyl, particularly preferably a hydrogen atom.

Y is preferably an oxygen atom or NH.

Examples of the "organic group having a hydrocarbon group" for Z' include a $C_{1-6}$ alkyl group such as methyl, ethyl, tert-butyl and the like, benzyl, p-nitrobenzyl, p-methoxybenzyl, diphenylmethyl, allyl, 1,1-dimethyl-2-phenyl-ethyl, 2,4-dimethoxybenzyl, bis(4-methoxyphenyl)methyl and the like. In addition, as the organic group having a hydrocarbon group, a group having a branched chain is preferable. When a group having a branched chain is used, liposolubility and solubility in a solvent (particularly, non-polar solvent) of an n-mer oligonucleotide and an n+p-mer oligonucleotide can be improved, step (1) can be performed smoothly, and an n+p-mer oligonucleotide can be easily transferred into a non-polar solvent in the extraction-isolation step of the below-mentioned step (4).

Preferable examples of the "group having a branched chain" for Z' include a group represented by the formula (a2):

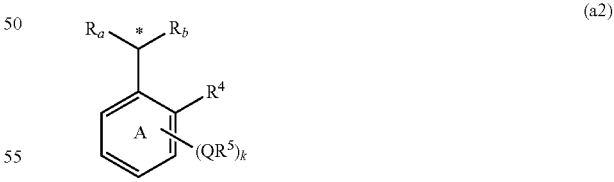

(a2)

wherein * shows the bonding position to Y;
$R^4$ is a hydrogen atom, or when $R_b$ is a group represented by the following formula (a3), then $R^4$ shows, in combination with $R^6$, a single bond or —O— to optionally form a fluorenyl group or a xanthenyl group together with ring B;
Q in the number of k are each independently a single bond, —O—, —S—, —OC(=O)—, —NHC(=O)— or —NH—;
$R^5$ in the number of k are each independently an organic group having at least one aliphatic hydrocarbon group having one or more branched chains and the total carbon number of not less than 14 and not more than 300;

k is an integer of 1 to 4;

ring A optionally further has, in addition to $R^4$, $QR^5$ in the number of k and *$C(R_a)(R_b)$, a substituent selected from the group consisting of a halogen atom, a $C_{1-6}$ alkyl group optionally substituted by one or more halogen atoms, and a $C_{1-6}$ alkoxy group optionally substituted by one or more halogen atoms;

$R_a$ is a hydrogen atom; and $R_b$ is a hydrogen atom, or a group represented by the formula (a3):

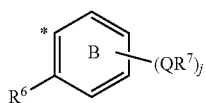

(a3)

wherein * indicates the bonding position;

j is an integer of 0 to 4;

Q in the number of j are each independently as defined above;

$R^7$ in the number of j are each independently an organic group having at least one aliphatic hydrocarbon group having one or more branched chains and the total carbon number of not less than 14 and not more than 300;

$R^6$ is a hydrogen atom, or shows, in combination with $R^4$, a single bond or —O— to form a fluorenyl group or a xanthenyl group together with ring A; and ring B optionally further has, in addition to $QR^7$ in the number of j and $R^6$, a substituent selected from the group consisting of a halogen atom, a $C_{1-6}$ alkyl group optionally substituted by one or more halogen atoms, and a $C_{1-6}$ alkoxy group optionally substituted by one or more halogen atoms.

That is, a preferable one embodiment of the 3'-hydroxyl-protecting group in the n-mer oligonucleotide in the present invention is represented by the following formula (III):

(III)

wherein

L and Y are as defined above, and

Z is the formula (a2):

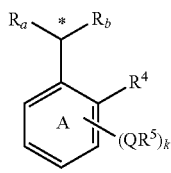

(a2)

wherein each symbol is as defined above.

When the nucleotide 3'-hydroxyl-protecting group is -L-Y—Z' and Z' is a "group having branched chain", preferably a group represented by the formula (a2), then a solvent, wherein solubility of the nucleoside or oligonucleotide is improved, is preferably a non-polar solvent.

Preferable embodiments of L and Y in the above-mentioned formula (III) are similar to those of the above-mentioned formula (III').

The preferable embodiment for Z' in the above-mentioned formula (III'), that is, a group represented by the formula (a2) for Z in the above-mentioned formula (III) is a particular benzyl group (in the formula (a2), both $R_a$ and $R_b$ are hydrogen atoms, and $R^4$ is a hydrogen atom); a particular diphenyl-methyl group (in the formula (a2), $R_a$ is a hydrogen atom, $R^4$ is a hydrogen atom, k is 1 to 3, and $R_b$ is a group represented by the formula (a3) wherein $R^6$ is a hydrogen atom, and j is 0 or 1); a particular fluorenyl group (in the formula (a2), $R_a$ is a hydrogen atom, k is 1, $R_b$ is a group represented by the formula (a3) wherein j is 0, and $R^6$ shows, together with $R^4$, a single bond to form a fluorine ring together with ring A); a particular xanthenyl group (in the formula (a2), $R_a$ is a hydrogen atom, k is 1, $R_b$ is a group represented by the formula (a3) wherein j is 0, and $R^6$ shows —O— together with $R^4$ to form a xanthine ring together with ring A).

In the formula (III), the "organic group having at least one aliphatic hydrocarbon group having one or more branched chains and a total carbon number of not less than 14 and not more than 300" for $R^5$ and $R^7$ is an organic group having at least one aliphatic hydrocarbon group having one or more branched chains in a molecular structure thereof, and a total carbon number of not less than 14 and not more than 300.

The "branched chain" of the "aliphatic hydrocarbon group having one or more branched chains" is a straight or branched saturated aliphatic hydrocarbon group. Preferred is a $C_{1-6}$ alkyl group, more preferred is a $C_{1-4}$ alkyl group, and still more preferred is a methyl group or an ethyl group. In addition, the "branched chain" is optionally substituted by one or more halogen atoms.

The "aliphatic hydrocarbon group" of the "aliphatic hydrocarbon group having one or more branched chains" is a straight saturated or unsaturated aliphatic hydrocarbon group, a $C_2$-$C_{300}$ alkyl group (preferably, a $C_3$-$C_{100}$ alkyl group, more preferably, a $C_3$-$C_{60}$ alkyl group), a $C_2$-$C_{300}$ alkenyl group (preferably, a $C_3$-$C_{100}$ alkenyl group, more preferably, a $C_3$-$C_{60}$ alkenyl group) or a $C_2$-$C_{300}$ alkynyl group (preferably, a $C_3$-$C_{100}$ alkynyl group, more preferably, a $C_3$-$C_{60}$ alkynyl group).

The moiety of the "aliphatic hydrocarbon group having one or more branched chains" of the "organic group having at least one aliphatic hydrocarbon group having one or more branched chains, and a total carbon number of not less than 14 and not more than 300" is not particularly limited, and it may be present at the terminal (monovalent group), or other site (e.g., divalent group).

Specific examples of the "aliphatic hydrocarbon group having one or more branched chains" include a monovalent group having one or more branched chain(s) of a branched isomer of a propyl group, a butyl group, a pentyl group, a hexyl group, a heptyl group, an octyl group, a nonyl group, a decyl group, an undecyl group, a dodecyl group (a lauryl group), a tridecyl group, a myristyl group, a cetyl group, a stearyl group, an arachyl group, a behenyl group, an oleyl group, a linolyl group, a lignoceryl group and the like, and a divalent group derived therefrom, preferably, a 3,7,11-trimethyldodecyl group, a 3,7,11,15-tetramethylhexadecyl group (hereinafter sometimes to be referred to as a 2,3-dihydrophytyl group), a 2,2,4,8,10,10-hexamethylundecan-5-yl group, and the like.

When plural "aliphatic hydrocarbon groups having one or more branched chains" are in the "organic group having at least one aliphatic hydrocarbon group having one or more branched chains, and a total carbon number of not less than 14 and not more than 300", each may be same or different.

The moiety other than the "aliphatic hydrocarbon group having one or more branched chains" of the "organic group having at least one aliphatic hydrocarbon group having one or more branched chains, and a total carbon number of not less than 14 and not more than 300" can be set freely. For example, the group optionally has moieties such as —O—, —S—, —CO—, —NH—, —COO—, —OCONH—, —CONH—, —NHCO—, hydrocarbon group (monovalent group or divalent group) and the like. Examples of the "hydrocarbon group" include an aliphatic hydrocarbon group, an aromatic aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferable and, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferable and, for example, vinyl, 1-propenyl, allyl, isopropenyl, butenyl, isobutenyl and the like can be mentioned. As the "alkynyl group", a $C_{2-6}$ alkynyl group and the like are preferable and, for example, ethynyl, propargyl, 1-propynyl and the like can be mentioned. As the "cycloalkyl group", a $C_{3-6}$ cycloalkyl group and the like are preferable and, for example, cyclopropyl, cyclobutyl, cyclopentyl and cyclohexyl can be mentioned. As the "aryl group", for example, a $C_{6-14}$ aryl group and the like are preferable and, for example, phenyl, 1-naphthyl, 2-naphthyl, biphenylyl, 2-anthryl and the like can be mentioned. Of these, a $C_{6-10}$ aryl group is more preferable, and phenyl is particularly preferable. As the "aralkyl group", a $C_{7-20}$ aralkyl group is preferable and, for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group ($C_{6-10}$ aryl-$C_{1-6}$ alkyl group) is more preferable, and benzyl is particularly preferable. The "hydrocarbon group" is optionally substituted by a substituent selected from a halogen atom (a chlorine atom, a bromine atom, a fluorine atom, an iodine atom), an oxo group and the like.

Z has a $QR^5$ group in the number of k. Here, Q is a single bond, or —O—, —S—, —C(=O)O—, —C(=O)NH— or —NH—, preferably O. The $QR^5$ group in the number of k may be the same or different.

In Z, the "organic group having at least one aliphatic hydrocarbon group having one or more branched chains, and a total carbon number of not less than 14 and not more than 300" for $R^5$ and $R^7$ preferably has a total carbon number of not less than 14, preferably not less than 16, more preferably not less than 18. The "organic group having at least one aliphatic hydrocarbon group having one or more branched chains, and a total carbon number of not less than 14 and not more than 300" for $R^5$ and $R^7$ preferably has a total carbon number of not more than 300, preferably not more than 200, more preferably not more than 160. In addition, in the compound of in the present invention, while a total number of the branched chain of the "organic group having at least one aliphatic hydrocarbon group having one or more branched chains, and a total carbon number of not less than 14 and not more than 300" for $R^5$ and $R^7$ is not particularly limited, it preferably has a total number of the branched chain of preferably two or more, more preferably not less than 3, more preferably not less than 4, more preferably not less than 8, more preferably not less than 10. When the total number of the branched chain is higher, an oligonucleotide wherein the 3'-hydroxyl group is protected by said protecting group becomes an oil showing good solubility in various organic solvents (particularly, non-polar solvents) even when the oligonucleotide chain becomes long.

As the "organic group having at least one aliphatic hydrocarbon group having one or more branched chains, and a total carbon number of not less than 14 and not more than 300" for $R^5$ and $R^7$, a group having the same or different divalent groups represented by the formula (b):

wherein * shows a bonding position with the adjacent atom;
$R^8$ and $R^9$ are each independently a hydrogen atom or a $C_{1-4}$ alkyl group;
$X_1$ is a single bond, or a $C_{1-4}$ alkylene group,
provided that $R^8$ and $R^9$ are not hydrogen atoms at the same time, is preferable and, for example, a group represented by any of the following formulas (c) to (e) can be mentioned.

The carbon number, repeat unit number ($m_1$, $n_0$ to $n_2$) and the like in the definition of each symbol in the formulas (c) to (e) are shown for convenience, and can be changed as appropriate within the range defined above, so that the total number of the carbon will be not less than 14 (preferably not less than 16, more preferably not less than 18) and not more than 300 (preferably not more than 200, more preferably not more than 160). In the following, the formulas (c) to (e) are successively explained.

The formula (c) is as described below.

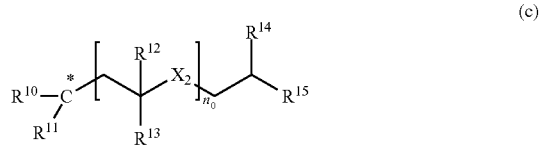

wherein * shows a bonding position to Q;
$R^{10}$ and $R^{11}$ are both hydrogen atoms, or show =O in combination;
$n_0$ is an integer of 2 to 40;
$R^{12}$ and $R^{13}$ in the number of $n_0$ are each independently a hydrogen atom or a $C_{1-4}$ alkyl group;
$X_2$ in the number of $n_0$ are each independently a single bond or a $C_{1-4}$ alkylene group;
$R^{14}$ is a hydrogen atom or a $C_{1-4}$ alkyl group; and
$R^{15}$ is a $C_{1-4}$ alkyl group;
provided that $R^{12}$ and $R^{13}$ are not hydrogen atoms at the same time, and when $n_0$ is 2, $R_{14}$ is a $C_{1-4}$ alkyl group.

In the group of the formula (c), a group wherein
$R^{10}$ and $R^{11}$ are both hydrogen atoms;
$n_0$ is an integer of 2 to 40;
$R^{12}$ and $R^{13}$ in the number of $n_0$ are each independently a hydrogen atom, a methyl group or an ethyl group;
$X_2$ in the number of $n_0$ are each independently a single bond, a methylene group or an ethylene group; and
$R^{14}$ is a hydrogen atom, a methyl group or an ethyl group is preferable, provided that $R^{12}$ and $R^{13}$ are not hydrogen atoms at the same time, and when $n_0$ is 2, $R^{14}$ is methyl or an ethyl group.

More preferable group of the formula (c) is a group of a branched isomer having a carbon number of 14 to 160, of a myristyl group, a cetyl group, a stearyl group, an arachyl group, a behenyl group and the like. Of these, a 2,3-dihydrophytyl group, a 3,7,11-trimethyldodecyl group and a 2,2,4,8,10,10-hexamethyl-5-dodecanoyl group are particularly preferable.

The formula (d) is as described below.

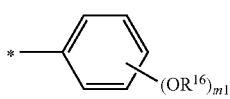

wherein * shows a bonding position to Q;
$OR^{16}$ in the number of $m_1$ are each independently hydroxyl group substituted by a group represented by the formula (c); and
$m_1$ is an integer of 1 to 3.

The group represented by the formula (c) is the same as the group represented by the above-mentioned formula (c) except that * does not show a bonding position to Q but shows a bonding position to O.

In the group of the formula (d), $R^{16}$ is more preferably a group of a branched isomer having a carbon number of 14 to 30 of a myristyl group, a cetyl group, a stearyl group, an arachyl group, a behenyl group and the like. Of these, a 2,3-dihydrophytyl group and a 3,7,11-trimethyldodecyl group are particularly preferable.

The formula (e) is as described below.

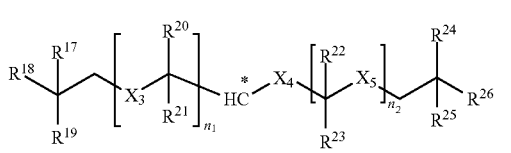

wherein * shows a bonding position to Q;
$n_1$ is an integer of 1 to 10;
$n_2$ is an integer of 1 to 10;
$R^{20}$ and $R^{21}$ in the number of $n_1$ are each independently a hydrogen atom or a $C_{1-4}$ alkyl group;
$X_3$ in the number of $n_1$ are each independently a single bond or a $C_{1-4}$ alkylene group;
$R^{22}$ and $R^{23}$ in the number of $n_2$ are each independently a hydrogen atom or a $C_{1-4}$ alkyl group;
$X_5$ in the number of $n_2$ are each independently a single bond or a $C_{1-4}$ alkylene group;
$X_4$ is a single bond or a $C_{1-4}$ alkylene group; and
$R^{17}$, $R^{18}$, $R^{19}$, $R^{24}$, $R^{25}$ and $R^{26}$ are each independently a hydrogen atom or a $C_{1-4}$ alkyl group,
provided that $R^{20}$ and $R^{21}$ and/or $R^{22}$ and $R^{23}$ are not hydrogen atoms at the same time, and when $n_1+n_2$ is 2, two or more of $R^{17}$, $R^{18}$ and $R^{19}$ are each independently a $C_{1-4}$ alkyl group, or two or more of $R^{24}$, $R^{25}$ and $R^{26}$ are each independently a $C_{1-4}$ alkyl group.
A group of the formula (e), wherein
$n_1$ is an integer of 1 to 5;
$n_2$ is an integer of 1 to 5;
$R^{20}$ and $R^{21}$ in the number of $n_1$ are each independently a hydrogen atom, a methyl group or an ethyl group;
$X_3$ in the number of $n_1$ are each independently a single bond, a methylene group or an ethylene group;
$R^{22}$ and $R^{23}$ in the number of $n_2$ are each independently a hydrogen atom, a methyl group or an ethyl group;
$X_5$ in the number of $n_2$ are each independently a single bond, a methylene group or an ethylene group;
$X_4$ is a single bond, a methylene group or an ethylene group; and
$R^{17}$, $R^{18}$, $R^{19}$, $R^{24}$, $R^{25}$ and $R^{26}$ are each independently a hydrogen atom or a $C_{1-4}$ alkyl group is more preferable,
provided that $R^{20}$ and $R^{21}$ and/or $R^{22}$ and $R^{23}$ are not hydrogen atoms at the same time, and when $n_1+n_2$ is 2, two or more of $R^{17}$, $R^{18}$ and $R^{19}$ are each independently a $C_{1-4}$ alkyl group, or two or more of $R^{24}$, $R^{25}$ and $R^{26}$ are each independently a $C_{1-4}$ alkyl group.
A group of the formula (e), wherein
$n_1$ is an integer of 1 to 5;
$n_2$ is an integer of 1 to 5;
$R^{20}$ and $R^{21}$ in the number of $n_1$ are each independently a hydrogen atom or a methyl group;
$X_3$ in the number of $n_1$ are each independently a single bond or a methylene group;
$R^{22}$ and $R^{23}$ in the number of $n_2$ are each independently a hydrogen atom or a methyl group;
$X_5$ in the number of $n_2$ are each independently a single bond or a methylene group;
$X_4$ is a single bond or a methylene group; and
$R^{17}$, $R^{18}$, $R^{19}$, $R^{25}$, $R^{25}$ and $R^{26}$ are each a methyl group, provided that $R^{20}$ and $R^{21}$ and/or $R^{22}$ and $R^{23}$ are not hydrogen atoms at the same time is particularly preferable.

Specific examples of the "organic group having at least one aliphatic hydrocarbon group having one or more branched chains, and a total carbon number of not less than 14 and not more than 300" for $R^5$ and $R^7$ include the following groups, wherein * in each group shows a bonding position, $n_3$ in the formula is an integer of not less than 3, and $n_4$ can be appropriately adjusted so that the total carbon number of the group will be not less than 14 and not more than 300.

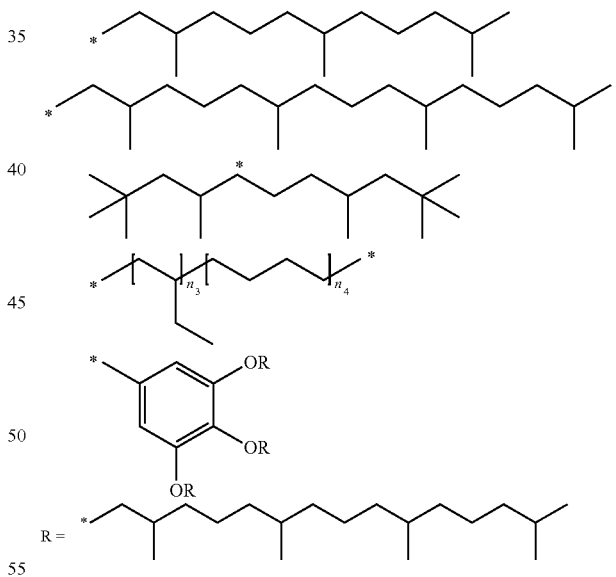

Specific preferable examples of the "organic group having at least one aliphatic hydrocarbon group having one or more branched chains, and a total carbon number of not less than 14 and not more than 300" for $R^5$ and $R^7$ include the following groups:
3,7,11,15-tetramethylhexadecyl group;
3,7,11-trimethyldodecyl group;
2,2,4,8,10,10-hexamethyl-5-dodecanoyl group;
3,4,5-tri(3',7',11',15'-tetramethylhexadecyloxy)benzyl group; and
3,5-di(3',7',11',15'-tetramethylhexadecyloxy)benzyl group.

Preferable examples of protecting group represented by the formula (III') or the formula (III) of the present invention include the following benzylsuccinyl group, or diphenylmethylsuccinyl group, which are not to be construed as limiting the present invention:

2-{2,4-di(2',3'-dihydrophytyloxy)benzylaminocarbonyl}ethylcarbonyl group; 3,5-di(2',3'-dihydrophytyloxy)benzylsuccinyl group; 4-(2',3'-dihydrophytyloxy)benzylsuccinyl group; 2-{1-[(2-chloro-5-(2',3'-dihydrophytyloxy)phenyl)]benzylaminocarbonyl}ethylcarbonyl group; 3,4,5-tri(2',3'-dihydrophytyloxy)benzylsuccinyl group; 2-{3,4,5-tri(2',3'-dihydrophytyloxy)benzylaminocarbonyl}ethylcarbonyl group; 2-{4-(2',3'-dihydrophytyloxy)benzylaminocarbonyl}ethylcarbonyl group; 2-{2-[3',4',5'-tri(2'',3''-dihydrophytyloxy)benzyloxy]-4-methoxybenzylaminocarbonyl}ethylcarbonyl group; 2-{4-(2',3'-dihydrophytyloxy)-2-methoxybenzylaminocarbonyl}ethylcarbonyl group; 4-(2',3'-dihydrophytyloxy)-2-methylbenzylsuccinyl group; 2-{4-(2',3'-dihydrophytyloxy)-2-methylbenzylaminocarbonyl}ethylcarbonyl group; 4-[2,2,4,8,10,10-hexamethyl-5-dodecanoylamino]benzylsuccinyl group; 2-{4-[2,2,4,8,10,10-hexamethyl-5-dodecanoylamino]benzylaminocarbonyl}ethylcarbonyl group; 4-(3,7,11-trimethyldodecyloxy)benzylsuccinyl group; 2-{4-(3,7,11-trimethyldodecyloxy)benzylaminocarbonyl}ethylcarbonyl group; 2-{3,5-di(2',3'-dihydrophytyloxy)benzylaminocarbonyl}ethylcarbonyl group; 2-{1-[2,3,4-tri(2',3'-dihydrophytyloxy)phenyl]benzylaminocarbonyl}ethylcarbonyl group; 2-{1-[4-(2',3'-dihydrophytyloxy)phenyl]-4'-(2',3'-dihydrophytyloxy)benzylaminocarbonyl}ethylcarbonyl group; 3,4,5-tris[3,4,5-tri(2',3'-dihydrophytyloxy)benzyl]benzylsuccinyl group; and 2-{3,4,5-tris[3,4,5-tri(2',3'-dihydrophytyloxy)benzyl]benzylaminocarbonyl}ethylcarbonyl group.

4-3. Explanation of "Optionally Protected Nucleic Acid Base"

The "optionally protected nucleic acid base" represented by Base in the formulas (i) and (ii) means, for example, that an amino group may be protected in an adenyl group, a guanyl group or a cytosyl group, which is a nucleic acid base having an amino group, or an imido group may be protected in a thymyl group, or an uracil group, which is a nucleic acid base having a cyclic imido group, a nucleic acid base wherein the amino group therein is protected by a protecting group sustainable under the deprotection conditions of the 5'-position is preferable. The "amino-protecting group" and "imide-protecting group" are not particularly limited, and examples thereof include the protecting groups described in Greene's PROTECTIVE GROUPS IN ORGANIC SYNTHESIS, 4th edition, JOHN WILLY&SONS, 2006 and the like. Specific examples of the "amino-protecting group" include a pivaloyl group, a pivaloyloxymethyl group, a trifluoroacetyl group, a phenoxyacetyl group, a 4-isopropylphenoxyacetyl group, a 4-tert-butylphenoxyacetyl group, an acetyl group, a benzoyl group, an isobutyryl group, a dimethylformamidinyl group, a 9-fluorenylmethyloxycarbonyl group and the like. Among them, a phenoxyacetyl group, a 4-isopropylphenoxyacetyl group, an acetyl group, a benzoyl group, an isobutyryl group and a dimethylformamidinyl group are preferable. In addition, the carbonyl group of the nucleic acid base is optionally protected, and can be protected, for example, by reacting phenol, 2,5-dichlorophenol, 3-chlorophenol, 3,5-dichlorophenol, 2-formylphenol, 2-naphthol, 4-methoxyphenol, 4-chlorophenol, 2-nitrophenol, 4-nitrophenol, 4-acetylaminophenol, pentafluorophenol, 4-pivaloyloxybenzyl alcohol, 4-nitrophenethyl alcohol, 2-(methylsulfonyl)ethanol, 2-(phenylsulfonyl)ethanol, 2-cyanoethanol, 2-(trimethylsilyl)ethanol, dimethylcarbamoyl chloride, diethylcarbamoyl chloride, ethylphenylcarbamoyl chloride, 1-pyrrolidinecarbonyl chloride, 4-morpholinecarbonyl chloride, diphenylcarbamoyl chloride and the'like. In some cases, the carbonyl-protecting group does not need to be particularly introduced.

Another preferable embodiment of the protecting group of the nucleic acid base includes a "group having a $C_{5-30}$ straight chain or branched chain alkyl group and/or a $C_{5-30}$ straight chain or branched chain alkenyl group". The "group having a $C_{5-30}$ straight chain or branched chain alkyl group and/or a $C_{5-30}$ straight chain or branched chain alkenyl group" is as defined for the "group having a $C_{5-30}$ straight chain or branched chain alkyl group and/or a $C_{5-30}$ straight chain or branched chain alkenyl group" of the "nucleic acid base protected by a group having a $C_{5-30}$ straight chain or brandied chain alkyl group and/or a $C_{5-30}$ straight chain or branched chain alkenyl group" for $Base^2$ in the above-mentioned formula (I).

Of these, a "group having a $C_{5-30}$ branched chain alkyl group and/or a $C_{5-30}$ branched chain alkenyl group" is preferable, and a "group having a $C_{5-30}$ branched chain alkyl group" is more preferable.

Protection of a nucleic acid base by a "group having a $C_{5-30}$ straight chain or branched chain alkyl group and/or a $C_{5-30}$ straight chain or branched chain alkenyl group" further confers liposolubility and solubility in an organic solvent (particularly, non-polar solvent) to an n-mer oligonucleotide, which is advantageous for the synthesis of a long chain oligonucleotide.

At least one nucleic acid base of an n-mer oligonucleotide is preferably protected by a group having a $C_{5-30}$ straight chain or branched chain alkyl group and/or a $C_{5-30}$ straight chain or branched chain alkenyl group, and more preferably protected by a group having a $C_{5-30}$ branched chain alkyl group and/or a $C_{5-30}$ branched chain alkenyl group.

In this case, at least one nucleic acid base of the n-mer oligonucleotide only needs to be protected by the protecting group, or all nucleic acid bases in the number of n may be is protected by the protecting group, or a part thereof may be protected by the protecting group and other nucleic acid bases may be protected by a protecting group conventionally used in the field of nucleic acid synthesis (e.g., pivaloyl group, pivaloyloxymethyl group, trifluoroacetyl group, phenoxyacetyl group, 4-isopropylphenoxyacetyl group, 4-tert-butylphenoxyacetyl group, acetyl group, benzoyl group, isobutyryl group, dimethylformamidinyl group, 9-fluorenylmethyloxycarbonyl group etc.).

Thus, when all or a part of the nucleic acid bases represented by Base are/is protected by a group having a $C_{5-30}$ straight chain or branched chain alkyl group and/or a $C_{5-30}$ straight chain or branched chain alkenyl group, the obtained n+p-mer oligonucleotide shows further improved liposolubility and solubility in an organic solvent (particularly, non-polar solvent), which facilitates the extraction operation in the next step (4) and enables synthesis of an oligonucleotide having a higher degree of polymerization.

In the nucleic acid base in the number of n, the ratio of protection by a group having a $C_{5-30}$ straight chain or branched chain alkyl group and/or a $C_{5-30}$ straight chain or branched chain alkenyl group can be appropriately set so that the n-mer oligonucleotide shows sufficient solubility in an organic solvent (particularly, non-polar solvent).

Preferable examples of the "group having a $C_{5-30}$ straight chain or branched chain alkyl group and/or a $C_{5-30}$ straight chain or branched chain alkenyl group" and "group having a $C_{5-30}$ branched chain alkyl group and/or a $C_{5-30}$ branched chain alkenyl group" are as explained for the aforementioned formula (I).

4-4. Oligonucleotide Protected by a Branched Chain-Containing Aromatic Group

A more preferable embodiment of the n-mer oligonucleotide in the present invention is a novel oligonucleotide represented by the following formula (II), wherein, in the aforementioned formulas (i) and (ii), a 3'-hydroxyl-protecting group represented by $P^3$ is a group represented by the aforementioned formula (III): -L-Y—Z (sometimes to be referred to as "branched chain-containing aromatic protecting group" in the present specification) (sometimes to be referred to as an "oligonucleotide protected by a branched chain-containing aromatic group" in the present specification).

When m is 0, the oligonucleotide protected by a branched chain-containing aromatic group, which is represented by the formula (II), is understood to mean a "nucleoside protected by a branched chain-containing aromatic group".

Since the oligonucleotide protected by a branched chain-containing aromatic group of the present invention is easily soluble in a non-polar solvent superior in the partitioning operability, which is a reaction solvent in the production method of the present invention, it is extremely useful as a novel compound usable for a production method of oligonucleotide wherein the reaction in each step can be performed smoothly, and the final resultant product can be obtained without crystallization and isolation of each intermediate but via an extraction separation alone (also referred to as one-pot synthesis method).

The compound should be clearly differentiated from the protecting group having a straight chain structure described in JP-A-2010-275254 since it shows good solubility particularly in heptane as a representative solvent of non-polar solvents.

In addition, as compared to conventional liquid phase methods, since the compound permits stable dissolution and transfer into a nonpolar solvent irrespective of the degree of polymerization (sequence and chain length) of oligonucleotide, it is advantageous in that the isolation and purification step can be simplified as for the steps, and high purity and high yield can be ensured as a total view.

While the lower limit of the solubility (=solute/(solvent+solute)×100) (mass %) of a nucleoside protected by a branched chain-containing aromatic group wherein m is 0 in heptane at 20° C. is not particularly limited as long as the binding to a reaction substrate and the reaction thereafter proceed, it is preferably 1 mass %, more preferably 2 mass %, further preferably 5 mass %, still more preferably 10 mass %, especially preferably 25 mass %, particularly preferably 50 mass %.

The upper limit of the solubility (=solute/(solvent+solute)×100) (mass %) of a nucleoside protected by a branched chain-containing aromatic group wherein m is 0 in heptane at 20° C. is preferably 80 mass %, more preferably 85 mass %, further preferably 90 mass %, still more preferably 95 mass %, particularly preferably 98 mass %, since the reaction can proceed stably irrespective of the industrial progress degree of the reaction.

In the present specification, the "solubility" means the percentage (mass %) of the mass of solute relative to the total mass of the solvent and the solute when the solute is saturated in the solvent.

The formula (II):

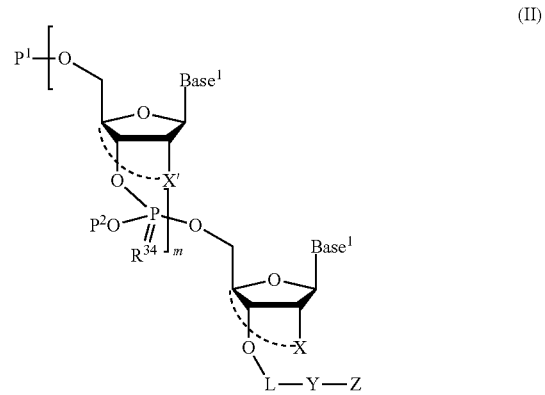

wherein m is an integer of 0 or more;

$Base^1$ in the number of m+1 are each independently an optionally protected nucleic acid base;

$P^1$ is a hydrogen atom, or a temporary protecting group removable under acidic conditions;

X is a hydrogen atom, an optionally protected hydroxyl group, a halogen atom or an organic group crosslinked with the 4-position carbon atom;

X' in the number of m are each independently a hydrogen atom, an optionally protected hydroxyl group, a halogen atom or an organic group crosslinked with the 4-position carbon atom;

$P^2$ in the number of m are each independently a protecting group removable under basic conditions;

$R^{34}$ in the number of m are each independently an oxygen atom or a sulfur atom; and L, Y and Z are as defined above.

In compound (II) of the present invention, p-mer oligonucleotide wherein the 3'-hydroxyl group is phosphoramidited and the 5'-hydroxyl group is protected by a temporary protecting group is bonded via oxygen atom of 5'-hydroxyl group to form m+1+p-mer oligonucleotide.

The compound (II) wherein m is 0 of the present invention is a starting compound of 3'-terminal in the oligonucleotide synthesis. In addition, the compound of the present invention also encompasses a compound wherein 5'-hydroxyl group is not protected ($P^1$ is a hydrogen atom) in a wide sense.

The definition, preferable embodiments and the like of $P^1$, $P^2$, X, X' and $R^{34}$ are similar to those of the above-mentioned compound (I).

The definition, preferable embodiments and the like of m are similar to those of the above-mentioned compound (i) and (ii).

The preferable embodiments of L, Y and Z in the formula (II) are similar to those of L, Y and Z in the aforementioned formula (III') or (III).

The "optionally protected nucleic acid base" represented by $Base^1$ is similar to that in the aforementioned formulas (i) and (ii).

Since the oligonucleotide protected by a branched chain-containing aromatic group, which is represented by the formula (II), is conferred with sufficient liposolubility by a branched chain-containing aromatic protecting group, it is not necessary; however, $Base^1$ is optionally protected by a group having a $C_{5-30}$ straight chain or branched chain alkyl group and/or a $C_{5-30}$ straight chain or branched chain alkenyl group, preferably a group having a $C_{5-30}$ branched chain alkyl group and/or a $C_{5-30}$ branched chain alkenyl group to further improve the liposolubility.

Preferable examples of the "group having a $C_{5-30}$ straight chain or branched chain alkyl group and/or a $C_{5-30}$ straight chain or branched chain alkenyl group" and the "group having a $C_{5-30}$ branched chain alkyl group and/or a $C_{5-30}$ branched chain alkenyl group" are as mentioned above.

A preferable embodiment of the compound represented by the formula (II) of the present invention is a compound of the formula (IIa), wherein m is 0;

$Base^1$ is a cytosyl group, a uracil group, a thyminyl group, an adenyl group, or a guanyl group, each of which is optionally protected;

$P^1$ is a di ($C_{1-6}$ alkoxy)trityl group, or a mono ($C_{1-6}$ alkoxy) trityl group;

X is a hydrogen atom, an optionally protected hydroxyl group, fluorine atom, —ORi (Ri is as defined above), —O—$NR^{37}$—Rj (Rj and $R^{37}$ are as defined above), or —O—Rk-C—Rl (Rk and Rl are as defined above); and L-Y—Z is the combination of each group shown as a preferable embodiment in the aforementioned formula (III') or the formula (III).

Another preferable embodiment of the compound represented by the formula (II) of the present invention is a compound of the formula (IIb), wherein m is 0;

$Base^1$ is a cytosyl group, a uracil group, a thyminyl group, an adenyl group, or a guanyl group, each of which is optionally protected;

$P^1$ is a dimethoxytrityl group or a monomethoxytrityl group;

X is a hydrogen atom, an optionally protected hydroxyl group, fluorine atom, —O—$CH_2$—, —O—$CH_2$—$CH_2$—, or —O—$NR^{37}$—$CH_2$— ($R^{37}$ is as defined above), —O—$CH_2$—O—$CH_2$— (in all of which the left side binds to the 2-position and the right side binds to the 4-position); and L-Y—Z is the combination of each group shown as a preferable embodiment in the aforementioned formula (III') or the formula (III).

A still another preferable embodiment of the compound represented by the formula (II) of the present invention is a compound of the formula (IIc), wherein m is 0;

$Base^1$ is a cytosyl group, a uracil group, a thyminyl group, an adenyl group, or a guanyl group, each of which is optionally protected;

$P^1$ is a dimethoxytrityl group;

X is a hydrogen atom, methoxy group, tert-butyldimethylsilyloxy group, fluorine atom, —O—$CH_2$—, —O—$CH_2$—$CH_2$—, —O—NH—$CH_2$—, —O—NMe-$CH_2$—, —O—$CH_2$—O—$CH_2$— (in all of which the left side binds to the 2-position and the right side binds to the 4-position); and L-Y—Z is the combination of each group shown as a preferable embodiment in the aforementioned formula (III') or the formula (III).

4-5. Production Method of Oligonucleotide Protected by Branched Chain-Containing Aromatic Group While the production method of a nucleoside protected by a branched chain-containing aromatic group represented by the formula (II'), which is an oligonucleotide protected by a branched chain-containing aromatic group represented by the formula (II) wherein m is 0, is not particularly limited, it can be produced by a method known per se (Richard T. Pon et al., Nucleic Acids Research 2004, 32, 623-631) or a method analogous thereto.

When a starting compound has a substituent (e.g., hydroxyl group, amino group, carboxy group) that influences the reaction, the starting compound is generally protected in advance by a suitable protecting group according to a known method and then subjected to the reaction. Such protecting group can be removed after the reaction by a known method such as an acid treatment, an alkali treatment, a catalytic reduction and the like.

A general production method of a nucleoside protected by a branched chain-containing aromatic group of the above-mentioned formula (II') wherein L is a succinyl group is shown below.

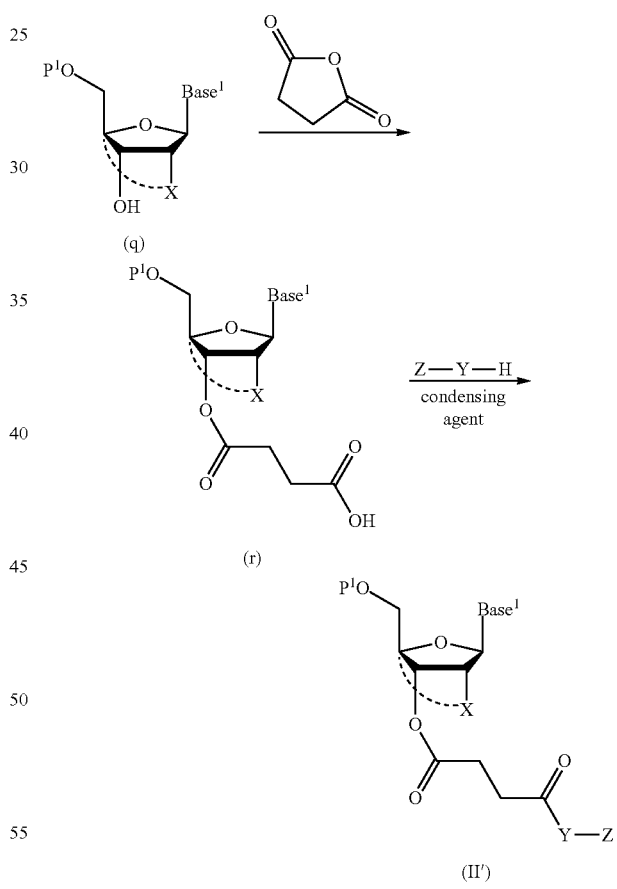

wherein each symbol is as defined above.

Nucleoside (q) wherein 5'-hydroxyl group is protected by protecting group $P^1$ is reacted with succinic anhydride in the presence of a base to give compound (r) wherein succinic acid is introduced into 3'-hydroxyl group. A nucleoside protected by a branched chain-containing aromatic group represented by the formula (II') can be obtained by dehydration condensation of compound (r) with Z—Y—H in the presence of a condensing agent.

The conversion step of the above-mentioned nucleoside (q) to compound (r) is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, aliphatic hydrocarbon solvents such as pentane, hexane, heptane, octane and the like, ether solvents such as diethyl ether, tetrahydrofuran, cyclopentyl methyl ether and the like, and mixed solvents thereof are preferable. Of these, dichloromethane and chloroform are particularly preferable.

While the base is not particularly limited, for example, an organic base mentioned below can be used, with preference given to triethylamine.

The above-mentioned dehydrating condensation step is advantageously performed in a solvent inert to the reaction. While such solvent is not particularly limited as long as the reaction proceeds, halogenated hydrocarbon solvents such as dichloromethane, 1,2-dichloroethane, chloroform, carbon tetrachloride and the like, aromatic hydrocarbon solvents such as benzene, toluene, xylene and the like, or aliphatic hydrocarbon solvents such as pentane, hexane, heptane, octane and the like, and mixed solvents thereof are preferable. Of these, dichloromethane and chloroform are particularly preferable.

Examples of the condensing agent used for the condensation reaction of compound (r) with Z—Y—H include dicyclohexylcarbodiimide (DCC), diisopropylcarbodiimide (DIC), N-ethyl-N'-3-dimethylaminopropylcarbodiimide and hydrochloride thereof (EDC HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-benzotriazole-N,N,N',N'-tetramethyluronium hexafluorophosphate (HBTU) and the like. Of these, HBTU, HCTU, N-ethyl-N'-3-dimethylaminopropylcarbodiimide and hydrochloride thereof (EDC HCl) are preferable.

The amount of the condensing agent to be used is 1 to 10 mol, preferably 1 to 5 mol, per 1 mol of compound (r). The amount of Z—Y—H to be used is 1 to 10 mol, preferably 1 to 5 mol, per 1 mol of compound (r). While the reaction temperature is not particularly limited as long as the reaction proceeds, it is preferably −10° C. to 50° C., more preferably 0° C. to 30° C. The reaction time is 30 min to 70 hr.

A compound of the above-mentioned formula (II') wherein 1 is other than a succinyl group can also be produced by performing a reaction similar to the above-mentioned production method except that a corresponding acid anhydride, a corresponding dicarboxylic halide, an activated ester of corresponding dicarboxylic acid and the like is used instead of succinic anhydride.

A compound of the above-mentioned formula (II) wherein m is one or more can be produced by repeating the 5'-terminal elongation process according to the following production method of the present invention and using a compound represented by the formula (II') as starting material.

4-6. Production Method of Z—Y—H (Alcohol or Amine)

While the production method of an alcohol compound or an amine compound represented by the formula: Z—Y—H, which is a starting compound used for the production of an oligonucleotide protected by a branched chain-containing aromatic group, is not particularly limited, for example, it can be produced by the following steps.

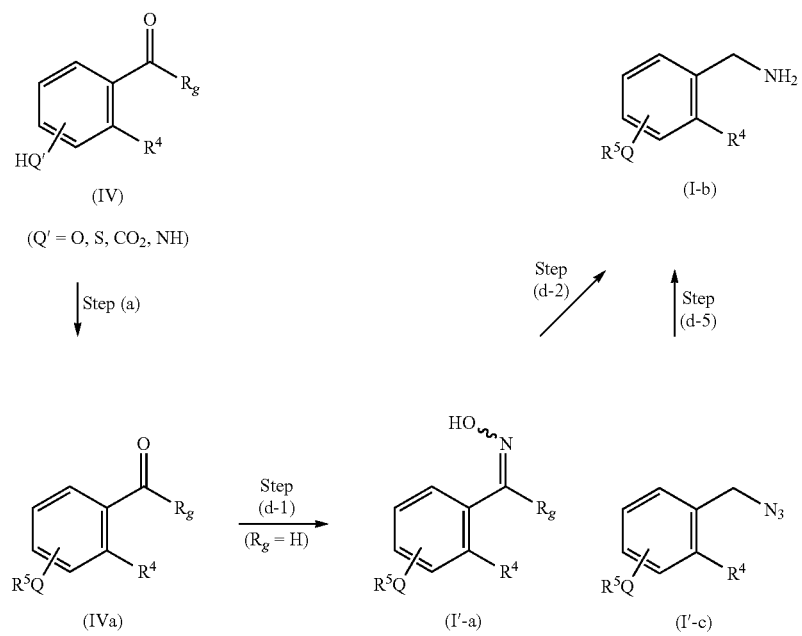

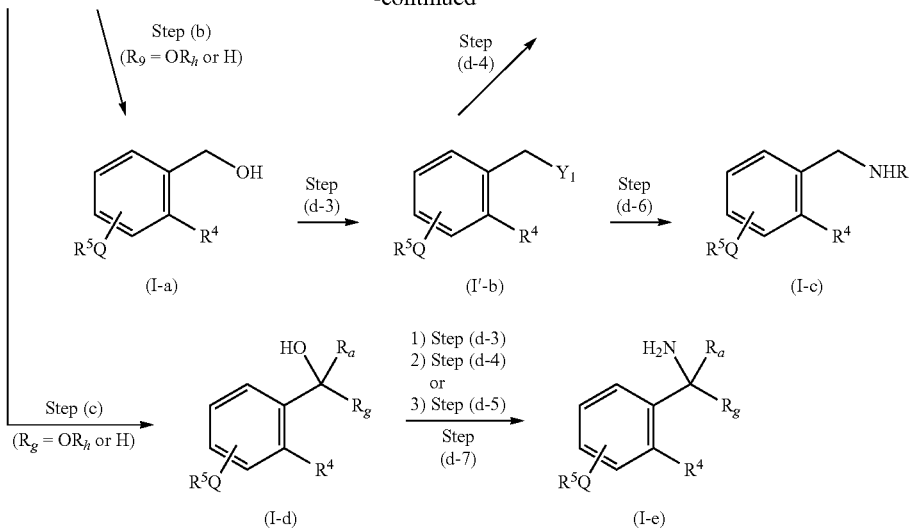

wherein Q' is —O—, —S—, —C(=O)O— or —NH—, $R_g$ is a hydrogen atom, an $OR_h$ group (wherein $R_h$ is an alkyl group such as a $C_{1-6}$ alkyl group and the like, an aralkyl group such as benzyl group and the like, and the like) or a group represented by the formula (a3):

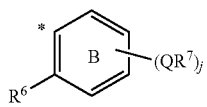

wherein each symbol is as defined above, $Y_1$ is a leaving group such as a halogen atom and the like, and other symbol is as defined above.

Step (a)

In this step, an $R^5$ group is introduced into a Q'H group wherein Q' is —O—, —S—, —C(=O)O— or —NH— of a compound represented by the formula (IV) (hereinafter to be abbreviated as compound (IV)) to give a compound represented by the formula (IVa) (hereinafter to be abbreviated as compound (IVa)).

When Q' is —O—, —S— or —NH—, the reaction is carried out in a solvent that does not influence the reaction, in the presence or absence of a base and using a halide corresponding to an $R^5$ group (chloride, bromide or iodide), a carboxylic acid or an acid halide corresponding to an $R^5$ group or alkylsulfonyloxylation product (e.g., methanesulfonyloxylation product etc.) or an arylsulfonyloxylation product (e.g., p-toluenesulfonyloxylation product etc.) corresponding to an $R^5$ group. In addition, when Q' is —O—, the reaction can be carried out under the conditions of Mitsunobu reaction including reacting compound (IV) with hydroxide corresponding to an $R^5$ group in the presence of triphenylphosphine and diisopropyl azodicarboxylate. Furthermore, when Q' is —C(=O)O—, for example, compound (IVa) can be synthesized by reacting compound (IV) with amine or hydroxide corresponding to an $R^5$ group in the presence of the below-mentioned condensing agent.

Examples of the base include alkali metal salt such as sodium carbonate, sodium hydrogen carbonate, potassium carbonate, sodium hydride, potassium hydride, potassium tert-butoxide and the like; amines such as pyridine, triethylamine, N,N-dimethylaniline, 1,8-diazabicyclo[5.4.0]undec-7-ene etc., and the like. Of these, sodium carbonate, potassium carbonate, sodium hydride and the like are preferable.

Examples of the solvent include aromatic hydrocarbons such as toluene, xylene and the like; ethers such as tetrahydrofuran, dioxane and the like; amides such as dimethylformamide, dimethylacetamide and the like; halogenated hydrocarbons such as chloroform, dichloromethane and the like; nitriles such as acetonitrile and the like, N-methylpyrrolidone, and a mixture thereof. Of these, dimethylformamide, tetrahydrofuran, toluene, N-methylpyrrolidone and the like are preferable.

The reaction temperature is preferably 50° C. to 150° C., more preferably 60° C. to 130° C. The reaction time is preferably 2 to 30 hr, more preferably 3 to 10 hr.

Step (b)

In this step, compound (IVa) is reduced to give a compound represented by the formula (I-a) (hereinafter to be abbreviated as compound (I-a)). The reduction reaction can be performed by a method using a reducing agent.

Examples of the reducing agent to be used for the reduction reaction include metal hydride (sodium borohydride, lithium borohydride, sodium cyanoborohydride, sodium triacetoxyborohydride, dibutylaluminum hydride, aluminum hydride, lithium aluminum hydride, etc.) and the like. Of these, sodium borohydride, dibutylaluminum hydride and the like are preferable.

The reaction is performed in a solvent that does not influence the reaction. Examples of the solvent include alcohols such as methanol, ethanol and the like; ethers such as diethyl ether, tetrahydrofuran, dioxane and the like; aromatic hydrocarbons such as toluene, xylene and the like; and a mixture thereof. Of these, tetrahydrofuran, toluene and the like are preferable.

The reaction temperature is preferably 0° C. to 100° C., more preferably 30° C. to 70° C., and the reaction time is preferably 1 to 24 hr, more preferably 2 to 5 hr.

Step (c)

In this step, compound (IVa) (in the formula (IVa), $R_g$ is not a hydrogen atom or an $OR_h$ group) is reduced in the same manner as in the above-mentioned step (b).

Step (d-1)

In this step, compound (IVa) (in the formula (IVa), Rg is a hydrogen atom) is oximated to give a compound represented by the formula (I'-a) (hereinafter to be abbreviated as compound (I'-a)).

The oximation reaction includes reacting compound (IVa) with hydroxylamine acid addition salt in a solvent that does not influence the reaction in the presence of a base.

Examples of the hydroxylamine acid addition salt include mineral acid salts such as hydrochloride, sulfate, nitrate and the like, organic acid salts such as acetate, trifluoroacetate, methanesulfonate, trifluoromethanesulfonate, p-toluenesulfonate etc., and the like, and hydrochloride is particularly preferable.

Examples of such base include alkali metal salts such as potassium hydroxide, sodium hydroxide, sodium hydrogen carbonate, potassium carbonate and the like; organic amines such as pyridine, triethylamine, diisopropylethylamine, N,N-dimethylaniline, 1,8-diazabicyclo[5.4.0]undec-7-ene etc., and the like. Of these, triethylamine, diisopropylethylamine and the like are preferable.

Examples of the solvent include halogen solvents such as chloroform, dichloromethane and the like; aromatic hydrocarbons such as toluene, xylene and the like; ethers such as tetrahydrofuran, dioxane and the like; and/or a mixture thereof. Of these, dichloromethane, chloroform, toluene and the like are preferable.

The reaction temperature is preferably 10° C. to 100° C., more preferably 20° C. to 60° C., and the reaction time is preferably 0.5 to 30 hr, more preferably 2 to 20 hr.

Step (d-2)

In this step, compound (I'-a) is reduced by a catalytic hydrogenation reaction in the presence of a metal catalyst such as palladium-carbon, Raney-nickel and the like, or by a reducing agent such as metal hydride and the like, which is similar to those in the aforementioned step (b), to give a compound represented by the formula (I-b) (hereinafter to be abbreviated as compound (I-b)), which is the compound of the present invention.

Compound (I-b) can also be produced from step (d-3) via step (d-4) and step (d-5).

Step (d-3)

In this step, compound (I-a) is halogenated with, for example, a chlorinating agent such as acetyl chloride, thionyl chloride and the like or, for example, a brominating agent such as acetyl bromide, phosphorus tribromide, diphenylphosphine/bromine and the like to give a compound represented by the formula (I'-b) (hereinafter to be abbreviated as compound (I'-b)).

Examples of the solvent include halogenated hydrocarbons such as chloroform, dichloromethane, and the like; aromatic hydrocarbons such as toluene, xylene, and the like; ethers such as tetrahydrofuran, dioxane, and the like; and a mixture thereof. Of these, chloroform, tetrahydrofuran, toluene, and the like are preferable.

The reaction temperature is preferably 10° C. to 150° C., more preferably 30° C. to 80° C., and the reaction time is preferably 0.5 to 30 hr, more preferably 2 to 20 hr.

Step (d-4)

In this step, compound (I'-b) is azidated with an azidating agent such as sodium azide and the like to give a compound represented by the formula (I'-c) (hereinafter to be abbreviated as compound (I'-c)).

The reaction includes reacting compound (I'-b) with an azidating agent in a solvent that does not influence the reaction.

Examples of the solvent include halogenated hydrocarbons such as chloroform, dichloromethane, and the like; aromatic hydrocarbons such as toluene, xylene, and the like; ethers such as tetrahydrofuran, dioxane, and the like; amides such as N,N-dimethylformamide and the like; and a mixture thereof. Of these, chloroform, N,N-dimethylformamide, and the like are preferable.

The reaction temperature is preferably 10° C. to 150° C., more preferably 20° C. to 100° C., and the reaction time is preferably 0.5 to 30 hr, more preferably 2 to 20 hr.

Step (d-5)

In this step, compound (I'-c) is aminated to give compound (I-b).

The reaction is carried out by reacting compound (I'-c) with triphenylphosphine in a solvent that does not influence the reaction in the presence of water or catalytic hydrogenation.

The amount of triphenylphosphine to be used is preferably 1 to 10 mol, particularly preferably 1 to 5 mol, per 1 mol of compound (I'-c).

The amount of water to be used is preferably 1 to 10 mol, particularly preferably 1 to 5 mol, per 1 mol of compound (I'-c).

Examples of the solvent include aromatic hydrocarbons such as toluene, xylene, and the like; ethers such as tetrahydrofuran, dioxane, and the like; and a mixture thereof. Of these, toluene, tetrahydrofuran, and the like are preferable.

The reaction temperature is preferably 10° C. to 150° C., more preferably 20° C. to 100° C., and the reaction time is preferably 0.5 to 30 hr, more preferably 2 to 20 hr.

Step (d-6)

In this step, compound (I'-b) is reacted with $RNH_2$ (wherein R is as defined above) to give a compound represented by the formula (I-c) (hereinafter to be abbreviated as compound (I-c)), which is the compound of the present invention wherein Y is an —NHR group.

The reaction includes reacting compound (I'-b) with amine represented by R—$NH_2$ in a solvent that does not influence the reaction in the presence of, where necessary, for example, a base such as tertiary amine (triethylamine, diisopropylethylamine etc.) and the like.

Examples of the solvent include aromatic hydrocarbons such as toluene, xylene, and the like; ethers such as tetrahydrofuran, dioxane, and the like; and, halogen solvents such as chloroform, dichloromethane, and the like and a mixture thereof. Of these, toluene, tetrahydrofuran, chloroform, and the like are preferable.

The reaction temperature is generally 10° C. to 100° C., preferably 20° C. to 60° C., and the reaction time is generally 0.5 to 30 hr, preferably 2 to 20 hr.

Step (d-7)

In this step, compound (I-d) is reacted with a compound having a —$CONH_2$ group or a —$OCONH_2$ group, and treated with a base to give compound (I-e).

The reaction of compound (I-d) with a compound having a —$CONH_2$ group or a —$OCONH_2$ group is carried out in a solvent that does not influence the reaction and under an acid catalyst.

Examples of the acid catalyst include methanesulfonic acid, trifluoromethanesulfonic acid, toluenesulfonic acid and the like. Of these, methanesulfonic acid and toluenesulfonic acid are preferable.

The amount of the acid catalyst to be used is preferably 0.05 to 0.5 mol, particularly preferably 0.1 to 0.3 mol, per 1 mol of compound (I-d).

Examples of the compound having a —$CONH_2$ group or a —$OCONH_2$ group include Fmoc-$NH_2$, $HCONH_2$, CF$_3$CONH$_2$, AcNH$_2$, EtOCONH$_2$, Cbz-NH$_2$ and the like. Of these, Fmoc-NH$_2$, EtOCONH$_2$ and the like are preferable.

Here, the "Fmoc-" means a 9-fluorenylmethoxycarbonyl group (hereinafter to be also referred to as a Fmoc group), and "Cbz-" means a benzyloxycarbonyl group (hereinafter to be also referred to as a Cbz group).

The R$^5$ forming-reagent to be used as a starting compound of step (a) [i.e., hydroxide, halide, an alkylsulfonyloxylation product (e.g., methanesulfonyloxylation product etc.) or an arylsulfonyloxylation product (e.g., p-toluenesulfonyloxylation product etc.) corresponding to R$^5$ group] may be a commercially available product. In addition, the R$^5$ forming-reagent can be produced by, for example,
(1) halogenation, alkylsulfonyloxylation or arylsulfonyloxylation of hydroxide corresponding to an R$^5$ group, or
(2) reduction reaction of unsaturated hydroxide corresponding to an R$^5$ group (e.g., catalytic hydrogenation reaction in the presence of a metal catalyst such as platinum-carbon (Pt/C), palladium-carbon (Pd/C), rhodium-carbon (Rh/C), Raney-nickel etc. and the like), and subsequently halogenation, alkylsulfonyloxylation or arylsulfonyloxylation.

In the production of the R$^5$ forming-reagent, examples of the reagent to be used for conversion to a leaving group from a hydroxyl group include, in addition to halogenating agent such as chlorinating agent (thionyl chloride, N-chlorosuccinimide (NCS) and the like), brominating agent (hydrobromic acid, acetyl bromide, N-bromosuccinimide (NBS), phosphorus tribromide, diphenylphosphine/bromine and the like) and the like, alkylsulfonylating agent such as methanesulfonyl chloride, trifluoromethanesulfonyl chloride and the like, arylsulfonylating agent such as benzenesulfonyl chloride, p-toluenesulfonyl chloride etc. and the like. Of these, thionyl chloride, hydrobromic acid and the like are preferable, which are the halogenating agents.

The reaction is performed in a solvent that does not influence the reaction. Examples of the solvent include water, halogenated hydrocarbons such as chloroform, dichloromethane and the like; aromatic hydrocarbons such as benzene, toluene, xylene and the like; nitriles such as acetonitrile, propionitrile and the like; ethers such as tetrahydrofuran, 1,4-dioxane, diethyl ether and the like. Of these, water, halogenated hydrocarbons such as chloroform and the like are preferable.

The reaction temperature is preferably 10 to 120° C., more preferably 50 to 100° C., and the reaction time is preferably 1 to 72 hr, more preferably 3 to 24 hr.

The compound represented by Z—Y—H wherein the aforementioned Q is a single bond can be also produced by, for example, the following method. That is, introduction of an R$^5$ group onto a benzene ring can be carried out by
(1) Friedel-Crafts reaction using halide corresponding to an R$^5$ group (chloride, bromide, or iodide), carboxylic acid or acid halide corresponding to an R$^5$ group,
(2) a method comprising subjecting a compound corresponding to the above-mentioned compound (II) (a compound wherein a Q'H group is substituted by a —CHO group) to carbon homologation by a Wittig reaction and, followed by catalytic hydrogenation and the like, or
(3) conventional organic synthesis reaction such as cross coupling using a metal catalyst and the like.

In each scheme above, the carbon number of an organic group for R$^5$, the kind of halogen atom, reaction reagents and the like are shown for the sake of convenience, and can be appropriately changed within the scope of the above-mentioned definitions.

4-7. Explanation of "Oligonucleotide Comprising a Protected Base Wherein the 3'-hydroxyl Group is Phosphoramidited, the 5'-hydroxyl Group is Protected by a Temporary Protecting Group Removable Under Acidic Conditions, and the Nucleic Acid Base is Protected by a Group Having a C$_{5-30}$ Straight Chain or Branched Chain Alkyl Group and/or a C$_{5-30}$ Straight Chain or Branched Chain Alkenyl Group"

The "p-mer oligonucleotide comprising a protected base (p is an integer of one or more) wherein the 3'-hydroxyl group is phosphoramidited, the 5'-hydroxyl group is protected by a temporary protecting group removable under acidic conditions, and the nucleic acid base is protected by a group having a C$_{5-30}$ straight chain or branched chain alkyl group and/or a C$_{5-30}$ straight chain or branched chain alkenyl group" used in step (2) is not particularly limited as long as it satisfies the structure requirements.

"3'-hydroxyl group is phosphoramidited" means that the oligonucleotide 3'-hydroxyl group is modified by, for example, a phosphoramiditing group represented by —P(OP$^2$)(NR$_e$R$_f$) wherein each symbol is as defined above.

The definitions, examples and preferable embodiments of P$^2$, R$_e$ and R$_f$ are as explained for the above-mentioned formula (I).

The definitions, examples and preferable embodiments of the "temporary protecting group removable under acidic conditions" are as explained for the above-mentioned formula (I).

The definitions, examples and preferable embodiments of the "group having a C$_{5-30}$ straight chain or branched chain alkyl group and/or a C$_{5-30}$ straight chain or branched chain alkenyl group" are as explained for the above-mentioned formula (I).

As the p-mer oligonucleotide comprising a protected base used in step (2), an oligonucleotide comprising a protected base represented by the above-mentioned formula (I) is preferable.

4-8. Explanation of Steps (1)-(5)

While steps (1)-(5) are explained below by reference to the formulas (i), (ii), (iii) and the like for convenience, they are not limited thereby.

Step (1) (Deprotection Step)

In this step, before condensation step (2), in a non-polar solvent, temporary protecting group P$^1$ (P$^1$ is a temporary protecting group removable under acidic conditions) of the 5'-terminal hydroxyl group of an n-mer oligonucleotide (i) wherein the 3'-hydroxyl group is protected, and the 5'-hydroxyl group is protected by a temporary protecting group removable under acidic conditions is removed by reaction with an acid (deprotection step).

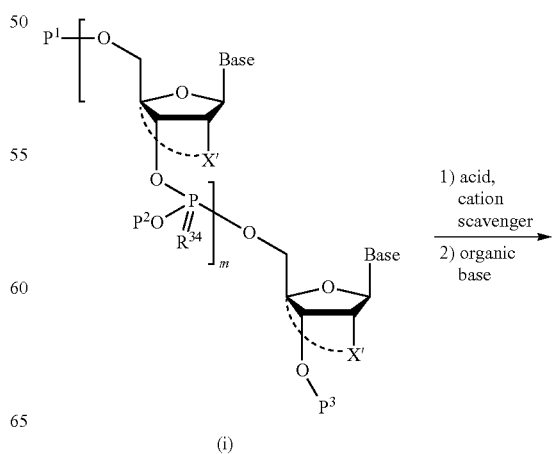

(i)

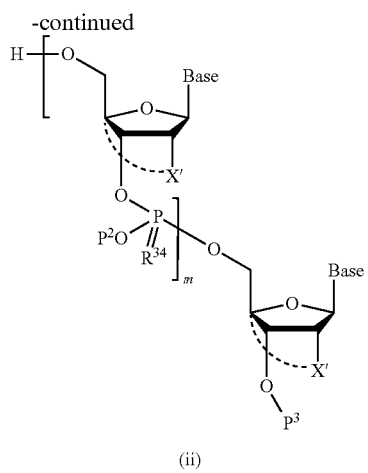

(ii)

wherein each symbol is as defined above.

This step is performed in a solvent that does not influence the reaction. Since a higher solubility of the solvent is expected to afford superior reactivity, a non-polar solvent showing high solubility of the n-mer oligonucleotide of the present invention is preferably selected. Specifically, examples thereof include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Two or more kinds of these solvents may be used in a mixture in an appropriate ratio. In addition, the above-mentioned non-polar solvent may be mixed with a polar solvent at an appropriate ratio, such as nitrile solvents such as acetonitrile, propionitrile and the like, amide solvents such as N,N-dimethylformamide, N,N-dimethylacetamide, N-methylpiperidone and the like, as long as n-mer oligonucleotide is dissolved. Of these, aromatic solvents, aliphatic solvents, or a combination of these is preferable, benzene, toluene, hexane, pentane, heptane, nonane, cyclohexane or a combination of these is preferable, toluene, heptane, nonane or a combination of these is more preferable, and toluene and heptane or a combination of these is particularly preferable.

In this step, the concentration of n-mer oligonucleotide (i) in a solvent is not particularly limited as long as the oligonucleotide is dissolved, it is preferably 1 to 30 mass %.

To continuously perform the deprotection step, subsequent condensation step, and oxidation step in a solution, it is preferable to use a cation scavenger in this step during or after the removal reaction of a temporary protecting group $P^1$ of 5'-hydroxyl group in n-mer oligonucleotide (i).

While the cation scavenger is not particularly limited as long as re-protection (returning to starting material) with the removed protecting group $P^1$ and side reaction with the deprotected functional group do not proceed, pyrrole derivatives such as pyrrole, 2-methylpyrrole, 3-methylpyrrole, 2,3-dimethylpyrrole, 2,4-dimethylpyrrole and the like; and indole derivatives such as indole, 4-methylindole, 5-methylindole, 6-methylindole, 7-methylindole, 5,6-dimethylindole, 6,7-dimethylindole and the like can be used. Since a good cation trap effect can be obtained, pyrrole, 3-methylpyrrole, 2,4-dimethylpyrrole, indole, 4-methylindole, 5-methylindole, 6-methylindole, 7-methylindole, 5,6-dimethylindole and 6,7-dimethylindole are preferable, pyrrole, 3-methylpyrrole and indole are more preferable, pyrrole and indole are more preferable, and pyrrole is particularly preferable.

The amount of cation scavenger to be used in this step is 1 to 50 mol, preferably 5 to 20 mol, per 1 mol of n-mer oligonucleotide (i).

While the acid to be used in this step is not particularly limited as long as good deprotection can be achieved, trifluoroacetic acid, dichloroacetic acid, trifluoromethanesulfonic acid, trichloroacetic acid, methanesulfonic acid, hydrochloric acid, acetic acid, p-toluenesulfonic acid and the like are preferably used.

Since good reaction can be achieved, trifluoroacetic acid, dichloroacetic acid, trifluoromethanesulfonic acid and trichloroacetic acid are more preferable, trifluoroacetic acid, dichloroacetic acid and trifluoromethanesulfonic acid are more preferable, trifluoroacetic acid and dichloroacetic acid are still more preferable, and trifluoroacetic acid is particularly preferable. These acids may be diluted with the above-mentioned non-polar solvent. When the aforementioned acid is used, it may be combined with a particular base to appropriately adjust the acidity before use.

The amount of the acid to be used in this step is 1 to 100 mol, preferably 1 to 40 mol, per 1 mol of n-mer oligonucleotide (i).

While the reaction temperature in this step is not particularly limited as long as the reaction proceeds, it is preferably −10° C. to 50° C., more preferably 0° C. to 40° C. While the reaction time varies depending on the kind of n-mer oligonucleotide to be used, the kind of acid, the kind of solvent, the reaction temperature and the like, it is 5 min to 5 hr.

To continuously perform the deprotection step, subsequent condensation step, and oxidation step in a solution, it is preferable to remove the temporary protecting group of the 5'-hydroxy group in this step and neutralize the compound with an organic base.

The organic base to be used for neutralization is not particularly limited as long as it can neutralize the above-mentioned acids, and the obtained salt can function as a condensing agent. Since the reaction proceeds smoothly, pyridine, benzimidazole, 1,2,4-triazole, N-phenylimidazole, 2-amino-4,6-dimethylpyrimidine, 1,10-phenanthroline, imidazole, N-methylimidazole, 2-chlorobenzimidazole, 2-bromobenzimidazole, 2-methylimidazole, 2-phenylbenzimidazole, N-phenylbenzimidazole and 5-nitrobenzimidazole are preferable, pyridine, benzimidazole, 1,2,4-triazole, N-phenylimidazole, N-methylimidazole, 2-amino-4,6-dimethylpyrimidine and 1,10-phenanthroline are more preferable, pyridine, benzimidazole, 1,2,4-triazole and N-phenylimidazole are further preferable, pyridine, benzimidazole and 1,2,4-triazole are still more preferable, and pyridine is particularly preferable.

The amount of the organic base to be used in this step is 1 to 10 mol, preferably 1 to 3 mol, per 1 mol of acid.

A particularly preferable combination of an acid and an organic base in this step is that of trifluoroacetic acid and pyridine and/or N-methylimidazole.

Step (2) (Condensation Step)

In this step, an n-mer oligonucleotide (ii) wherein the 5'-hydroxyl group is not protected, and the 3'-hydroxyl group is protected is condensed with a p-mer oligonucleotide comprising a protected base (iii) wherein the 3'-hydroxyl group is phosphoramidited, the 5'-hydroxyl group is protected by a temporary protecting group removable under acidic conditions, and the nucleic acid base is protected by a group having a $C_{5-30}$ straight chain or branched chain alkyl group and/or a $C_{5-30}$ straight chain or branched chain alkenyl group.

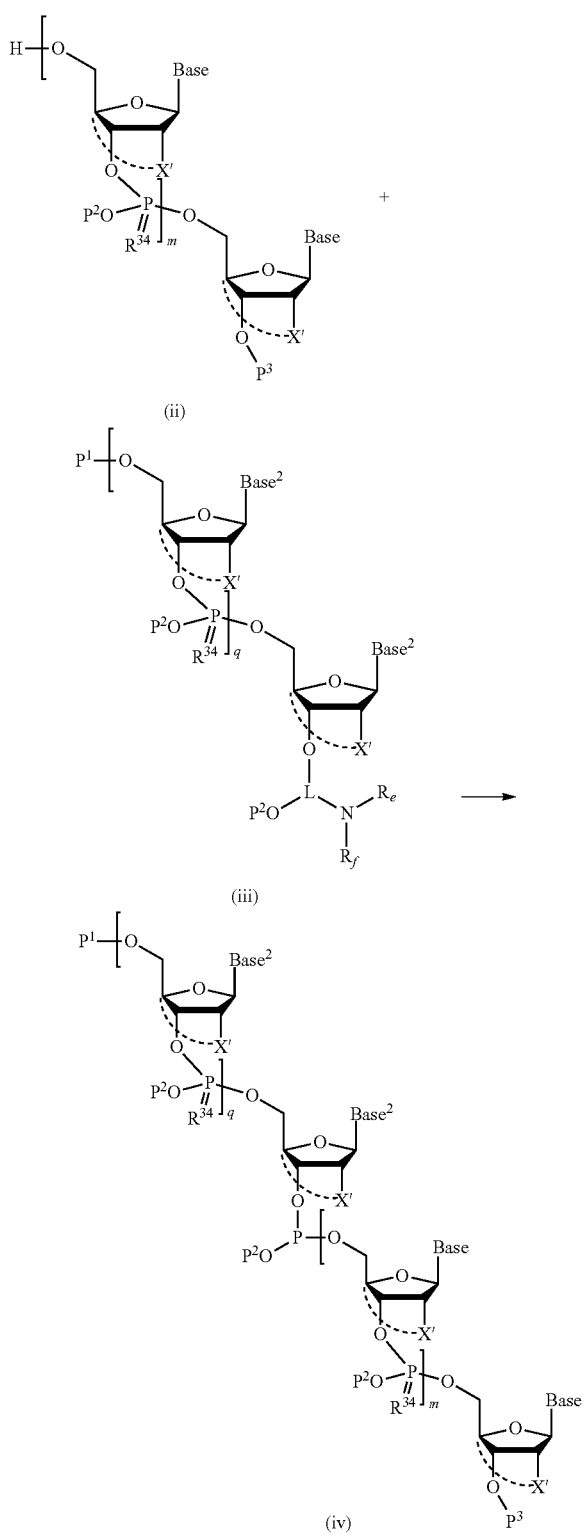

wherein X' means the same as X, and other symbols are as defined above.

In this step, the n-mer oligonucleotide (ii) is not particularly limited, and one obtained in the aforementioned step (1) can be preferably used. In this case, a p-mer oligonucleotide comprising a protected base (iii) only needs to to be added directly to the reaction mixture after step (1), without isolating the n-mer oligonucleotide (ii). In this condensation step, the salt (e.g., pyridine trifluoroacetate), which is formed by the acid added during deprotection step (1) and the organic base added during neutralization reaction, acts as a condensing agent. Therefore, steps (1) and (2) continuously performed in a solution provide advantages of not only omission of an isolation operation but also improved reaction efficiency.

The reaction efficiency can also be improved by adding a condensing agent (e.g., pyridine trifluoroacetate, tetrazole, 5-benzylthio-1H-tetrazole, 4,5-dicyanoimidazole etc.) in this condensation reaction.

In this step, moreover, when the acidity of the reaction mixture becomes high, a side reaction removing temporary protecting group $P^1$ may occur. Therefore, N-methylimidazole is preferably added to suppress acidification of the reaction mixture.

The amount of N-methylimidazole to be added to adjust the acidity is 0.1 to 1 mol, preferably 0.5 mol, per 1 mol of organic base used for neutralization.

As the p-mer oligonucleotide comprising a protected base (iii) used in this step, an oligonucleotide comprising a protected base represented by the above-mentioned formula (I) can be preferably used.

This step is performed in a solvent that does not influence the reaction. Specifically, a non-polar solvent similar to the one used in the aforementioned step (1) can be mentioned. For efficient activation of a phosphoramidite group of the p-mer oligonucleotide comprising a protected base (iii), a mixture of the above-mentioned non-polar solvent and a polar solvent, for example, nitrile solvents such as acetonitrile, propionitrile and the like; ketone solvents such as acetone, 2-butanone and the like; N,N-dimethylformamide, N,N-dimethylacetamide, polar ether solvents such as 1,4-dioxane, tetrahydrofuran and the like, amide solvents such as N-methylpyrrolidone and the like; sulfoxide solvents such as dimethyl sulfoxide and the like, and the like at an appropriate ratio is preferably used as long as the n-mer oligonucleotide (ii) after removal of the temporary protecting group of the 5'-hydroxyl group can be dissolved.

In this case, as the polar solvent, amide solvent, nitrile solvent, and a combination thereof are preferable, acetonitrile, N,N-dimethylformamide, N-methylpiperidone, and a combination thereof are more preferable, and acetonitrile is particularly preferable.

The polar solvent may be added as a solution of a p-mer oligonucleotide comprising a protected base (iii), a condensing agent and the like.

The amount of a p-mer oligonucleotide comprising a protected base (iii) to be used is 1 to 10 mol, preferably 1 to 5 mol, per 1 mol of an n-mer oligonucleotide (ii).

While the reaction temperature is not particularly limited as long as the reaction proceeds, 0° C. to 100° C. is preferable, and 20° C. to 50° C. is more preferable. While the reaction time varies depending on the kind of n-mer oligonucleotide to be condensed, the reaction temperature and the like, it is 30 min to 24 hr.

Step (3) (Oxidation Step or Sulfurization Step)

The n+p-mer oligonucleotide (iv) obtained in step (2) is reacted with an oxidizing agent or sulfurizing agent to convert the phosphite triester bond in the n+p-mer oligonucleotide (iv) to a phosphate triester bond or a thiophosphate triester bond.

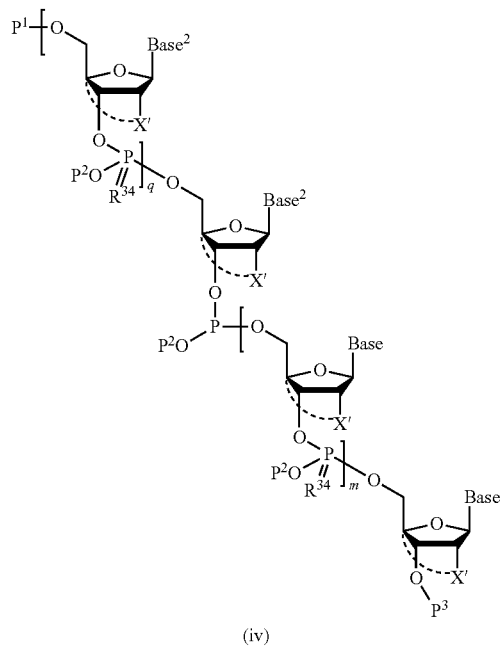

(iv)

oxidizing agent or sulfurizing agent →

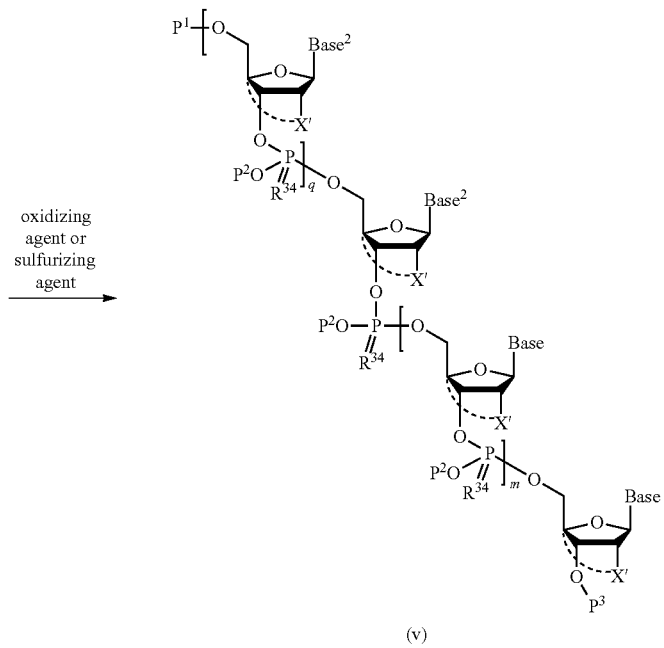

(v)

wherein the symbols are as defined above.

This step can be simply performed by directly adding an oxidizing agent or sulfurizing agent to the reaction mixture after step (2), without isolating the n+p-mer oligonucleotide (iv) obtained in step (2).

While the "oxidizing agent" to be used in this step is not particularly limited as long as it can oxidize a phosphite triester bond into a phosphate triester bond without oxidizing other moieties, iodine, (1S)-(+)-(10-camphorsulfonyl)oxaziridine, tert-butyl hydroperoxide (TBHP), 2-butanone peroxide, 1,1-dihydroperoxycyclododecane, bis(trimethylsilyl) peroxide, m-chloroperbenzoic acid or hydrogen peroxide is preferably used. Since good oxidation reaction can be achieved, iodine, (1S)-(+)-(10-camphorsulfonyl)oxaziridine, tert-butyl hydroperoxide, 2-butanone peroxide and 1,1-dihydroperoxycyclododecane are more preferable, iodine, (1S)-(+)-(10-camphorsulfonyl)oxaziridine, tert-butyl hydroperoxide and 2-butanone peroxide are more preferable, iodine and tert-butyl hydroperoxide are still more preferable, and iodine is particularly preferable. The oxidizing agent can be used after diluting with a suitable solvent to achieve a concentration of 0.05 to 2M. While the dilution solvent is not particularly limited as long as it is inert to the reaction, for example, pyridine, THF, dichloromethane, water, nonane and a mixed solvent of any of them can be mentioned. Of these, for example, iodine/water/pyridine-THF, iodine/pyridine-acetic acid, peroxide (TBHP)/dichloromethane, tert-butyl hydroperoxide/nonane or hydrogen peroxide/potassium iodide/phosphoric acid buffer are preferably used.

The "sulfurizing agent" to be used in this step is not particularly limited as long as it can convert a phosphite triester bond to a thiophosphate triester bond, 3-((N,N-dimethylaminomethylidene)amino)-3H-1,2,4-dithiazole-5-thione (DDTT), 3H-1,2-benzodithiol-3-one-1,1-dioxide (Beaucage reagent), 3H-1,2-benzodithiol-3-one, phenylacetyl disulfide (PADS), tetraethylthiuram disulfide (TETD), 3-amino-1,2,4-dithiazole-5-thione (ADTT) or sulfur is preferably used. Since a good reaction proceeds, 3-((N,N-dimethylaminomethylidene)amino)-3H-1,2,4-dithiazole-5-thione (DDTT), 3H-1,2-benzodithiol-3-one-1,1-dioxide (Beaucage reagent), 3H-1,2-benzodithiol-3-one and phenylacetyl disulfide (PADS) are more preferable, 3-((N,N-dimethylaminomethylidene)amino)-3H-1,2,4-dithiazole-5-thione and 3H-1,2-benzodithiol-3-one-1,1-dioxide are further preferable, and 3-((N,N-dimethylaminomethylidene)amino)-3H-1,2,4-dithiazole-5-thione is particularly preferable. The sulfurizing agent can be used after diluting with a suitable solvent to achieve a concentration of 0.05 to 2M. While the dilution solvent is not particularly limited as long as it is inert to the reaction, for example, dichloromethane, acetonitrile, pyridine and a mixed solvent of any of them can be mentioned.

The amount of the oxidizing agent or sulfurizing agent to be used is 1 to 50 mol, preferably 1 to 5 mol, per 1 mol of the n+p-mer oligonucleotide (iv) obtained in step (2).

While the reaction temperature is not particularly limited as long as the reaction proceeds, 0° C. to 100° C. is preferable, and 20° C. to 50° C. is more preferable. While the reaction time varies depending on the kind of n+p-mer oligonucleotide (iv), the kind of oxidizing agent or sulfurizing agent to be used, the reaction temperature and the like, it is 1 min to 3 hr.

Step (4) (Extraction Isolation Step)

This step is a method of isolating and purifying an n+p-mer oligonucleotide (v) from a reaction mixture containing n+p-mer oligonucleotide (v) having a phosphate triester bond or a thiophosphate triester bond, which is obtained from step (3), by an extraction operation alone.

While the extraction operation is not particularly limited, it is preferably performed by adding a polar solvent and/or a non-polar solvent as necessary to the reaction mixture obtained in step (3), partitioning the mixture between polar solvent-non-polar solvent, and transferring the n+p-mer oligonucleotide to the non-polar solvent. When the reaction is performed by mixing a non-polar solvent with a polar solvent in step (2), the reaction mixture is preferably partitioned by adding a non-polar solvent.

The extraction operation can remove impurities such as the remaining starting materials, reagents (e.g., acid, cation scavenger, organic base, p-mer oligonucleotide wherein 3'-hydroxyl group is phosphoramidited and the 5'-hydroxyl group is protected by a temporary protecting group removable under acidic conditions, oxidant and sulfurizing agent) and the like into a polar solvent.

Examples of the non-polar solvent to be added as necessary to transfer an n+p-mer oligonucleotide into a non-polar solvent in this step include halogenated solvents such as chloroform, dichloromethane, 1,2-dichloroethane and the like; aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like; non-polar ether solvents such as diethyl ether, cyclopentyl methyl ether, tert-butyl methyl ether and the like. Two or more kinds of these solvents may be used in a mixture in an appropriate ratio. Of these, aromatic solvents, aliphatic solvents, or a combination of these is preferable, benzene, toluene, hexane, pentane, heptane, nonane, cyclohexane or a combination of these is preferable, toluene, heptane, nonane or a combination of these is more preferable, toluene, heptane or a combination of these is further preferable, and heptane is particularly preferable.

Examples of the polar solvent to be added as necessary to transfer impurities in this step into a polar solvent include alcohol solvent methanol, ethanol, isopropanol and the like, nitrile solvents such as acetonitrile, propionitrile and the like, ketone solvents such as acetone, 2-butanone and the like, polar ether solvents such as 1,4-dioxane, tetrahydrofuran and the like, amide solvents such as N,N-dimethylformamide, N,N-dimethylacetamide, N-methylpiperidone and the like, sulfoxide solvents such as dimethyl sulfoxide and the like, water and the like, and a mixed solvent of two or more kinds of these. Of these, amide solvents, nitrile solvents, and a combination of these are preferable, acetonitrile, N,N-dimethylformamide, N-methylpiperidone, and a combination of these are more preferably used. The polar solvent in the present invention is particularly preferably acetonitrile from the practical aspects.

The impurity can be removed by removing polar solvents after partitioning between polar solvent-non-polar solvent.

Moreover, the impurity remaining in a small amount can be further removed by adding a polar solvent to a non-polar solvent after removal of the polar solvent, stirring the mixture and removing the polar solvent by partitioning (washing in the present invention).

While the number of washing with a polar solvent is not particularly limited, it may be repeated until the impurity in the non-polar solvent layer decreases to the extent the nucleotide elongation reaction in the next cycle is not inhibited by the analysis of the non-polar solvent by thin layer silica gel chromatography, high performance liquid chromatography and the like.

The polar solvent to be used for partitioning and washing may contain water to improve partitioning performance from the non-polar solvent.

In this case, the water content of the polar solvent is preferably 1-10% (v/v), more preferably 3-8% (v/v). When the water content is too low, the partitioning performance may be insufficient, and when the water content is too high, the solubility of the byproduct, the remaining starting material, reagent and the like to be removed in a polar solvent trends to decrease to degrade the removal efficiency.

The n+p-mer oligonucleotide (v) can be isolated by concentrating the non-polar solvent layer after washing with a polar solvent. In this case, nucleotide elongation can be repeated in one-pot by adding the solvent and reagent for the next cycle to a reaction vessel containing the concentrate.

Alternatively, it is also possible to apply, without concentration, the non-polar solvent layer after washing to the nucleotide elongation in the next cycle.

The production method of oligonucleotide of the present invention can afford the object long oligonucleotide with high purity and in a high yield by repeating the above-mentioned steps (1) to (4) a desired number of times.

Step (5) (Deprotection, Oligonucleotide Isolation Step)

In the production method of oligonucleotide of the present invention, deprotection is performed after step (4) according to the kind and properties of the protecting group, whereby oligonucleotide is isolated. All protecting groups can be removed from oligonucleotide according to the deprotection method described in Greene's PROTECTIVE GROUPS IN ORGANIC SYNTHESIS, 4th ed., JOHN WILLY&SONS (2006) and the like. To be specific, nucleotide 3'-hydroxyl-protecting group, as well as phenoxyacetyl group, acetyl group, a group having a $C_{5-30}$ straight chain or branched chain alkyl group and/or a $C_{5-30}$ straight chain or branched chain alkenyl group and the like, which are nucleic acid base-protecting groups, cyanoethyl group bonded to phosphate group and the like in the present invention can all be removed by treating with aqueous ammonia/ethanol solution, aqueous ammonia/aqueous methylamine solution, ethylenediamine and the like. In addition, nucleotide 5' hydroxyl-protecting group can be removed by a treatment with the acid used in step (1) or an appropriately diluted solution of such acid.

Since oligonucleotide without a protecting group is easily degraded by an enzyme, oligonucleotide is preferably isolated under appropriate air contamination control.

The progress of the reaction in each of the above-mentioned steps can be confirmed by a method similar to conventional liquid phase organic synthesis reaction. That is, the reaction can be traced by thin layer silica gel chromatography, high performance liquid chromatography and the like.

The oligonucleotide obtained by step (4) or step (5) can also be led to a desired oligonucleotide derivative by further applying an organic synthesis reaction.

5. Explanation of Steps (1')-(5')

Another embodiment of the production method of oligonucleotide of the present invention is a method including the following step (2').

(2') A step of producing an n'+p'-mer oligonucleotide by condensing a p'-mer oligonucleotide (p' is an integer of one or more) wherein the 3'-hydroxyl group is phosphoramidited, the 5'-hydroxyl group is protected by a temporary protecting group removable under acidic conditions, and the nucleic acid base is optionally protected, with an n'-mer oligonucleotide (n' is an integer of one or more) wherein the 5'-hydroxyl group is not protected, and the 3'-hydroxyl group is protected by a protecting group represented by the above-mentioned formula (III) to form a phosphite triester bond via the 5'-hydroxyl group thereof.

This method preferably further includes the following step (3'), wherein the phosphite triester bond of the n'+p'-mer oligonucleotide obtained in step (2') is converted to a phosphate triester bond or a thiophosphate triester bond: (3') a step of adding an oxidizing agent or a sulfurizing agent to the reaction mixture obtained in the condensation step (2') to convert the phosphite triester bond of the n'+p'-mer oligonucleotide obtained in the condensation step to a phosphate triester bond or a thiophosphate triester bond.

This method preferably further includes the following step (1') by which an n'-mer oligonucleotide used in step (2') wherein the 5'-hydroxyl group is not protected and the 3'-hydroxyl group is protected by a protecting group represented by the above-mentioned formula (III) is prepared.

(1') a step of removing a temporary protecting group removable under acidic conditions of the 5'-hydroxyl group by reacting, in a non-polar solvent prior to the condensation step (2'), the n'-mer oligonucleotide wherein the 3'-hydroxyl group is protected by the protecting group represented by the above-mentioned formula (III), and the 5'-hydroxyl group is protected by the temporary protecting group, with an acid.

Step (1') is preferably performed in the presence of at least one kind of cation scavenger selected from a pyrrole derivative and an indole derivative, and further includes a step of neutralization with an organic base after removal of the temporary protecting group of the 5'-hydroxyl group. As a result, steps (1'), (2') and (3') can be continuously performed in a liquid, and an oligonucleotide wherein nucleoside in the number of p' is elongated can be isolated and purified by an extraction operation alone.

Furthermore, by including the following step (4'), an n'+p'-mer oligonucleotide is purified by removing an excess starting material and by-product conveniently and effectively, without the need for complicated solidification-isolation, and can be led to the next step without taking out the resultant product from the reaction vessel:

(4') a step of isolating the n'+p'-mer oligonucleotide from the reaction mixture obtained in step (3') by an extraction operation alone.

When the amount of the by-product generated can be controlled by the management of equivalent of the starting materials and controlling the reaction, it is preferable to repeat step (1') to step (3') as a basic unit, which includes step (4').

Since the generation of by-product can be strictly managed and controlled and highly pure oligonucleotide can be obtained, it is preferable to repeat step (1') to step (4') as a basic unit.

By repeating such cycle in the liquid phase method, the final oligonucleotide can be produced in one-pot, without changing the reaction vessel.

In the production method of the present invention, oligonucleotide can be isolated and produced by further including step (5'):

(5') a step of removing all the protecting groups of the n'+p'-mer oligonucleotide obtained in step (4).

n' is an integer of one or more. While the upper limit of n is not particularly limited, it is generally 100 or less, preferably 75 or less, more preferably 50 or less, and more preferably 30 or less p' is an integer of one or more, preferably 1. While the upper limit of p is not particularly limited, it is preferably 50 or less, more preferably 30 or less, more preferably 20 or less, still more preferably 5 or less, and particularly preferably 3 or less.

The n'-mer oligonucleotide used in step (1') is, for example, an n'-mer oligonucleotide represented the following formula (i') wherein $P^1$ is a temporary protecting group removable under acidic conditions, the 3'-hydroxyl group is protected by a protecting group represented by the above-mentioned formula (III) and the 5'-hydroxyl group is protected by a temporary protecting group removable under acidic conditions, and the n'-mer oligonucleotide used in step (2') is, for example, an n'-mer oligonucleotide represented by the following formula (ii') wherein the 5'-hydroxyl group is not protected, and the 3'-hydroxyl group is protected by a protecting group represented by the above-mentioned formula (III).

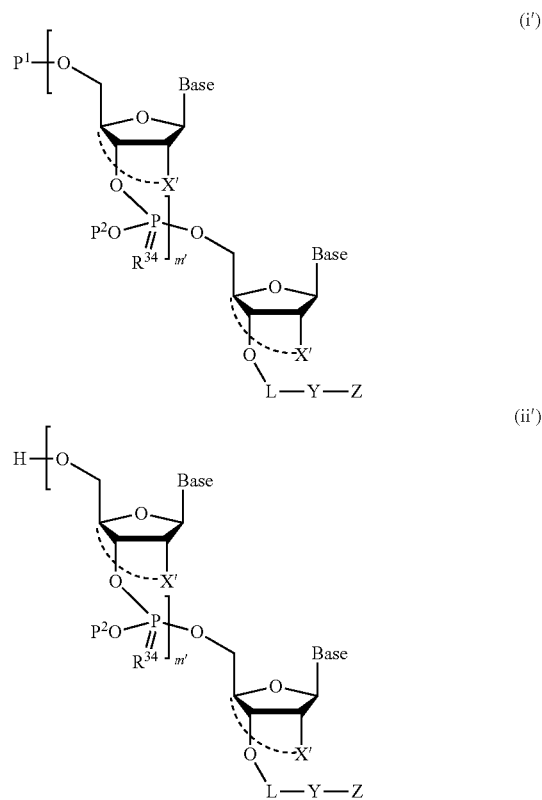

wherein m' is any integer of not less than 0, and each of other symbols is as defined above.

While the upper limit of m' is not particularly limited, it is generally 99 or less, preferably 74 or less, more preferably 49 or less, more preferably 29 or less.

The definition, example and preferable embodiment of each of other symbols are the same as those in the explanation on the formulas (i) and (ii).

The "a p'-mer oligonucleotide wherein the 3'-hydroxyl group is phosphoramidited, the 5'-hydroxyl group is protected by a temporary protecting group removable under acidic conditions, and the nucleic acid base is optionally protected" used in step (2') is not particularly limited as long as the structural requirements are satisfied.

The "3'-hydroxyl group is phosphoramidited" means that oligonucleotide 3'-hydroxyl group is modified by, for example, a phosphoramidite group represented by —P(OP$^2$)(NR$_e$R$_f$) wherein each symbol is as defined above.

The definitions, examples and preferable embodiments of P$^2$, R$_e$ and R$_f$ are as explained for the above-mentioned formula (I).

The definitions, examples and preferable embodiments of "temporary protecting group removable under acidic conditions" are as explained for the above-mentioned formula (I).

The protecting group of the "nucleic acid base is optionally protected" are the same as the protecting groups exemplified for the "optionally protected nucleic acid base" for Base in the above-mentioned formulas (i) and (ii).

The protecting group is preferably a group free of a $C_{5-30}$ straight chain or branched chain alkyl group and/or a $C_{5-30}$ straight chain or branched chain alkenyl group and, for example, pivaloyl group, pivaloyloxymethyl group, trifluoroacetyl group, phenoxyacetyl group, 4-isopropylphenoxyacetyl group, 4-tert-butylphenoxyacetyl group, acetyl group, benzoyl group, isobutyryl group, dimethylformamidinyl group, 9-fluorenylmethyloxycarbonyl group and the like are preferable. Of these, phenoxyacetyl group, 4-isopropylphenoxyacetyl group, acetyl group, benzoyl group, isobutyryl group, and dimethylformamidinyl group are more preferable.

Examples of the p'-mer oligonucleotide having optionally protected nucleic acid base wherein the 3'-hydroxyl group is phosphoramidited, and the 5'-hydroxyl group is protected by a temporary protecting group removable under acidic conditions include the following formula (iii').

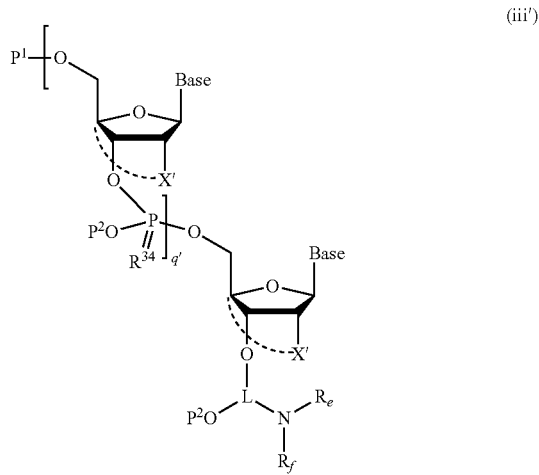

wherein
Base is optionally substituted nucleic acid base, q' is any integer of not less than 0, and other symbol is as defined above.

"optionally substituted nucleic acid base" for Base is as defined for the "optionally protected nucleic acid base" for Base in the formulas (i) and (ii).

q' is any integer of 0 or more, preferably 0. While the upper limit of q' is not particularly limited, it is preferably 49 or less, more preferably 29 or less, more preferably 19 or less, still more preferably 4 or less, still more preferably 2 or less, and particularly preferably 1.

Steps (1')-(5') can be performed under similar conditions as in the above-mentioned steps (1)-(5) by reading the formulas (i), (ii) and (iii) as the formulas (i'), (ii') and (iii'), respectively.

6. Use of Oligonucleotide

The oligonucleotide produced by the present invention can be used for various applications such as various veterinary pharmaceutical products (RNA, DNA, oligonucleic acid medicine, etc.) for human or animal, functional food, food for specified health uses, food, chemical product, polymer material for human or industrial use, and the like.

EXAMPLES

The present invention is explained in more detail in the following by referring to Preparation Examples and Examples, which are not to be construed as limiting the scope of the present invention. The reagents, apparatuses and materials used in the present invention are commercially available unless otherwise specified. In the present specification, when indicated by abbreviation, each indication is based on the abbreviation of the IUPAC-IUB Commission on Biochemical Nomenclature or conventional abbreviations in the art.

The yield in the following Preparation Examples and Examples shows mol/mol %. Unless particularly specified, "%" means "mass %" in the present specification. In addition, the ratio of the solvent in the following Preparation Examples and Examples is volume ratio. For $^1$H-NMR spectrum, tetramethylsilane was used as the internal standard, and $CDCl_3$ was used as a measurement solvent. NMR spectrum was measured using Bruker AVANCE AV300 (300 MHz) nuclear magnetic resonance apparatus or Bruker AVANCE 400 (400 MHz) nuclear magnetic resonance apparatus.

For electrospray ionization liquid chromatography/mass spectrometry (hereinafter to be abbreviated as LC/MS), flow injection analysis (FIA) (solvent: 0.1 mol/l TEAA buffer pH 7.0, acetonitrile, ionization mode: ESI, ion node: negative, mass analyzer: quadrupole, fragmentor voltage: 200V) was performed using 6130 Quadrupole LC/MS (Agilent Technologies).

For quadrupole mass spectrometry, flow injection analysis (FIA) (solvent: acetonitrile, ionization mode: ESI, ion mode: positive•negative, mass analyzer: quadrupole, fragmentor voltage: 71V) was performed using ZQ2000 (manufactured by Nihon Waters K.K.).

The abbreviations used in the following Preparation Examples and Examples are as described below. When nucleic acid base of nucleoside is protected, the protecting group is shown in superscript after each nucleoside.
dT: 2'-deoxythymidine
dC: 2'-deoxycytidine
dG: 2'-deoxyguanosine
dA: 2'-deoxyadenosine
U(M): 2'-methoxyuridine
U(F): 2'-fluorouridine
(LNA)T: 2'-O,4'-C-methylenethymidine
DMTr: 4,4'-dimethoxytrityl
PA: (2-cyanoethyl)-N,N-diisopropylphosphoramidite
suc: succinyl
TPB: 3,4,5-tris(3,7,11,15-tetramethyl-1-hexadecanyloxy)benzyl (same as 3,4,5-tris(2,3-phytyloxy)benzyl)
Phy: 2,3-dihydrophytyl (wherein "2,3-dihydrophytyl" means "3,7,11,15-tetramethyl-1-hexadecanyl")
PhyOM: (3,7,11,15-tetramethyl-1-hexadecanoyloxy)methyl (same as 2,3-phytyloxymethyl)
4-Cit-Bz: 4-(3,7-dimethyl-1-octyloxy)benzoyl (same as 4-(dihydrocitronellyloxy)-benzyl)
2Et-Hex: 2-ethyl-1-hexanoyl
3,5,5-Me3Hex: 3,5,5-trimethyl-1-hexanoyl
Me6Dodecanoyl: 2,2,4,8,10,10-hexamethyl-5-dodecanoyl
2-HepUndecanoyl: 2-heptyl-1-undecanoyl
2-HexDecanoyl: 2-hexyl-1-decanoyl
Myr: tetradecanoyl (same as myristoyl)
Me6Dodecanoyl: 2,2,4,8,10,10-hexamethyl-5-dodecanoyl
N,N-Cit2-methylene: bis(3,7-dimethyl-octyl)amino-methylene (same as N,N-bis-dihydrocitronellyl-methylene)
Bz: benzoyl
ibu: isobutyryl Preparation Example 1

Synthesis of 2,3-dihydrophytol

Phytol (10.00 g, 33.7 mmol) was dissolved in methanol, Pt/C (2%, 1.00 g) was suspended therein and the suspension was stirred overnight under a hydrogen atmosphere. After completion of the reaction, the suspension was filtered to remove Pt/C, and the filtrate was concentrated to give 2,3-dihydrophytol. This was used for the next reaction without purification.

Preparation Example 2

Synthesis of 2,3-dihydrophytyl bromide 2,3-Dihydrophytol (33.7 mmol) was suspended in 48% hydrobromic acid (100 ml), concentrated sulfuric acid (0.17 ml) was added dropwise and the mixture was stirred at 100° C. overnight. The reaction mixture was cooled to room temperature, extracted with hexane (200 ml), and washed twice with 5% aqueous sodium hydrogen carbonate solution (70 ml) and once with 20% brine (70 ml). The organic layer was dried over sodium sulfate, and the solvent in the filtrate was evaporated. The obtained residue was purified by silica gel column chromatography (short column, hexane alone) to give 2,3-dihydrophytyl bromide ("2,3-dihydrophytyl group" is sometimes to be referred to as "Phy" hereunder) (10.41 g, 28.8 mmol, 85% vs. phytol).

Preparation Example 3

Synthesis of 3,7,11-trimethyldodecan-1-ol

Using Farnesol (3.00 g, 13.5 mmol) and in the same manner as in Preparation Example 1, 3,7,11-trimethyldodecan-1-ol was obtained. This was used for the next reaction without purification.

Preparation Example 4

Synthesis of 1-bromo-3,7,11-trimethyldodecane

Using 3,7,11-trimethyldodecan-1-ol obtained in Preparation Example 3 and in the same manner as in Preparation Example 2, 1-bromo-3,7,11-trimethyldodecane (2.98 g, 10.2 mmol, 76% vs. Farnesol) was obtained.

Preparation Example 5

Synthesis of 1-[(2-chloro-5-(2,3-dihydrophytyloxy)phenyl)]-1-phenylmethanamine

To 2,3-dihydrophytyl bromide (1.02 g, 2.82 mmol) were added DMF (15 ml), 2-chloro-5-hydroxybenzophenone (0.99 g, 4.23 mmol) and $K_2CO_3$ (0.78 g, 5.64 mmol), and the mixture was stirred at 90° C. for 3 hr. The reaction mixture was cooled to room temperature, ethyl acetate (25 ml) and 1 mol/l hydrochloric acid (25 ml) were added and the mixture was stirred to allow layer separation. The aqueous layer was separated and discarded. The organic layer was washed twice with purified water (25 ml), and the organic layer was evaporated under reduced pressure to give 2-chloro-5-(2,3-dihydrophytyloxy)benzophenone.

To the aforementioned 2-chloro-5-(2,3-dihydrophytyloxy)benzophenone were added chloroform (20 ml), methanol (2 ml) and sodium borohydride (440 mg, 11.6 mmol), and the mixture was stirred at 50° C. overnight. The reaction mixture was cooled to room temperature, 1 mol/l hydrochloric acid (15 ml) was added dropwise in an ice bath to decompose unreacted sodium borohydride. The aqueous layer was discarded, and the organic layer was washed twice with purified water (10 ml). The organic layer was evaporated under reduced pressure, and moisture was azeotropically distilled with acetonitrile to give 2-chloro-5-(2,3-dihydrophytyloxy)benzhydrol.

To 2-chloro-5-(2,3-dihydrophytyloxy)benzhydrol were added chloroform (20 ml), DMF (43 μl, 559 μmol) and thionyl chloride (1.03 ml, 14.1 mmol), and the mixture was stirred at 50° C. for 4 hr. The reaction mixture was cooled to room temperature. The solvent was evaporated under reduced pressure, and the remaining thionyl chloride was azeotropically distilled with toluene to give 1-chloro-1-[(2-chloro-5-(2,3-dihydrophytyloxy)phenyl)phenylmethane.

To the aforementioned 1-chloro-1-[(2-chloro-5-(2,3-dihydrophytyloxy)phenyl)phenylmethane were added DMF (15 ml) and sodium azide (786 mg, 12.1 mmol), and the mixture was stirred at 80° C. overnight. The reaction mixture was cooled to room temperature, ethyl acetate (20 ml) and hexane (20 ml) were added, and the mixture was washed once with purified water (30 ml), and twice with purified water (15 ml). The organic layer was evaporated under reduced pressure to give 1-azido-1-[(2-chloro-5-(2,3-dihydrophytyloxy)phenyl)phenylmethane.

To the aforementioned 1-azido-1-[(2-chloro-5-(2,3-dihydrophytyloxy)phenyl)phenylmethane were added THF (20 ml), purified water (2 ml) and triphenylphosphine (813 mg, 3.10 mmol), and the mixture was stirred at 50° C. for 2 hr. The reaction mixture was cooled to room temperature, THF was evaporated, and liquid-separated three times with heptane (30 ml)-50% aqueous acetonitrile solution (15 ml) and the heptane layer was evaporated under reduced pressure. The residue was purified by silica gel column chromatography (hexane:ethyl acetate=100:0→5:1) to give 1-[(2-chloro-5-(2',3'-dihydrophytyloxy)phenyl)]-1-phenylmethanamine as an oil (1.35 g, 2.63 mmol, yield 93% vs. 2,3-dihydrophytyl bromide).

Preparation Example 6

Synthesis of 4,4'-bis(2,3-dihydrophytyloxy)benzhydryl alcohol

To 2,3-dihydrophytyl bromide (14.3 g, 39.6 mmol) were added DMF (120 ml), 4,4'-dihydroxybenzophenone (4.04 g, 18.9 mmol) and potassium carbonate (7.82 g, 56.6 mmol), and the mixture was stirred at 80° C. for 5 hr. The reaction mixture was cooled to room temperature, ethyl acetate (300 ml) and 1 mol/l hydrochloric acid (100 ml) were added and the mixture was stirred to allow layer separation. The aqueous layer was separated and discarded. The organic layer was washed twice with purified water (100 ml), and the organic layer was evaporated under reduced pressure to give 4,4'-bis(2,3-dihydrophytyloxy)benzophenone oil. This was dissolved in chloroform (60 ml) and methanol (10 ml), sodium borohydride (4.49 g, 119 mmol) was added, and the mixture was stirred at 60° C. for 3 hr. To the reaction mixture was added 1 mol/l hydrochloric acid (80 ml), and the mixture was concentrated. Ethyl acetate (100 ml) was added, and the mixture was washed successively with 1 mol/l hydrochloric acid and water. The organic layer was concentrated to give 4,4'-bis(2,3-dihydrophytyloxy)benzhydryl alcohol oil.

Preparation Example 7

Synthesis of 3,4,5-tri(2,3-dihydrophytyloxy)benzyl alcohol 2,3-Dihydrophytyl bromide (40.6 g, 112 mmol), methyl gallate (5.90 g, 32.0 mmol) and potassium carbonate (22.14 g, 160 mmol) were suspended in DMF (400 ml), and the mixture was stirred at 110° C. overnight. The reaction mixture was extracted with hexane (800 ml), washed with 1 mol/l hydrochloric acid (400 ml), 5% aqueous sodium hydrogen carbonate solution (400 ml) and 20% brine (400 ml), dried over sodium sulfate and the solvent in the filtrate was evaporated to give methyl 3,4,5-tri(2,3-dihydrophytyloxy)benzoate (29.3 g, yield 93%).

The aforementioned methyl 3,4,5-tri(2,3-dihydrophytyloxy)benzoate (29.3 g, 30.0 mmol) was dissolved in THF (400 ml), and diisobutylaluminum hydride (DIBAL) (1.0 mol/l toluene solution, 96 ml, 96 mmol) was added dropwise over 30 min under a nitrogen atmosphere at 0° C. After stirring at room temperature overnight, 0.2 mol/l hydrochloric acid (50 ml) was added dropwise at 0° C. to quench the reaction. The solvent was evaporated to about half, and the residue was dissolved in ethyl acetate (600 ml). The mixture was washed three times with 1 mol/l hydrochloric acid (300 ml), once with 5% aqueous sodium hydrogen carbonate solution (300 ml), and once with 20% brine (300 ml), and dried over sodium sulfate. The solvent in the filtrate was evaporated to give 3,4,5-tri(2,3-dihydrophytyloxy)benzyl alcohol (26.8 g, yield 94%).

Preparation Example 8

Synthesis of 3,4,5-tri(2,3-dihydrophytyloxy)benzyl amine 3,4,5-Tri(2,3-dihydrophytyloxy)benzyl chloride (6.46 g, 6.63 mmol) was dissolved in DMF-chloroform (60+20 ml), sodium azide (861 mg, 13.2 mmol) was added and the mixture was stirred at 70° C. for 2 hr. The reaction mixture was cooled to room temperature, ethyl acetate (160 ml) was added, and the mixture was washed twice with water (80 ml) and three times with 20% brine (50 ml), and dried over sodium sulfate. The solvent in the filtrate was evaporated to give 3,4,5-tri(2,3-dihydrophytyloxy)benzyl azide oil, which was directly used for the next step.

The aforementioned 3,4,5-tri(2,3-dihydrophytyloxy)benzyl azide oil was dissolved in THF (80 ml), water (1.19 ml, 66.1 mmol) and triphenylphosphine (1.91 g, 7.28 mmol) were added and the mixture was stirred at 70° C. for 1 hr. After cooling to room temperature, the solvent was evaporated, and the residue was dissolved in heptane (160 ml). The mixture was washed three times with 50% aqueous acetonitrile solution (50 ml) and twice with 20% brine (50 ml), and dried over sodium sulfate. The solvent in the filtrate was evaporated. The obtained residue was purified by silica gel column chromatography (hexane:ethyl acetate=5:1→chloroform:methanol: aqueous ammonia=100:10:1) to give 3,4,5-tri(2,3-dihydrophytyloxy)benzyl amine (5.31 g, 5.32 mmol, yield 80% vs. chloride product).

Preparation Example 9

Synthesis of 3,5-bis(2,3-dihydrophytyloxy)benzyl alcohol 2,3-Dihydrophytyl bromide (895 mg, 2.48 mmol), methyl 3,5-dihydroxybenzoate (204 mg, 1.21 mmol), and potassium carbonate (513 mg, 3.71 mmol) were suspended in DMF (10 ml), and the suspension was stirred at 100° C. for 7 hr. The reaction mixture was extracted with ethyl acetate (30 ml), and the extract was washed three times with 1 mol/l hydrochloric acid (10 ml) and 20% brine (10 ml), and dried over sodium sulfate. The solvent in the filtrate was evaporated to give methyl 3,5-bis(2,3-dihydrophytyloxy)benzoate (0.78 g, yield 92%).

The aforementioned methyl 3,5-bis(2,3-dihydrophytyloxy)benzoate (0.70 g, 1.00 mmol) was dissolved in THF (10 ml), and lithium aluminum hydride (2.0 mol/l THF solution, 1.2 ml, 2.4 mmol) was added dropwise under a nitrogen atmosphere at 0° C. After stirring at room temperature for 5 hr, water was added dropwise at 0° C. to quench the reaction. The solution was dissolved in ethyl acetate (30 ml), and the mixture was washed three times with 1 mol/l hydrochloric acid (10 ml), and once with 20% brine (20 ml), and dried over sodium sulfate. The solvent in the filtrate was evaporated. The obtained residue was purified by silica gel column chromatography (hexane alone→hexane:ethyl acetate=5:1) to give 3,5-bis(2,3-dihydrophytyloxy)benzyl alcohol (0.61 g, yield 90%).

Preparation Example 10

Synthesis of 4-(2,3-dihydrophytyloxy)benzyl alcohol 2,3-Dihydrophytyl bromide (600 mg, 1.66 mmol), 4-hydroxybenzaldehyde (223 mg, 1.83 mmol) and potassium carbonate (344 mg, 2.49 mmol) were suspended in DMF (6 ml), and the suspension was stirred at 60° C. for 3 days. The reaction mixture was cooled to room temperature, and extracted with ethyl acetate (30 ml). The extract was washed three times with 1 mol/l hydrochloric acid (6 ml), three times with 5% aqueous sodium hydrogen carbonate solution (6 ml), and once with 20% brine (6 ml), and dried over sodium sulfate. The solvent in the filtrate was evaporated. The obtained residue was purified by silica gel column chromatography (hexane:ethyl acetate=15:1→5:1) to give 4-(2,3-dihydrophytyloxy)benzaldehyde (640 mg, yield 100% vs. 2,3-dihydrophytyl bromide).

The aforementioned 4-(2,3-dihydrophytyloxy)benzaldehyde (640 mg, 1.66 mmol) was dissolved in THF-methanol mixed solution (7+0.3 ml), sodium borohydride (110 mg, 90%, 2.62 mmol) was added at 0° C., and the mixture was stirred at room temperature for 30 min. The reaction mixture was cooled to 0° C., and the reaction was quenched with 1 mol/l hydrochloric acid. Ethyl acetate (30 ml) was added and the mixture was washed three times with 1 mol/l hydrochloric acid (5 ml), three times with 5% aqueous sodium hydrogen carbonate solution (5 ml), and once with 20% brine (5 ml), and dried over sodium sulfate. The solvent in the filtrate was evaporated to give 4-(2,3-dihydrophytyloxy)benzyl alcohol (619 mg, 1.53 mmol, yield 92% vs. 2,3-dihydrophytyl bromide).

Preparation Example 11

Synthesis of 4-(2,3-dihydrophytyloxy)benzyl amine 4-(2,3-Dihydrophytyloxy)benzyl alcohol (619 mg, 1.53 mmol) was dissolved in chloroform (6 ml), thionyl chloride (167 µl, 2.29 mmol) was added and the mixture was stirred for 5 hr. After completion of the reaction, the solvent was evaporated to give 4-(2,3-dihydrophytyloxy)-benzyl chloride oil, which was directly used for the next step.

The aforementioned 4-(2,3-dihydrophytyloxy)benzyl chloride (1.53 mmol) was dissolved in DMF-CHCl$_3$ mixed solvent (6+3 ml), sodium azide (298 mg, 4.58 mmol) was added and the mixture was stirred at 70° C. overnight. The reaction mixture was cooled to room temperature, ethyl acetate (20 ml) was added, and the mixture was washed 5 times with water (10 ml) and dried over sodium sulfate. The solvent in the filtrate was evaporated to give 4-(2,3-dihydrophytyloxy)benzyl azide (632 mg, yield 96% vs. 4-(2,3-dihydrophytyloxy)benzyl alcohol).

The aforementioned 4-(2,3-dihydrophytyloxy)benzyl azide (632 mg, 1.47 mmol) was dissolved in THF (6 ml), water (265 µl, 14.7 mmol) and triphenylphosphine (424 mg, 1.62 mmol) were added and the mixture was stirred at 70° C. overnight. After cooling to room temperature, the solvent was evaporated, and the residue was dissolved in hexane (10 ml), and the mixture was washed 3 times with 50% aqueous acetonitrile solution (5 ml). The solvent was evaporated. The obtained residue was purified by silica gel column chromatography (hexane:ethyl acetate=5:1→chloroform:methanol:aqueous ammonia=50:5:1) to give 4-(2,3-dihydrophytyloxy)benzyl amine (555 mg, 1.37 mmol, yield 94%).

Preparation Example 12

Synthesis of
2-methoxy-4-(2,3-dihydrophytyloxy)benzyl amine 2,3-Dihydrophytyl bromide (2.00 g, 5.53 mmol), 2-methoxy-4-hydroxybenzaldehyde (884 mg, 5.81 mmol) and potassium carbonate (1.15 g, 8.32 mmol) were suspended in DMF (20 ml), and the suspension was stirred at 80° C. overnight. The reaction mixture was cooled to room temperature, and extracted with ethyl acetate (50 ml). The extract was washed three times with 1 mol/l hydrochloric acid (20 ml), three times with 5% aqueous sodium hydrogen carbonate solution (20 ml), and once with 20% brine (20 ml), and dried over sodium sulfate. The solvent in the filtrate was evaporated. The obtained residue was purified by silica gel column chromatography (hexane:ethyl acetate=20:1) to give 2-methoxy-4-(2,3-dihydrophytyloxy)benzaldehyde oil, which was used for the next step.

The aforementioned 2-methoxy-4-(2,3-dihydrophytyloxy)benzaldehyde, and hydroxylamine hydrochloride (1.15 g, 16.5 mmol) were suspended in dichloromethane (25 ml), triethylamine (3.84 ml, 27.7 mmol) was added at 0° C. and the suspension was stirred at room temperature for 3 hr. To the reaction mixture was added chloroform (30 ml) and the mixture was washed three times with 1 mol/l hydrochloric acid (15 ml), three times with 5% aqueous sodium hydrogen carbonate solution (15 ml), and once with 20% brine (15 ml), and the solvent was evaporated to give 2-methoxy-4-(2,3-dihydrophytyloxy)benzaldoxime. After confirmation of the structure by NMR, it was used for the next step.

The aforementioned 2-methoxy-4-(2,3-dihydrophytyloxy)benzaldoxime was dissolved in methanol-THF mixed solvent (20+10 ml), 10% palladium-carbon(K) (200 mg) was added and the mixture was stirred under a hydrogen atmosphere at room temperature overnight. The solvent in the filtrate was evaporated. The obtained residue was purified by silica gel column chromatography (chloroform:methanol:aqueous ammonia=100:10:1) to give 2-methoxy-4-(2,3-dihydrophytyloxy)benzyl amine (1.87 g, 4.31 mmol, yield 78% vs. 2,3-dihydrophytyl bromide).

Preparation Example 13

Synthesis of
4-(2,3-dihydrophytyloxy)-2-methylbenzyl alcohol

To methanol (10 ml) was added dropwise thionyl chloride (1.92 ml, 26.3 mmol) at 0° C., 4-hydroxy-2-methylbenzoic acid (2.00 g, 13.1 mmol) was added, and the mixture was stirred at 60° C. overnight. After completion of the reaction, the solvent was evaporated, and the residue was dissolved in ethyl acetate (20 ml). The mixture was washed twice with 5% aqueous sodium hydrogen carbonate solution (10 ml), once with 1 mol/l hydrochloric acid (10 ml), and once with water (10 ml), and the solvent was evaporated to give methyl 4-hydroxy-2-methylbenzoate (2.24 g, yield 100%).

The aforementioned methyl 4-hydroxy-2-methylbenzoate (269 mg, 1.62 mmol), 2,3-dihydrophytyl bromide (389 mg, 1.08 mmol) and potassium carbonate (297 mg, 2.15 mmol) were suspended in DMF (5 ml), and the suspension was stirred at 90° C. for 5 hr. The reaction mixture was cooled to room temperature, extracted with hexane-ethyl acetate (10+10 ml), and washed once with 1 mol/l hydrochloric acid (15 ml) and twice with water (10 ml). The solvent was evaporated to give methyl 4-(2,3-dihydrophytyloxy)-2-methylbenzoate. After confirmation of the structure by NMR, it was used for the next step.

The aforementioned methyl 4-(2,3-dihydrophytyloxy)-2-methylbenzoate (1.08 mmol) was dissolved in THF (6 ml), DIBAL (1.0M, 4.9 ml, 4.9 mmol) was added, and the mixture was stirred at room temperature for 100 min. The reaction mixture was cooled to 0° C., and the reaction was quenched with 1 mol/l hydrochloric acid (15 ml). Hexane (10 ml) and ethyl acetate (10 ml) were added to allow liquid-separation, and the mixture was washed once with 0.5 mol/l hydrochloric acid (10 ml) and once with water (10 ml), and the solvent was evaporated to give 4-(2,3-dihydrophytyloxy)-2-methylbenzyl alcohol.

Preparation Example 14

Synthesis of
4-(2,3-dihydrophytyloxy)-2-methylbenzyl amine 4-(2,3-Dihydrophytyloxy)-2-methyl-benzyl alcohol (1.08 mmol) was dissolved in chloroform (8 ml), thionyl chloride (393 µl, 5.38 mmol) was added and the mixture was stirred at 50° C. for 4.5 hr. After completion of the reaction, the solvent was evaporated to give 4-(2,3-dihydrophytyloxy)-2-methylbenzyl chloride. After confirmation of the structure by NMR, it was used for the next step.

The aforementioned 4-(2,3-dihydrophytyloxy)-2-methylbenzyl chloride (1.08 mmol) was dissolved in DMF (6 ml), sodium azide (350 mg, 5.38 mmol) was added and the mixture was stirred at 70° C. overnight. The reaction mixture was cooled to room temperature, hexane (10 ml) and ethyl acetate (5 ml) were added, and the mixture was washed 3 times with water (10 ml).

The solvent in the filtrate was evaporated to give 4-(2,3-dihydrophytyloxy)-2-methylbenzyl azide. After confirmation of the structure by NMR, it was used for the next step.

The aforementioned 4-(2,3-dihydrophytyloxy)-2-methylbenzyl azide (1.08 mmol) was dissolved in THF (10 ml), water (2 ml) and triphenylphosphine (565 mg, 2.15 mmol) were added and the mixture was stirred at 60° C. for 3 hr. After cooling to room temperature, the solvent was evaporated, and the residue was dissolved in heptane (10 ml), and washed 3 times with 50% aqueous acetonitrile solution (10 ml). The solvent was evaporated and the obtained residue was purified by silica gel column chromatography (hexane:ethyl acetate=5:1→chloroform:methanol:aqueous ammonia=50:5:1) to give 4-(2,3-dihydrophytyloxy)-2-methylbenzyl amine (281 mg, 0.67 mmol, yield 62% vs. 2,3-dihydrophytyl bromide).

Preparation Example 15

Synthesis of 2,2,4,8,10,10-hexamethyl-5-dodecanoic acid (4-hydroxymethyl)phenylamide 2,2,4,8,10,10-Hexamethyl-5-dodecanoic acid (2.81 g, 9.88 mmol), 4-aminobenzyl alcohol (1.00 g, 8.12 mmol) and 3,4-dihydro-3-hydroxy-4-oxo-1,2,3-benzotriazine (HOOBt) (133 mg, 0.812 mmol) were suspended in chloroform (10 ml), EDC HCl (2.05 g, 10.7 mmol) was added at 0° C., and the suspension was stirred at room temperature overnight. The solvent was removed, and the residue was purified by silica gel column chromatography (hexane:ethyl acetate=2:1) to give 2,2,4,8,10,10-hexamethyl-5-dodecanoic acid (4-hydroxymethyl)phenylamide (2.69 g, 6.67 mmol, yield 82%).

Preparation Example 16

Synthesis of 4-(3,7,11-trimethyldodecyloxy)benzyl alcohol

1-Bromo-3,7,11-trimethyldodecane (1.00 g, 3.43 mmol) obtained in Reference Example 4 was dissolved in DMF (5 ml), 4-hydroxybenzyl alcohol (0.85 g, 6.85 mmol) and potassium carbonate (1.42 g, 10.3 mmol) were added and the mixture was stirred at 120° C. overnight. The reaction mixture was cooled to room temperature, extracted with chloroform (50 ml), and the extract was washed three times with 1 mol/l hydrochloric acid (30 ml), once with 5% aqueous sodium hydrogen carbonate solution (30 ml), and once with purified water (30 ml). The solvent of the organic layer was evaporated to give 4-(3,7,11-trimethyldodecyloxy)benzyl alcohol (1.09 g, 3.26 mmol, yield 95% vs. 1-bromo-3,7,11-trimethyldodecane).

Preparation Example 17

Synthesis of 3,7,11,15-tetramethyl-1-hexadecanoic acid 3,7,11,15-Tetramethyl-hexadecan-1-ol (8.96 g, 30.0 mmol) was dissolved in a mixed solvent of acetone (360 ml) and acetic acid (180 ml), a solution of anhydrous chromic acid (7.27 g, 72.7 mmol) in water (9.0 ml) was added dropwise, and the mixture was stirred at room temperature for 1 hr. A solution of sodium disulfite (100 g, 526 mmol) in water (450 ml) was added to the reaction mixture after completion of the reaction, the mixture was stirred at room temperature overnight and extracted 6 times with diethyl ether (135 ml). The solvent of the obtained organic layer was evaporated under reduced pressure. Diethylether (450 ml) and water (150 ml) were added to the oil after concentration to allow partitioning, and the aqueous layer was extracted 3 times with ethyl acetate (150 ml). The combined organic layer was dried over anhydrous sodium sulfate, and the solvent was evaporated under reduced pressure. The oil (10.1 g) after concentration was purified by chromatography (silica gel; 250 g, eluate; 50:1→3:1 hexane-ethyl acetate) to give the title compound (6.78 g, 72.3%) as a pale-blue oil.

Preparation Example 18

Synthesis of 3,7,11,15-tetramethyl-1-hexadecanoyl chloride

The compound (2.81 g, 9.0 mmol) synthesized in Preparation Example 17 was dissolved in anhydrous chloroform (4.5 ml), thionyl chloride (1.31 ml, 18.0 mmol) was added and the mixture was stirred at room temperature for 1 hr. After completion of the reaction, the solvent was evaporated under reduced pressure and the obtained oil (3.07 g) was directly used for the next reaction as the title compound.

Preparation Example 19

Synthesis of chloromethyl 3,7,11,15-tetramethyl-1-hexadecanoate

The compound (6.56 g, 21.0 mmol) synthesized in Preparation Example 17 was dissolved in anhydrous chloroform (10 ml), thionyl chloride (3.06 ml, 42.0 mmol) was added and the mixture was stirred at room temperature for 1 hr. After completion of the reaction, the solvent was evaporated under reduced pressure, and the obtained oil was added dropwise to a to mixed solid of 90% para-formaldehyde (840 mg, 25.2 mmol) and zinc chloride (42.9 mg, 0.32 mmol) over 30 min under cooling in an ice bath. The obtained mixed solution was stirred with heating at 60° C. for 5 hr and allowed to cool to room temperature. 10% Aqueous sodium hydrogen carbonate solution (30 ml) and dichloromethane (15 ml) were added to allow layer separation, and the mixture was further extracted twice with an equal amount of dichloromethane. The combined organic layer was washed with saturated brine (30 ml), dried over anhydrous sodium sulfate and the solvent was evaporated under reduced pressure. The oil (7.40 g) after concentration was purified by chromatography (silica gel; 120 g, eluate; 10:1 hexane-dichloromethane) to give the title compound (5.01 g, 66.1%) as a colorless oil.

Preparation Example 20

Synthesis of 4-(3,7-dimethyl-1-octyloxy)benzoic acid (1) Synthesis of 1-bromo-3,7-dimethyloctane 3,7-Dimethyloctan-1-ol (10.0 g, 63.2 mmol) was suspended in 48% aqueous hydrobromic acid solution, concentrated sulfuric acid (0.17 ml) was added dropwise and the mixture was stirred at 100° C. for 16 hr. The reaction mixture was allowed to cool to room temperature, extracted with hexane (200 ml), and washed twice with 5% aqueous sodium hydrogen carbonate solution (100 ml) and once with 20% brine (100 ml). The organic layer was dried over sodium sulfate, and the solvent in the filtrate was evaporated to give the title compound (13.3 g, 95.1%) as a colorless oil.

(2) Synthesis of methyl [4-(3,7-dimethyl-1-octyloxy)]benzoate

Under an argon atmosphere, potassium carbonate (12.5 g, 90.3 mmol) was suspended in anhydrous N,N-dimethylformamide (100 ml), 1-bromo-3,7-dimethyloctane (13.3 g, 60.1 mmol) and methyl (4-hydroxy)benzoate (8.74 g, 57.4 mmol) were added, and the mixture was stirred at 70° C. for 16 hr. The reaction mixture was filtered to remove potassium carbonate. Water (50 ml) was added and the mixture was extracted with hexane (250 ml). The extract was washed successively with 1.0 mol/l aqueous hydrochloric acid solution (100 ml), aqueous sodium hydrogen carbonate solution (100 ml) and saturated brine (100 ml). The obtained organic layer was dried over sodium sulfate, filtered and concentrated under reduced pressure to give the title compound (16.1 g, 95.7%) as a colorless oil.

(3) Synthesis of 4-(3,7-dimethyl-1-octyloxy)benzoic acid

Methyl[4-(3,7-dimethyl-1-octyloxy)]benzoate (16.1 g, 54.9 mmol) was dissolved in 1,4-dioxane (300 ml), 50% aqueous potassium hydroxide solution (25 ml) was added and the mixture was stirred at 100° C. for 6 hr. To acidify the reaction mixture, concentrated hydrochloric acid was added dropwise, and the mixture was extracted with ethyl acetate (200 ml), and washed with 10% aqueous sodium hydroxide solution (100 ml) and saturated brine (100 ml). The organic layer was dried over sodium sulfate, filtered and concentrated under reduced pressure to give the title compound (14.2 g, 92.8%) as a white solid.

Preparation Example 21

Synthesis of 5'-O-(4,4'-dimethoxytrityl)-2'-deoxycytidine-3'-O-[(2-cyanoethyl)-N,N-diisopropylphosphoramidite]

Under an argon atmosphere, 5'-O-(4,4'-dimethoxytrityl)-$N^4$-acetyl-2'-deoxycytidine-3'-O-[(2-cyanoethyl)-N,N-diisopropylphosphoramidite] (3.5 g, 4.5 mmol) was dissolved in 2.0 mol/l ammonia/methanol solution (40 ml) and the mixture was stirred at room temperature for 2 hr. The reaction mixture was concentrated under reduced pressure to give the title compound (3.4 g) quantitatively.

Preparation Example 22

Synthesis of 5'-O-(4,4'-dimethoxytrityl)-2'-deoxyguanosine-3'-O-[(2-cyanoethyl)-N,N-diisopropylphosphoramidite]

Under an argon atmosphere, 5'-O-(4,4'-dimethoxytrityl)-$N^2$-(2-methyl-1-oxopropyl)-2'-deoxyguanosine-3'-O-[(2-cyanoethyl)-N,N-diisopropylphosphoramidite] (5.0 g, 5.9 mmol) was dissolved in 2.0 mol/l ammonia/methanol solution (60 ml) and the mixture was stirred at room temperature overnight. The reaction mixture was concentrated under reduced pressure, and the obtained oil was purified by silica gel column chromatography to give the title compound (4.6 g) quantitatively.
(Preparation of Amidine-Type Protecting Group Reagent)

Preparation Example 23

Synthesis of N,N-di(3,7-dimethyl-octyl)formamide dimethylacetal (1) Synthesis of 3,7-dimethyl-1-octyl bromide 48% HBr (200 ml) and concentrated sulfuric acid (0.46 ml) were added to 3,7-dimethyl-1-octanol (21.0 g, 157.9 mmol), and the mixture was heated overnight. After allowing to cool to room temperature, the mixture was extracted with hexane. The organic layer was washed with 5% aqueous sodium hydrogen carbonate solution and saturated brine, dried and concentrated to give the title compound (28.7 g, 82.1%).

(2) Synthesis of di(3,7-dimethyl-octyl)benzyl amine

Benzyl amine (7.1 ml, 64.8 mmol), potassium carbonate (17.9 g, 129.6 mmol) and the compound (28.7 g, 129.6 mmol) obtained in Preparation Example 23-(1) were dissolved in dry acetonitrile (80 ml) and the mixture was heated overnight. The reaction mixture was concentrated, dichloromethane (200 ml) was added and the mixture was washed with water. The organic layer was concentrated and the obtained oil was purified by silica gel column chromatography to give the title compound (13.2 g, 52.2%).

(3) Synthesis of N,N-di(3,7-dimethyl-octyl)amine

The compound (13.2 g, 33.8 mmol) obtained in Preparation Example 23-(2) was dissolved in ethanol (150 ml), 5% palladium carbon (53% wetted, 2.86 g) was added and the mixture was stirred overnight under a hydrogen atmosphere. The reaction mixture was filtered through celite to remove the palladium catalyst, and the filtrate was concentrated to give the title compound (10.0 g, 99.3%) quantitatively.

(4) Synthesis of N,N-di(3,7-dimethyl-octyl)formamide dimethylacetal

To the compound (7.0 g, 23.4 mmol) obtained in Preparation Example 23-(3) were added N,N-dimethylformamide dimethyl acetal (2.8 g, 23.4 mmol) and a catalytic amount of pyridinium p-toluenesulfonate, and the mixture was heated to 160° C. and stirred overnight. The reaction mixture was evaporated under reduced pressure to give the title compound (1.4 g, 16%).

Preparation Example 24

Synthesis of 2,3,4-tris(2,3-dihydrophytyloxy)benzhydryl amine (1) Synthesis of 2,3,4-tris(2,3-dihydrophytyloxy)benzophenone Under an argon atmosphere, 2,3,4-trihydroxybenzophenone (0.94 g, 4.07 mmol), 2,3-dihydrophytyl bromide (6.01 g, 16.6 mmol) and potassium carbonate (2.57 g, 138.2 mmol) were added to anhydrous N,N-dimethylformamide (25 ml), and the mixture was stirred at 80° C. overnight. The reaction mixture was allowed to cool to room temperature, extracted with hexane (50 ml), washed successively with 1 mol/l aqueous hydrochloric acid (20 ml), 5% aqueous sodium hydrogen carbonate solution (20 ml) and saturated brine (20 ml), and dried over sodium sulfate. The solvent in the filtrate was evaporated and the obtained residue was purified by silica gel column chromatography (hexane:ethyl acetate=100:0-95/5 (v/v)). The object fractions were collected and concentrated to give the title compound (3.90 g, 88.9%) as an oil.

(2) Synthesis of 2,3,4-tris(2,3-dihydrophytyloxy)benzhydryl alcohol 2,3,4-Tris(2,3-dihydrophytyloxy)benzophenone (3.90 g, 3.64 mmol) synthesized in Preparation Example 24-(1) was dissolved in a mixed solvent of chloroform (35 ml) and methanol (3.5 ml), sodium borohydride (0.41 g, 10.9 mmol) was added, and the mixture was stirred at 45° C. for 2 hr. After completion of the reaction, 0.1 mol/l aqueous hydrochloric acid was added dropwise to decompose unreacted sodium borohydride, and the mixture was washed with 1.0 mol/l aqueous hydrochloric acid. The organic layer was dried over sodium sulfate and filtered, and the filtrate was concentrated under reduced pressure. The solvent in the filtrate was evaporated and the obtained residue was purified by silica gel column chromatography (hexane:ethyl acetate=98:2-90/10 (v/v)). The object fractions were collected and concentrated to give the title compound (3.56 g, 91.0%) as an oil.

(3) Synthesis of N-(9-fluorenylmethoxycarbonyl)-2,3,4-tris(2,3-dihydrophytyloxy)benzhydryl amine Under an argon atmosphere, 2,3,4-tris(2,3-dihydrophytyloxy)benzhydryl alcohol (3.56 g, 3.31 mmol) synthesized in Preparation Example 24-(2) and 9-fluorenylmethyl carbamate (1.42 g, 5.96 mmol) were dissolved in anhydrous toluene (40 ml) at 50° C., methanesulfonic acid (64 µl, 993 µmol) was added and the mixture was stirred at 100° C. for 2 hr. The reaction mixture was allowed to cool to room temperature, washed with 5% aqueous sodium hydrogen carbonate solution (20 ml) and saturated brine (20 ml), and dried over sodium sulfate. The solvent in the filtrate was evaporated and the obtained residue was purified by silica gel column chromatography (hexane:ethyl acetate=98:2-90/10 (v/v)). The object fractions were collected and concentrated to give the title compound (4.00 g, 93.3%) as an oil.

(4) Synthesis of 2,3,4-tris(2,3-dihydrophytyloxy)benzhydryl amine

N-(9-Fluorenylmethoxycarbonyl)-2,3,4-tris(2,3-dihydrophytyloxy)benzhydryl amine (4.00 g, 3.09 mmol) synthesized in Preparation Example 24-(3) was dissolved in a mixed solvent of chloroform (30 ml) and acetonitrile (15 ml), 20% piperidine [1-methyl-2-pyrrolidone solution] (30.5 ml, 61.8 mmol) was added, and the mixture was stirred at room temperature for 30 min. After completion of the reaction, ethyl acetate (60 ml), hexane (30 ml) and water (10 ml) were added to allow layer separation. The organic layer was washed with saturated brine and dried over sodium sulfate. The solvent in the filtrate was evaporated and the obtained residue was purified by silica gel column chromatography (hexane:ethyl acetate=100:0-80/20 (v/v)). The object fractions were collected and concentrated to give the title compound (2.92 g, 88.2%) as an oil.

Preparation Example 25

Synthesis of 4,4'-bis(2,3-dihydrophytyloxy)benzhydryl amine (1) Synthesis of N-(9-fluorenylmethoxycarbonyl)-bis-4-(2,3-dihydrophytyloxy)benzhydryl amine To 4,4'-bis(2,3-dihydrophytyloxy)benzhydryl alcohol (3.80 g, 4.89 mmol) described in Preparation Example 6 were added toluene (50 ml) and 9-fluorenylmethyl carbamate (2.11 g, 8.81 mmol), and the mixture was dissolved by heating to 50° C. Methanesulfonic acid (95.3 µl, 1.47 mmol) was added and the mixture was stirred at 100° C. for 2 hr. The completion of the reaction was confirmed and the reaction mixture was allowed to cool to room temperature. 5% Aqueous sodium hydrogen carbonate solution (20 ml) was added and the mixture was stirred. After partitioning, the organic layer was further washed with water (20 ml) and saturated brine (20 ml). The organic layer was evaporated under reduced pressure to give the title compound (5.10 g, quant).

(2) Synthesis of 4,4'-bis(2,3-dihydrophytyloxy)benzhydryl amine

N-(9-Fluorenylmethoxycarbonyl)-4-bis(2,3-dihydrophytyloxy)benzhydryl amine (5.10 g, 5.27 mmol) obtained in Preparation Example 25-(1) was dissolved in a mixed solvent of chloroform (50 ml) and acetonitrile (25 ml), 20% piperidine [1-methyl-2-pyrrolidone solution] (52.1 ml, 105.4 mol) was added, and the mixture was stirred at room temperature for 30 min. After completion of the reaction, ethyl acetate (100 ml), hexane (60 ml) and water (15 ml) were added to allow layer separation. The organic layer was washed with saturated brine and dried over sodium sulfate. The solvent in the filtrate was evaporated and the obtained residue was purified by silica gel column chromatography (hexane:ethyl acetate=100:0-30/70 v/v)). The object fractions were collected and concentrated to give the title compound (3.56 g, 86.8%) as an oil.

Preparation Example 26

Synthesis of 3,5-bis(2,3-dihydrophytyloxy)benzyl amine (1) Synthesis of 3,5-bis(2,3-dihydrophytyloxy)benzyl chloride Under an argon atmosphere, 3,5-bis(2,3-dihydrophytyloxy)benzyl alcohol (4.70 g, 6.70 mmol) described in Preparation Example 9 was dissolved in chloroform (34 ml), pyridine (a few drops) and thionyl chloride (0.97 ml, 13.4 mmol) were added, and the mixture was stirred at room temperature for 90 min. The reaction mixture was concentrated under reduced pressure to give the title compound (4.93 g, quant) as an oil.

(2) Synthesis of 3,5-bis(2,3-dihydrophytyloxy)benzyl azide 3,5-Bis(2,3-dihydrophytyloxy)benzyl chloride (4.93 g, 6.85 mmol) obtained in Preparation Example 26-(1) was dissolved in a mixed solvent of chloroform (27 ml) and N,N-dimethylformamide (81 ml), sodium azide (0.90 g, 13.7 mmol) was added and the mixture was stirred at 80° C. for 2.5 hr. After completion of the reaction, the reaction mixture was allowed to cool to room temperature, ethyl acetate (250 ml) and purified water (180 ml) were added to allow layer separation, and the organic layer was washed with purified water (180 ml) and saturated brine (130 ml). The organic layer was dried over sodium sulfate and filtered to give the title compound (4.79 g, 96.4%).

(3) Synthesis of 3,5-bis(2,3-dihydrophytyloxy)benzyl amine

Under an argon atmosphere, 3,5-bis(2,3-dihydrophytyloxy)benzyl azide (4.79 g, 6.60 mmol) obtained in Preparation Example 26-(2) was dissolved in anhydrous tetrahydrofuran (33 ml), lithium aluminum hydride (0.50 g, 13.2 mmol) was added under ice-cooling, and the reaction mixture was stirred at room temperature for 2 hr. To the reaction mixture after completion of the reaction were added dropwise 1 mol/l aqueous hydrochloric acid (25 ml) and ethyl acetate (50 ml) to allow layer separation, and the aqueous layer was extracted with ethyl acetate (50 ml). The organic layers were combined, washed twice with water (90 ml), and further washed with 5% aqueous sodium hydrogen carbonate solution (90 ml) and saturated brine (90 ml). The organic layer was dried over magnesium sulfate, and the filtrate was concentrated under reduced pressure and purified by silica gel column chromatography to give the title compound (3.29 g, 71.1%) as an oil.

Preparation Example 27

Synthesis of 5'-O-(4,4'-dimethoxytrityl)-2'-deoxy-2'-fluorouridine-3'-O-[(2-cyanoethyl)-N,N-diisopropylphosphoramidite]

(1) Synthesis of 5'-O-(4,4'-dimethoxytrityl)-2'-deoxy-2'-fluorouridine

An operation of dissolving 2'-Deoxy-2'-fluorouridine (3.00 g, 12.2 mmol) in dry pyridine, followed by concentration under reduced pressure was repeated 3 times to perform dehydrative azeotropic distillation. Thereafter, under an argon atmosphere, the reaction mixture was dissolved in dry pyridine (120 ml), 4,4'-dimethoxytrityl chloride (4.55 g, 13.4 mmol) was added, and the mixture was stirred at room temperature for 3 hr. The completion of the reaction was confirmed, and ethyl acetate (150 ml) and water (60 ml) were added to the reaction mixture to allow layer separation. The organic layer was washed 3 times with 5% aqueous sodium hydrogen carbonate solution (20 ml), washed with water (20 ml) and saturated brine (20 ml), and the obtained organic layer was dried over sodium sulfate. The solvent in the filtrate was evaporated and the obtained residue was purified by silica gel column chromatography (hexane:ethyl acetate=50:50-0/100 (v/v), containing 1% triethylamine). The object fractions were collected and concentrated to give the title compound (8.48 g, quant).

(2) Synthesis of 5'-O-(4,4'-dimethoxytrityl)-2'-deoxy-2'-fluorouridine-3'-O-[(2-cyanoethyl)-N,N-diisopropylphosphoramidite]

5'-O-(4,4'-Dimethoxytrityl)-2'-deoxy-2'-fluorouridine (3.00 g, 5.47 mmol) obtained in Preparation Example 27-(1) was dissolved in anhydrous dichloromethane (50 ml) under an argon atmosphere, N,N-diisopropylethylamine (0.55 ml, 3.18 mmol), 1H-tetrazole (0.45 g, 6.45 mmol) and 2-cyanoethyl-N,N,N',N'-tetraisopropylphosphordiamidite (1.92 g, 6.36 mmol) were added, and the mixture was stirred at room temperature overnight. The completion of the reaction was confirmed, 5% aqueous sodium hydrogen carbonate solution (20 ml) was added to the reaction mixture to allow layer separation, and the organic layer was washed with saturated brine (20 ml). The organic layer was dried over sodium sulfate, the filtrate was concentrated and the obtained crude product was purified by silica gel chromatography (hexane:ethyl acetate=75:25-30/70 (v/v), containing 3% triethylamine). The object fractions were collected and concentrated to give the title compound (2.76 g, 67.3%).

Example 1

Synthesis of 5'-O-(4,4'-dimethoxytrityl)-2'-deoxythymidin-3'-yl-O-[3,4,5-tris(3,7,11,15-tetramethyl-1-hexadecanyloxy)benzyl]succinate [5'-O-DMTr-dT-suc-TPB]

(1) Synthesis of 5'-O-(4,4'-dimethoxytrityl)-2'-deoxythymidine-3'-O-succinate

Under an argon atmosphere, 5'-O-(4,4'-dimethoxytrityl)-2'-deoxythymidine (4.98 g, 9.14 mmol) and tetrahydrofuran-2,5-dione (1.39 g, 13.9 mmol) were dissolved in anhydrous dichloromethane (100 ml), triethylamine (3.80 ml, 27.3 mmol) was added and the mixture was stirred at room temperature for 16 hr. The reaction mixture after completion of the reaction was washed 3 times with 2.0 mol/l aqueous triethylammonium phosphate solution (70 ml), and the organic layer was dried over sodium sulfate, filtered and concentrated under reduced pressure. The obtained residue was azeotropically distilled 3 times with toluene (10 ml) to quantitatively give a triethylamine salt of the title compound (7.15 g) as a white solid.

(2) Synthesis of 5'-O-(4,4'-dimethoxytrityl)-2'-deoxythymidin-3'-yl-O-[3,4,5-tris(3,7,11,15-tetramethyl-1-hexadecanyloxy)benzyl]succinate [5'-O-DMTr-dT-suc-TPB]

The compound synthesized in Example 1-(1) (6.55 g, 8.78 mmol) and 3,4,5-tris(3,7,11,15-tetramethyl-1-hexadecanyloxy)benzyl alcohol (5.19 g, 5.16 mmol) synthesized in Preparation Example 7 were dissolved in anhydrous dichloromethane (15 ml), 2-(1H-benzotriazol-1-yl) 1,1,3,3-tetramethyluronium hexafluorophosphate [HBTU] (11.8 g, 30.8 mmol) and N,N-diisopropylethylamine (5.53 ml, 31.2 mmol) were added, and the mixture was stirred at room temperature for 1 hr. The mixture was washed with saturated aqueous sodium hydrogen carbonate solution and saturated brine, and the obtained organic layer was dried over sodium sulfate and filtered. The filtrate was concentrated under reduced pressure and the obtained residue was purified by silica gel column chromatography (hexane/ethyl acetate, 1% v/v triethylamine) to give the title compound (3.83 g, 45.3%) as a viscous solid.

Example 2

Synthesis of 5'-O-(4,4'-dimethoxytrityl)-2'-deoxythymidin-3'-yl-N-[3,4,5-tris(3,7,11,15-tetramethyl-1-hexadecanyloxy)benzyl]succinamate [5'-O-DMTr-dT-suc-NH-TPB]

Using a triethylamine salt (1.45 g, 1.94 mmol) of 5'-O-(4,4'-dimethoxytrityl)-2'-deoxythymidine-3'-O-succinate, and 3,4,5-tris(3,7,11,15-tetramethyl-1-hexadecanyloxy)benzyl amine (1.02 g, 1.10 mmol) synthesized in Preparation Example 8, and in the same manner as in Example 1-(2), the title compound (1.22 g, 72.4%) was obtained as a viscous solid.

Example 3

Synthesis of 5'-O-(4,4'-dimethoxytrityl)-N$^4$-(3,7,11,15-tetramethyl-1-hexadecanoyl)-2'-deoxycytidine-3'-O-[(2-cyanoethyl)-N,N-diisopropylphosphoramidite] [5'-O-DMTr-dC$^{Phy}$-PA]

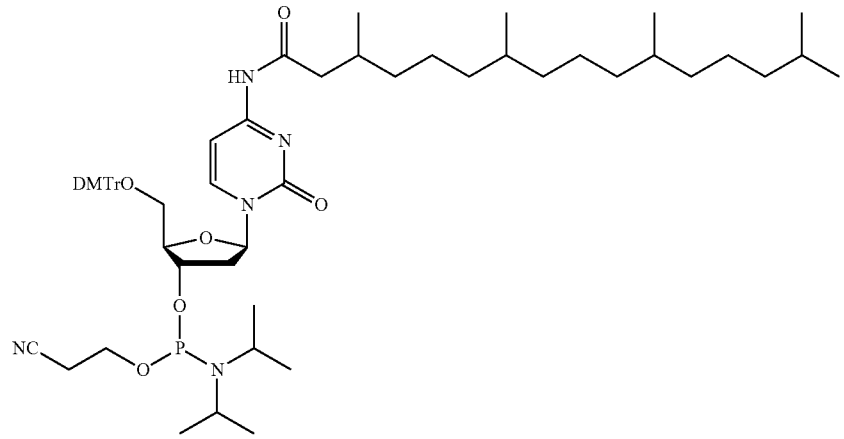

Under an argon atmosphere, 5'-O-(4,4'-dimethoxytrityl)-2'-deoxycytidine-3'-O-[(2-cyanoethyl)-N,N-diisopropylphosphoramidite] (1.46 g, 2.00 mmol) was dissolved in anhydrous tetrahydrofuran (10 ml), N,N-diisopropylethylamine (720 μl, 4.00 mmol) and the compound synthesized in Preparation Example 18 (990 mg, 3.00 mmol) were added, and the mixture was stirred at room temperature for 3 hr. After completion of the reaction, ethyl acetate (60 ml) and 5% aqueous sodium hydrogen carbonate solution (15 ml) were added to the reaction mixture to allow phase separation, and the aqueous phase was extracted with ethyl acetate (30 ml). The combined organic phase was dried over anhydrous sodium sulfate, and the solvent was evaporated under reduced pressure. The concentrated oil (2.70 g) was purified by chromatography (silica gel; 50 g, eluate; 1% triethylamine-containing 10:1→1:1 hexane-ethyl acetate) to give the title compound (1.08 g, 52.6%) as a colorless oil.

$^1$H-NMR (400 MHz, CDCl$_8$): δ0.84 (d, 6H, J=6.6 Hz), 0.86 (d, 6H, J=6.6 Hz), 0.97 (d, 3H, J=6.6 Hz), 1.00-1.41 (m, 32H), 1.46-1.56 (m, 1H), 1.94-2.18 (m, 2H), 2.21-2.33 (m, 1H), 2.34-2.46 (m, 2H), 2.62 (t, 1H, J=6.3 Hz), 2.67-2.83 (m, 1H), 3.34-3.67 (m, 5H), 3.69-3.86 (m, 1H), 3.80 (s, 3H), 3.81 (s, 3H), 4.20-4.24 (m, 1H), 4.55-4.66 (m, 1H), 6.22-6.29 (m, 1H), 6.82-6.87 (m, 4H), 7.10-7.14 (m, 1H), 7.21-7.33 (m, 7H), 7.36-7.42 (m, 2H), 7.94 (brs, 1H), 8.17-8.29 (m, 1H)

$^{31}$P-NMR (160 MHz, CDCl$_3$): δ 150.0, 150.6 m/z(ESI-MS): Anal. Calc. for C$_{59}$H$_{86}$N$_5$O$_8$P: 1023.6. Found 1022.3 (M–H)$^-$ Example 4

Synthesis of N$^3$-[4-(3,7-dimethyl-1-octyloxy)benzoyl]-2'-deoxythymidine (1) Synthesis of 4-(3,7-dimethyl-1-octyloxy)benzoyl chloride Under an argon atmosphere, 4-(3,7-dimethyl-1-octyloxy) benzoic acid was dissolved in anhydrous chloroform (25 ml), and after ice-cooling, thionyl chloride (6.72 ml, 92.7 mmol) was added dropwise. The reaction mixture was stirred at room temperature overnight and concentrated under reduced pressure to give the title compound as an oil. The present compound was directly used for the next step.

(2) Synthesis of 3',5'-O-bis(trimethylsilyl)-N$^3$-[4-(3,7-dimethyl-1-octyloxy)benzoyl]2'-deoxythymidine 2'-Deoxythymidine (5.00 g, 20.6 mmol) was azeotropically distilled 3 times with anhydrous pyridine (10 ml), and under an argon atmosphere, the mixture was dissolved in anhydrous pyridine (60 ml), N,N-diisopropylethylamine (17.9 ml, 103 mmol) and trimethylsilyl chloride (6.50 ml, 51.5 mmol) were added, and the mixture was stirred at room temperature for 30 min. After stirring, an oil of the aforementioned 4-(3,7-dimethyl-1-octyloxy)benzoyl chloride was added dropwise over 25 min, and thereafter the mixture was stirred at room temperature for 4 hr. The reaction mixture after completion of the reaction was ice-cooled, potassium dihydrogen phosphate (17 g) and water (80 ml) were added, and the mixture was stirred for 5 min. The mixture was extracted with diethyl ether (100 ml), washed with saturated aqueous potassium dihydrogen phosphate solution (50 ml) and saturated brine (50 ml), the obtained organic layer was dried over sodium sulfate and filtered, and the filtrate was concentrated under reduced pressure to give the title compound. The present compound was directly used for the next step.

(3) Synthesis of N$^3$-[4-(3,7-dimethyl-1-octyloxy) benzoyl]-2'-deoxythymidine

3',5'-O-bis-(trimethylsilyl)-N$^3$-[4-(3,7-dimethyl-1-octyloxy)benzoyl]-2'-deoxythymidine was dissolved in a mixed solvent of chloroform (70 ml) and methanol (70 ml), trifluoroacetic acid (350 μl) was added, and the mixture was stirred at room temperature for 30 min. After completion of the reaction, the solvent was evaporated and dissolved again in ethyl acetate (150 ml). The mixture was washed with 5% aqueous sodium hydrogen carbonate solution (75 ml) and saturated brine (75 ml), and the organic layer was dried over sodium sulfate and filtered. The solvent in the filtrate was evaporated and the obtained residue was purified by silica gel column chromatography (dichloromethane/methanol) to give the title compound (7.10 g, 68.5%) as a white solid.

Example 5

Synthesis of 5'-O-(4,4'-dimethoxytrityl)-N$^3$-[4-(3,7-dimethyl-1-octyloxy)benzoyl]-2'-deoxythymidine Under an argon atmosphere, N$^3$-[4-(3,7-dimethyl-1-octyloxy)benzoyl]-2'-deoxythymidine (7.10 g, 14.1 mmol) was azeotropically distilled 3 times with anhydrous pyridine (10 ml) and dissolved in anhydrous pyridine (130 ml). 4,4'-Dimethoxytrityl chloride (4.83 g, 14.3 mmol) was added, and the mixture was stirred overnight. Water (130 ml) was added to the reaction mixture after completion of the reaction, and the mixture was extracted with diethyl ether (260 ml) and washed with water (130 ml). The organic layer was dried over sodium sulfate and filtered, the filtrate was concentrated, and the obtained residue was purified by silica gel column chromatography (dichloromethane/methanol, 1% v/v triethylamine) to give the title compound (10.2 g, 90.1%) as a white solid.

Example 6

Synthesis of 5'-O-(4,4'-dimethoxytrityl)-N$^3$-[4-(3,7-dimethyl-1-octyloxy)benzoyl]-2'-deoxythymidine-3'-O-[(2-cyanoethyl)-N,N-diisopropylphosphoramidite] [5'-O-DMTr-dT$^{(4\text{-}Cit\text{-}Bz)}$-PA]

Under an argon atmosphere, 5'-O-(4,4'-dimethoxytrityl)-N$^3$-[4-(3,7-dimethyl-1-octyloxy)benzoyl]-2'-deoxythymidine (6.47 g, 8.03 mmol) was azeotropically distilled 3 times with anhydrous acetonitrile (10 ml) and dissolved in anhydrous dichloromethane (40 ml). Under ice-cooling, N,N-diisopropylethylamine (5.60 ml, 32.0 mmol) was added, and a solution of chloro-2-cyanoethyl-N,N-diisopropylphosphoramidite (2.36 ml, 10.0 mmol) in dichloromethane (40 ml) was added dropwise over 20 min. The reaction mixture was stirred at room temperature for 30 min and concentrated under reduced pressure, and the obtained residue was purified by silica gel column chromatography (hexane/ethyl acetate, 3% v/v triethylamine) to give the title compound (7.32 g, 91.0%) as a white solid.

Example 7

Synthesis of 5'-O-(4,4'-dimethoxytrityl)-3'-O-levulinoyl-N$^3$-(3,7,11,15-tetramethyl-1-hexadecanoyloxy) methyl-2'-deoxythymidine Under an argon atmosphere, potassium carbonate (2.10 g, 15.2 mmol) was suspended in anhydrous N,N-dimethylformamide (50 ml), the compound synthesized in Preparation Example 19 (3.65 g, 10.1 mmol) and 5'-O-(4,4'-dimethoxytrityl)-3'-O-levulinoyl-2'-deoxythymidine (3.25 g, 5.06 mmol) were dissolved therein, and the mixture was stirred at 40° C. for 24 hr. The reaction mixture was filtered, water (50 ml) was added, and the mixture was extracted twice with diethyl ether (100 ml). The organic layer was washed with water (100 ml), dried over sodium sulfate, filtered and concentrated under reduced pressure. The obtained residue was purified by silica gel column chromatography (dichloromethane, 1% v/v triethylamine) to give the title compound (4.80 g, 98%) as a pale-yellow viscous solid.

Example 8

Synthesis of 5'-O-(4,4'-dimethoxytrityl)-N$^3$-(3,7,11, 15-tetramethyl-1-hexadecanoyloxy)methyl-2'-deoxythymidine The compound synthesized in Example 7 (4.80 g, 4.96 mmol) was dissolved in a mixed solvent of pyridine (40 ml) and acetic acid (10 ml), anhydrous hydrazine (244 µl, 7.71 mmol) was added, and the mixture was stirred at room temperature for 30 min. Acetylacetone (1.07 ml, 10.3 mmol) was added and the mixture was stirred at room temperature for 5 min. Diethyl ether (100 ml) was added, and the mixture was washed successively with 10% aqueous hydrogen sulfate potassium solution (50 ml), 10% aqueous sodium hydrogen carbonate solution (50 ml) and saturated brine (50 ml). The organic layer was concentrated to give the title compound (3.58 g, 83.0%) as a pale-yellow viscous solid.

Example 9

Synthesis of 5'-O-(4,4'-dimethoxytrityl)-N$^3$-(3,7,11, 15-tetramethyl-1-hexadecanoyloxy)methyl-2'-deoxythymidine-3'-O-[(2-cyanoethyl)-N,N-diisopropylphosphoramidite] [5'-O-DMTr-dT$^{PhyOM}$-PA]

Under an argon atmosphere, the compound synthesized in Example 8 (3.58 g, 4.12 mmol) was azeotropically distilled 3 times with anhydrous acetonitrile (10 ml) and dissolved in anhydrous dichloromethane (22 ml). N,N-diisopropylethylamine (2.49 ml, 16.5 mmol) was added dropwise, and chloro-2-cyanoethyl-N,N-diisopropylphosphoramidite (1.15 ml, 5.15 mmol) was dissolved in anhydrous dichloromethane (22 ml) was added dropwise over 20 min. After stirring at room temperature for 30 min, the mixture was concentrated under reduced pressure and the obtained residue was purified by silica gel column chromatography (hexane/ethyl acetate=8/2, 3% v/v triethylamine) to give the title compound (3.90 g, 88.6%) as a pale-yellow viscous solid.

Example 10

Synthesis of 5'-O-(4,4'-dimethoxytrityl)-N$^3$-(3,7,11, 15-tetramethyl-1-hexadecanoyloxy)methyl-2'-deoxythymidine-3'-O-[(2-cyanoethyl)-N,N-diisopropylphosphoramidite] [5'-O-DMTr-dr$^{PhyOM}$-PA]

Under an argon atmosphere, 5'-O-(4,4'-dimethoxytrityl)-2'-deoxythymidine-3'-O-[(2-cyanoethyl)-N,N-diisopropylphosphoramidite] (1.00 g, 1.34 mmol) was dissolved in anhydrous N,N-dimethylformamide (15 ml), potassium carbonate (279 mg, 2.02 mmol) and (3,7,11,15-tetramethyl-1-hexadecanoyloxy)methyl chloride (970 mg, 2.69 mmol) were added, and the mixture was stirred at room temperature for 16 hr. The reaction mixture was filtered, water (20 ml) was added and the mixture was extracted with diethyl ether (50 ml). The organic layer was dried over sodium sulfate and filtered, the filtrate was concentrated under reduced pressure, and the obtained residue was purified by silica gel column chromatography (ethyl acetate/hexane, 3% v/v triethylamine) to give the title compound (929 mg, 65.0%) as a pale-yellow viscous solid.

Example 11

Synthesis of 5'-O-(4,4'-dimethoxytrityl)-N$^2$-(3,7,11, 15-tetramethyl-1-hexadecanoyl)-2'-deoxyguanosine-3'-O-[(2-cyanoethyl)-N,N-diisopropylphosphoramidite] [5'-O-DMTr-dG$^{Phy}$-PA]

Under an argon atmosphere, 5'-O-(4,4'-dimethoxytrityl)-2'-deoxyguanosine-3'-O-[(2-cyanoethyl)-N,N-diisopropylphosphoramidite] (1.52 g, 1.98 mmol) was dissolved in anhydrous tetrahydrofuran (20 ml), N,N-diisopropylethylamine (696 µl, 4.00 mmol) was added, and 3,7,11,15-tetramethyl-1-hexadecanoyl chloride (993 mg, 3.00 mmol) synthesized in Preparation Example 18 was added dropwise. After stirring at room temperature for 1.5 hr, the reaction mixture was concentrated and the obtained residue was purified by silica gel column chromatography (dichloromethane/methanol, 1% v/v triethylamine) to give the title compound (1.73 g, 82.0%) as a pale-yellow viscous solid.

Example 12

Synthesis of 5'-O-(4,4'-dimethoxytrityl)-N$^6$-(3,7,11, 15-tetramethyl-1-hexadecanoyl)-2'-deoxyadenosine-3'-O-[(2-cyanoethyl)-N,N-diisopropylphosphoramidite] [5'-O-DMTr-dA$^{Phy}$-PA]

Using 5'-O-(4,4'-dimethoxytrityl)-2'-deoxyadenosine-3'-O-[(2-cyanoethyl)-N,N-diisopropylphosphoramidite] (1.76 g, 2.33 mmol) and in the same manner as in Example 11, the title compound (1.12 g, 45.8%) was obtained as a pale-yellow viscous solid.

Example 13

Synthesis of deoxythymidinyl-[3→5']-deoxythymidinyl-[3'→5']-deoxythymidine (5'-d[TTT]-3')

(1) Synthesis of 5'-O-DMTr-dT$^{PhyOM}$-dT-suc-NH-TPB

Under an argon atmosphere, 5'-O-DMTr-dT-suc-NH-TPB (206 mg, 127 µmol) synthesized in Example 2 was dissolved in a mixed solvent of anhydrous heptane (650 µl) and anhydrous toluene (650 µl), trifluoroacetic acid (26.0 µl, 350 µmol) and 1H-pyrrole (17.5 µl, 254 µmol) were added, and the mixture was stirred for 5 min. The completion of the deprotection was confirmed by thin layer chromatography, pyridine (28.3 µl, 350 µmol) and N-methylimidazole (13.9 µl, 175 µmol) were added, and the mixture was stirred for 5 min. To the reaction mixture after neutralization was added the compound synthesized in Example 10 (271 mg, 254 µmol) dissolved in 0.25 mol/l 5-(benzylthio)-1H-tetrazole/acetonitrile solution (1.0 ml), and the mixture was stirred for 10 min. 0.2 mol/l Iodine pyridine/tetrahydrofuran/water=49/49/2 solution (1.27 ml) was added and the mixture was stirred for 5 min. To the reaction mixture after completion of the reaction was added heptane (5.0 ml) to allow phase separation. The lower layer was extracted, washed with a mixed solution of acetonitrile (1.0 ml) and water (80 µl), and the obtained organic layer was concentrated under reduced pressure to give the title compound (291 mg, 99.5%) as a viscous solid.

(2) Synthesis of 5'-O-DMTr-dT$^{PhyOM}$-dT$^{PhyOM}$-dT-suc-NH-TPB

Using the compound synthesized in Example 13-(1) (291 mg, 126 µmol) and the compound synthesized in Example 10

(271 mg, 254 μmol), and in the same manner as in Example 13-(1), the title compound (369 mg, 98.0%) was obtained as a viscous solid.

(3) Synthesis of deoxythymidinyl-[3'→5']-deoxythymidinyl-[3'→5']-deoxythymidine (5'-d[TTT]-3')

The compound synthesized in Example 13-(2) and a solution (4.0 ml) of 28% aqueous ammonia solution:40% aqueous methylamine solution=1:1 were placed in an autoclave, the mixture was heated at 65° C. for 16 hr, and concentrated by a rotary evaporator under reduced pressure. The mixture was adsorbed to C-18 reversed-phase cartridge column and washed with 0.1 mol/L aqueous ammonium acetate solution. A dimethoxytrityl group bonded to the hydroxyl group at the 5'-terminal was deprotected with 2% aqueous trifluoroacetic acid solution and eluted with 20% aqueous acetonitrile solution to give the title compound.

m/z(ESI-MS): Anal. Calc. for $C_{30}H_{40}N_6O_{19}P_2$: 850.2. Found 849.1 $(M-H)^-$ Example 14

Synthesis of deoxythymidinyl-[3'→5']-deoxythymidinyl-[3'→5']-deoxythymidine (5'-d[TTT]-3')

(1) Synthesis of 5'-O-DMTr-dT$^{(4-Cit-Bz)}$-dT-suc-NH-TPB

Using 5'-O-DMTr-dT-suc-NH-TPB synthesized in Example 2 (206 mg, 127 μmol) and the compound synthesized in Example 6 (256 mg, 254 μmol), and in the same manner as in Example 13-(1), the title compound (273 mg, 96.0%) was obtained as a viscous solid.

(2) Synthesis of 5'-O-DMTr-dT$^{(4-Cit-Bz)}$-dT$^{(4-Cit-Bz)}$-dT-suc-NH-TPB

Using the compound synthesized in Example 14-(1) (273 mg, 122 μmol) and the compound synthesized in Example 6 (256 mg, 254 μmol), and in the same manner as in Example 13-(1), the title compound (339 mg, 97.5%) was obtained as a viscous solid.

(3) Synthesis of deoxythymidinyl-[3'→5']-deoxythymidinyl-[3'→5']-deoxythymidine (5'-d[TTT]-3')

Using the compound synthesized in Example 14-(2) and in the same manner as in Example 13-(3), the title compound was obtained.

m/z(ESI-MS): Anal. Calc. for $C_{30}H_{40}N_6O_{19}P_2$: 850.18. Found 849.1 $(M-H)^-$ Example 15

Synthesis of deoxyadenylyl-[3'→5']-deoxyadenylyl-[3'→5']-deoxythymidine (5'-d[AAT]-3')

(1) Synthesis of 5'-O-DMTr-dA$^{Phy}$-dT-suc-NH-TPB

Under an argon atmosphere, 5'-O-DMTr-dT-suc-NH-TPB (213 mg, 131 μmol) synthesized in Example 2 was dissolved in a mixed solvent of anhydrous heptane (700 μl) and anhydrous toluene (700 μl), trifluoroacetic acid (28.0 μl, 377 μmol) and 1H-pyrrole (18.1 μl, 262 μmol) were added, and the mixture was stirred for 5 min. The completion of the deprotection was confirmed by thin layer chromatography, pyridine (30.5 μl, 377 μmol) and N-methylimidazole (15.0 μl, 189 μmol) were added, and the mixture was stirred for 5 min. To the reaction mixture after neutralization was added the compound synthesized in Example 12 (275 mg, 262 μmol) dissolved in a mixed solvent of 0.25 mol/l 5-(benzylthio)-1H-tetrazole/acetonitrile solution (1.0 ml) and anhydrous toluene (300 μl), and the mixture was stirred for 10 min. 5.78 mol/l tert-Butyl hydroperoxide/nonane solution (45.3 μl) was added and the mixture was stirred for 5 min. To the reaction mixture after completion of the reaction was added heptane (4.0 ml) to allow layer separation. The lower layer was extracted and washed with a mixed solution of acetonitrile (1.0 ml) and water (80 μl), and the obtained organic layer was concentrated under reduced pressure to give the title compound (301 mg) as a viscous solid quantitatively.

(2) Synthesis of 5'-O-DMTr-dA$^{Phy}$-dA$^{Phy}$-dT-suc-NH-TPB

Using the compound synthesized in Example 15-(1) (301 mg, 131 μmol) and the compound synthesized in Example 12 (275 mg, 262 μmol), and in the same manner as in Example 15-(1), the title compound (387 mg) was obtained as a viscous solid quantitatively.

(3) Synthesis of deoxyadenylyl-[3'→5']-deoxyadenylyl-[3'-35']-deoxythymidine (5'-d[AAT]-3')

The compound synthesized in Example 15-(2) and 28% aqueous ammonia solution (4.0 ml) were placed in an autoclave, the mixture was heated at 65° C. for 16 hr, and concentrated by a rotary evaporator under reduced pressure. The concentrated solution was adsorbed to C-18 reversed-phase cartridge column and washed with 0.1 mol/L aqueous ammonium acetate solution. A dimethoxytrityl group bonded to the hydroxyl group at the 5'-terminal was deprotected with 2% aqueous trifluoroacetic acid solution and eluted with 20% aqueous acetonitrile solution to give the title compound.

m/z(ESI-MS): Anal. Calc. for $C_{30}H_{38}N_{12}O_{15}P_2$: 868.21. Found 867.1 $(M-H)^-$ Example 16

Synthesis of deoxyguanosinyl-[3'→5']-deoxyguanosinyl-[3'→5']-deoxythymidine (5'-d[GGT]-3')

(1) Synthesis of 5'-O-DMTr-dG$^{Phy}$-dT-suc-NH-TPB

Using 5'-O-DMTr-dT-suc-NH-TPB (201 mg, 124 μmol) synthesized in Example 2 and the compound (266 mg, 250 μmol) synthesized in Example 11, and in the same manner as in Example 15-(1), the title compound (303 mg) was obtained as a viscous solid quantitatively.

(2) Synthesis of 5'-O-DMTr-dG$^{Phy}$-dG$^{Phy}$-dT-suc-NH-TPB

Under an argon atmosphere, using the compound synthesized in Example 16-(1) (303 mg, 124 μmol) and the compound synthesized in Example 11 (265 mg, 249 μmol), and in the same manner as in Example 15-(1), the title compound (400.0 mg) was obtained as a viscous solid quantitatively.

(3) Synthesis of deoxyguanosinyl-[3'→5']-deoxyguanosinyl-[3'→5']-deoxythymidine (5'-d[GGT]-3')

Using the compound synthesized in Example 16-(2) (23.8 mg, 7.37 mmol) and in the same manner as in Example 15-(3), the title compound was obtained.

m/z(ESI-MS): Anal. Calc. for $C_{30}H_{38}N_{12}O_{17}P_2$: 900.20. Found 900.8 $(M+H)^+$

Example 17

Synthesis of deoxycytidinyl-[3'-5']-deoxycytidinyl-[3'→5']-deoxythymidine (5'-d[CCT]-3')

(1) Synthesis of 5'-O-DMTr-dC$^{Phy}$-dT-suc-NH-TPB

Under an argon atmosphere, using 5'-O-DMTr-dT-suc-NH-TPB (203 mg, 125 µmol) synthesized in Example 2 and the compound synthesized in Example 3 (260 mg, 254 µmol), and in the same manner as in Example 15-(1), the title compound (366.9 mg) was obtained as a viscous solid quantitatively.

(2) Synthesis of 5'-O-DMTr-dC$^{Phy}$-dC$^{Phy}$-dT-suc-NH-TPB

Under an argon atmosphere, using the compound synthesized in Example 17-(1) (367 mg, 125 µmol) and the compound synthesized in Example 3 (262 mg, 256 µmol), and in the same manner as in Example 15-(1), the title compound (394 mg) was obtained as a viscous solid quantitatively.

(3) Synthesis of deoxycytidinyl-[3'→5']-deoxycytidinyl-[3'→5']-deoxythymidine (5'-d[CCT]-3')

Using the compound synthesized in Example 17-(2) (20.8 mg, 6.59 mmol) and in the same manner as in Example 13-(3), the title compound was obtained.
m/z(ESI-MS): Anal. Calc. for $C_{28}H_{38}N_8O_{17}P_2$: 820.2. Found 819.1 (M−H)⁻

Example 18

Synthesis of 5'-O-DMTr-dT$^{PhyOM}$-dT$^{PhyOM}$-dT$^{PhyOM}$-dT$^{PhyOM}$-dT$^{PhyOM}$-dT$^{PhyOM}$-dT$^{PhYOM}$-dT$^{PhyOM}$-dT$^{PhyOM}$-dT$^{PhyOM}$-dT$^{PhyOM}$-dT$^{PhyOM}$-dT$^{PhyOM}$-dT$^{PhyOM}$-dT$^{PhyOM}$-dT$^{PhyOM}$-dT$^{PhyOM}$-dT$^{PhyOM}$-dT-suc-NH-TPB (1) Under an argon atmosphere, 5'-O-DMTr-dT-suc-NH-TPB (208 mg, 128 µmol) synthesized in Example 2 was dissolved in a mixed solvent of anhydrous heptane (650 µl) and anhydrous toluene (650 µl), trifluoroacetic acid (26.0 µl, 350 µmol) and 1H-pyrrole (17.7 µl, 256 µmol) were added, and the mixture was stirred for 5 min. The completion of the deprotection was confirmed by thin layer chromatography, pyridine (28.3 µl, 350 µmol) and N-methylimidazole (13.9 µl, 175 µmol) were added, and the mixture was stirred for 5 min. To the reaction mixture after neutralization was added the compound synthesized in Example 9 (273 mg, 256 µmol) dissolved in 0.25 mol/l 5-(benzylthio)-1H-tetrazole/acetonitrile solution (1.0 ml), and the mixture was stirred for 10 min. 5.78 mol/l tert-Butyl hydroperoxide/nonane solution (383 µmol, 66.3 µl) was added and the mixture was stirred for 5 min. The reaction mixture after completion of the reaction was partitioned by adding heptane (3.0 ml), the lower layer was extracted, washed with a mixed solution of acetonitrile (1.0 ml) and water (80 µl), and the obtained organic layer was concentrated under reduced pressure to give a compound same as that synthesized in Example 14-(1) (291 mg, 98.8%) as a viscous solid.
(2) By repeating a similar operation 18 times, the title compound (1.67 g, 89.6%) was obtained as an orange solid.

Example 19

Synthesis of 5'-O-(4,4'-dimethoxytrityl)-N$^4$-(2-ethyl-1-hexanoyl)-2'-deoxycytidine-3'-O-[(2-cyanoethyl)-N,N-diisopropylphosphoramidite] [5'-O-DMTr-dC$^{(2Et-Hex)}$-PA]

Under an argon atmosphere, 5'-O-(4,4'-dimethoxytrityl)-2'-deoxycytidine-3'-O-[(2-cyanoethyl)-N,N-diisopropylphosphoramidite] (20.4 g, 28.0 mmol) was dissolved in tetrahydrofuran (200 ml), N,N-diisopropylethylamine (7.4 g, 57.0 mmol) and 2-ethyl-1-hexanoic anhydride (11.4 g, 42.0 mmol) were added, and the mixture was stirred at room temperature for 3 days. To the reaction mixture after completion of the reaction were added ethyl acetate and water, and the mixture was extracted. The ethyl acetate layer was washed with 5% aqueous sodium hydrogen carbonate solution and saturated brine. The organic layer was dried over anhydrous sodium sulfate, the solvent was evaporated under reduced pressure, and the obtained crude product was purified by silica gel column chromatography (eluate; 1% triethylamine-containing 10:1→1:1 heptane-ethyl acetate) to give the title compound (15.9 g, 66.5%).

Example 20

Synthesis of 5'-O-(4,4'-dimethoxytrityl)-N$^4$-(3,5,5-trimethyl-1-hexanoyl)-2'-deoxycytidine-3'-O-[(2-cyanoethyl)-N,N-diisopropylphosphoramidite] [5'-O-DMTr-dC$^{(3,5,5-Me3Hex)}$-PA]

(1) Synthesis of N$^4$-(3,5,5-trimethyl-1-hexanoyl)-2'-deoxycytidine

Suspending 2'-Deoxycytidine (2.3 g, 10.0 mmol) in dry pyridine, followed by concentration under reduced pressure was repeated 3 times to perform dehydrative azeotropic distillation, the concentrate was suspended again in dry pyridine (60 ml), and trimethylsilyl chloride (6.4 ml, 50 mmol) was added dropwise over 5 min. To the reaction mixture was added 3,5,5-trimethyl-1-hexanoyl chloride (9.5 ml, 50.0 mmol) over 5 min. After completion of the reaction, under ice-cooling, aqueous ammonia (25 ml) was added and the mixture was reacted for 20 min. The reaction mixture was concentrated under reduced pressure. Water (150 ml) was added to the concentrate, and the mixture was extracted 3 times with ethyl acetate (100 ml). The organic layer was concentrated and the obtained oil was purified by silica gel column chromatography to give the title compound (4.7 g).

(2) Synthesis of 5'-O-(4,4'-dimethoxytrityl)-N$^4$-(3,5,5-trimethyl-1-hexanoyl)-2'-deoxycytidine Dissolving the compound obtained in Example 20-(1) (4.7 g) in dry pyridine, followed by concentration under reduced pressure was repeated 3 times to perform dehydrative azeotropic distillation, and the concentrate was dissolved in dry pyridine (40 ml). 4,4'-Dimethoxytrityl chloride (3.8 g, 11.0 mmol) was added and the mixture was stirred for 30 min. Water (100 ml) was added to the reaction mixture and the mixture was extracted 3 times with ethyl acetate (100 ml). The organic layer was further washed with water and concentrated under reduced pressure, and the obtained oil was purified by silica gel column chromatography to give the title compound (5.2 g, 77.3%).

(3) Synthesis of 5'-O-(4,4'-dimethoxytrityl)-N⁴-(3,5,5-trimethyl-1-hexanoyl)-2'-deoxycytidine-3'-O-[(2-cyanoethyl)-N,N-diisopropylphosphoramidite] [5'-O-DMTr-dC$^{(3,5,5\text{-}Me3Hex)}$-PA]

Dissolving the compound obtained in Example 20-(2) in dry acetonitrile (5 ml), followed by concentration under reduced pressure was repeated 3 times to perform dehydrative azeotropic distillation and the concentrate was dissolved in dry dichloromethane (30 ml). N,N-diisopropylethylamine (5.4 ml, 30.9 mmol) was added dropwise over 5 min, and a solution of chloro-2-cyanoethyl-N,N-diisopropylphosphoramidite (2.2 ml, 9.7 mmol) in dichloromethane (30 ml) was added dropwise over 15 min. After reaction at room temperature for 30 min, the reaction mixture was concentrated under reduced pressure, and the obtained oil was purified by silica gel column chromatography (dichloromethane/methanol/triethylamine=94/3/3). The fractions containing the object product were concentrated to dryness to give the title compound (3.7 g, 55.3%) as a white solid.

Example 21

Synthesis of 5'-O-(4,4'-dimethoxytrityl)-N⁴-(2,2,4,8,10,10-hexamethyl-5-dodecanoyl)-2'-deoxycytidine-3'-O-[(2-cyanoethyl)-N,N-diisopropylphosphoramidite] [5'-O-DMTr-dC$^{(Me6Dodecanoyl)}$-PA]

According to the method described in Example 19, the title compound (16.5 g, 47.3%) was prepared from 5'-O-(4,4'-dimethoxytrityl)-2'-deoxycytidine-3'-O-[(2-cyanoethyl)-N,N-diisopropylphosphoramidite] (25.6 g, 35.1 mmol) using 2,2,4,8,10,10-hexamethyl-5-dodecanoyl chloride (16.5 g, 54.5 mmol) as an acylating agent.

Example 22

Synthesis of 5'-O-(4,4'-dimethoxytrityl)-N⁴-(2-heptyl-1-undecanoyl)-2'-deoxycytidine-3'-O-[(2-cyanoethyl)-N,N-diisopropylphosphoramidite] [5'-O-DMTr-dC$^{(2\text{-}HepUndecanoyl)}$-PA]

According to the method described in Example 19, 5'-O-(4,4'-dimethoxytrityl)-2'-deoxycytidine-3'-O-[(2-cyanoethyl)-N,N-diisopropylphosphoramidite] (1.8 g, 2.5 mmol) was reacted with 2-heptyl-1-undecanoic anhydride (2.1 g, 3.8 mmol) as an acylating agent. Since the reaction proceeds slowly, 2-heptyl-1-undecanoyl chloride (1.2 g, 3.8 mmol) was added again as an acylating agent, and the mixture was reacted for 30 min. After completion of the reaction, the mixture was extracted with chloroform, and the organic layer was washed with 5% aqueous sodium hydrogen carbonate solution, concentrated and purified by silica gel column chromatography to prepare the title compound (1.7 g, 67.5%).

Example 23

Synthesis of 5'-O-(4,4'-dimethoxytrityl)-N⁴-(2-hexyl-1-decanoyl)-2'-deoxycytidine-3'-O-[(2-cyanoethyl)-N,N-diisopropylphosphoramidite] [5'-O-DMTr-dC$^{(2\text{-}HexDecanoyl)}$-PA]

According to the method described in Example 19, the title compound (12.6 g, 47.0%) was prepared from 5'-O-(4,4'-dimethoxytrityl)-2'-deoxycytidine-3'-O-[(2-cyanoethyl)-N, N-diisopropylphosphoramidite] (20.2 g, 28.0 mmol), using 2-hexyl-1-decanoylchloride (11.4 g, 41.0 mmol) as an acylating agent.

Example 24

Synthesis of 5'-O-(4,4'-dimethoxytrityl)-N⁴-n-tetradecanoyl-2'-deoxycytidine-3'-O-[(2-cyanoethyl)-N,N-diisopropylphosphoramidite][5'-O-DMTr-dC$^{Myr}$-PA]

According to the method described in Example 19, the title compound (1.3 g, 49.2%) was prepared from 5'-O-(4,4'-dimethoxytrityl)-2'-deoxycytidine-3'-O-[(2-cyanoethyl)-N,N-diisopropylphosphoramidite] (2.0 g, 2.7 mmol), using the corresponding tetradecanoyl chloride (751 mg, 3.0 mmol) as an acylating agent.

Example 25

Synthesis of 5'-O-(4,4'-dimethoxytrityl)-N²-[bis(3,7-dimethyl-octyl)amino-methylene]-2'-deoxyguanosine-3'-O-[(2-cyanoethyl)-N,N-diisopropylphosphoramidite] [5'-O-DMTr-dG$^{(N,N\text{-}Cit2\text{-}methylene)}$-PA]

Suspending 5'-O-(4,4'-dimethoxytrityl)-2'-deoxyguanosine-3'-O-[(2-cyanoethyl)-N,N-diisopropylphosphoramidite] (1.0 g, 1.3 mmol) obtained in Preparation Example 22 in dry pyridine, followed by concentration under reduced pressure was repeated twice, the concentrate was further dissolved in toluene, concentrated under reduced pressure, and subjected to dehydrative azeotropic distillation. Thereafter, in dry methanol (2.6 ml), the concentrate was reacted with the compound synthesized in Preparation Example 23 overnight and concentrated under reduced pressure, and the obtained oil was purified by silica gel column chromatography to give the title compound (184 mg, 13.1%).

Example 26

Synthesis of dA$^{Bz}$-dC$^{Bz}$-dA$^{Bz}$-dT-dG$^{ibu}$-dC$^{Bz}$-dA$^{Bz}$-dT-dT-suc-NH-TPB (1) Synthesis of dT-dT-suc-NH-TPB Under an argon atmosphere, 5'-O-DMTr-dT-suc-NH-TPB (225 mg, 139 µmol) was dissolved in anhydrous cyclopentyl methyl ether (1.0 ml), and 1H-pyrrole (9.6 µl, 139 µmol) was added. Furthermore, 20 µl of a solution (2.0 ml) of trifluoromethanesulfonic acid (24.4 µl, 2.78 µmol) in cyclopentyl methyl ether, prepared separately, was added, and the mixture was stirred at room temperature for 10 min. The completion of the deprotection was confirmed by thin layer chromatography, and the mixture was neutralized with a solution (14.0 µl, 176 µmol) of 0.2 mol/l N-methylimidazole in cyclopentyl methyl ether. dT-CE Phosphoramidite (5'-O-(4,4'-dimethoxytrityl)deoxythymidine-3'-[O-(2-cyanoethyl)-(N,N-diisopropyl)]-phosphoramidite) (207 mg, 278 µmol) dissolved in 0.3 mol/l 4,5-dicyanoimidazole/acetonitrile solution was added and the mixture was stirred for 10 min. Thereafter, pH 6.8 phosphoric acid buffer (1.0 ml), aqueous hydrogen peroxide (47 µl, 417 µmol) and potassium iodide (23.1 mg, 139 µmol) were added to the reaction mixture, and the mixture was stirred for 15 min. The reaction mixture was washed with 10% aqueous sodium thiosulfate solution. To the obtained organic layer were added 1H-pyrrole (9.6 µl, 139 µmol) and trifluoroacetic acid (206 µl, 2.8 mmol) and the mixture was stirred for 10 min. The organic layer was washed with 10% aqueous potassium hydrogen sulfate solution, 10% aqueous sodium hydrogen carbonate solution and brine. The obtained organic layer was concentrated under reduced pressure to give the title compound (316 mg) as a viscous solid quantitatively.

(2) Synthesis of dA$^{Bz}$-dT-dT-suc-NH-TPB

The compound obtained in Example 26-(1) (316 mg) was dissolved in dichloromethane (2.0 ml), dA-CE phosphoramidite (5'-O-(4,4'-dimethoxytrityl)-N$^6$-benzoyl-2'-deoxyadenosine-3'-[O-(2-cyanoethyl)-(N,N-diisopropyl)]-phosphoramidite) (239 mg, 278 µmol) dissolve in 0.3 mol/l 4,5-dicyanoimidazole/acetonitrile solution was added, and the mixture was stirred for 10 min. Thereafter, pH 6.8 phosphoric acid buffer (1.0 ml), potassium iodide (20.0 mg, 97.4 µmol) and aqueous hydrogen peroxide (16.0 µl, 139 µmol) were added to the reaction mixture, and the mixture was stirred for 15 min. The reaction mixture was washed with 10% aqueous sodium thiosulfate solution. To the obtained organic layer were added 1H-pyrrole (9.6 µl, 139 µmol) and trifluoroacetic acid (206 µl, 2.8 mmol) and the mixture was stirred for 10 min. The organic layer was washed with 10% aqueous potassium hydrogen sulfate solution, 10% aqueous sodium hydrogen carbonate solution and brine. The obtained organic layer was concentrated under reduced pressure to give the title compound (442 mg) as a viscous solid quantitatively.

(3) Synthesis of dA$^{Bz}$-dC$^{Bz}$-dA$^{Bz}$-dT-dG$^{ibu}$-dC$^{Bz}$-dA$^{Bz}$-dT-dT-suc-NH-TPB The title compound was synthesized by repeating the method described in Example 26-(2).

Example 27

Synthesis of 5'-O-DMTr-dC$^{(2Et-Hex)}$-dC$^{(2Et-Hex)}$-dT-suc-NH-TPB (1) Synthesis of 5'-O-DMTr-dC$^{(2Et-Hex)}$-dT-suc-NH-TPB Using 5'-O-DMTr-dT-suc-NH-TPB (207 mg, 127 µmol) and the phosphoramidite monomer synthesized in Example 19 (336 mg, 393 µmol), and in the same manner as in Example 15-(1), the title compound (226 mg, 84.9%) was obtained as a viscous solid.

(2) Synthesis of 5'-O-DMTr-dC$^{(2Et-Hex)}$-dC$^{(2Et-Hex)}$-dT-suc-NH-TPB

Under conditions similar to those of Example 27-(1), cytidine derivative was elongated by further using the phosphoramidite monomer synthesized in Example 19 to give the title compound (249 mg, 90.0%).

thin layer chromatography: Rf 0.18 (eluent=ethyl acetate)

Example 28

Synthesis of 5'-O-DMTr-dC$^{(3,5,5-Me3Hex)}$-dC$^{(3,5,5-Me3Hex)}$-dC$^{(3,5,5-Me3Hex)}$-dC$^{(3,5,5-Me3Hex)}$-dT-suc-NH-TPB Based on the method described in Example 27, the title compound (314 mg, 72.2%) was obtained from 5'-O-DMTr-dT-suc-NH-TPB (198.6 mg, 122 µmol) by repeating elongation of cytidine derivative 4 times using the phosphoramidite monomer described in Example 20.

thin layer chromatography: Rf 0.21 (eluent=toluene/acetonitrile=9/1 (v/v))

Example 29

Synthesis of 5'-O-DMTr-dC$^{(2-HepUndecanoyl)}$-dC$^{(2-HepUndecanoyl)}$-dC$^{(2-HepUndecanoyl)}$-dC$^{(2-HepUndecanoyl)}$-dC$^{(2-HepUndecanoyl)}$-dC$^{(2-HepUndecanoyl)}$-dC$^{(2-HepUndecanoyl)}$-dC$^{(2-HepUndecanoyl)}$-dC$^{(2-HepUndecanoyl)}$-dT-suc-NH-TPB Based on the method described in Example 27, the title compound (210 mg, 49.1%) was obtained from 5'-O-DMTr-dT-suc-NH-TPB (203 mg, 125 µmol) by repeating elongation of cytidine derivative 9 times using the phosphoramidite monomer described in Example 22.

thin layer chromatography: Rf 0.13 (eluent=ethyl acetate)

Example 30

Synthesis of 5'-O-DMTr-dC$^{Myr}$-dC$^{Myr}$-dC$^{Myr}$-dC$^{Myr}$-dT-suc-NH-TPB Based on the method described in Example 27, the title compound (199 mg, 82.2%) was obtained from 5'-O-DMTr-dT-suc-NH-TPB (102 mg, 63.1 µmol) by repeating elongation of cytidine derivative 4 times using the phosphoramidite monomer described in Example 24.

thin layer chromatography: Rf 0.14 (eluent=ethyl acetate)

Example 31

Synthesis of 5'-O-DMTr-dC$^{(Me6Dodecanoyl)}$-dC$^{(Me6Dodecanoyl)}$-dC$^{(Me6Dodecanoyl)}$-dC$^{(Me6Dodecanoyl)}$-dC$^{(Me6Dodecanoyl)}$-dC$^{Phy}$-dC$^{Phy}$-dC$^{Phy}$-dC$^{Phy}$-dT-suc-NH-TPB Based on the method described in Example 27, 5'-O-DMTr-dC$^{Phy}$-dC$^{Phy}$-dC$^{Phy}$-dC$^{Phy}$-dT-suc-NH-TPB (534 mg, 97.9%) was obtained from 5'-O-DMTr-dT-suc-NH-TPB (210 mg, 129 µmol) by repeating elongation of cytidine derivative 4 times using 5'-O-DMTr-dC$^{Phy}$-PA. Furthermore, based on the method described in Example 27, the title compound (598 mg, 64.6%) was obtained by repeating elongation of cytidine derivative 5 times using 5'-O-DMTr-dC$^{(Me6Dodecanoyl)}$-PA described in Example 21.

Example 32

Synthesis of 2'-deoxycytidine-[3'→5']-2'-deoxycytidine-[3'→5']-2'-deoxycytidine-[3'→5']-2'-deoxycytidine-[3'→5']-2'-deoxycytidine-[3'→5']-deoxycytidine-[3'→5']-2'-deoxycytidine-[3'→5']-2'-deoxycytidine-[3'→5']-2'-deoxycytidine-[3'→5']-2'-deoxythymidine [5'-d(CCCCCCCCCT)-3']

To the compound synthesized in Example 31 (20.0 mg, 2.8 µmol) were added 40% aqueous methylamine solution (2.0 ml) and 28% aqueous ammonia (2.0 ml), and the mixture was reacted in an autoclave at 65° C. for 1 hr. The reaction mixture was concentrated with a rotary evaporator under reduced pressure, adsorbed on C-18 reversed-phase cartridge column, and washed with 0.1 mol/l aqueous ammonium acetate solution. The dimethoxytrityl group bonded to the 5'-terminal hydroxyl group was removed with aqueous 2% trifluoroacetic acid solution, and the mixture was eluted with 20% aqueous acetonitrile solution to give the title compound.

IEX-HPLC (DNA Pac PA200 (4×250 mm)), flow rate 1 ml/min, eluent A 20 mM Tris-HCl (pH 7.5), eluent B 400 mM NaClO$_4$/20 mM Tris-HCl (pH 7.5), gradient 20% to 70% for 30 min, λ=260 nm: RT=6.68 min (94.0 area %)

MALDI-TOF/MS: 2843.87 [M−H]$^-$

Example 33

Synthesis of 5'-O-(4,4'-dimethoxytrityl)-2'-deoxythymidin-3'-yl-N-[2,3,4-tris(2,3-dihydrophytyloxy)benzhydryl]succinamate Using a triethylamine salt (3.52 g, 4.63 mmol) of 5'-O-(4,4'-dimethoxytrityl)-2'-deoxythymidine-3'-O-succinate and 2,3,4-tris(2,3-dihydrophytyloxy)benzhydryl amine (2.92 g, 2.73 mmol) obtained in Preparation Example 24, and in the same manner as in Example 1-(2), a filtrate of the reaction solution was obtained. Said filtrate was concentrated under reduced pressure and the obtained oil was purified by silica gel column chromatography (hexane:ethyl acetate=75:25-50/50 (v/v), containing 3% triethylamine) to give the title compound (3.60 g, 77.6%) as an oil.

Example 34

Synthesis of 5'-O-(4,4'-dimethoxytrityl)-2'-deoxythymidin-3'-yl-N-[4,4'-bis(2,3-dihydrophytyloxy)benzhydryl]succinamate Using a triethylamine salt (2.88 g, 3.79 mmol) of 5'-O-(4,4'-dimethoxytrityl)-2'-deoxythymidine-3'-O-succinate and 4,4'-bis(2,3-dihydrophytyloxy)benzhydryl amine (1.73 g, 2.23 mmol) obtained in Preparation Example 25, and in the same manner as in Example 1-(2), a filtrate of the reaction solution was obtained. Said filtrate was concentrated under reduced pressure and the obtained oil was purified by silica gel column chromatography (hexane:ethyl acetate=100:0-30/70 (v/v), containing 3% triethylamine) to give the title compound (1.87 g, 59.8%) as an oil.

Example 35

Synthesis of 5'-O-(4,4'-dimethoxytrityl)-2'-deoxythymidin-3'-yl-N-[3,5-bis(2,3-dihydrophytyloxy)benzyl]succinamate Using a triethylamine salt (2.84 g, 3.74 mmol) of 5'-O-(4,4'-dimethoxytrityl)-2'-deoxythymidine-3'-O-succinate and 3,5-bis(2,3-dihydrophytyloxy)benzyl amine (1.54 g, 2.20 mmol) obtained in Preparation Example 26, and in the same manner as in Example 1-(2), a filtrate of the reaction solution was obtained. Said filtrate was concentrated under reduced pressure and the obtained oil was purified by silica gel column chromatography (hexane:ethyl acetate=90:10-20/80 (v/v), containing 1% triethylamine) to give the title compound (0.97 g, 33%) as an oil.

Example 36

Synthesis of 2'-deoxythymidinyl-[3'→5']-2'-deoxythymidine (5'-d[TT]-3') using 5'-O-(4,4'-dimethoxytrityl)-2'-deoxythymidin-3'-yl-N-[2,3,4-tris(2,3-dihydrophytyloxy)benzhydryl]succinamate (1) Synthesis of 5'-O-(4,4'-dimethoxytrityl)-2'-deoxythymidine-3'-[O-(2-cyanoethyl)]phosphoryl-2'-deoxythymidin-3'-yl-N-[2,3,4-tris(2,3-dihydrophytyloxy)benzhydryl]succinamate Using the compound synthesized in Example 33 (199.0 mg, 117.1 μmol) and a dT-CE phosphoramidite reagent (5'-O-(4,4'-dimethoxytrityl)deoxythymidine-3'-[O-(2-cyanoethyl)-(N,N-diisopropyl)]-phosphoramidite) (223.8 mg, 0.30 mmol), and in the same manner as in Example 18-(1), the title compound (213.8 mg, 88.1%) was obtained as a viscous oil.

(2) Synthesis of 2'-deoxythymidinyl-[3'→5']-2'-deoxythymidine (5'-d[TT]-3')

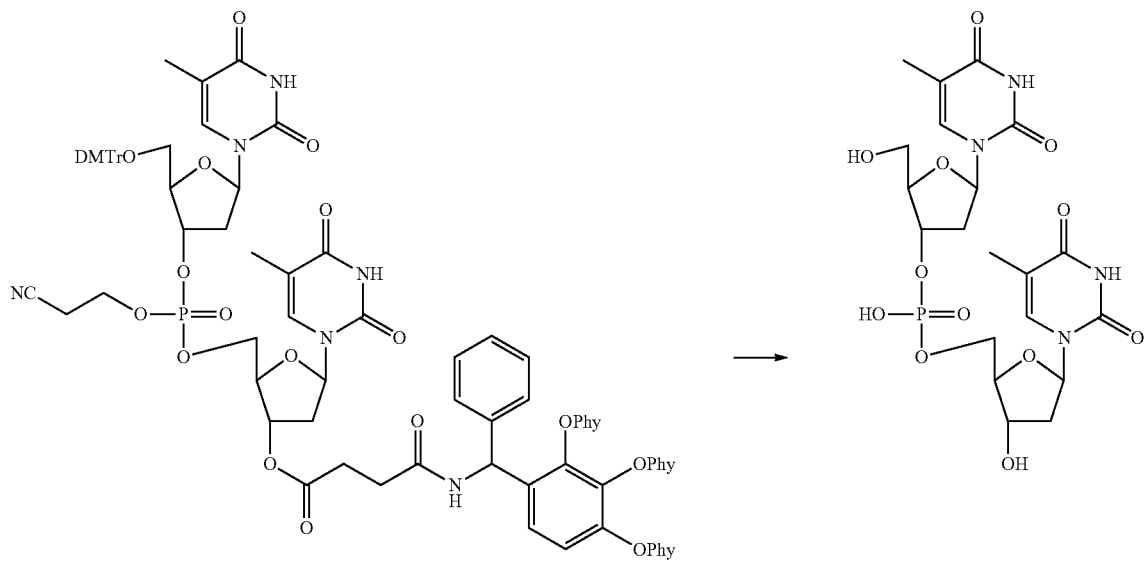

To the compound synthesized in Example 36-(1) (about 50 mg) was added a mixture (5.0 ml) of 28% aqueous ammonia solution:40% aqueous methylamine solution=1:1 (v/v), and the mixture was incubated at room temperature for 1 hr. The reaction mixture was concentrated in a rotary evaporator, the obtained crude product was adsorbed to C-18 reversed-phase cartridge column and washed with 0.1 mol/l aqueous ammonium acetate solution. The dimethoxytrityl group bonded to the 5'-terminal hydroxyl group was removed with aqueous 2% trifluoroacetic acid solution, and the mixture was eluted with 20% aqueous acetonitrile solution to give the title compound.

m/z(ESI-MS): Anal. Calc. for $C_{20}H_{27}N_4O_{12}P$: 546.12. Found 545.1 (M−H)⁻

Example 37

Synthesis of 2'-methoxyuridinyl-[3'→5']-2'-deoxythymidine (5'-U(M)dT-3') using 5'-O-(4,4'-dimethoxytrityl)-2'-deoxythymidin-3'-yl-N-[2,3,4-tris(2,3-dihydrophytyloxy)benzhydryl]succinamate (1) Synthesis of 5'-O-(4,4'-dimethoxytrityl)-2'-methoxyuridine-3'-[O-(2-cyanoethyl)]phosphoryl-2'-deoxythymidin-3'-yl-N-[2,3,4-tris(2,3-dihydrophytyloxy)benzhydryl]succinamate Using the compound synthesized in Example 33 (200.4 mg, 117.9 μmol) and a 2'-OMe-U-CE phosphoramidite reagent (5'-O-(4,4'-dimethoxytrityl)-2'-methoxyuridine-3'-[O-(2-cyanoethyl)-(N,N-diisopropyl)]-phosphoramidite) (222.3 mg, 0.30 mmol), and in the same manner as in Example 18-(1), the title compound (219.1 mg, 89.2%) was obtained as a viscous oil.

(2) Synthesis of 2'-methoxyuridinyl-[3'→5']-2'-deoxythymidine (5'-U(M)dT-3')

Using the compound synthesized in Example 37-(1) (about 50 mg) and in the same manner as in Example 36-(2), the title compound was obtained.

m/z(ESI-MS): Anal. Calc. for $C_{20}H_{27}N_4O_{13}P$: 562.13. Found 561.1 (M−H)⁻

Example 38

Synthesis of 2'-deoxythymidinyl-[3'→5']-2'-deoxythymidine (5'-d[TT]-3') using 5'-O-(4,4'-dimethoxytrityl)-2'-deoxythymidin-3'-yl-N-[4,4'-bis(2,3-dihydrophytyloxy)benzhydryl]succinamate (1) Synthesis of 5'-O-(4,4'-dimethoxytrityl)-2'-deoxythymidine-3'-[O-(2-cyanoethyl)]phosphoryl-2'-deoxythymidin-3'-yl-N-[4,4'-bis(2,3-dihydrophytyloxy)benzhydryl]succinamate Using the compound synthesized in Example 34 (200.1 mg, 0.14 mmol) and a 2'-dT-CE phosphoramidite reagent (5'-O-(4,4'-dimethoxytrityl)-2'-deoxythymidine-3'-[O-(2-cyanoethyl)-(N,N-diisopropyl)]-phosphoramidite) (267.3 mg, 0.36 mmol), and in the same manner as in Example 18-(1), the title compound (154.3 mg, 61.0%) was obtained as a viscous oil.

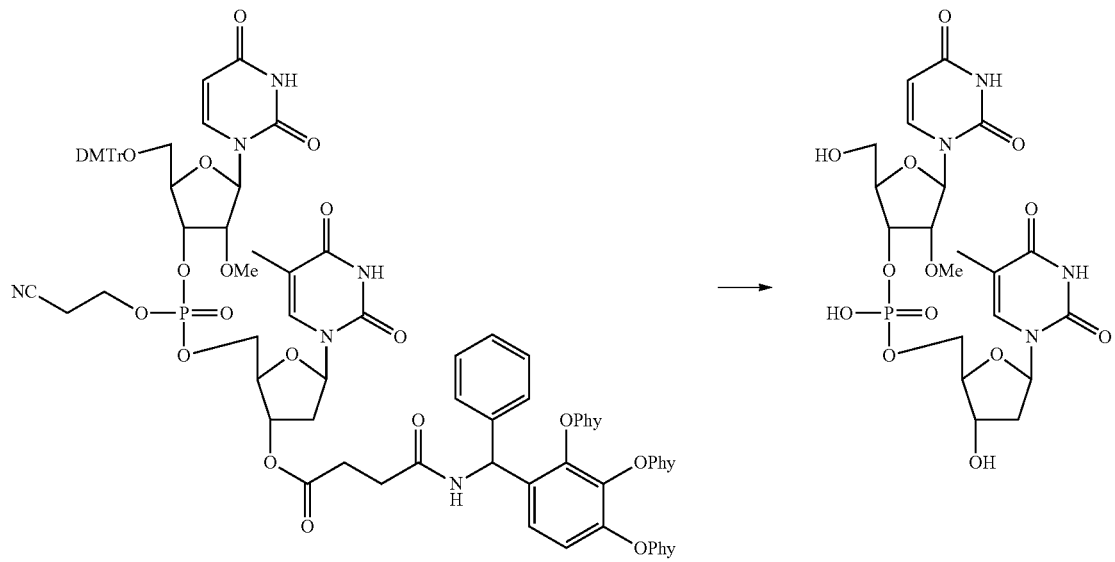

(2) Synthesis of 2'-deoxythymidinyl-[3'→5']-2'-deoxythymidine (5'-d[TT]-3')

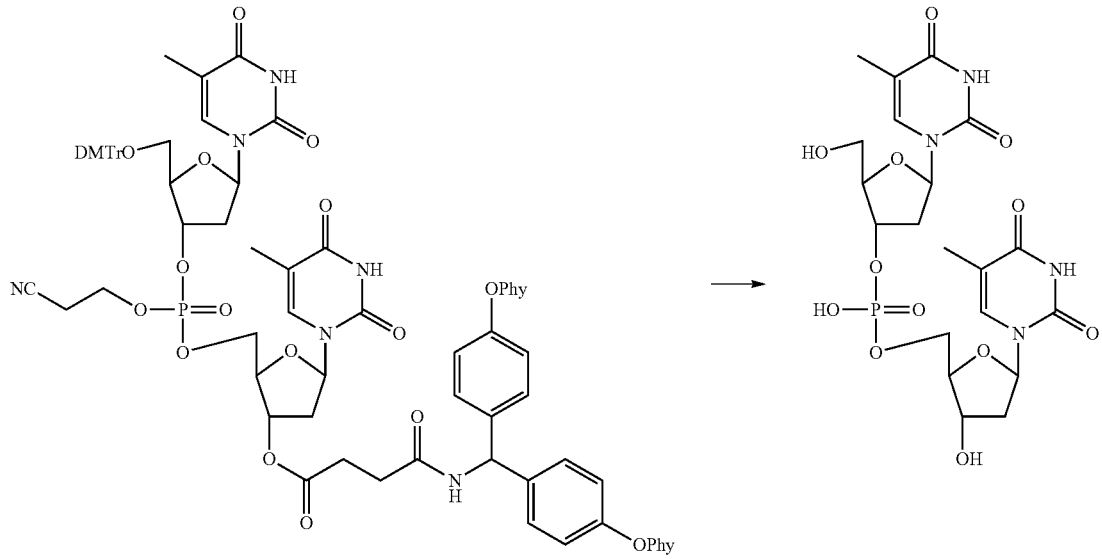

Using the compound synthesized in Example 38-(1) (about 50 mg) and in the same manner as in Example 36-(2), the title compound was obtained.

m/z(ESI-MS): Anal. Calc. for $C_{20}H_{27}N_4O_{12}P$: 546.12. Found 545.1 (M–H)⁻

Example 39

Synthesis of 2'-methoxyuridinyl-[3'→5']-2'-deoxythymidine (5'-U(M)dT-3') using 5'-O-(4,4'-dimethoxytrityl)-2'-deoxythymidin-3'-yl-N-[4,4'-bis(2,3-dihydrophytyloxy)benzhydryl]succinamate (1) Synthesis of 5'-O-(4,4'-dimethoxytrityl)-2'-methoxyuridine-3'-[O-(2-cyanoethyl)]phosphoryl-2'-deoxythymidin-3'-yl-N-[4,4'-bis(2,3-dihydrophytyloxy)benzhydryl]succinamate Using the compound synthesized in Example 34 (201.7 mg, 0.14 mmol) and a 2'-OMe-U-CE phosphoramidite reagent (5'-O-(4,4'-dimethoxytrityl)-2'-methoxyuridine-3'-[O-(2-cyanoethyl)-(N,N-diisopropyl)]-phosphoramidite) (278.9 mg, 0.37 mmol), and in the same manner as in Example 18-(1), the title compound (137.3 mg, 53.3%) was obtained as a viscous oil.

(2) Synthesis of 2'-methoxyuridinyl-[3'→5']-2'-deoxythymidine (5'-U(M)dT-3')

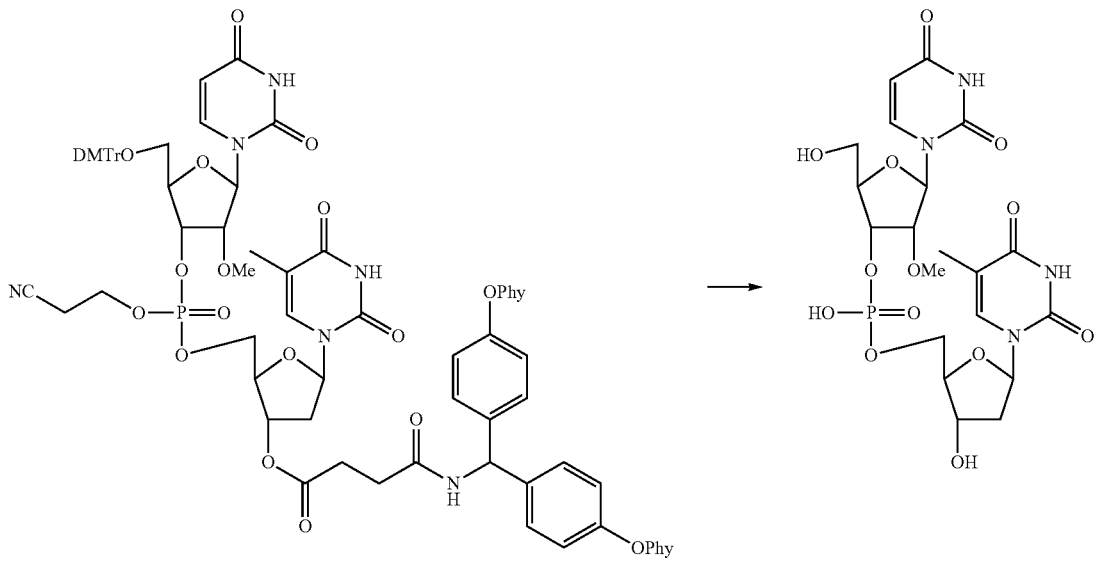

Using the compound synthesized in Example 39-(1) (about 50 mg) and in the same manner as in Example 36-(2), the title compound was obtained.

m/z(ESI-MS): Anal. Calc. for $C_{20}H_{27}N_4O_{13}P$: 562.13. Found 561.1 $(M-H)^-$

Example 40

Synthesis of 2'-deoxythymidinyl-[3'→5']-2'-deoxythymidine (5'-d[TT]-3') using 5'-O-(4,4'-dimethoxytrityl)-2'-deoxythymidin-3'-yl-N-[3,5-bis(2,3-dihydrophytyloxy)benzyl]succinamate (1) Synthesis of 5'-O-(4,4'-dimethoxytrityl)-2'-deoxythymidine-3'-[O-(2-cyanoethyl)]phosphoryl-2'-deoxythymidin-3'-yl-N-[3,5-bis(2,3-dihydrophytyloxy)benzyl]succinamate Using the compound synthesized in Example 35 (196.7 mg, 0.15 mmol) and a 2'-dT-CE phosphoramidite reagent (5'-O-(4,4'-dimethoxytrityl)-2'-deoxythymidine-3'-[O-(2-cyanoethyl)-(N,N-diisopropyl)]-phosphoramidite) (288.2 mg, 0.39 mmol), and in the same manner as in Example 18-(1), the title compound (76.7 mg, 30.5%) was obtained as a viscous oil.

(2) Synthesis of 2'-deoxythymidinyl-[3'→5']-2'-deoxythymidine (5'-d[TT]-3')

Using the compound synthesized in Example 40-(1) (about 50 mg) and in the same manner as in Example 36-(2), the title compound was obtained.

m/z(ESI-MS): Anal. Calc. for $C_{20}H_{27}N_4O_{12}P$: 546.12. Found 545.1 $(M-H)^-$

Example 41

Synthesis of 2'-deoxy-2'-fluorouridinyl[3'→5']-2'-deoxythymidine (5'-U(F)dT-3') using 5'-O-(4,4'-dimethoxytrityl)-2'-deoxythymidin-3'-yl-N-[3,4,5-tris(2,3-dihydrophytyloxy)benzyl]succinamate (1) Synthesis of 5'-O-(4,4'-dimethoxytrityl)-2'-deoxy-2'-fluorouridine-3'-[O-(2-cyanoethyl)]phosphoryl-2'-deoxythymidin-3'-yl-N-[3,4,5-tris(2,3-dihydrophytyloxy)benzyl]succinamate Using the compound synthesized in Example 2 (202.4 mg, 0.13 mmol) and the 2'-F-U-CE phosphoramidite reagent (5'-O-(4,4'-dimethoxytrityl)-2'-deoxy-2'-fluorouridine-3'-[O-(2-cyanoethyl)-(N,N-diisopropyl)]-phosphoramidite) (291.5 mg, 0.39 mmol) obtained in Preparation Example 27, and in the same manner as in Example 18-(1), the title compound (198.9 mg, 78.8%) was obtained as a viscous oil.

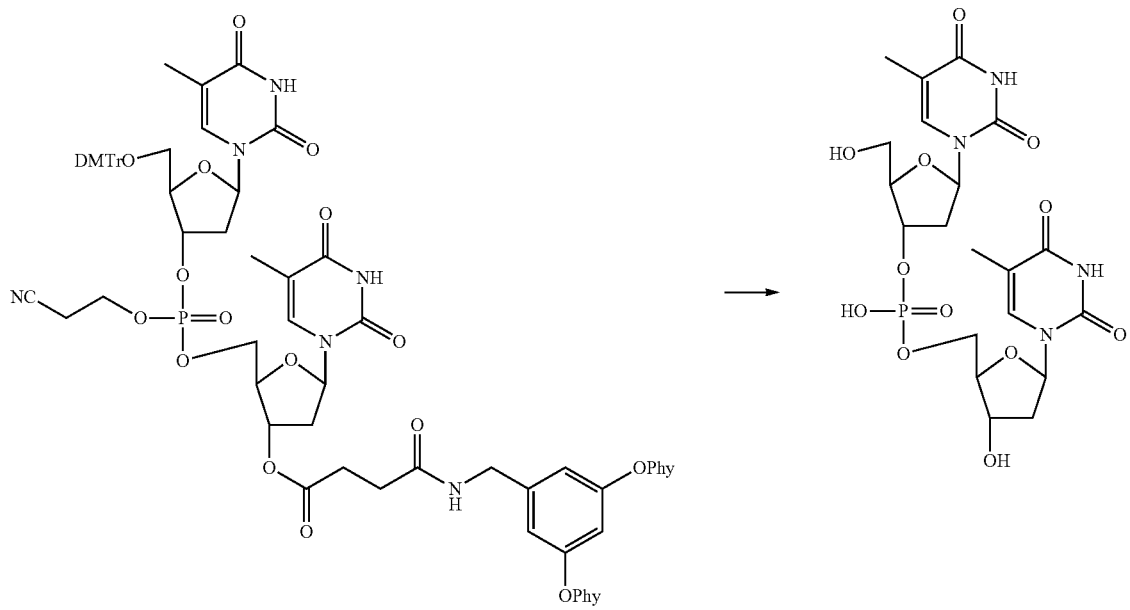

(2) Synthesis of 2'-deoxy-2'-fluorouridinyl[3'→5']-2'-deoxythymidine (5'-U(F)dT-3')

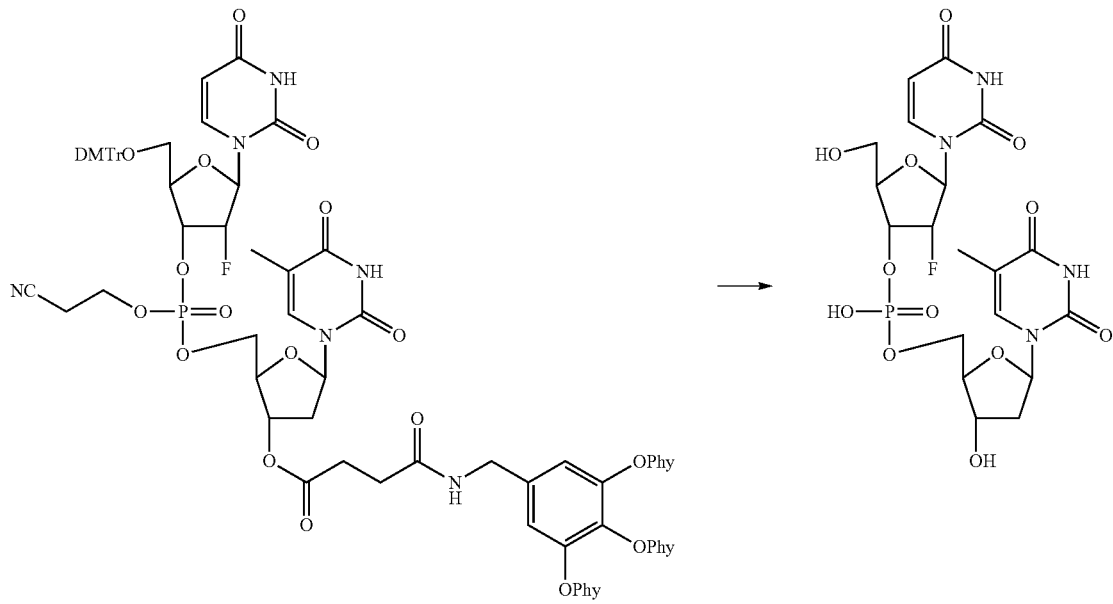

Using the compound synthesized in Example 41-(1) (about 50 mg) and in the same manner as in Example 36-(2), the title compound was obtained.

m/z (ESI-MS): Anal. Calc. for $C_{19}H_{24}FN_4O_{12}P$: 550.11. Found 549.1 (M−H)⁻

Example 42

Synthesis of 2'-O,4'-C-methylenethymidinyl[3'->5']-2'-deoxythymidine (5'-(LNA)TdT-3') using 5'-O-(4,4'-dimethoxytrityl)-2'-deoxythymidin-3'-yl-N-[3,4,5-tris(2,3-dihydrophytyloxy)benzyl]succinamate (1) Synthesis of 5'-O-(4,4'-dimethoxytrityl)-2'-O,4'-C-methylenethymidine-3'-[O-(2-cyanoethyl)]phosphoryl-2'-deoxythymidin-3'-yl-N-[3,4,5-tris(2,3-dihydrophytyloxy)benzyl]succinamate Using the compound synthesized in Example 2 (197.8 mg, 0.13 mmol) and an LNA-T-CE phosphoramidite reagent (5'-O-(4,4'-dimethoxytrityl)-2'-O,4'-C-methylenethymidine-3'-[O-(2-cyanoethyl)-(N,N-diisopropyl)]-phosphoramidite) (250.7 mg, 0.32 mmol), and in the same manner as in Example 18-(1), the title compound (220.3 mg, 88.3%) was obtained as a viscous oil.

(2) Synthesis of 2'-O,4'-C-methylenethymidinyl[3'→5']-2'-deoxythymidine (5'-(LNA)TdT-3')

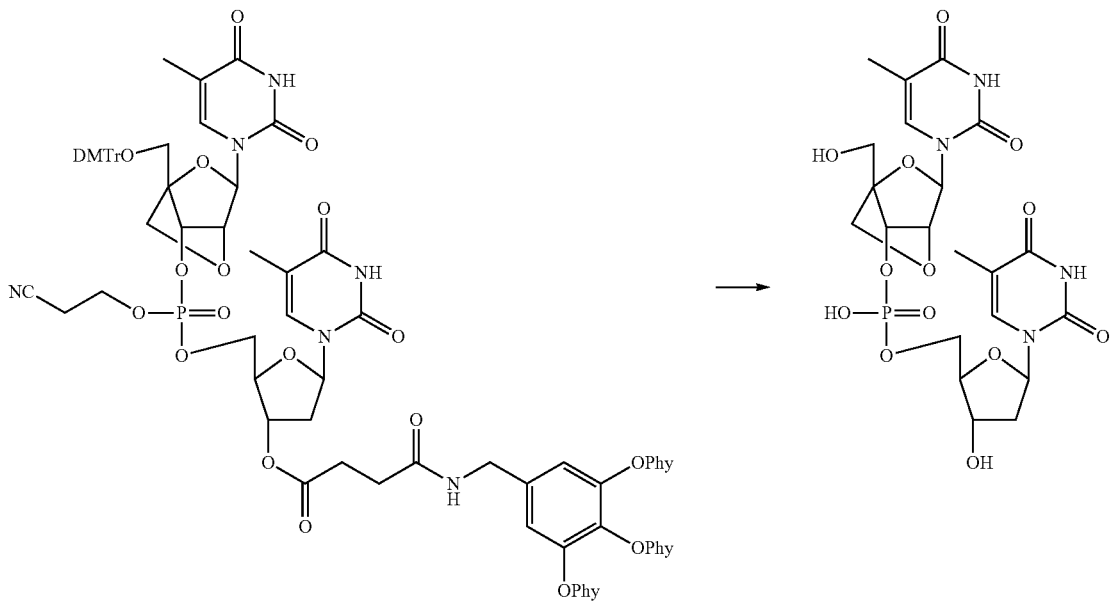

To the compound synthesized in Example 42-(1) (about 50 mg) was added a solution (5.0 ml) of 10% (v/v) tert-butylamine dissolved in 28% aqueous ammonia solution, and the mixture was heated to 65° C. in an autoclave and reacted overnight. The reaction mixture was concentrated in a rotary evaporator, the obtained crude product was adsorbed to C-18 reversed-phase cartridge column, and washed with 0.1 mol/l aqueous ammonium acetate solution. The dimethoxytrityl group bonded to the 5'-terminal hydroxyl group was removed with aqueous 2% trifluoroacetic acid solution, and the mixture was eluted with 20% aqueous acetonitrile solution to give the title compound.

m/z(ESI-MS): Anal. Calc. for $C_{21}H_{27}N_4O_{13}P$: 574.13. Found 573.1 (M−H)⁻

Example 43

Synthesis of 5'-O-(4,4'-dimethoxytrityl)-N³-[4-(2,3-dihydrophytyloxy)benzoyl]-2'-O,4'-C-methylenethymidine-3'-O-[(2-cyanoethyl)-N,N-diisopropylphosphoramidite]

(1) Synthesis of 4-(2,3-dihydrophytyloxy)benzoic acid

In the same manner as in Preparation Example 20, the title compound was prepared using 2,3-dihydrophytyl bromide and methyl (4-hydroxy)benzoate described in Preparation Example 2.

¹H-NMR (400 MHz, CDCl₃): δ 0.83-0.98 (m, 15H), 1.01-1.92 (m, 24H), 4.01-4.12 (m, 2H), 6.91-6.96 (m, 2H), 8.03-8.08 (m, 2H)

(2) Synthesis of 4-(2,3-dihydrophytyloxy)benzoyl chloride

The benzoic acid compound prepared in the above-mentioned Example 43-(1) was converted to the corresponding acid chloride in the same manner as in Example 4-(1) to give an oily compound. The present compound was directly used for the next step.

(3) Synthesis of 5'-O-(4,4'-dimethoxytrityl)-N³-[4-(2,3-dihydrophytyloxy)benzoyl]-2'-O,4'-C-methylenethymidine-3'-O-[(2-cyanoethyl)-N,N-diisopropylphosphoramidite]

An operation of dissolving commercially available LNA-T-CE phosphoramidite reagent (5'-O-(4,4'-dimethoxytrityl)-2'-O,4'-C-methylenethymidine-3'-[O-(2-cyanoethyl)-(N,N-diisopropyl)]-phosphoramidite) (701.7 mg, 0.91 mmol) in anhydrous pyridine (5.0 ml), followed by concentration under reduced pressure was repeated 3 times to perform dehydrative azeotropic distillation of adhesive water. Thereafter, under an argon atmosphere, the reaction mixture was dissolved in dry pyridine (8.0 ml), N,N-diisopropylethylamine (0.17 ml, 1.12 mmol) and acid chloride (0.6 g, 1.36 mmol) prepared in the above-mentioned Example 42-(2) were added, and the mixture was stirred at room temperature for 9 hr. Ethyl acetate (50 ml) and water (10 ml) were added to the reaction mixture to allow layer separation. The organic layer was washed 3 times with 10% aqueous sodium hydrogen carbonate solution and once with brine (10 ml), and the obtained organic layer was dried over sodium sulfate. The filtered filtrate was concentrated and the obtained crude product was purified by silica gel column chromatography (hexane:ethyl acetate=100:0-30/70 (v/v), containing 1% triethylamine). The object fractions were collected and concentrated, and the concentrated residue was azeotropically distilled with toluene and dried to solidness to give the title compound (0.77 g, 65.5%).

Example 44

Synthesis of 2'-O,4'-C-methylenethymidinyl[3'→5']-2'-deoxythymidine (5'-(LNA)TdT-3')

(1) Synthesis of 5'-O-(4,4'-dimethoxytrityl)-2'-O,4'-C-methylenethymidine-3'-[O-(2-cyanoethyl)]phosphoryl-2'-deoxythymidin-3'-yl-N-[3,4,5-tris(2,3-dihydrophytyloxy)benzyl]succinamate Using the compound synthesized in Example 2 (200 mg, 0.12 mmol) and the phosphoramidite monomer synthesized in Example 43 (362 mg, 0.31 mmol), and in the same manner as in Example 18-(1), the title compound (295 mg, 99.4%) was synthesized.

(2) Synthesis of 2'-O,4'-C-methylenethymidinyl [3'→5']-2'-deoxythymidine (5'-(LNA)TdT-3')

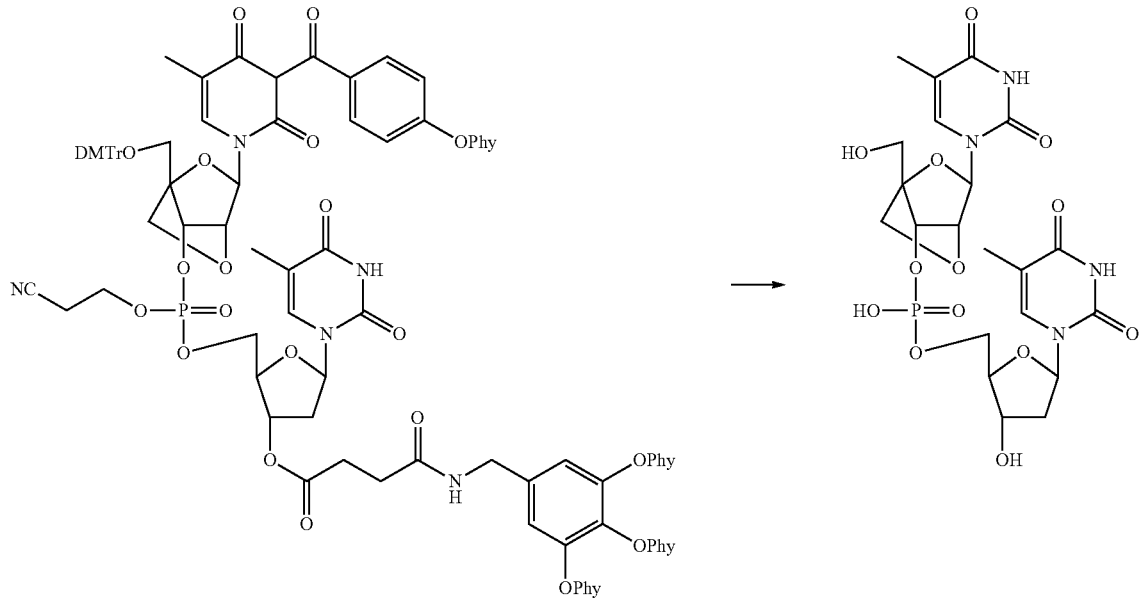

The compound (about 20 mg) synthesized in Example 44-(1) was treated according to a method similar to that in Example 32, the title compound was obtained by deprotection and cutout from the anchor.

m/z(ESI-MS): Anal. Calc. for $C_{21}H_{27}N_4O_{13}P$: 574.13. Found 573.1 (M–H)⁻

Comparative Example 1

Synthesis of 5'-O-(4,4'-dimethoxytrityl)-2'-deoxythymidine-3'-[O-(2-cyanoethyl)]phosphoryl-N²-isobutyryl-2'-deoxyguanosine-3'-[O-(2-cyanoethyl)]phosphoryl-N⁴-benzoyl-2'-deoxycytidine-3'-[O-(2-cyanoethyl)]phosphoryl-N⁶-benzoyl-2'-deoxyadenosine-3'-[O-(2-cyanoethyl)]phosphoryl-2'-deoxythymidine-3'-[O-(2-cyanoethyl)]phosphoryl-2'-deoxythymidin-3'-yl-[3,4,5-tris(3,7,11,15-tetramethyl-1-hexadecanyloxy)benzyl]succinate Under an argon atmosphere, 5'-O-(4,4'-dimethoxytrityl)-2'-deoxythymidin-3'-yl-[3,4,5-tris(3,7,11,15-tetramethyl-1-hexadecanyloxy)benzyl]succinate (509 mg, 313 μmol) was dissolved in a mixed solvent of anhydrous heptane (3.6 ml) and anhydrous toluene (3.6 ml), trifluoroacetic acid (279 μl, 3.76 mmol) and 1H-pyrrole (217 μl, 3.13 mmol) were added, and the mixture was stirred for 15 min. The completion of the deprotection was confirmed by thin layer chromatography, acetonitrile (1.2 ml), pyridine (304 μl, 3.76 mmol) and N-methylimidazole (149 μl, 1.88 mmol) were added, and the mixture was stirred for 5 min. To the reaction mixture after neutralization was added a solution (1.2 ml) of 5'-O-(4,4'-dimethoxytrityl)-2'-deoxythymidine-3'-O-(2-cyanoethyl-N,N-diisopropylphosphoramidite) (466 mg, 626 μmol) in acetonitrile, and the mixture was stirred for 1 hr. 2,6-Lutidine (350 μl), N-methylimidazole (350 μl) and acetic anhydride (350 μl) were added and the mixture was stirred for 5 min. 1.0M iodine pyridine/THF/H₂O solution (1.25 ml) was added and the mixture was stirred at room temperature for 10 min. The reaction mixture after completion of the reaction was partitioned by adding heptane (7.2 ml) and water (480 μl), the lower layer was extracted, and the heptane layer was washed with acetonitrile containing water, and the obtained organic layer was concentrated under reduced pressure to give 5'-O-(4,4'-dimethoxytrityl)-2'-deoxythymidine-3'-[O-(2-cyanoethyl)]phosphoryl-deoxythymidin-3'-yl-[3,4,5-tris(3,7,11,15-tetramethyl-1-hexadecanyloxy)benzyl]succinate (620 mg, 99.8%).

According to the nucleic acid base sequence of the object product, a similar operation was repeated using the corresponding commercially available phosphoramidite monomer to synthesize the title compound. When deoxyguanosine was elongated, the resultant product showed insufficient liposolubility, and the yield after extraction operation decreased to 90%. When deoxythymidine was further elongated, it could not be dissolved in a heptane/toluene mixed solvent, and the yield after reaction and extraction decreased to 85%. The following Tables show phosphoramidite monomers used in each stage and the yield thereof.

TABLE 1

| Monomer | product | Yield |
| --- | --- | --- |
| 5'-O-(4,4'-dimethoxytrityl)-deoxythymidine-3'-O-(2-cyanoethyl-N,N-diisopropylphosphoramidite) | DMTr-dTT-suc-TPB | 99.8% |

TABLE 1-continued

| Monomer | product | Yield |
| --- | --- | --- |
| N⁶-benzoyl-5'-O-(4,4'-dimethoxytrityl)-deoxyadenosine-3'-O-(2-cyanoethyl-N,N-diisopropylphosphoramidite) | DMTr-d(A$^{Bz}$TT)-suc-TPB | 99.2% |
| N⁴-benzoyl-5'-O-(4,4'-dimethoxytrityl)-deoxycytidine-3'-O-(2-cyanoethyl-N,N-diisopropylphosphoramidite) | DMTr-d(C$^{Bz}$A$^{Bz}$TT)-suc-TPB | 98.3% |
| N²-isobutyryl-5'-O-(4,4'-dimethoxytrityl)-deoxyguanosine-3'-O-(2-cyanoethyl-N,N-diisopropylphosphoramidite) | DMTr-d(G$^{ibu}$C$^{Bz}$A$^{Bz}$TT)-suc-TPB | 90.3% |
| 5'-O-(4,4'-dimethoxytrityl)-deoxythymidine-3'-O-(2-cyanoethyl-N,N-diisopropylphosphoramidite) | DMTr-d(TG$^{ibu}$C$^{Bz}$A$^{Bz}$TT)-suc-TPB | 85.2% |

Comparative Example 2

Synthesis of 5'-O-(4,4'-dimethoxytrityl)-2'-deoxythymidin-3'-yl-N-(3,4,5-tris(octadecyloxy)benzyl)succinamate (1) Synthesis of 5'-O-(4,4'-dimethoxytrityl)-2'-deoxythymidine-3'-O-succinate Under an argon atmosphere, 5'-O-(4,4'-dimethoxytrityl)-2'-deoxythymidine (5.00 g, 9.18 mmol), succinic anhydride (1.38 g, 13.8 mmol) and triethylamine (3.85 mL, 27.5 mmol) were dissolved in dichloromethane (95 mL), and the mixture was stirred at room temperature for 8 hr. The completion of the reaction was confirmed by thin layer chromatography, and the reaction mixture was partitioned and washed three times with 2.0M phosphoric acid-triethylamine buffer (pH 7.50). The organic layer was evaporated under reduced pressure to give a triethylamine salt (7.02 g, 98%) of 5'-O-(4,4'-dimethoxytrityl)deoxythymidine-3'-O-succinate as a colorless frothy solid.

(2) Synthesis of 5'-O-(4,4'-dimethoxytrityl)-2'-deoxythymidin-3'-yl-N-(3,4,5-tris(octadecyloxy)benzyl)succinamate A triethylamine salt (1.45 g, 1.94 mmol) of 5'-O-(4,4'-dimethoxytrityl)-2'-deoxythymidine-3'-O-succinate and 3,4,5-tris(octadecyloxy)benzyl amine (1.02 g, 1.10 mmol) were dissolved in anhydrous dichloromethane (15 mL), 2-(1H-benzotriazol-1-yl)-1,1,3,3-tetramethyluronium hexafluorophosphate [HBTU] (2.53 g, 6.60 mmol) and N,N-diisopropylethylamine (1.17 mL, 6.60 mmol) were added, and the mixture was stirred at room temperature for 1 hr. The disappearance of the starting material was confirmed by thin layer chromatography, and the mixture was washed with saturated aqueous sodium hydrogen carbonate solution and saturated brine. The organic layer was dried over sodium sulfate and filtered, and the filtrate was concentrated under reduced pressure. Methanol was added to the concentrated solution, the mixture was filtered, and the obtained solid was purified by silica gel column chromatography (dichloromethane/methanol, 1% v/v triethylamine) to give the title compound (1.22 g, 72.4%) as a white solid.

In the following, Table 2 to Table 13 show the structural formulas and compound data of the compounds produced in Preparation Examples 1 to 27, Examples 1, 2, 4 to 12, 19 to 25, 33 to 35, 43, and Comparative Example 2.

TABLE 2

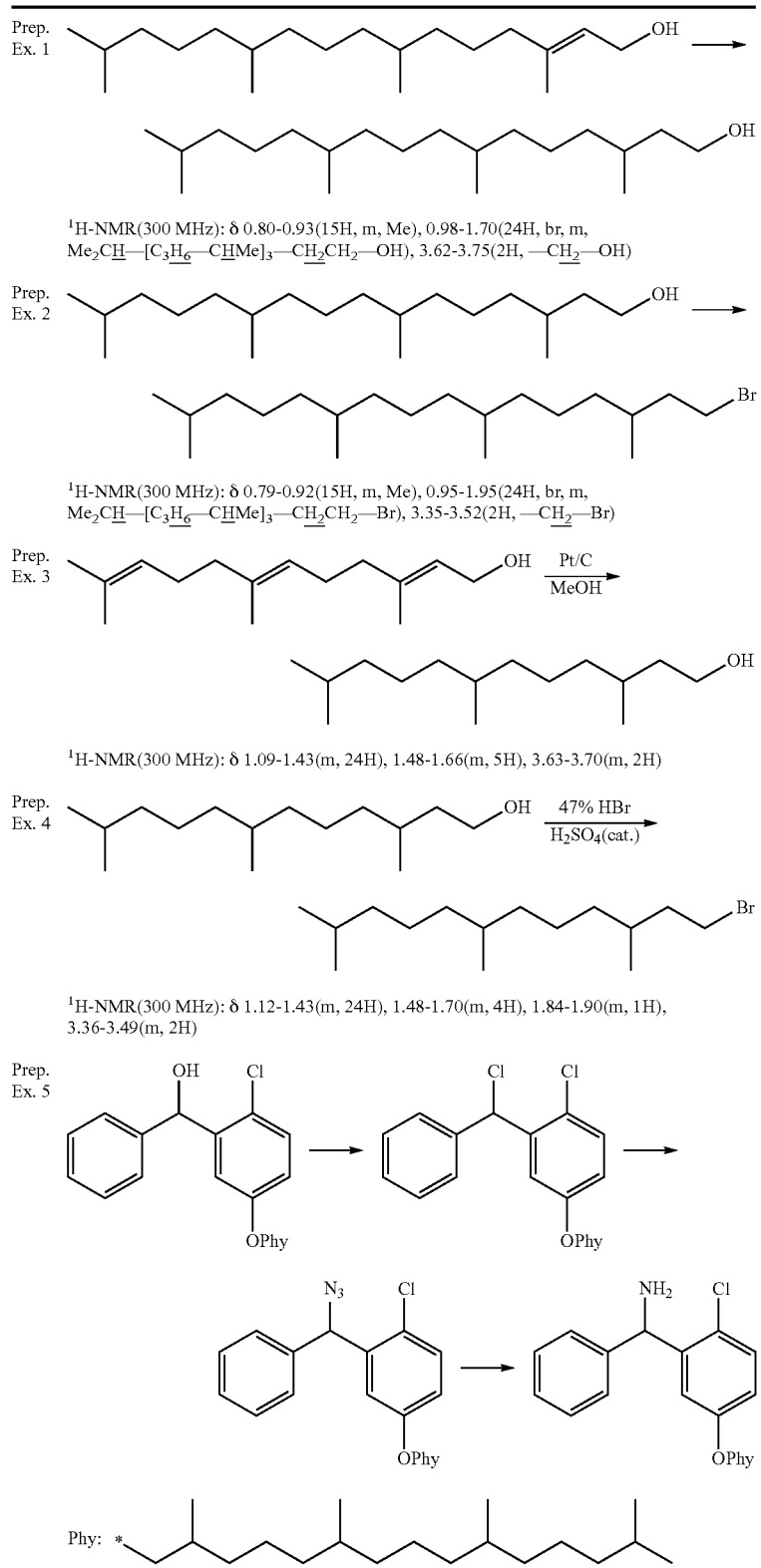

Prep. Ex. 1

¹H-NMR(300 MHz): δ 0.80-0.93(15H, m, Me), 0.98-1.70(24H, br, m, Me₂C$\underline{H}$—[C₃$\underline{H_6}$—C$\underline{H}$Me]₃—C$\underline{H_2}$CH₂—OH), 3.62-3.75(2H, —C$\underline{H_2}$—OH)

Prep. Ex. 2

¹H-NMR(300 MHz): δ 0.79-0.92(15H, m, Me), 0.95-1.95(24H, br, m, Me₂C$\underline{H}$—[C₃$\underline{H_6}$—C$\underline{H}$Me]₃—C$\underline{H_2}$CH₂—Br), 3.35-3.52(2H, —C$\underline{H_2}$—Br)

Prep. Ex. 3

¹H-NMR(300 MHz): δ 1.09-1.43(m, 24H), 1.48-1.66(m, 5H), 3.63-3.70(m, 2H)

Prep. Ex. 4

¹H-NMR(300 MHz): δ 1.12-1.43(m, 24H), 1.48-1.70(m, 4H), 1.84-1.90(m, 1H), 3.36-3.49(m, 2H)

Prep. Ex. 5

2-chloro-5-(2,3-dihydrophytyloxy)benzophenone
¹H-NMR(300 MHz): δ 0.75-0.90(15H, m, $\underline{Me}$), 0.95-1.70(24H, br, Me₂C$\underline{H}$—[C₃$\underline{H_6}$—C$\underline{H}$Me]₃—C$\underline{H_2}$CH₂—O—Ar), 3.82-3.92(2H, br, —O—C$\underline{H_2}$—C₁₉H₃₉), 6.89(1$\underline{H}$, d, J = 8.3 Hz, C₃—$\underline{H}$), 7.35-7.80(7H, m, C4,6-$\underline{H}$, Ph—$\underline{H}$)
2-chloro-5-(2,3-dihydrophytyloxy)benzhydrol
¹H-NMR(300 M Hz): δ 0.82-0.90(15H, m, $\underline{Me}$), 1.00-1.90(24H, br, TABLE 2-continued Me$_2$C<u>H</u>—[C$_3$<u>H</u>$_6$—C<u>H</u>Me]$_3$—CH$_2$CH$_2$—O—Ar), 3.88-4.00(2H, br, —O—C<u>H</u>$_2$—C$_{19}$H$_{39}$), 5.98(1H, s, Ar—C<u>H</u>OH—Ph), 6.75-6.90(1H, m, C3-<u>H</u>), 7.10-7.45(7H, m, C4,6-<u>H</u>, Ph—<u>H</u>)

1-chloro-1-[(2-chloro-5-(2,3-dihydrophytyloxy)phenyl)phenylmethane
$^1$H-NMR(300 MHz): δ 0.80-0.90(15H, m, <u>Me</u>), 1.00-1.90(24H, br, Me$_2$C<u>H</u>—[C$_3$<u>H</u>$_6$—C<u>H</u>Me]$_3$—CH$_2$CH$_2$—O—Ar), 3.88-4.05(2H, m, —O—C<u>H</u>$_2$—C$_{19}$H$_{39}$), 6.48(1H, d, J = 1.6 Hz, Ar—C<u>H</u>Cl—Ph), 6.77(1H, d, J = 8.7 Hz, C3-<u>H</u>), 7.10-7.55(7H, m, C4,6-<u>H</u>, Ph—<u>H</u>)

1-azido-1-[(2-chloro-5-(2,3'-dihydrophytyloxy)phenyl)phenylmethane
1H-NMR(300 MHz): δ 0.85-0.95(15H, m, <u>Me</u>), 0.95-1.85(24H, br, Me$_2$C<u>H</u>—[C$_3$<u>H</u>$_6$—C<u>H</u>Me]$_3$—CH$_2$CH$_2$—O—Ar), 3.75-4.02(2H, m, —O—C<u>H</u>$_2$—C$_{19}$H$_{39}$), 5.90-6.10(1H, m, Ar—C<u>H</u>N$_3$—Ph), 6.79(1H, d, J = 9.0 Hz, C3-<u>H</u>), 7.10-7.50(7H, m, C4,6-<u>H</u>, Ph—<u>H</u>)

1-[(2-chloro-5-(2,3-dihydrophytyloxy)phenyl)]-1-phenylmethanamine
$^1$H-NMR(300 MHz): δ 0.85-0.95(15H, m, <u>Me</u>), 0.95-1.85(24H, br, Me$_2$C<u>H</u>—[C$_3$<u>H</u>$_6$—C<u>H</u>Me]$_3$—CH$_2$CH$_2$—O—Ar), 3.85-4.00(2H, br, —O—C<u>H</u>$_2$—C$_{19}$H$_{39}$), 5.43(1H, s, Ar—C<u>H</u>NH$_2$—Ph), 6.75(1H, d, J = 8.7 Hz, C3-<u>H</u>), 7.10-7.50(7H, m, C4,6-<u>H</u>, Ph—<u>H</u>)

TABLE 3

Prep. Ex. 6

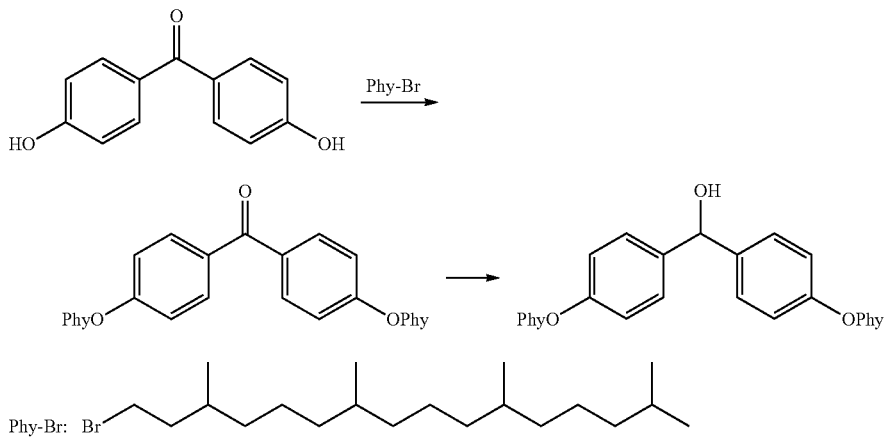

$^1$H-NMR(300 MHz): δ 0.86-0.90(24H, m, <u>Me</u>), 1.10-1.40(48H, br, Me$_2$C<u>H</u>—[C$_3$<u>H</u>$_6$—C<u>H</u>Me]$_3$—CH$_2$CH$_2$—O—Ar), 2.03(1H, s, OH), 3.90-3.94(4H, m, —O—C<u>H</u>$_2$—C$_{19}$H$_{39}$), 5.76(1H, s, Ar—C<u>H</u>N$_3$—Ph), 6.85(4H, m, C3-<u>H</u>), 7.20-7.26(4H, m, C4,6-<u>H</u>, Ph—<u>H</u>)

Prep. Ex. 7

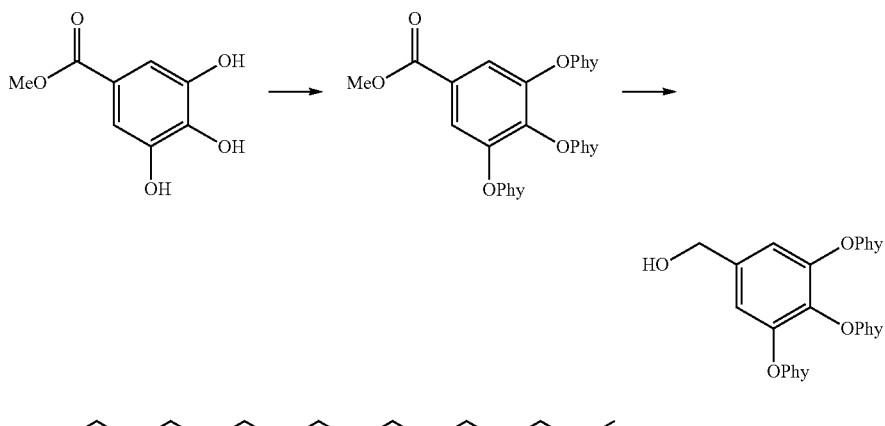

$^1$H-NMR(300 MHz): δ 0.85(36H, t, J = 6.3 Hz, Me), 0.94(9H, t, J = 6.3 Hz, Me), 1.00-2.00(72H, br, m, Me$_2$C<u>H</u>—[C$_3$<u>H</u>$_6$—C<u>H</u>Me]$_3$—CH$_2$CH$_2$—O—Ar), 3.93-4.07(6H, m, —C<u>H</u>$_2$—O—Ar), 4.60(2H, s, —O—C<u>H</u>$_2$—OH), 6.57(2H, s, C2,6-<u>H</u>)

TABLE 3-continued

Prep. Ex. 8

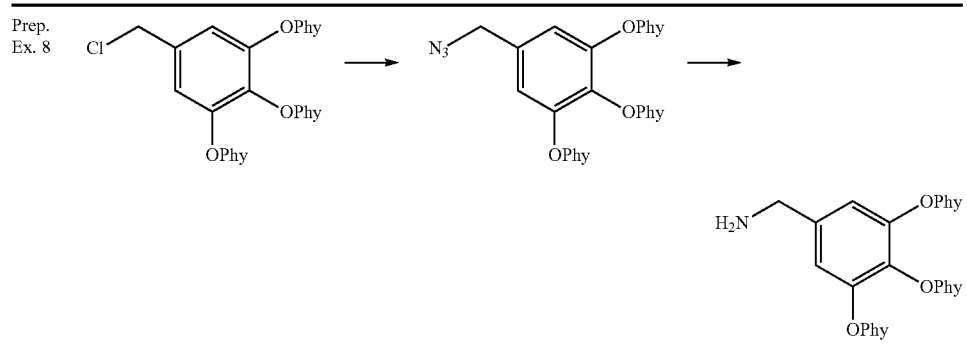

$^1$H-NMR(300 MHz): δ 0.85(36H, t, J = 6.3 Hz, Me), 0.93(9H, t, J = 6.3 Hz, Me), 1.00-2.00(72H, br, m, Me$_2$C$\underline{H}$—[C$_3$$\underline{H}_6$—C$\underline{H}$Me]$_3$—C$\underline{H}_2$C$\underline{H}_2$—O—Ar), 3.79(2H, s, benzyl-$\underline{H}$), 3.85-4.10(6H, m, —C$\underline{H}_2$—O—Ar), 6.52(2H, s, C$\overline{2,6}$-$\underline{H}$)

Prep. Ex. 9

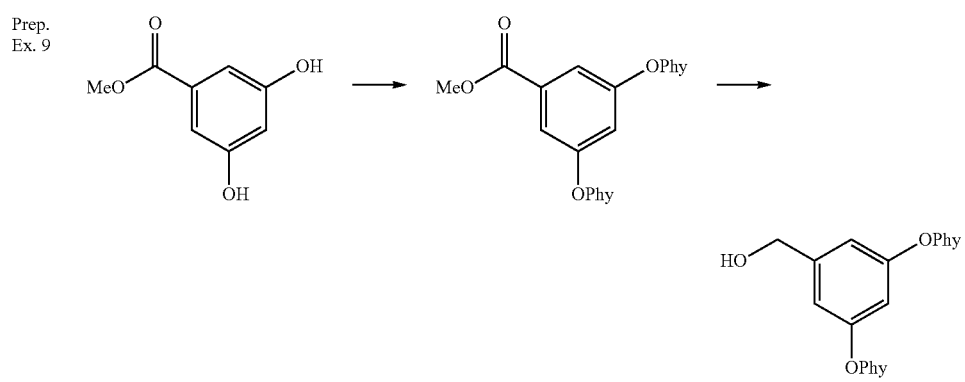

$^1$H-NMR(300 MHz): δ 0.80-0.90(24H, m, Me), 0.93(6H, d, J = 6.3 Hz, Me), 1.00-1.90(48 H, br, m, Me$_2$C$\underline{H}$—[C$_3$$\underline{H}_6$—C$\underline{H}$Me]$_3$—C$\underline{H}_2$C$\underline{H}_2$—O—Ar), 3.92-4.02(4H, m, C$_{19}$H$_{39}$—C$\underline{H}_2$—O—Ar), 4.62(2H, s, Ar—C$\underline{H}_2$—$\overline{\text{OH}}$), 6.38(1H, t, $\overline{J}$ = 2.1 Hz, C4-H), 6.50(2H, d, J = 2.0 Hz, C2,6-$\underline{H}$)

Prep. Ex. 10

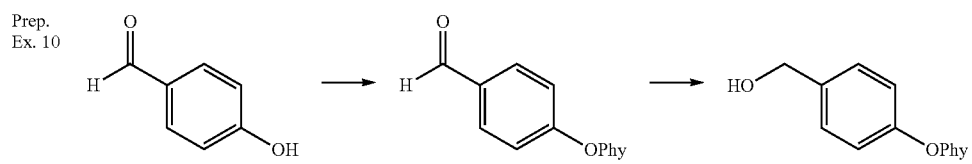

4-(2,3-dihydrophytyloxy)benzaldehyde
$^1$H-NMR(300 MHz): δ 0.82-0.89(12H, m, Me), 0.95(3H, d, J = 6.4 Hz, Me), 1.00-1.95(24 H, m, Me$_2$C$\underline{H}$—[C$_3$$\underline{H}_6$—C$\underline{H}$Me]$_3$—C$\underline{H}_2$C$\underline{H}_2$—O—Ar), 4.03-4.13(2H, m, —O—C$\underline{H}_2$—C$_{19}$H$_{39}$), 4.62 (2H, s, Ar—C$\underline{H}_2$—$\overline{\text{OH}}$), 6.99(2H, m, $\overline{C3,5}$-$\underline{H}$), 7.83(2H, m, C2,6-$\underline{H}$), 9.88(1H, s, C$\overline{HO}$)
4-(2,3-dihydrophytyloxy)benzyl alcohol
$^1$H-NMR(300 MHz): δ 0.81-0.90(12H, m, Me), 0.94(3H, d, J = 6.4 Hz, Me), 1.00-1.90(24 H, m, Me$_2$C$\underline{H}$—[C$_3$$\underline{H}_6$—C$\underline{H}$Me]$_3$—C$\underline{H}_2$C$\underline{H}_2$—O—Ar), 3.94-4.05(2H, m, —O—C$\underline{H}_2$—C$_{19}$H$_{39}$), 6.89 (2H, m, C3,5-$\underline{H}$), 7.28(2H, m, C2,6-$\underline{H}$)

TABLE 4

Prep. Ex. 11

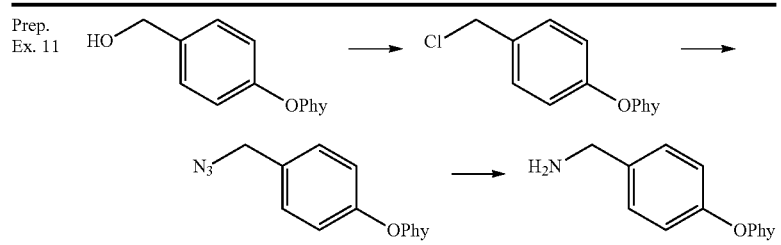

4-(2,3-dihydrophytyloxy)benzyl azide
$^1$H-NMR(300 MHz): δ 0.81-0.90(12H, m, Me), 0.94(3H, d, J = 6.4 Hz, Me), 1.00-1.90(24 H, m, Me$_2$C$\underline{H}$—[C$_3$$\underline{H}_6$—C$\underline{H}$Me]$_3$—C$\underline{H}_2$C$\underline{H}_2$—O—Ar), 3.94-4.04(2H, m, —O—C$\underline{H}_2$—C$_{19}$H$_{39}$), 4.26(2H, s, Ar—C$\underline{H}_2$—N$_3$), 6.90(2H, d, J = 8.6 Hz, C3,5-$\underline{H}$), 7.23

(2H, d, J = 8.6 Hz, C2,6-H)
4-(2,3-dihydrophytyloxy)benzylamine
¹H-NMR(300 MHz): δ 0.86(12H, t, J = 6.0 Hz, Me), 0.94(3H, d, J = 6.6 Hz, Me), 1.00-1.90(24H, m, Me₂CH—[C₃H₆—CHMe]₃—CH₂CH₂—O—Ar), 3.80(2H, s, Ar—CH₂—NH₂), 3.92-4.04(2H, m, —O—CH₂—C₁₉H₃₉), 6.87(2H, d, J = 8.6 Hz, C3,5-H), 7.21 (2H, d , J = 8.6 Hz, C2,6-H)

Prep. Ex. 12

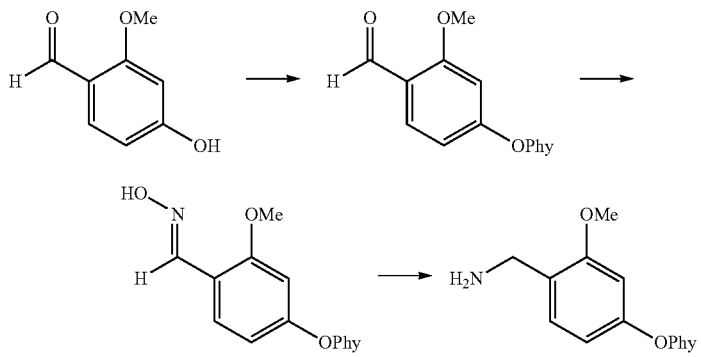

2-methoxy-4-(2,3-dihydrophytyloxy)benzaldoxime
¹H-NMR(300 MHz): δ 0.82-0.92(12H, m, Me), 0.95(3H, d, J = 6.4 Hz, Me), 1.00-1.95(24H, m, Me₂CH—[C₃H₆—CHMe]₃—CH₂CH₂—O—Ar), 3.83(3H, s, OMe), 3.97-4.10(2H, m, —O—CH₂—C₁₉H₃₉), 6.44(1H, d, J = 2.2 Hz, C3-H), 6.49(1H, dd, J = 2.2, 8.6 Hz, C5-H), 7.15(1H, s, —CHNOH), 7.62(1H, d, J = 8.6 Hz, C6-H), 8.41(1H, s, —CHNOH)
2-methoxy-4-(2,3-dihydrophytyloxy)benzylamine
¹H-NMR(300 MHz): δ 0.80-0.90(12H, m, Me), 0.94(3H, d, J = 6.4 Hz, Me), 1.00-1.90(24H, m, Me₂CH—[C₃H₆—CHMe]₃—CH₂CH₂—O—Ar), 3.74(2H, s, Ar—CH₂—NH₂), 3.82(3H, s, OMe), 3.90-4.05(2H, m, —O—CH₂—C₁₉H₃₉), 6.42(1H, dd, J = 2.3, 8.1 Hz, C5-H), 6.46(1H, d, J = 2.1 Hz, C3-H), 7.09(1H, d, J = 8.1 Hz, C6-H)

Prep. Ex. 13

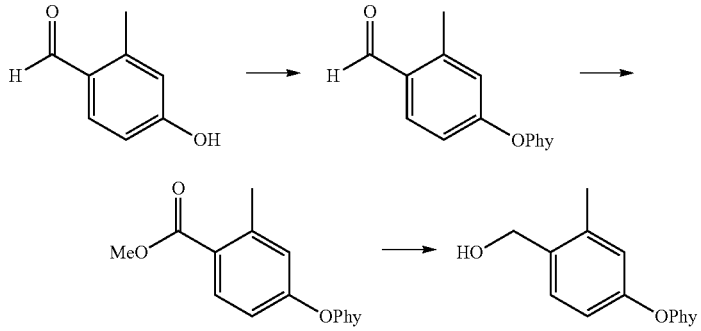

methyl 4-hydroxy-2-methylbenzoate
¹H-NMR(300 MHz): δ 2.57(3H, s, C2-Me), 3.86(3H, s, —COOMe), 5.68(1H, s, br, —OH), 6.66-6.72(2H, m, C3,5-H), 7.89(1H, dd, J = 2.4, 6.9 Hz, C6-H)
methyl 4-(2,3-dihydrophytyloxy)-2-methylbenzoate
¹H-NMR(300 MHz): δ 0.85(12H, t, J = 6.6 Hz, Me), 0.94(3H, d, J = 6.6 Hz, Me), 1.00-1.90(24H, m, Me₂CH—[C₃H₆—CHMe]₃—CH₂CH₂—O—Ar), 2.59(3H, s, C2-Me), 3.85(3H, s, —COOMe), 4.02(2H, dt, J = 3.0, 6.7 Hz, O—CH₂—C₁₉H₃₉), 6.65-6.76(2H, m, C3,5-H), 7.85-7.96(1H, m, C6-H)
4-(2,3-dihydrophytyloxy)-2-methylbenzyl alcohol
¹H-NMR(300 MHz): δ 0.86(12H, t, J = 6.3 Hz, Me), 0.94(3H, d, J = 6.4 Hz, Me), 1.00-1.90(24H, m, Me₂CH—[C₃H₆—CHMe]₃—CH₂CH₂—O—Ar), 2.36(3H, s, C2-Me), 3.98(2H, dt, J = 3.0, 6.7 Hz, O—CH₂—C₁₉H₃₉), 4.63(2H, d, J = 4.7 Hz, Ar—CH₂—OH), 6.60-6.77(2H, m, C3,5-H), 7.15-7.25(1H, m, C6-H)

TABLE 5

Prep. Ex. 14

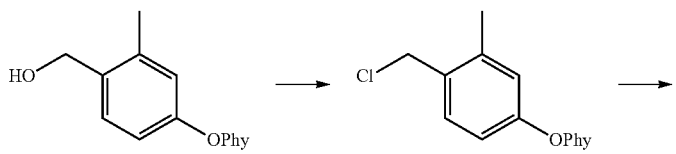

TABLE 5-continued

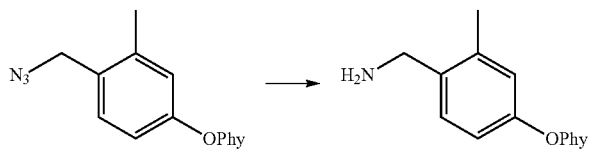

4-(2,3-dihydrophytyloxy)-2-methylbenzyl chloride
$^1$H-NMR(300 MHz): δ 0.86(12H, t, J = 6.3 Hz, Me), 0.93(3H, d, J = 6.3 Hz, Me), 1.00-1.90 (24H, m, Me$_2$CH—[C$_3$H$_6$—CHMe]$_3$—CH$_2$CH$_2$—O—Ar), 2.40(3H, s, C2-Me), 3.97(2H, dt, J = 2.7, 6.7 Hz, O—CH$_2$—C$_{19}$H$_{39}$), 4.59(2H, s, Ar—CH$_2$—Cl), 6.69(1H, dd, J = 2.4, 8.3 Hz, C5-H), 6.74(1H, d, J = 2.3 Hz, C3-H), 7.21(1H, d, J = 8.3 Hz, C6-H)

4-(2,3-dihydrophytyloxy)-2-methylbenzyl azide
$^1$H-NMR(300 MHz): δ 0.86(12H, t, J = 6.3 Hz, Me), 0.94(3H, d, J = 6.3 Hz, Me), 1.00-1.90 (24H, m, Me$_2$CH—[C$_3$H$_6$—CHMe]$_3$—CH$_2$CH$_2$—O—Ar), 2.34(3H, s, C2-Me), 3.98(2H, dt, J = 3.0, 6.6 Hz, O—CH$_2$—C$_{19}$H$_{39}$), 4.28(2H, s, Ar—CH$_2$—N3), 6.71(1H, dd, J = 2.6, 8.2 Hz, C5-H), 6.77(1H, d, J = 2.3 Hz, C3-H), 7.15(1H, d, J = 8.3 Hz, C6-H)

4-(2,3-dihydrophytyloxy)-2-methylbenzylamine
$^1$H-NMR(300 MHz): δ 0.86(12H, t, J = 6.3 Hz, Me), 0.93(3H, d, J = 6.6 Hz, Me), 1.00-1.90 (24H, m, Me$_2$CH—[C$_3$H$_6$—CHMe]$_3$—CH$_2$CH$_2$—O—Ar), 2.32(3H, s, C2-Me), 3.79(2H, s, Ar—CH$_2$—NH$_2$), 3.97(2H, dt, J = 3.0, 6.7 Hz, O—CH$_2$—C$_{19}$H$_{39}$), 6.71(1H, dd, J = 2.6, 8.2 Hz, C5-H), 6.68-6.75(2H, br, C3,5-H), 7.17(1H, d, J = 8.7 Hz, C6-H)

Prep. Ex. 15

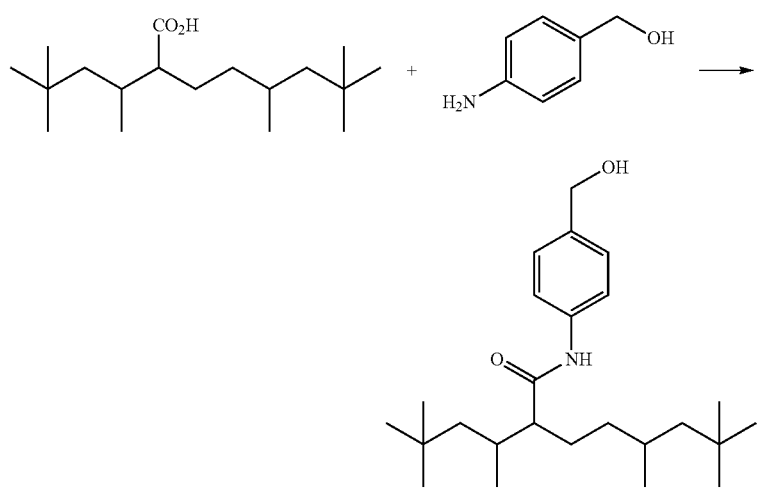

$^1$H-NMR(300 MHz): δ 0.92-0.99(m, 24H), 1.01-1.09(m, 6H), 1.19-1.23(m, 4H), 4.58(s, 2H), 7.21(d, 2H, J = 6 Hz), 7.43(d, 2H, J = 9 Hz), 7.53-7.66(b, 1H)

Prep. Ex. 16

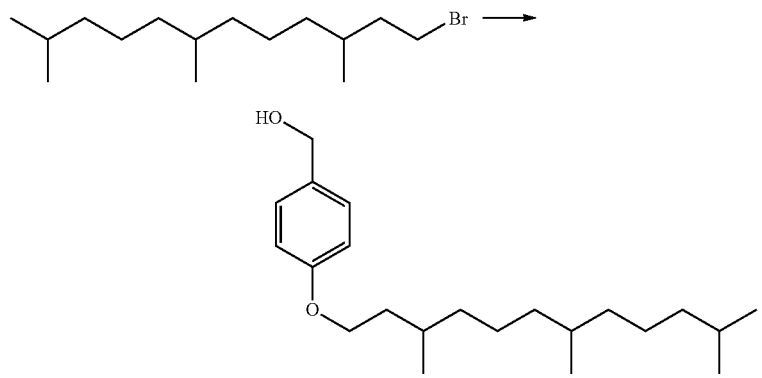

$^1$H-NMR(300 MHz): δ 0.81-0.89(m, 12H), 1.08-1.37(m, 12H), 1.48-1.83(m, 5H), 3.96-4.02(m, 2H), 4.62(s, 2H), 6.89(d, 2H, J = 9 Hz), 7.29(d, 2H, J = 9 Hz)

Prep. Ex. 17

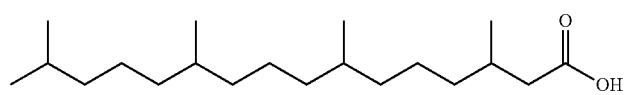 [SMILES: CC(C)CCCC(C)CCCC(C)CCCC(C)CC(=O)O]

$^1$H-NMR(400 MHz, CDCl$_3$): δ 0.84(d, 6H, J = 6.6 Hz), 0.87(d, 6H, J = 6.6 Hz), 0.92(d, 3H, J = 6.6 Hz), 1.00-1.44(m, 21H), 1.47-1.58(m, 1H), 1.91-1.99(m, 1H), 2.15(ddd, 1H, J = 15.0, 8.2, 2.0 Hz), 2.36(ddd, 1H, J = 15.0, 5.9, 1.9 Hz)

TABLE 6

Prep. Ex. 18

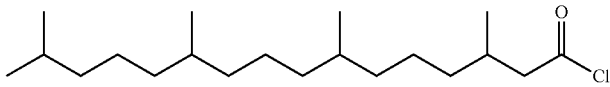 [SMILES: CC(C)CCCC(C)CCCC(C)CCCC(C)CC(=O)Cl]

$^1$H-NMR(400 MHz, CDCl$_3$): δ 0.84(d, 6H, J = 6.6 Hz), 0.87(d, 6H, J = 6.6 Hz), 0.92(d, 3H, J = 6.6 Hz), 1.00-1.44(m, 21H), 1.47-1.58(m, 1H), 1.91-1.99(m, 1H), 2.15(ddd, 1H, J = 15.0, 8.2, 2.0 Hz), 2.36(ddd, 1H, J = 15.0, 5.9, 1.9 Hz)

Prep. Ex. 19

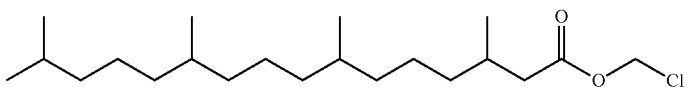 [SMILES: CC(C)CCCC(C)CCCC(C)CCCC(C)CC(=O)OCCl]

$^1$H-NMR(400 MHz, CDCl$_3$): δ 0.84(d, 6H, J = 6.6 Hz), 0.87(d, 6H, J = 6.6 Hz), 0.96(d, 3H, J = 6.6 Hz), 1.01-1.42(m, 20H), 1.45-1.57(m, 1H), 1.93-2.02(m, 1H), 2.18(ddd, 1H, J = 14.9, 8.1, 1.8 Hz), 2.37(ddd, 1H, J = 14.9, 5.9, 1.8 Hz), 5.70(d, 1H, J = 6.0 Hz), 5.71(d, 1H, J = 6.0 Hz)

Prep. Ex. 20

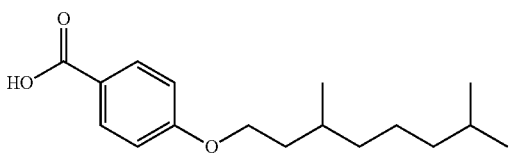 [SMILES: CC(C)CCCC(C)CCOc1ccc(C(=O)O)cc1]

$^1$H-NMR(400 MHz, CDCl$_3$): δ 0.87(d, 6H, J = 6.6 Hz), 0.95(d, 3H, J = 6.5 Hz), 1.12-1.38(m, 6H), 1.50-1.63(m, 3H), 1.82-1.90(m, 1H), 4.04-4.11(m, 1H), 6.93(d, 2H, J = 8.8 Hz), 8.06(d, 2H, J = 8.8 Hz)

Prep. Ex. 21

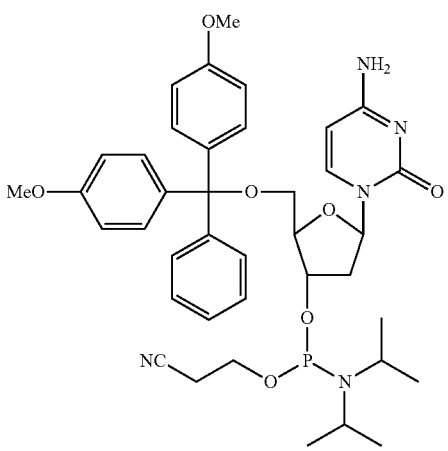 [SMILES: COc1ccc(C(OCC2OC(n3ccc(N)nc3=O)CC2OP(OCCC#N)N(C(C)C)C(C)C)(c2ccccc2)c2ccc(OC)cc2)cc1]

$^1$H-NMR(300 MHz, CDCl$_3$): δ 0.99-1.16 (m, 12H), 2.14-2.35(m, 1H), 2.42(t, 1H, J = 6.5 Hz), 2.55-2.74(m, 2H), 3.30-3.40 (m, 1H), 3.45-3.66(m, 4H), 3.70-3.87(m, 7H), 4.10-4.14(m, 1H), 4.52-4.69(m, 1H), 5.35(d, 1H, J = 7.2 Hz), 6.27-6.38(m, 1H), 6.79-6.88(m, 4H), 7.20-7.35(m, 7H), 7.35-7.44(m, 2H), 7.94, 8.03(2d, 1H, J = 7.4 Hz)
$^{31}$P-NMR(120 MHz, CDCl$_3$): δ 149.7, 149.1

Prep. Ex. 22

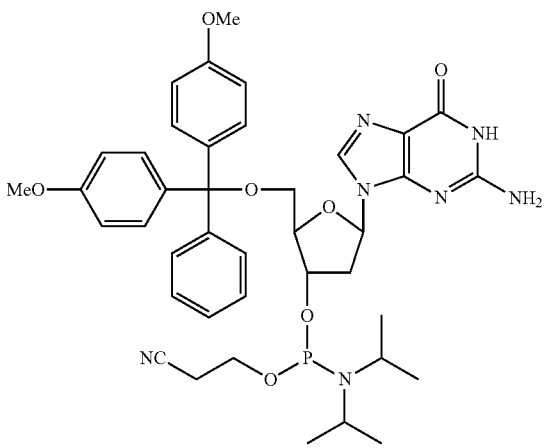 [SMILES: COc1ccc(C(OCC2OC(n3cnc4c(=O)[nH]c(N)nc43)CC2OP(OCCC#N)N(C(C)C)C(C)C)(c2ccccc2)c2ccc(OC)cc2)cc1]

$^1$H-NMR(400 MHz, CDCl$_3$): δ 1.04-1.19 (m, 12H), 2.44-2.61(m, 3H), 2.72-2.85(m, 1H), 3.29-3.40(m, 2H), 3.53-3.90(m, 10H), 4.24(s, 1H), 4.70-4.73(m, 1H), 6.02(brs, 2H), 6.21(t, 1H, J = 7.02 Hz), 6.78(dd, 4H, J = 2.70, 8.64 Hz), 7.14-7.30(m, 7H), 7.38-7.41(m, 2H), 7.65(d, 1H, J = 4.05 Hz)
$^{31}$P-NMR(160 MHz, CDCl$_3$): δ 149.5, 149.3

TABLE 6-continued

| Prep. Ex. 23 | 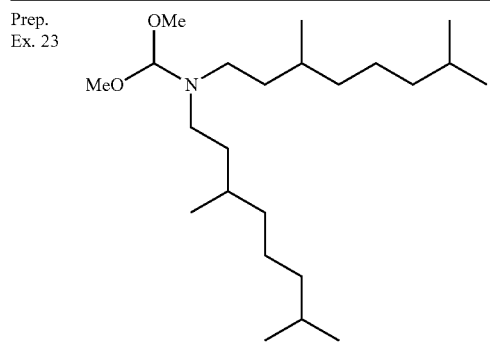 |

TABLE 7

| Prep. Ex. 24 | 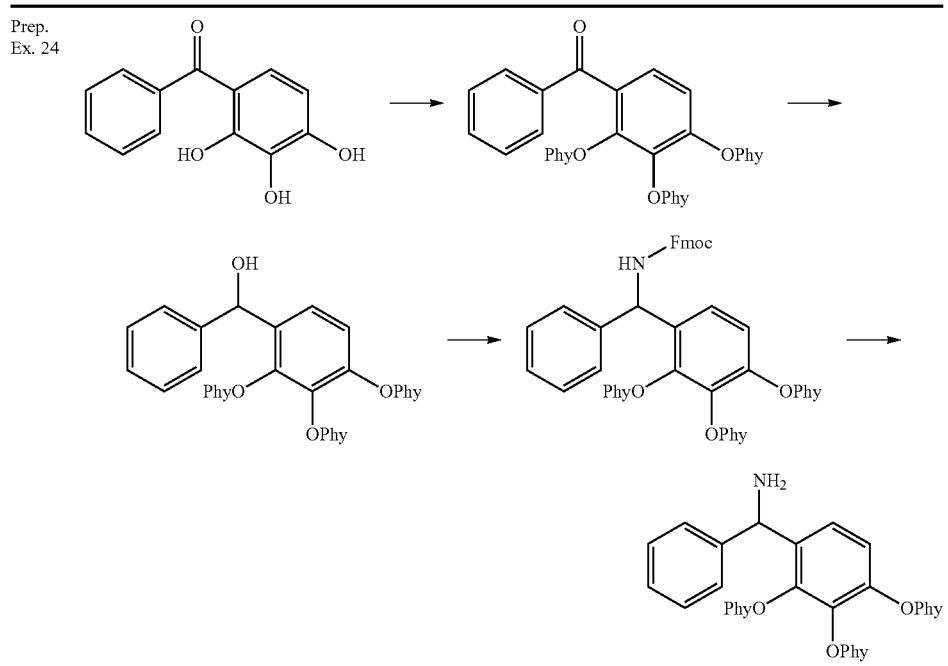 |

2,3,4-tris(2,3-dihydrophytyloxy)benzophenone
¹H-NMR(400 MHz, CDCl₃): δ 0.68-1.95(m, 117H), 3.88-3.95(m, 2H), 3.97-4.11(m, 4H), 6.71(d, 1H, J = 8.7 Hz), 7.14(d, 1H, J = 8.6 Hz), 7.38-7.44(m, 2H), 7.50-7.55(m, 1H), 7.76-7.79(m, 2H)
2,3,4-tris(2,3-dihydrophytyloxy)benzhydrylalcohol
¹H-NMR(400 MHz, CDCl₃): δ 0.78-1.95(m, 117H), 3.05-3.10(m, 1H), 3.68-3.78(m, 1H), 3.93-4.05(m, 5H), 5.89-5.94(m, 1H), 6.61(d, 1H, J = 8.6 Hz), 6.82-6.86(m, 1H), 7.20-7.28(m, 1H), 7.29-7.34(m, 2H), 7.35-7.39(m, 2H)
N-(9-fluorenylmethoxycarbonyl)-2,3,4-tris(2,3-dihydrophytyloxy)benzhydrylamine
¹H-NMR(400 MHz, CDCl₃): δ 0.83-1.90(m, 117H), 3.37-3.45(m, 1H), 3.92-4.06(m, 5H), 4.22-4.28(m, 1H), 4.35-4.42(m, 1H), 4.42-4.50(m, 1H), 5.90-5.98(m, 1H), 6.01-6.08(m, 1H), 6.63(d, 1H, J = 8.5 Hz), 6.89-6.94(m, 1H), 7.14-7.43(m, 9H), 7.58-7.65(m, 2H), 7.73-7.78(m, 2H)
2,3,4-tris(2,3-dihydrophytyloxy)benzhydrylamine
¹H-NMR(400 MHz, CDCl₃): δ 0.83-1.90(m, 117H), 3.77-3.91(m, 2H), 3.91-4.02(m, 4H), 5.40(s, 1H), 6.60(d, 1H, J = 8.6 Hz), 6.90(d, 1H, J = 8.4 Hz), 7.20-7.37(m, 5H)

| Prep. Ex. 25 | 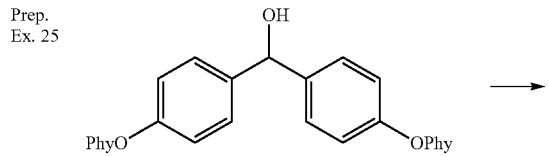 |

TABLE 7-continued

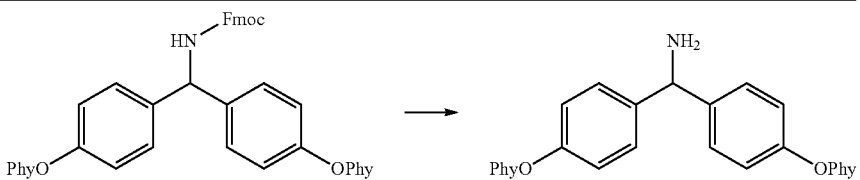

N-(9-fluorenylmethoxycarbonyl)-bis-4-(2,3-dihydrophytyloxy)benzhydrylamine
$^1$H-NMR(400 MHz, CDCl$_3$): δ 0.83-1.85(m, 78H), 3.90-4.02(m, 4H), 4.18-4.25(m, 1H), 4.35-4.44(m, 2H), 5.20-5.30(m, 1H), 5.83-5.91(m, 1H), 6.84(d, 4H, J = 8.9 Hz), 7.11(d, 4H, J = 8.6 Hz), 7.24-7.43(m, 4H), 7.53-7.62(m, 2H), 7.70-7.78(m, 2H)
4,4'-bis(2,3-dihydrophytyloxy)benzhydrylamine
$^1$H-NMR(400 MHz, CDCl$_3$) δ 0.80-0.93(m, 30H), 1.01-1.85(m, 52H), 3.93-3.98(m, 4H), 5.12(s, 1H), 6.83(d, 4H, J = 8.7 Hz), 7.24(d, 4H, J = 8.9 Hz)

Prep. Ex. 26

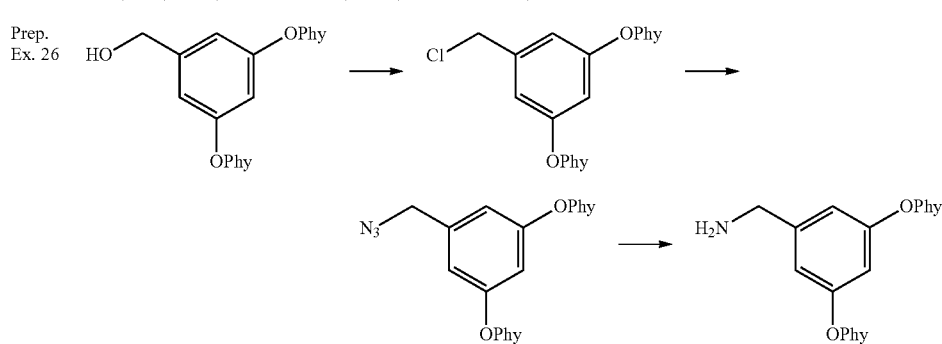

3,5-bis(2,3-dihydrophytyloxy)benzyl chloride
$^1$H-NMR(400 MHz, CDCl$_3$): δ 0.83-1.85(m, 78H), 3.90-4.02(m, 4H), 4.50(s, 2H), 6.40(d, 1H, J = 2.2 Hz), 6.51(d, 2H, J = 2.2 Hz)
3,5-bis(2,3-dihydrophytyloxy)benzyl azide
$^1$H-NMR(400 MHz, CDCl$_3$): δ 0.83-1.85(m, 78H), 3.90-4.02(m, 4H), 4.50(s, 2H), 6.40-6.45(m, 3H)
3,5-bis(2,3-dihydrophytyloxy)benzyl amine
$^1$H-NMR(400 MHz, CDCl$_3$): δ 0.82-1.88(m, 78H), 3.79(s, 2H), 3.92-4.01(m, 4H), 6.34(t, 1H, J = 2.2 Hz), 6.45(d, 2H, J = 2.2 Hz)

TABLE 8

Prep. Ex. 27

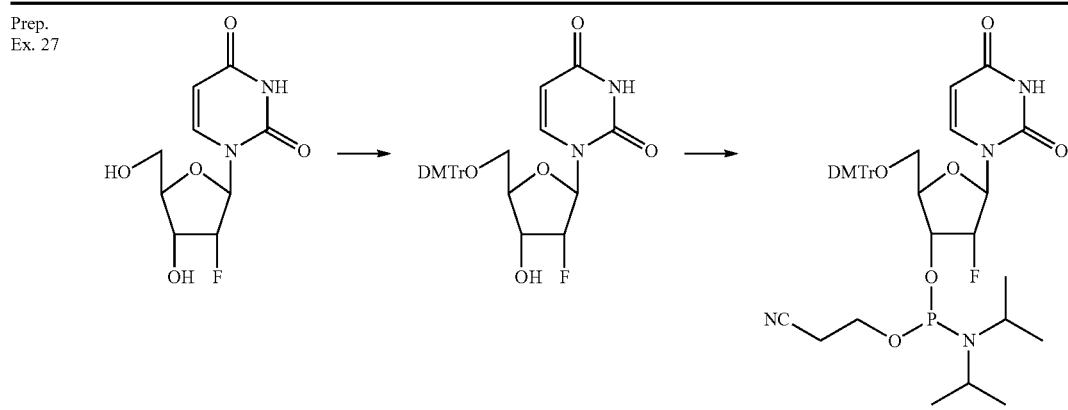

5'-O-(4,4'-dimethoxytrityl)-2'-deoxy-2'-fluorouridine
$^1$H-NMR(400 MHz, CDCl$_3$): δ 3.50-3.64(m, 2H), 3.80(s, 6H), 4.08(m, 1H), 4.49-4.60(m, 1H), 5.03(dd, 1H, J = 4.2, 51.2 Hz), 5.33(d, 1H, J = 8.2 Hz), 6.07(d, 1H, J = 14.9 Hz), 6.83-7.40(m, 13H), 7.90(d, 1H, J = 8.2 Hz)
5'-O-(4, 4'-dimethoxytrityl)-2'-deoxy-2'-fluorouridine-3'-O-[(2-cyanoethyl)-N,N-diisopropylphosphoramidite]
$^1$H-NMR(400 MHz, CDCl$_3$): δ 0.99-1.32(m, 12H), 2.40-2.65(m, 2H), 3.40-3.93(m, 6H), 3.80(m, 6H), 4.20-4.30(m, 1H), 4.55-4.80(m, 1H), 5.00-5.23(m, 1H), 5.24-5.29(m, 1H), 6.07(d, 2H, J = 16.1 Hz), 6.82-7.44(m, 13H), 7.92-8.04(m, 1H)
$^{31}$P-NMR(160 MHz, CDCl$_3$): δ 149.7, 150.3

TABLE 8-continued
Ex. 1
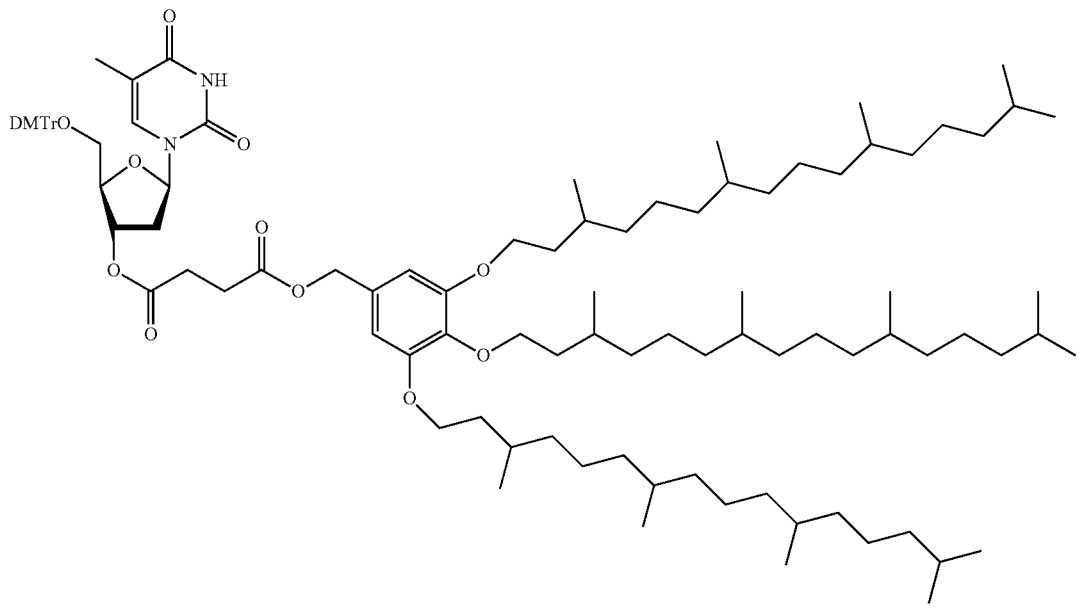
¹H-NMR(400 MHz, CDCl₃): δ 0.83-0.97(m, 45H), 0.98-(m, 75H), 2.38-2.48(m, 2H), 2.60-
2.71(m, 4H), 3.39-3.51(m, 2H), 3.79(s, 6H), 3.85-4.20(m, 6H), 4.13-4.15(m, 1H), 5.40-
5.50(m, 1H), 6.38-6.45(m, 1H), 6.54(s, 2H), 6.84(d, 4H, J = 8.9 Hz), 7.20-7.39(m, 9H),
7.60(s, 1H)
Ex. 2
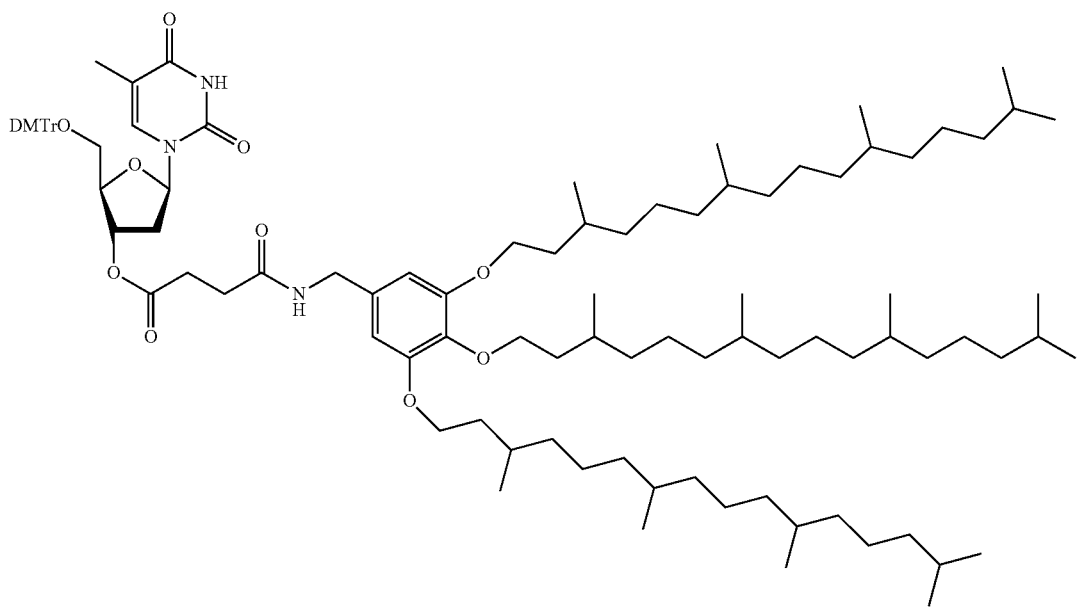
¹H-NMR(400 MHz, CDCl₃): δ 0.83-0.97(m, 45H), 1.00-2.00(m, 75H), 2.42-2.48(m, 2H),
2.52(t, 2H, J = 6.6 Hz), 2.71(t, 2H, J = 6.6 Hz), 3.79(s, 6H), 3.47(ddt, 2H, J = 2.4, 5.6, 16.2
Hz), 3.91-4.00(m, 6H), 4.13-4.17(m, 1H), 5.46-5.50(m, 1H), 6.40-6.45(m, 1H), 6.47(s,
2H), 6.82-6.85(m, 4H), 7.22-7.39(m, 9H), 7.61(d, 1H, J = 1.2 Hz)

TABLE 9
Ex. 4
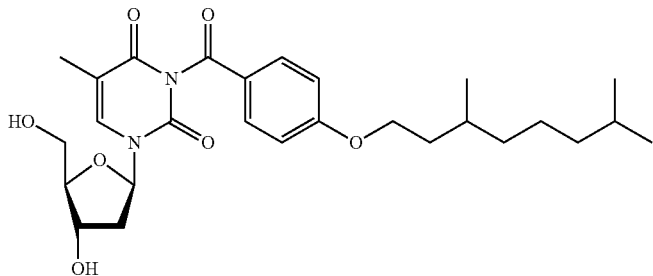 [SMILES: Cc1cn([C@H]2C[C@@H](O)[C@@H](CO)O2)c(=O)n(C(=O)c2ccc(OCCC(C)CCCC(C)C)cc2)c1=O]
$^1$H-NMR(400 MHz, CDCl$_3$): δ 0.87(d, 6H, J = 6.6 Hz), 0.93(d, 3H, J = 6.4 Hz), 1.10-1.89(m, 10H), 1.93(s, 3H), 2.25-2.40(m, 2H), 2.81(brs, 1H), 3.48(dd, 1H, J = 7.1, 14.0 Hz), 3.72-3.91(m, 2H), 3.92(d, 1H, J = 2.9 Hz), 4.00-4.12(m, 2H), 4.49(m, 1H), 6.19(m, 1H), 6.93(d, 2H, J = 8.7 Hz), 7.60(s, 1H), 7.86(d, 2H, J = 8.7 Hz)
Ex. 5
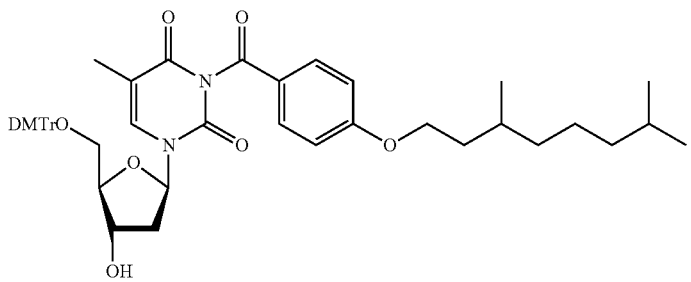
$^1$H-NMR(400 MHz, CDCl$_3$): δ 0.87(d, 6H, J = 6.6), 0.93(d, 3H, J = 6.5 Hz), 1.12-1.88(m, 13H), 2.38-2.46(m, 2H), 3.39(dd, 1H, J = 3.1, 10.6 Hz), 3.51(dd, 1H, J = 3.1, 10.6 Hz), 3.80(s, 6H), 4.01-4.10(m, 3H), 4.57-4.62(m, 1H), 6.39(t, 1H, J = 6.6 Hz), 6.83-6.88(m, 4H), 6.92(d, 2H, J = 9.0 Hz), 7.24-7.42(m, 9H), 7.68(s, 1H), 7.88(d, 2H, J = 9.0 Hz)
Ex. 6
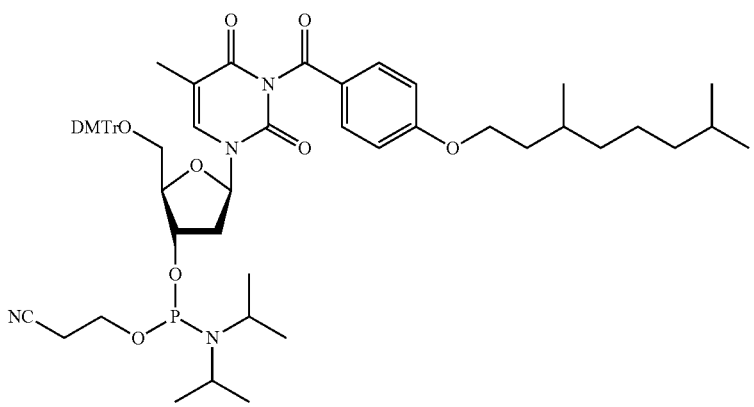
$^1$H-NMR(400 MHz, CDCl$_3$): δ 0.87(d, 6H, J = 6.6 Hz), 0.93(d, 3H, J = 6.4 Hz), 1.14-1.17(m, 12H), 1.17-1.90(m, 13H), 2.32-2.43(m, 1H), 2.45-2.55(m, 1H), 2.43(t, 2H, J = 6.3 Hz), 2.60 (t, 2H, J = 6.3 Hz), 3.32-3.38(m, 1H), 3.49-3.85(m, 5H), 3.80, 3.81(2s, 6H), 4.02-4.09 (m, 2H), 4.13, 4.19(2m, 1H), 4.63-4.71(m, 1H), 6.36-6.42(m, 1H), 6.84-6.87(m, 4H), 6.93 (d, 2H, J = 8.8 Hz), 7.13-7.19(m, 2H), 7.22-7.35(m, 5H), 7.39-7.44(m, 2H), 7.70, 7.75(2s, 1H), 7.89(d, 2H, J = 8.8 Hz), 7.90(d, 2H, J = 8.8 Hz)
$^{31}$P-NMR(400 MHz, CDCl$_3$): δ 149.7, 150.3

TABLE 9-continued
Ex. 7
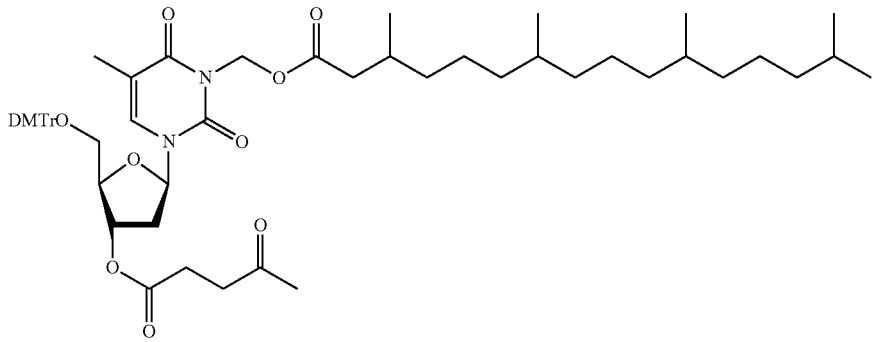
$^1$H-NMR(400 MHz, CDCl$_3$): δ 0.83-0.87(m, 12H), 0.94(d, 3H, J = 6.6 Hz), 1.04-1.58(m, 21H), 1.89-2.01(m, 1H), 2.11(ddd, 1H, J = 2.6, 8.5, 14.9 Hz), 2.19(s, 3H), 2.31-2.37(m, 1H), 2.42-2.51(m, 2H), 2.57(t, 2H, J = 6.2 Hz), 2.75(dt, 2H, J = 2.4, 6.4 Hz), 3.45(dd, 1H, J = 2.4, 10.5 Hz), 3.48(dd, 1H, J = 2.4, 10.5 Hz), 3.79(s, 6H), 4.12-4.15(m, 1H), 5.46-5.50(m, 1H), 5.98(t, 2H, J = 7.3 Hz), 6.46(dd, 1H, J = 5.7, 8.8 Hz), 6.81-6.85(m, 4H), 7.14-7.39(m, 9H), 7.64(d, 1H, J = 1.1 Hz)
TABLE 10
Ex. 8
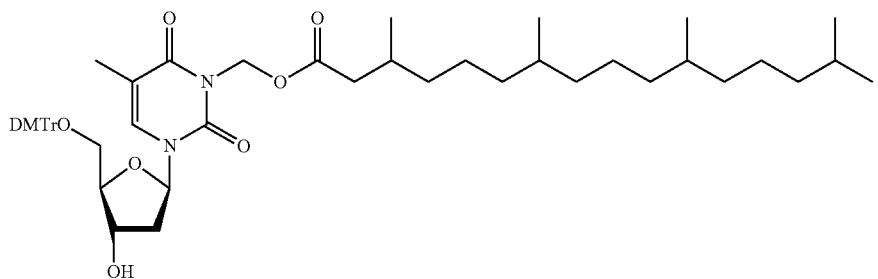
$^1$H-NMR(400 MHz, CDCl$_3$): δ 0.83-0.87(m, 12H), 0.93(d, 3H, J = 6.6 Hz), 1.02-1.56(m, 24H), 1.88-1.99(m, 1H), 2.10(ddd, 1H, J = 3.0, 6.9, 15.9 Hz), 2.31-2.36(m, 2H), 2.42(ddd, 1H, J = 3.0, 6.9, 15.9 Hz), 3.38(dd, 1H, J = 3.0, 10.5 Hz), 3.49(dd, 1H, J = 3.0, 10.5 Hz), 3.75-3.81(m, 2H), 3.79(s, 6H), 4.04(dt, 1H, J = 3.1, 6.2 Hz), 4.56-4.60(m, 1H), 5.98(dt, 2H, J = 1.9, 11.2 Hz), 6.42(dt, 1H, J = 1.2, 7.3 Hz), 6.72-6.78(m, 1H), 6.82-6.86(m, 4H), 7.10-7.41(m, 9H), 7.60(d, 1H, J = 1.2 Hz)
Ex. 9
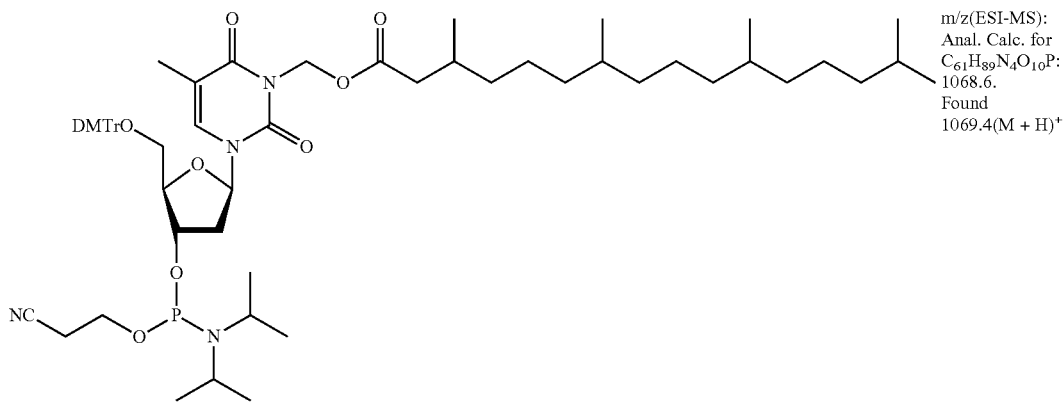
m/z(ESI-MS):
Anal. Calc. for
C$_{61}$H$_{89}$N$_4$O$_{10}$P:
1068.6.
Found
1069.4(M + H)$^+$ Ex. 10
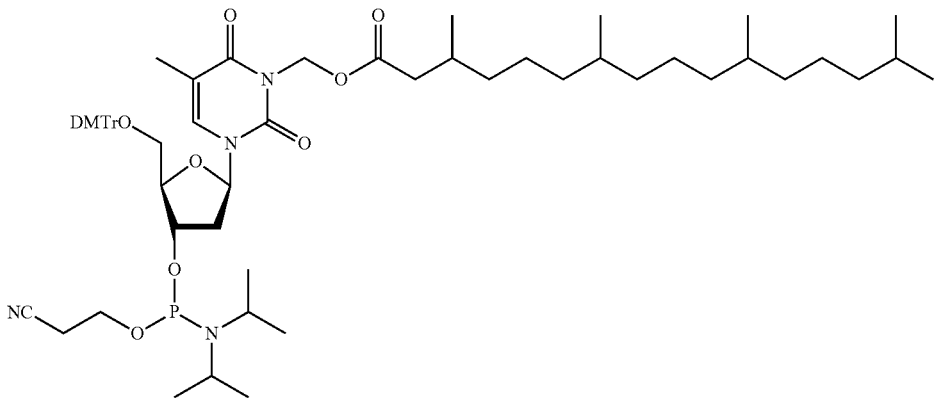
¹H-NMR(400 MHz, CDCl₃): δ 0.83-0.87(m, 12H), 0.94(d, 3H, J = 6.6 Hz), 1.03-1.58(m, 37H), 1.94-1.97(m, 1H), 2.07-2.14(m, 1H), 2.29-2.37(m, 1H), 2.41(t, 1H, J = 6.3 Hz), 2.46-2.59(m, 1H), 2.61(t, 1H, J = 6.3 Hz), 3.31-3.35(m, 1H), 3.47-3.64(m, 4H), 3.74-3.85(m, 1H), 3.78, 3.79(2s, 6H), 4.14, 4.18(2d, 1H, J = 2.2 Hz), 4.63-4.69(m, 1H), 5.98(s, 2H), 6.40-6.46(m, 1H), 6.82-6.86(m, 4H), 7.15-7.18(m, 2H), 7.23-7.32(m, 5H), 7.39-7.41(m, 2H), 7.63, 7.68(2d, 1H, J = 1.1 Hz)
³¹P-NMR(400 MHz, CDCl₃): δ 149.7, 150.3
Ex. 11
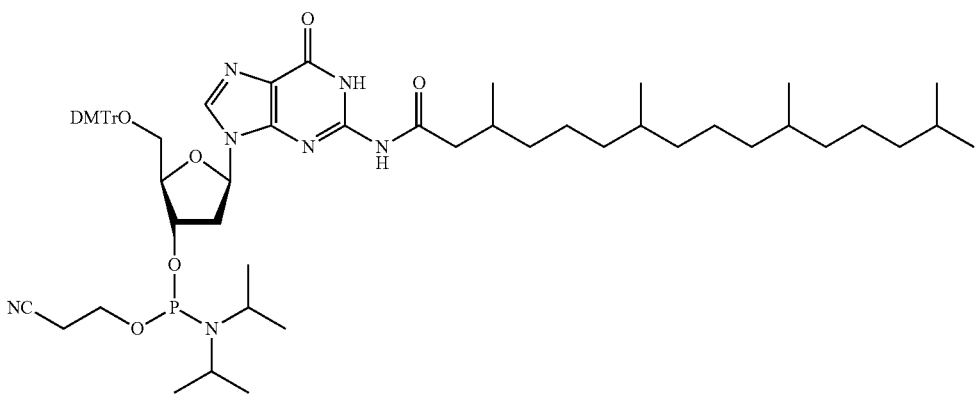
¹H-NMR(400 MHz, CDCl₃): δ 0.83-0.87(m, 27H), 1.09-1.52(m, 22H), 2.08-2.19(m, 1H), 2.43-2.49(m, 2H), 2.62(t, 1H, J = 6.3 Hz), 2.70-2.76(m, 1H), 2.86-2.95(m, 1H), 3.29-3.88 (m, 6H), 3.77(s, 6H), 4.26-4.30(m, 1H), 4.73-4.76(m, 1H), 6.27-6.30(m, 1H), 6.75-7.42 (m, 13H), 7.85, 7.86(2S, 1H)
³¹P-NMR(400 MHz, CDCl₃): δ 149.9, 150.0
m/z(ESI-MS): Anal. Calc. for C₆₀H₈₆N₇O₈P: 1063.6. Found 1062.4(M − H)⁻

TABLE 11
Ex. 12
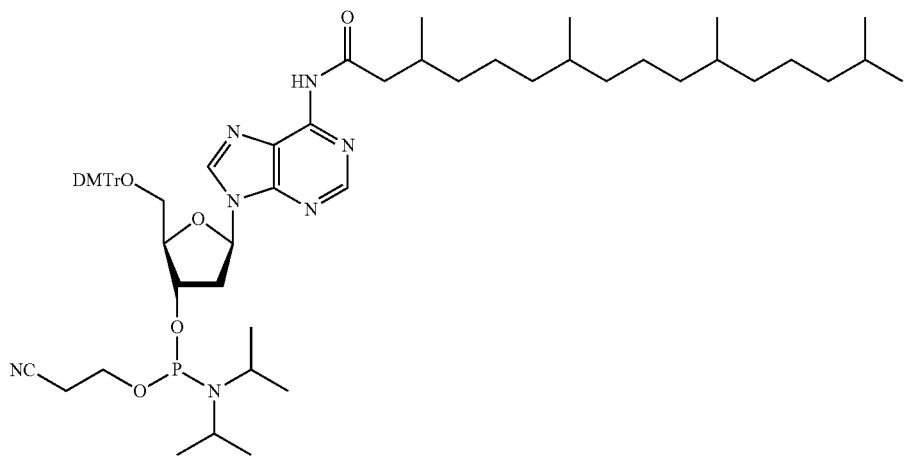
¹H-NMR(400 MHz, CDCl₃): δ 0.82-0.87(m, 24H), 0.93(d, 3H, J = 6.6 Hz), 1.02-1.55(m, 22H), 1.87-1.93(m, 1H), 1.99-2.02(m, 1H), 2.22-2.26(m, 1H), 2.38-2.49(m, 1H), 2.45(t, 1H, J = 6.5 Hz), 2.60(t, 1H, J = 6.5 Hz), 3.31-3.42(m, 2H), 3.57-3.63(m, 2H), 3.66-3.86(m, 2H), 3.76, 3.77(2s, 6H), 4.26-4.33(m, 1H), 4.70-4.78(m, 1H), 6.41-6.49(m, 1H), 6.76-6.81 (m, 4H), 7.15-7.48(m, 9H), 7.97, 7.99(2s, 1H), 8.61, 8.85(2s, 1H)
³¹P-NMR(400 MHz, CDCl₃): δ 149.9, 150.0
m/z(ESI-MS): Anal. Calc. for $C_{60}H_{86}N_7O_7P$: 1047.6. Found 1046.3(M − H)⁻
Ex. 19
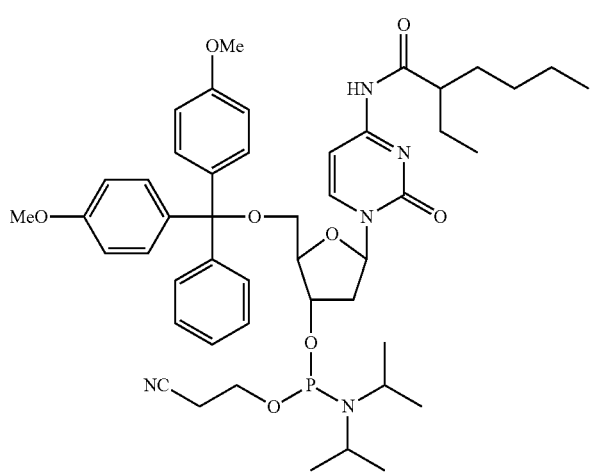 [SMILES: CCCCC(CC)C(=O)Nc1ccn(C2CC(OP(OCCC#N)N(C(C)C)C(C)C)C(COC(c3ccccc3)(c3ccc(OC)cc3)c3ccc(OC)cc3)O2)c(=O)n1]
¹H-NMR(300 MHz, CDCl₃): δ 0.83-0.95 (m, 6H), 1.03-1.35(m, 16H), 1.42-1.73 (m, 4H), 2.10-2.33(m, 2H), 2.44(t, 1H, J = 6.5 Hz), 2.62(t, 1H, J = 6.3 Hz), 2.68-2.85 (m, 1H), 3.30-3.90(m, 6H), 3.81(s, 6H), 4.20-4.24(m, 1H), 4.53-4.65(m, 1H), 6.18-6.28(m, 1H), 6.82-6.89(m, 4H), 7.13-7.44(m, 9H), 7.79(brs, 1H), 8.19, 8.29(2d, 1H, J = 7.4 Hz)
³¹P-NMR(120 MHz, CDCl₃): δ 149.9, 149.2
Ex. 20
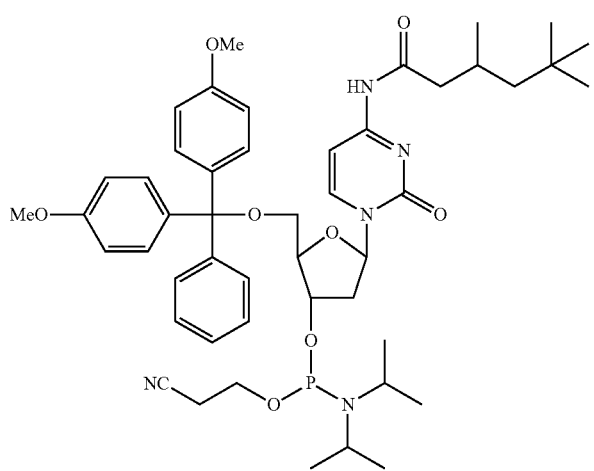 [SMILES: COc1ccc(C(OCC2OC(n3ccc(NC(=O)CC(C)CC(C)(C)C)nc3=O)CC2OP(OCCC#N)N(C(C)C)C(C)C)(c2ccccc2)c2ccc(OC)cc2)cc1]
¹H-NMR(400 MHz, CDCl₃): δ 0.90(s, 9H), 0.99-1.30(m, 18H), 2.03-2.83(m, 6H), 3.33-3.88(m, 12H), 3.34-3.67(m, 5H), 3.69-3.86(m, 1H), 4.18-4.4.24(m, 1H), 4.54-4.68(m, 1H), 6.22-6.29(m, 1H), 6.82-6.88(m, 4H), 7.10-7.43(m, 18H), 8.17-8.29(m, 2H)
³¹P-NMR(160 MHz, CDCl₃): δ 150.6, 150.0

TABLE 11-continued
| Ex. 21 | 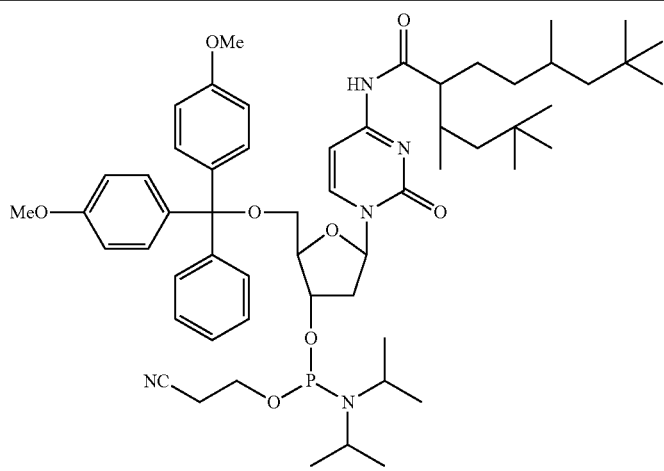 | ¹H-NMR(300 MHz, CDCl₃): δ 0.78-1.50 (m, 46H), 2.13-2.85(m, 5H), 3.34-3.95 (m, 12H), 4.20-4.24(m, 1H), 4.53-4.68 (m, 1H), 6.22-6.31(m, 1H), 6.78-6.92 (m, 4H), 7.10-7.45(m, 9H), 7.80-7.89 (m, 1H), 8.12-8.32(m, 1H) ³¹P-NMR(120 MHz, CDCl₃): δ 149.8, 149.1 |
TABLE 12
| Ex. 22 | 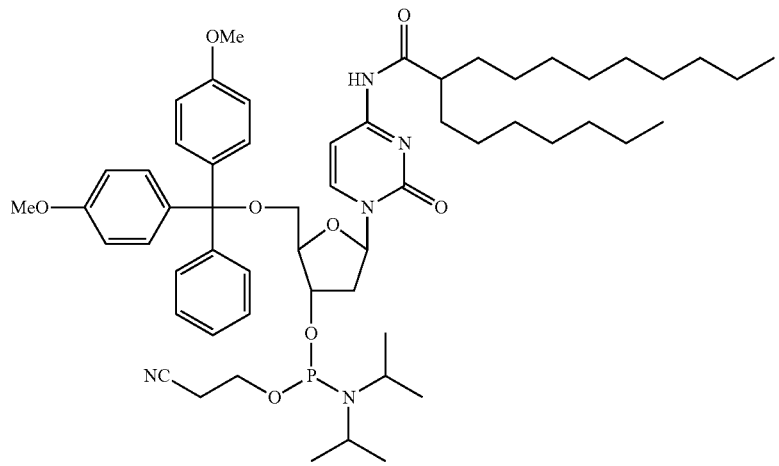 [SMILES: CCCCCCCCCC(CCCCCCC)C(=O)Nc1ccn(C2CC(OP(OCCC#N)N(C(C)C)C(C)C)C(COC(c3ccccc3)(c3ccc(OC)cc3)c3ccc(OC)cc3)O2)c(=O)n1] | ¹H-NMR(400 MHz, CDCl₃): δ 0.84-0.92(m, 6H), 1.05-1.20(m, 12H), 1.21-1.75(m, 28H), 2.07-2.85(m, 5H), 3.34-3.88(m, 6H), 3.80, 3.81(2s, 6H), 4.20-4.24 (m, 1H), 4.53-4.66(m, 1H), 6.23-6.30(m, 1H), 6.82-6.88 (m, 4H), 7.12-7.42(m, 10H), 7.89-7.99(m, 1H), 8.18, 8.27(2d, 1H, J = 7.4 Hz) ³¹P-NMR(160 MHz, CDCl₃): δ 150.0, 150.6 |
| Ex. 23 | 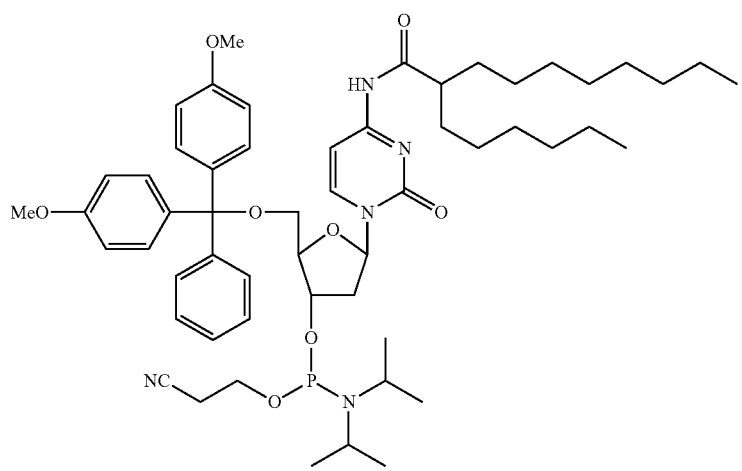 [SMILES: CCCCCCCCC(CCCCCC)C(=O)Nc1ccn(C2CC(OP(OCCC#N)N(C(C)C)C(C)C)C(COC(c3ccccc3)(c3ccc(OC)cc3)c3ccc(OC)cc3)O2)c(=O)n1] | ¹H-NMR(300 MHz, CDCl₃): δ 0.81-0.93(m, 6H), 1.05-1.20(m, 12H), 1.20-1.80(m, 24H), 2.18-2.85(m, 5H), 3.32-3.88(m, 6H), 3.80, 3.81(2s, 6H), 4.19-4.24 (m, 1H), 4.53-4.68(m, 1H), 6.22-6.31(m, 1H), 6.81-6.88 (m, 4H), 7.13-7.45(m, 10H), 8.02-8.12(m, 1H), 8.19, 8.29(2d, 1H, J = 7.5 Hz) ³¹P-NMR(120 MHz, CDCl₃): δ 149.2, 149.8 |

TABLE 12-continued
Ex. 24 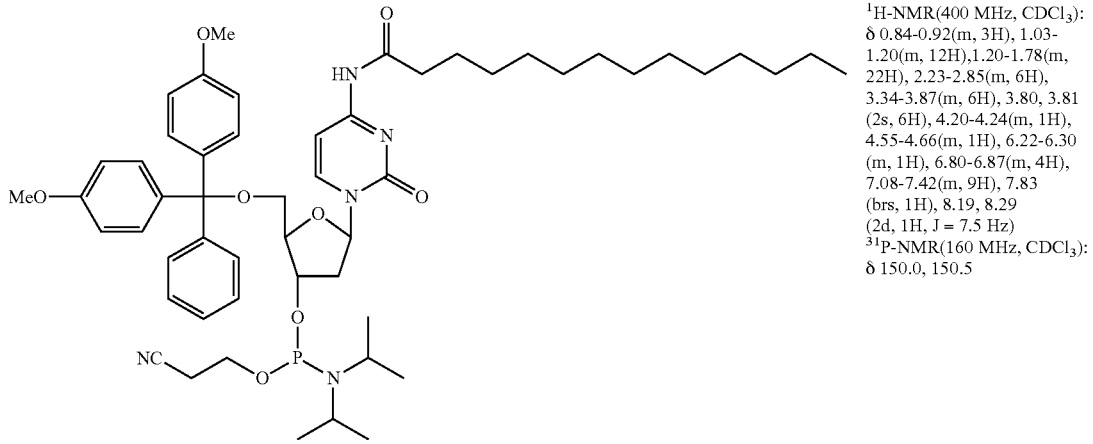
¹H-NMR(400 MHz, CDCl₃):
δ 0.84-0.92(m, 3H), 1.03-
1.20(m, 12H),1.20-1.78(m,
22H), 2.23-2.85(m, 6H),
3.34-3.87(m, 6H), 3.80, 3.81
(2s, 6H), 4.20-4.24(m, 1H),
4.55-4.66(m, 1H), 6.22-6.30
(m, 1H), 6.80-6.87(m, 4H),
7.08-7.42(m, 9H), 7.83
(brs, 1H), 8.19, 8.29
(2d, 1H, J = 7.5 Hz)
³¹P-NMR(160 MHz, CDCl₃):
δ 150.0, 150.5
Ex. 25 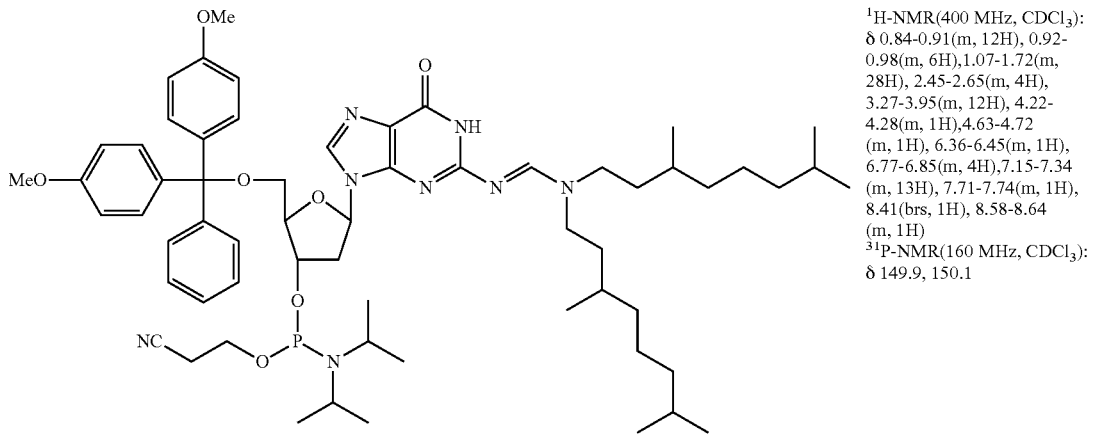
¹H-NMR(400 MHz, CDCl₃):
δ 0.84-0.91(m, 12H), 0.92-
0.98(m, 6H),1.07-1.72(m,
28H), 2.45-2.65(m, 4H),
3.27-3.95(m, 12H), 4.22-
4.28(m, 1H),4.63-4.72
(m, 1H), 6.36-6.45(m, 1H),
6.77-6.85(m, 4H),7.15-7.34
(m, 13H), 7.71-7.74(m, 1H),
8.41(brs, 1H), 8.58-8.64
(m, 1H)
³¹P-NMR(160 MHz, CDCl₃):
δ 149.9, 150.1
Ex. 33 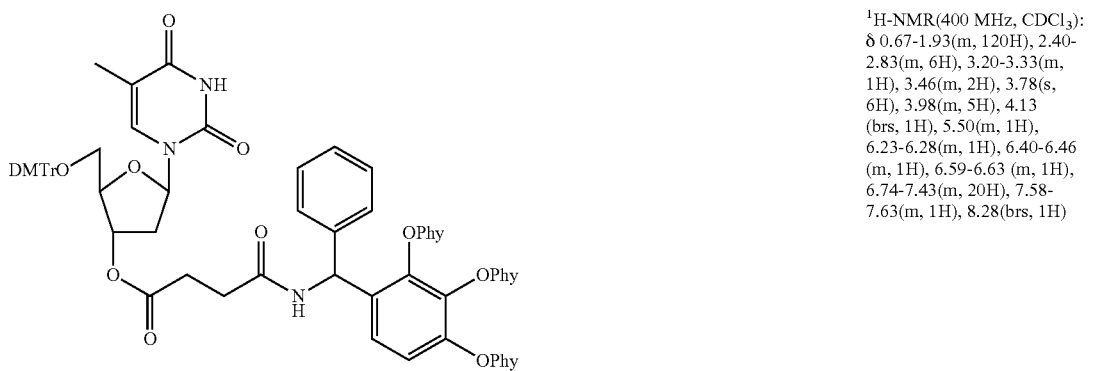
¹H-NMR(400 MHz, CDCl₃):
δ 0.67-1.93(m, 120H), 2.40-
2.83(m, 6H), 3.20-3.33(m,
1H), 3.46(m, 2H), 3.78(s,
6H), 3.98(m, 5H), 4.13
(brs, 1H), 5.50(m, 1H),
6.23-6.28(m, 1H), 6.40-6.46
(m, 1H), 6.59-6.63 (m, 1H),
6.74-7.43(m, 20H), 7.58-
7.63(m, 1H), 8.28(brs, 1H)

TABLE 13

| Ex. 34 | 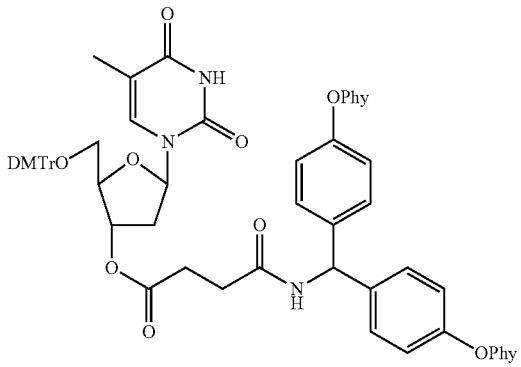 | ¹H-NMR(400 MHz, CDCl₃): δ 0.83-0.95 (m, 30H), 1.00-1.85(m, 51H), 2.40-2.45 (m, 2H), 2.52-2.58(m, 2H), 2.67-2.74 (m, 2H), 3.45(d, 2H, J = 2.3 Hz), 3.78(s, 6H), 3.85-3.97(m, 4H), 4.10(brs, 1H), 5.48 (m, 1H), 6.09(dd, 2H, J = 7.9, 13.6 Hz), 6.40(m, 1H), 6.78-7.41(m, 21H), 7.60 (m, 1H), 8.14(brs, 1H) |
|---|---|---|
| Ex. 35 | 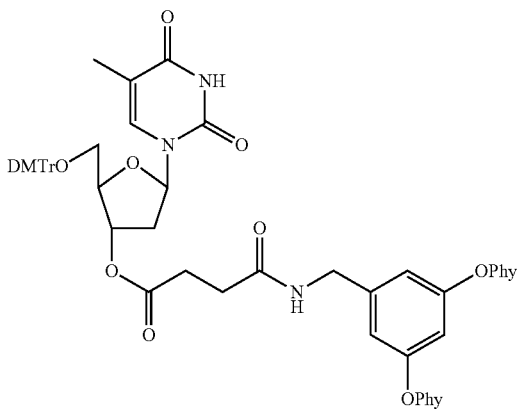 | ¹H-NMR(400 MHz, CDCl₃): δ 0.83-0.95 (m, 30H), 1.00-1.85(m, 51H), 2.40-2.55 (m, 4H), 2.67-2.74(m, 2H), 3.43-3.50 (m, 1H), 3.78(s, 6H), 3.88-3.97(m, 4H), 4.14(m, 1H), 4.35(d, 1H, J = 5.5 Hz), 5.45-5.50(m, 1H), 5.72-5.77(m, 1H), 6.35-6.45(m, 4H), 6.80-7.40(m, 13H), 7.60(m, 1H), 7.94(brs, 1H) |
| Ex. 43 | 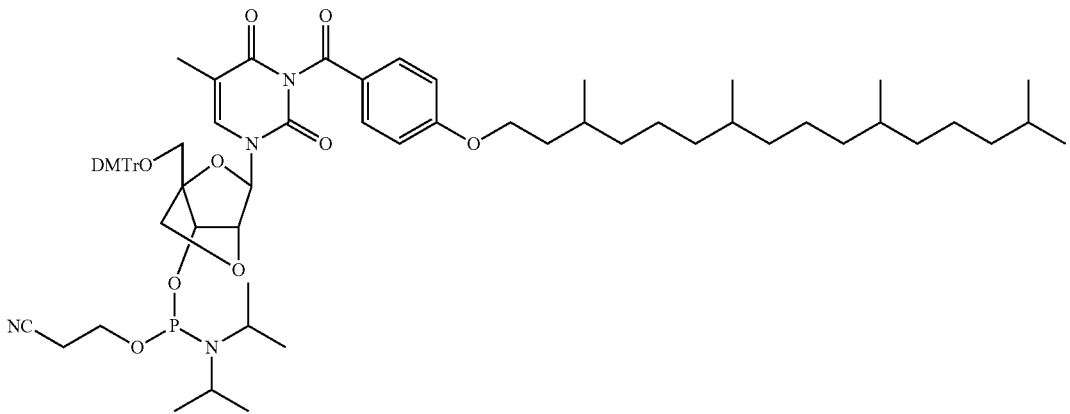 | |
| | 1H-NMR(400 MHz, CDCl₃): δ 0.83-0.95(m, 15H), 0.97-1.93(m, 39H), 2.35-2.40(m, 1H), 2.52-2.63(m, 1H), 3.37-3.60(m, 6H), 3.78-3.90(m, 8H), 4.03-4.13(m, 2H), 4.33-4.42 (m, 1H), 4.59(d, 1H, J = 26.5 Hz), 5.67(d, 1H, J = 2.2 Hz), 6.81-6.88(m, 4H), 6.90-6.95(m, 2H), 4.01-4.12(m, 2H), 6.91-6.96(m, 2H), 7.23-7.36(m, 7H), 7.42-7.49(m, 2H), 7.68-7.74 (m, 1H), 8.03-8.08(m, 2H) | |
| Comp. Ex. 2 | TLC: Rf = 0.50(dichloromethane:methanol = 4:1) ¹H-NMR(400 MHz): δ 0.89(t, 9H, J = 7.0 Hz, H3C(octadecyloxy)), 1.25-1.79(m, 102H, —CH2-(octadecyloxy)), 1.35(s, 3H, N5—CH3-thymidine), 2.45(m, 2H, 2'-thymidine), 2.51(m, 2H, succinyl), 2.70(m, 2H, succinyl), 3.46(m, 2H, 5'-thymidine), 3.79(s, 6H, H3CO-DMTr), 3.79-3.95(m, 6H, Bn-O—CH2—), 4.15(m, 1H, 4'-thymidine), 4.32(d, 2H, J = 5.5 Hz, —NH—CH2-benzyl), 5.47(m, 1H, 3'-thymidine), 5.72(d, 2H, J = 5.5 Hz, —NH—CH2-benzyl), 6.41(m, 1H, 1'-Thymidine), 6.45(s, 2H, -benzyl), 6.83(d, 4H, J = 9.0 Hz, DMTr), 7.24-7.38 (m, 9H, DMTr), 7.61(s, 1H, N6-thymidine), 7.95(br•s, N3—NH-thymidine) | |

Experimental Example 1

Solubility Test of Nucleoside with Protected 3'-hydroxyl Group

The solubility (=solute/(solvent+solute)×100) (mass %) at 20° C., shown in the following Table 2, of the compound representing the present invention, thymidine wherein the 5'-hydroxyl group is protected by dimethoxytrityl group, and the 3'-hydroxyl group is protected by the branched chain-containing aromatic protecting group (Example 2), and thymidine wherein the 5'-hydroxyl group is protected by dimethoxytrityl group, and the 3'-hydroxyl group is protected by the corresponding group containing the straight chain structure (Comparative Example 2) as a comparison target thereof was measured.

[Solubility Measurement Method]
1) A solute (100 parts by mass) was added to a solvent (100 parts by mass) to saturation at 20° C.
2) When the solute remained by visual observation, the supernatant was quantitatively analyzed under the following HPLC conditions, and the concentration was determined and taken as the solubility (=solute/(solvent+solute)×100) (mass %).
3) When the solute was absent by visual observation, the solubility was >50 mass %.

[HPLC Analysis Conditions]
use instrument: Hitachi high performance liquid chromatography LaChrom Elite L-2000 series
column: YMC-PACK 5 μm 150×4.6 mm
column temperature: 40° C.
eluent: THF/CH$_3$CN/H$_2$O
flow rate: 1.0 ml/min extraction solvents in the present invention, and a solvent of an appropriate mixture of heptane with toluene (non-polar solvent with different polarity from heptane) or acetonitrile (polar solvent), as compared to a nucleoside protected by a group having a straight chain structure similar to that of a known nucleotide 3'-hydroxyl-protecting group (described in JP-A-2010-275254).

Industrial Applicability

Using the particular oligonucleotide comprising a protected base of the present invention, a production method of oligonucleotide by a phosphoramidite method wherein the oligonucleotide can be purified by a liquid-liquid extraction operation efficiently and in a high yield can be provided.

Using the particular oligonucleotide comprising a protected base of the present invention, liposolubility and solubility in an organic solvent (particularly, non-polar solvent) of an intermediate oligonucleotide obtained in each step of a nucleotide elongation reaction are strikingly improved to enable isolation and purification by an extraction operation alone, and therefore, a complicated, time-consuming operation such as solidification isolation and the like is not required, the speed increases, and the efficiency and producibility of synthesis of oligonucleotide with high polymerization degree is strikingly improved.

Furthermore, by using the (oligo)nucleotide comprising a protected base of the present invention, which is imparted with liposoluble and solubility in organic solvents (particularly, non-polar solvents), adding a particular cation scavenger during or after deprotection of the 5'-terminal hydroxyl group protected by a temporary protecting group, applying a neutralization treatment after completion of the deprotection reaction, and using a particular oxidizing agent or sulfurizing agent in an oxidation step or a sulfurization step, for a nucle-

TABLE 14

| Solvent | Example 2 | Comparative Example 2 |
|---|---|---|
| heptane | >50% by mass | 0% by mass |
| heptane/toluene = 1/1 | >50% by mass | 22.3% by mass |
| heptane/toluene/acetonitrile = 1/1/1 | >50% by mass | 13.7% by mass |

The nucleoside protected by a branched chain-containing aromatic group wherein the nucleoside 3'-hydroxyl group is protected by a branched chain-containing aromatic protecting group of the present invention was found to show a remarkable solubility in heptane (the most representative non-polar solvent) which is preferably used for reaction solvents and otide elongation reaction including (1) a deprotection step of 5'-terminal hydroxyl group protected by a temporary protecting group, (2) an elongation step of 5'-terminal by the addition of an oligonucleotide comprising a protected base, and (3) a phosphite triester moiety oxidizing step or sulfurizing step, steps (1), (2) and (3) can be performed in a liquid and oligonucleotide, which is an elongated nucleotide, can be isolated and purified by an extraction operation alone, and therefore, the elongation reaction in the next cycle can be sequentially performed without taking out the resultant product from the reaction apparatus, whereby oligonucleotide can be produced continuously in one pot.

In addition, since in the production method of oligonucleotide of the present invention, the oligonucleotide can be stably dissolved in or transferred to a non-polar solvent irrespective of the sequence and chain length of oligonucleotide even as compared to conventional liquid phase methods, it is advantageous in that the isolation and purification step can be simplified as for the steps, and high purity and high yield can be ensured as a total view.

This application is based on a patent application Nos. 2012-033429 and 2012-254718 filed in Japan, the contents of which are incorporated in full herein.

The invention claimed is:

1. A compound comprising a protected base, which is represented by the formula (I):

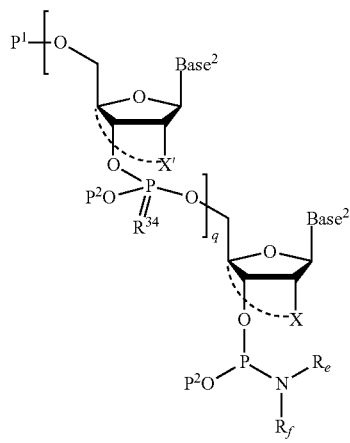

(I)

wherein q is any integer of not less than 0;

Base$^2$ in the number of q+1 are each independently a nucleic acid base protected by a group having a $C_{5-30}$ straight chain or branched chain alkyl group and/or a $C_{5-30}$ straight chain or branched chain alkenyl group;

$P^1$ is a hydrogen atom, or a temporary protecting group removable under acidic conditions;

X is a hydrogen atom, an optionally protected hydroxyl group, a halogen atom or an organic group crosslinked with the 4-position carbon atom;

X' in the number of q are each independently a hydrogen atom, an optionally protected hydroxyl group, a halogen atom or an organic group crosslinked with the 4-position carbon atom;

$P^2$ in the number of q+1 are each independently a protecting group removable under basic conditions;

$R^{34}$ in the number of q are each independently an oxygen atom or a sulfur atom; and $R_e$ and $R_f$ are each independently a $C_{1-6}$ alkyl group, or a 5- or 6-membered saturated cyclic amino group formed together with the adjacent nitrogen atom.

2. The compound comprising a protected base of according to claim 1, wherein q is 0.

3. The compound comprising a protected base according to claim 1 or 2, wherein the group having a $C_{5-30}$ straight chain or branched chain alkyl group and/or a $C_{5-30}$ straight chain or branched chain alkenyl group is a group represented by the formula (k):

(k)

wherein * indicates the bonding position to a nucleic acid base;
$R^{27}$ is a $C_{5-30}$ straight chain or branched chain alkyl group or a $C_{5-30}$ straight chain or branched chain alkenyl group;

a group represented by the formula (l):

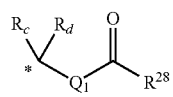

(l)

wherein * indicates the bonding position to a nucleic acid base;
$Q_1$ is —O—, —S— or —NR$^{30}$— wherein R$^{30}$ is a hydrogen atom or a $C_{1-22}$ alkyl group;
$R_c$ and $R_d$ are each independently a hydrogen atom or a $C_{1-22}$ alkyl group; and
$R^{28}$ is a $C_{5-30}$ straight chain or branched chain alkyl group or a $C_{5-30}$ straight chain or branched chain alkenyl group;

a group represented by the formula (m):

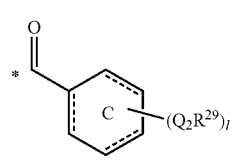

(m)

wherein * indicates the bonding position to a nucleic acid base;
l is an integer of 1 to 5;
$Q_2$ in the number of l are each independently a single bond, or —O—, —S—, —OC(=O)—, —C(=O)O—, —O—CH$_2$—, —NH—, —NHC(=O)—, —C(=O)NH—, —NH—CH$_2$— or —CH$_2$—;
$R^{29}$ in the number of l are each independently a $C_{5-30}$ straight chain or branched chain alkyl group or a $C_{5-30}$ straight chain or branched chain alkenyl group;
ring C is a benzene ring or a cyclohexane ring, each optionally having, in addition to $Q_2R^{29}$ in the number of l and *C=O, a substituent selected from the group consisting of a halogen atom, a $C_{1-6}$ alkyl group optionally substituted by one or more halogen atoms, and a $C_{1-6}$ alkoxy group optionally substituted by one or more halogen atoms; or a group represented by the formula (s):

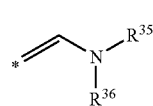

(s)

wherein * indicates the position at which an imino bond is formed with an amino group of a nucleic acid base; and $R^{35}$ and $R^{36}$ are each independently a $C_{5-30}$ straight chain or branched chain alkyl group or a $C_{5-30}$ straight chain or branched chain alkenyl group.

4. The compound comprising a protected base according to claim 3, wherein $R^{27}$, $R^{28}$, $R^{29}$ in the number of 1, $R^{35}$ and $R^{36}$ are each independently a branched chain alkyl group or branched chain alkenyl group selected from the group consisting of a 2,6,10,14-tetramethylpentadecyl group, a 2,6,10-trimethylundecyl group, a 2,2,4,8,10,10-hexamethyl-5-undecyl group, a 2,6,10-trimethylundeca-1,5,9-trienyl group, a 2,6-dimethylheptyl group, a 2,6-dimethylhept-5-enyl group, a 2,6-dimethylhepta-1,5-dienyl group, a 9-nonadecyl group, a 12-methyltridecyl group, an 11-methyltridecyl group, an 11-methyldodecyl group, a 10-methylundecyl group, an 8-heptadecyl group, a 7-pentadecyl group, a 7-methyloctyl group, a 3-methyloctyl group, a 3,7-dimethyloctyl group, a 3-methylheptyl group, a 3-ethylheptyl group, a 5-undecyl group, a 2-heptyl group, a 2-methyl-2-hexyl group, a 2-hexyl group, a 3-heptyl group, a 4-heptyl group, a 4-methyl-pentyl group, a 3-methyl-pentyl group, and a 2,4,4-trimethylpentyl group; or a straight chain alkyl group selected from the group consisting of a tetradecyl group, a tridecyl group, a dodecyl group, an undecyl group, a decyl group, a nonyl group, an octyl group, a heptyl group, a hexyl group, and a pentyl group.

5. The compound comprising a protected base according to claim 1, wherein the $C_{5-30}$ straight chain or branched chain alkyl group and/or $C_{5-30}$ straight chain or branched chain alkenyl group is a $C_{5-30}$ branched chain alkyl group and/or a $C_{5-30}$ branched chain alkenyl group.

6. The compound comprising a protected base according to claim 1, wherein $P^1$ is a monomethoxytrityl group or a dimethoxytrityl group.

7. A method of producing an n+p-mer oligonucleotide, comprising (2) a step of condensing a p-mer oligonucleotide comprising a protected base, wherein p is any integer of one or more, wherein the 3'-hydroxyl group is phosphoramidited, the 5'-hydroxyl group is protected by a temporary protecting group removable under acidic conditions, and the nucleic acid base is protected by a group having a $C_{5-30}$ straight chain or branched chain alkyl group and/or a $C_{5-30}$ straight chain or branched chain alkenyl group, with an n-mer oligonucleotide, wherein n is an integer of one or more, wherein the 5'-hydroxyl group is not protected and the 3'-hydroxyl group is protected, by forming a phosphite triester bond via the 5'-hydroxyl group thereof in a liquid phase.

8. The production method according to claim 7, wherein p is 1.

9. The production method according to claim 7 or 8, further comprising the following step (3):
(3) a step of converting the phosphite triester bond of the n+p-mer oligonucleotide obtained in the condensation step to a phosphate triester bond or a thiophosphate triester bond by adding an oxidizing agent or a sulfurizing agent to the reaction mixture obtained in the condensation step (2).

10. The production method according to claim 7, further comprising the following step (1):
(1) a step of removing the temporary protecting group removable under acidic conditions of the 5'-hydroxyl group by reacting, in a non-polar solvent prior to the condensation step (2), an n-mer oligonucleotide wherein the 3'-hydroxyl group is protected, and the 5'-hydroxyl group is protected by a temporary protecting group, with an acid.

11. The production method according to claim 10, wherein the step (1) is performed in the presence of at least one kind of cation scavenger selected from a pyrrole derivative and an indole derivative, and further comprises a step of neutralization with an organic base after removal of the temporary protecting group of the 5'-hydroxyl group.

12. The production method according to claim 9, further comprising the following step (4):
(4) a step of isolating the n+p-mer oligonucleotide from the reaction mixture obtained in step (3) by an extraction operation alone.

13. The production method according to claim 12, further comprising the following step (5):
(5) a step of removing all the protecting groups of the n+p-mer oligonucleotide obtained in step (4).

14. The production method according to claim 7, wherein the p-mer oligonucleotide comprising a protected base, wherein the 3'-hydroxyl group is phosphoramidited, the 5'-hydroxyl group is protected by a temporary protecting group removable under acidic conditions, and the nucleic acid base is protected by a group having a $C_{5-30}$ straight chain or branched chain alkyl group and/or a $C_{5-30}$ straight chain or branched chain alkenyl group, is the oligonucleotide comprising a protected base according to any one of claims 1 to 6.

15. The production method according to claim 7, wherein the 3'-hydroxyl group of the n-mer oligonucleotide is protected by a group represented by the formula (III):

$$\text{-L-Y-Z} \tag{III}$$

wherein
L is a group represented by the formula (a1):

wherein * shows the bonding position to Y; ** indicates the bonding position to a 3'-hydroxy group of the nucleotide; $L_1$ is an optionally substituted divalent $C_{1-22}$ hydrocarbon group; and
$L_2$ is a single bond, or a group represented by C(=O)N($R^2$)—$R^1$—N($R^3$)* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond,
Y is an oxygen atom or NR wherein R is a hydrogen atom, an alkyl group or an aralkyl group, and
Z is a group represented by the formula (a2):

wherein * shows the bonding position to Y;
$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;
Q in the number of k are each independently a single bond, or —O—, —S—, —OC(=O)—, —NHC(=O)— or —NH—;
$R^5$ in the number of k are each independently an organic group having at least one aliphatic hydrocarbon group having one or more branched chains and the total carbon number of not less than 14 and not more than 300;

k is an integer of 1 to 4;

ring A optionally further has, in addition to $R^4$, $QR^5$ in the number of k and $*C(R_a)(R_b)$, a substituent selected from the group consisting of a halogen atom, a $C_{1-6}$ alkyl group optionally substituted by one or more halogen atoms, and a $C_{1-6}$ alkoxy group optionally substituted by one or more halogen atoms;

$R_a$ is a hydrogen atom; and $R_b$ is a hydrogen atom, or a group represented by the formula (a3):

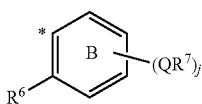

(a3)

wherein * indicates a bonding position;

j is an integer of 0 to 4;

Q in the number of j are each independently as defined above;

$R^7$ in the number of j are each independently an organic group having at least one aliphatic hydrocarbon group having one or more branched chains and the total carbon number of not less than 14 and not more than 300;

$R^6$ is a hydrogen atom, or optionally a single bond or —O— in combination with $R^4$ to form a fluorenyl group or a xanthenyl group together with ring A; and ring B optionally further has, in addition to $QR^7$ in the number of j and $R^6$, a substituent selected from the group consisting of a halogen atom, a $C_{1-6}$ alkyl group optionally substituted by one or more halogen atoms, and a $C_{1-6}$ alkoxy group optionally substituted by one or more halogen atoms.

16. The production method according to claim 7, wherein at least one nucleic acid base of the n-mer oligonucleotide is protected by a group having a $C_{5-30}$ straight chain or branched chain alkyl group and/or a $C_{5-30}$ straight chain or branched chain alkenyl group.

17. The production method according to claim 7, wherein the $C_{5-30}$ straight chain or branched chain alkyl group and/or $C_{5-30}$ straight chain or branched chain alkenyl group are/is a $C_{5-30}$ branched chain alkyl group and/or a $C_{5-30}$ branched chain alkenyl group.

18. A compound protected by a branched chain-containing aromatic group, which is represented by the formula (II):

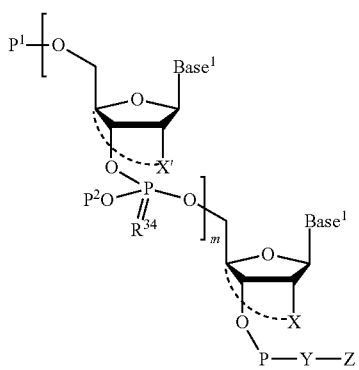

(II)

wherein m is any integer of 0 or more;

Base³ in the number of m+1 are each independently an optionally protected nucleic acid base;

$P^1$ is a hydrogen atom, or a temporary protecting group removable under acidic conditions;

X is a hydrogen atom, an optionally protected hydroxyl group, a halogen atom or an organic group crosslinked with the 4-position carbon atom;

X' in the number of m are each independently a hydrogen atom, an optionally protected hydroxyl group, a halogen atom or an organic group crosslinked with the 4-position carbon atom;

$P^2$ in the number of m are each independently a protecting group removable under basic conditions;

$R^{34}$ in the number of m are each independently an oxygen atom or a sulfur atom;

L is a group represented by the formula (a1):

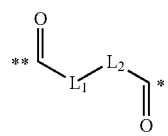

(a1)

wherein * shows the bonding position to Y;  indicates the bonding position to a 3'-hydroxy group of the nucleotide; $L_1$ is an optionally substituted divalent $C_{1-22}$ hydrocarbon group; and $L_2$ is a single bond, or a group represented by C(=O)N($R^2$)—$R^1$—N($R^3$)* wherein shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond, Y is an oxygen atom or NR wherein R is a hydrogen atom, an alkyl group or an aralkyl group, and Z is a group represented by the formula (a2):

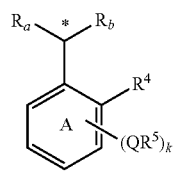

(a2)

wherein * shows the bonding position to Y;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

Q in the number of k are each independently a single bond, or —O—, —S—, —OC(=O)—, —NHC(=O)— or —NH—;

$R^5$ in the number of k are each independently an organic group having at least one aliphatic hydrocarbon group having one or more branched chains, and the total carbon number of not less than 14 and not more than 300;

k is an integer of 1 to 4;

ring A optionally further has, in addition to $R^4$, $QR^5$ in the number of k and $*C(R_a)(R_b)$, a substituent selected from the group consisting of a halogen atom, a $C_{1-6}$ alkyl group optionally substituted by one or more halogen atoms, and a $C_{1-6}$ alkoxy group optionally substituted by one or more halogen atoms;

$R_a$ is a hydrogen atom; and $R_b$ is a hydrogen atom, or a group represented by the formula (a3):

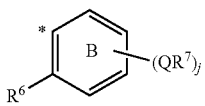

(a3)

wherein * indicates the bonding position;

j is an integer of 0 to 4;

Q in the number of j are each independently as defined above;

$R^7$ in the number of j are each independently an organic group having at least one aliphatic hydrocarbon group having one or more branched chains and the total carbon number of not less than 14 and not more than 300;

$R^6$ is a hydrogen atom, or optionally a single bond or —O— in combination with $R^4$ to form a fluorenyl group or a xanthenyl group together with ring A; and ring B optionally further has, in addition to $QR^7$ in the number of j and $R^6$, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms.

19. The compound according to claim 18, wherein m is 0.

20. The compound according to claim 18 or 19, wherein at least one of the nucleic acid bases is protected by a group having a $C_{5-30}$ straight chain or branched chain alkyl group and/or a $C_{5-30}$ straight chain or branched chain alkenyl group.

21. A method of producing an n'+p'-mer oligonucleotide comprising:

(2') a step of condensing a p'-mer oligonucleotide, wherein p' is any integer of one or more, wherein the 3'-hydroxyl group is phosphoramidited, the 5'-hydroxyl group is protected by a temporary protecting group removable under acidic conditions, and the nucleic acid base is optionally protected, with an n'-mer oligonucleotide, wherein n' is any integer of one or more, wherein the 5'-hydroxyl group is not protected, and the 3'-hydroxyl group is protected by the protecting group represented by the formula (III):

L-Y—Z  (II)

wherein

L is a group represented by the formula (a1):

(a1)

wherein * shows the bonding position to Y; ** indicates the bonding position to a 3'-hydroxy group of the nucleotide;

$L_1$ is an optionally substituted divalent $C_{1-22}$ hydrocarbon group; and $L_2$ is a single bond, or a group represented by C(=O)N($R^2$)—$R^1$—N($R^3$)* wherein  shows the bonding position to $L_1$, * shows the bonding position to C=O, $R^1$ is an optionally substituted $C_{1-22}$ alkylene group, and $R^2$ and $R^3$ are each independently a hydrogen atom or an optionally substituted $C_{1-22}$ alkyl group, or $R^2$ and $R^3$ are optionally joined to form an optionally substituted $C_{1-22}$ alkylene bond, Y is an oxygen atom or NR wherein R is a hydrogen atom, an alkyl group or an aralkyl group, and Z is a group represented by the formula (a2):

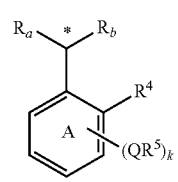

(a2)

wherein * shows the bonding position to Y;

$R^4$ is a hydrogen atom, or when $R_b$ is a group represented by the following formula (a3), $R^4$ is optionally a single bond or —O— in combination with $R^6$ to form a fluorenyl group or a xanthenyl group together with ring B;

Q in the number of k are each independently a single bond, or —O—, —S—, —OC(=O)—, —NHC(=O)— or —NH—;

$R^5$ in the number of k are each independently an organic group having at least one aliphatic hydrocarbon group having one or more branched chains and the total carbon number of not less than 14 and not more than 300;

k is an integer of 1 to 4;

ring A optionally further has, in addition to $R^4$, $QR^5$ in the number of k and *C($R_a$)($R_b$), a substituent selected from the group consisting of a halogen atom, a $C_{1-6}$ alkyl group optionally substituted by one or more halogen atoms, and a $C_{1-6}$ alkoxy group optionally substituted by one or more halogen atoms;

$R_a$ is a hydrogen atom; and $R_b$ is a hydrogen atom, or a group represented by the formula (a3):

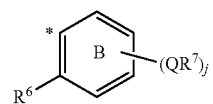

(a3)

wherein * indicates the bonding position;

j is an integer of 0 to 4;

Q in the number of j are each independently as defined above;

$R^7$ in the number of j are each independently an organic group having at least one aliphatic hydrocarbon group having one or more branched chains and the total carbon number of not less than 14 and not more than 300;

$R^6$ is a hydrogen atom, or optionally a single bond or —O— in combination with $R^4$ to form a fluorenyl group or a xanthenyl group together with ring A; and ring B optionally further has, in addition to $QR^7$ in the number of j and $R^6$, a substituent selected from the group consisting of a halogen atom, a $C_{1-6}$ alkyl group optionally substituted by one or more halogen atoms, and a $C_{1-6}$ alkoxy group optionally substituted by one or more halogen atoms, by forming a phosphite triester bond via the 5'-hydroxyl group thereof.

22. The compound comprising a protected base according to claim 1, wherein $Base^2$ in the number of q+1 are each independently a nucleic acid base protected by a group having a $C_{5-30}$ straight chain or branched chain alkyl group and/or a $C_{5-30}$ branched chain alkenyl group.

* * * * *